(12) United States Patent
Jovanovich et al.

(10) Patent No.: US 8,394,642 B2
(45) Date of Patent: Mar. 12, 2013

(54) UNIVERSAL SAMPLE PREPARATION SYSTEM AND USE IN AN INTEGRATED ANALYSIS SYSTEM

(75) Inventors: Stevan B. Jovanovich, Livermore, CA (US); William D. Nielsen, San Jose, CA (US); David S. Cohen, San Bruno, CA (US); Michael Recknor, Oakland, CA (US); Mattias Vangbo, Fremont, CA (US); Ezra Van Gelder, Palo Alto, CA (US); Lars Majlof, San Jose, CA (US); Omar El-Sissi, Fremont, CA (US)

(73) Assignee: IntegenX Inc., Pleasanton, CA (US)

( * ) Notice: Subject to any disclaimer, the term of this patent is extended or adjusted under 35 U.S.C. 154(b) by 50 days.

(21) Appl. No.: 12/795,515

(22) Filed: Jun. 7, 2010

(65) Prior Publication Data

US 2011/0005932 A1 Jan. 13, 2011

Related U.S. Application Data

(60) Provisional application No. 61/184,759, filed on Jun. 5, 2009, provisional application No. 61/235,664, filed on Aug. 20, 2009, provisional application No. 61/349,680, filed on May 28, 2010.

(51) Int. Cl.
| | | |
|---|---|---|
| *G01N 15/06* | (2006.01) | |
| *G01N 33/00* | (2006.01) | |
| *G01N 33/48* | (2006.01) | |

(52) U.S. Cl. ............. 436/94; 422/68.1; 422/50; 422/81; 436/63

(58) Field of Classification Search .................... 422/50, 422/68.1, 81; 436/43, 63, 94
See application file for complete search history.

(56) References Cited

U.S. PATENT DOCUMENTS

| | | |
|---|---|---|
| 3,352,643 A | 11/1967 | Ando et al. |
| 3,433,257 A | 3/1969 | Jensen |
| 3,568,692 A | 3/1971 | Metzger et al. |
| 4,113,665 A | 9/1978 | Law et al. |
| 4,847,120 A | 7/1989 | Gent |
| 4,963,498 A | 10/1990 | Hillman et al. |
| 5,085,757 A | 2/1992 | Karger et al. |
| 5,275,645 A | 1/1994 | Ternoir et al. |

(Continued)

FOREIGN PATENT DOCUMENTS

| | | |
|---|---|---|
| EP | 0459241 B1 | 12/1991 |
| EP | 0637999 A1 | 2/1995 |

(Continued)

OTHER PUBLICATIONS

Datasheet Cycle Sequencing, Retrieved from the internet, URL:http//answers.com/topic/cycle sequencing. Printed Sep. 3, 2010, pp. 1-2.

(Continued)

*Primary Examiner* — Brian J Sines

(57) ABSTRACT

The invention provides a system that can process a raw biological sample, perform a biochemical reaction and provide an analysis readout. For example, the system can extract DNA from a swab, amplify STR loci from the DNA, and analyze the amplified loci and STR markers in the sample. The system integrates these functions by using microfluidic components to connect what can be macrofluidic functions. In one embodiment the system includes a sample purification module, a reaction module, a post-reaction clean-up module, a capillary electrophoresis module and a computer. In certain embodiments, the system includes a disposable cartridge for performing analyte capture. The cartridge can comprise a fluidic manifold having macrofluidic chambers mated with microfluidic chips that route the liquids between chambers. The system fits within an enclosure of no more than 10 ft$^3$. and can be a closed, portable, and/or a battery operated system. The system can be used to go from raw sample to analysis in less than 4 hours.

43 Claims, 80 Drawing Sheets

U.S. PATENT DOCUMENTS

| | | |
|---|---|---|
| 5,364,759 A | 11/1994 | Caskey et al. |
| 5,376,252 A | 12/1994 | Ekström et al. |
| 5,387,505 A | 2/1995 | Wu |
| 5,453,163 A | 9/1995 | Yan |
| 5,482,836 A | 1/1996 | Cantor et al. |
| 5,523,231 A | 6/1996 | Reeve |
| 5,571,410 A | 11/1996 | Swedberg et al. |
| 5,587,128 A | 12/1996 | Wilding et al. |
| 5,635,358 A | 6/1997 | Wilding et al. |
| 5,639,428 A | 6/1997 | Cottingham |
| 5,681,946 A | 10/1997 | Reeve |
| 5,705,628 A | 1/1998 | Hawkins |
| 5,705,813 A | 1/1998 | Apffel et al. |
| 5,726,026 A | 3/1998 | Wilding et al. |
| 5,741,462 A | 4/1998 | Nova et al. |
| 5,750,015 A | 5/1998 | Soane et al. |
| 5,770,029 A | 6/1998 | Nelson et al. |
| 5,775,371 A | 7/1998 | Pan et al. |
| 5,776,748 A | 7/1998 | Singhvi et al. |
| 5,830,662 A | 11/1998 | Soares et al. |
| 5,842,787 A | 12/1998 | Kopf-sill et al. |
| 5,856,174 A | 1/1999 | Lipshutz et al. |
| 5,863,502 A | 1/1999 | Southgate et al. |
| 5,872,010 A | 2/1999 | Karger et al. |
| 5,885,470 A | 3/1999 | Parce et al. |
| 5,898,071 A | 4/1999 | Hawkins |
| 5,908,552 A | 6/1999 | Zimmerman et al. |
| 5,922,591 A | 7/1999 | Anderson et al. |
| 5,942,443 A | 8/1999 | Parce et al. |
| 5,948,684 A | 9/1999 | Weigl et al. |
| 5,971,158 A | 10/1999 | Yager et al. |
| 5,994,064 A | 11/1999 | Staub et al. |
| 6,001,229 A | 12/1999 | Ramsey |
| 6,007,690 A | 12/1999 | Nelson et al. |
| 6,007,775 A | 12/1999 | Yager |
| 6,010,607 A | 1/2000 | Ramsey |
| 6,027,031 A | 2/2000 | Reason et al. |
| 6,048,100 A | 4/2000 | Thrall et al. |
| 6,056,860 A | 5/2000 | Amigo et al. |
| 6,073,482 A | 6/2000 | Moles |
| 6,074,827 A | 6/2000 | Nelson et al. |
| 6,103,199 A | 8/2000 | Bjornson et al. |
| 6,110,343 A | 8/2000 | Ramsey et al. |
| 6,120,184 A | 9/2000 | Laurence et al. |
| 6,136,212 A | 10/2000 | Mastrangelo et al. |
| 6,168,948 B1 | 1/2001 | Anderson et al. |
| 6,176,962 B1 | 1/2001 | Soane et al. |
| 6,190,616 B1 | 2/2001 | Jovanovich et al. |
| 6,197,595 B1 | 3/2001 | Anderson et al. |
| 6,207,031 B1 | 3/2001 | Adourian et al. |
| 6,235,471 B1 | 5/2001 | Knapp et al. |
| 6,238,538 B1 | 5/2001 | Parce et al. |
| 6,251,343 B1 | 6/2001 | Dubrow et al. |
| 6,280,589 B1 | 8/2001 | Manz et al. |
| 6,319,476 B1 | 11/2001 | Victor, Jr. et al. |
| 6,321,791 B1 | 11/2001 | Chow |
| 6,322,683 B1 | 11/2001 | Wolk et al. |
| 6,342,142 B1 | 1/2002 | Ramsey |
| 6,348,318 B1 | 2/2002 | Valkirs |
| 6,379,929 B1 | 4/2002 | Burns et al. |
| 6,387,234 B1 | 5/2002 | Yeung et al. |
| 6,387,707 B1 | 5/2002 | Seul et al. |
| 6,403,338 B1 | 6/2002 | Knapp et al. |
| 6,408,878 B2 | 6/2002 | Unger et al. |
| 6,423,536 B1 | 7/2002 | Jovanovich et al. |
| 6,429,025 B1 | 8/2002 | Parce et al. |
| 6,432,191 B2 | 8/2002 | Schutt |
| 6,432,290 B1 | 8/2002 | Harrison et al. |
| 6,454,924 B2 | 9/2002 | Jedrzejewski et al. |
| 6,489,112 B1 | 12/2002 | Hadd et al. |
| 6,521,188 B1 | 2/2003 | Webster |
| 6,524,456 B1 | 2/2003 | Ramsey et al. |
| 6,527,003 B1 | 3/2003 | Webster |
| 6,531,041 B1 | 3/2003 | Cong et al. |
| 6,531,282 B1 * | 3/2003 | Dau et al. ............... 435/6.11 |
| 6,532,997 B1 | 3/2003 | Bedingham et al. |
| 6,533,914 B1 | 3/2003 | Liu |
| 6,534,262 B1 | 3/2003 | Mckernan et al. |
| 6,537,757 B1 | 3/2003 | Langmore et al. |
| 6,544,734 B1 | 4/2003 | Briscoe et al. |
| 6,551,839 B2 | 4/2003 | Jovanovich et al. |
| 6,581,441 B1 | 6/2003 | Paul |
| 6,581,899 B2 | 6/2003 | Williams |
| 6,605,454 B2 | 8/2003 | Barenburg et al. |
| 6,613,525 B2 | 9/2003 | Nelson et al. |
| 6,614,228 B2 | 9/2003 | Hofmann et al. |
| 6,618,679 B2 | 9/2003 | Loehrlein |
| 6,623,613 B1 | 9/2003 | Mathies et al. |
| 6,627,446 B1 | 9/2003 | Roach et al. |
| 6,629,820 B2 | 10/2003 | Kornelsen |
| 6,632,619 B1 | 10/2003 | Harrison et al. |
| 6,632,655 B1 | 10/2003 | Mehta et al. |
| 6,663,833 B1 | 12/2003 | Stave et al. |
| 6,685,442 B2 | 2/2004 | Chinn et al. |
| 6,685,809 B1 | 2/2004 | Jacobson et al. |
| 6,752,922 B2 | 6/2004 | Huang et al. |
| 6,764,648 B1 | 7/2004 | Roach et al. |
| 6,782,746 B1 | 8/2004 | Hasselbrink et al. |
| 6,786,708 B2 | 9/2004 | Brown et al. |
| 6,787,111 B2 | 9/2004 | Roach et al. |
| 6,793,753 B2 | 9/2004 | Unger et al. |
| 6,802,342 B2 | 10/2004 | Fernandes et al. |
| 6,803,019 B1 | 10/2004 | Bjornson et al. |
| 6,807,490 B1 | 10/2004 | Perlin |
| 6,824,663 B1 | 11/2004 | Boone |
| 6,829,753 B2 | 12/2004 | Lee et al. |
| 6,833,246 B2 | 12/2004 | Balasubramanian |
| 6,852,287 B2 | 2/2005 | Ganesan |
| 6,870,185 B2 | 3/2005 | Roach et al. |
| 6,885,982 B2 | 4/2005 | Harris et al. |
| 6,899,137 B2 | 5/2005 | Unger et al. |
| 6,923,907 B2 | 8/2005 | Hobbs et al. |
| 6,929,030 B2 | 8/2005 | Unger et al. |
| 6,951,632 B2 | 10/2005 | Unger et al. |
| 6,953,058 B2 | 10/2005 | Fernandes et al. |
| 6,960,437 B2 | 11/2005 | Enzelberger et al. |
| 6,994,986 B2 | 2/2006 | Swartz et al. |
| 7,005,292 B2 | 2/2006 | Wilding et al. |
| 7,005,493 B2 | 2/2006 | Huang et al. |
| 7,015,030 B1 | 3/2006 | Fouillet et al. |
| 7,046,357 B2 | 5/2006 | Weinberger et al. |
| 7,049,558 B2 | 5/2006 | Baer et al. |
| 7,087,380 B2 | 8/2006 | Griffiths et al. |
| 7,097,809 B2 | 8/2006 | Van Dam et al. |
| 7,118,910 B2 | 10/2006 | Unger et al. |
| 7,157,228 B2 | 1/2007 | Hashmi et al. |
| 7,169,557 B2 | 1/2007 | Rosenblum et al. |
| 7,198,759 B2 | 4/2007 | Bryning et al. |
| 7,211,388 B2 | 5/2007 | Cash et al |
| 7,232,656 B2 | 6/2007 | Balasubramanian et al. |
| 7,244,961 B2 | 7/2007 | Jovanovich et al. |
| 7,258,774 B2 | 8/2007 | Chou et al. |
| 7,279,146 B2 | 10/2007 | Nassef et al. |
| 7,282,361 B2 | 10/2007 | Hodge |
| 7,312,085 B2 | 12/2007 | Chou et al. |
| 7,312,611 B1 | 12/2007 | Harrison et al. |
| 7,323,305 B2 | 1/2008 | Leamon et al. |
| 7,361,471 B2 | 4/2008 | Gerdes et al. |
| 7,438,856 B2 | 10/2008 | Jedrzejewski et al. |
| 7,445,926 B2 | 11/2008 | Mathies et al. |
| 7,488,603 B2 | 2/2009 | Gjerde et al. |
| 7,501,237 B2 | 3/2009 | Solus et al. |
| 7,526,741 B2 | 4/2009 | Lee et al. |
| 7,537,886 B1 | 5/2009 | Nazarenko et al. |
| 7,575,865 B2 | 8/2009 | Leamon et al. |
| 7,645,580 B2 | 1/2010 | Barber et al. |
| 7,691,614 B2 | 4/2010 | Senapathy |
| 7,745,207 B2 | 6/2010 | Jovanovich et al. |
| 7,763,453 B2 | 7/2010 | Clemmens et al. |
| 7,766,033 B2 | 8/2010 | Mathies et al. |
| 7,799,553 B2 | 9/2010 | Mathies et al. |
| 7,803,281 B2 | 9/2010 | Davies |
| 7,817,273 B2 | 10/2010 | Bahatt et al. |
| 7,832,429 B2 | 11/2010 | Young et al. |
| 7,863,357 B2 | 1/2011 | Madabhushi et al. |
| 7,867,713 B2 | 1/2011 | Nasarabadi |
| 7,885,770 B2 | 2/2011 | Gill et al. |

| | | |
|---|---|---|
| 7,892,856 B2 | 2/2011 | Grate et al. |
| 7,942,160 B2 | 5/2011 | Jeon et al. |
| 7,943,305 B2 | 5/2011 | Korlach et al. |
| 7,959,875 B2 | 6/2011 | Zhou et al. |
| 7,976,789 B2 | 7/2011 | Kenis et al. |
| 7,976,795 B2 | 7/2011 | Zhou et al. |
| 8,007,746 B2 | 8/2011 | Unger et al. |
| 8,018,593 B2 | 9/2011 | Tan et al. |
| 8,053,192 B2 | 11/2011 | Bignell et al. |
| 2001/0041357 A1 | 11/2001 | Fouillet et al. |
| 2002/0022587 A1 | 2/2002 | Ferguson et al. |
| 2002/0025529 A1 | 2/2002 | Quake et al. |
| 2002/0025576 A1 | 2/2002 | Northrup et al. |
| 2002/0047003 A1 | 4/2002 | Bedingham et al. |
| 2002/0048536 A1 | 4/2002 | Bergh et al. |
| 2002/0051992 A1 | 5/2002 | Bridgham et al. |
| 2002/0058332 A1 | 5/2002 | Quake et al. |
| 2002/0068357 A1 | 6/2002 | Mathies et al. |
| 2002/0098097 A1 | 7/2002 | Singh |
| 2002/0110900 A1 | 8/2002 | Jovanovich et al. |
| 2002/0119480 A1 | 8/2002 | Weir et al. |
| 2002/0119482 A1 | 8/2002 | Nelson et al. |
| 2002/0139084 A1 | 10/2002 | Tobolka |
| 2002/0157951 A1 | 10/2002 | Foret et al. |
| 2002/0160361 A1 | 10/2002 | Loehrlein et al. |
| 2003/0008308 A1 | 1/2003 | Enzelberger et al. |
| 2003/0021734 A1 | 1/2003 | Vann et al. |
| 2003/0029724 A1 | 2/2003 | Derand et al. |
| 2003/0070677 A1 | 4/2003 | Handique et al. |
| 2003/0095897 A1 | 5/2003 | Grate et al. |
| 2003/0217923 A1 | 11/2003 | Harrison et al. |
| 2004/0003997 A1 | 1/2004 | Anazawa et al. |
| 2004/0013536 A1 | 1/2004 | Hower et al. |
| 2004/0014091 A1 | 1/2004 | Duck et al. |
| 2004/0017981 A1 | 1/2004 | Jovanovich et al. |
| 2004/0018611 A1 | 1/2004 | Ward et al. |
| 2004/0021068 A1 | 2/2004 | Staats |
| 2004/0037739 A1 | 2/2004 | Mcneely et al. |
| 2004/0038385 A1 | 2/2004 | Langlois et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0086870 A1 | 5/2004 | Tyvoll et al. |
| 2004/0086872 A1 | 5/2004 | Childers et al. |
| 2004/0132170 A1 | 7/2004 | Storek et al. |
| 2004/0151629 A1 | 8/2004 | Pease et al. |
| 2004/0185484 A1 | 9/2004 | Costa et al. |
| 2004/0197845 A1 | 10/2004 | Hassibi et al. |
| 2004/0200724 A1 | 10/2004 | Fujii et al. |
| 2004/0209354 A1 | 10/2004 | Mathies et al. |
| 2004/0224380 A1 | 11/2004 | Chou et al. |
| 2005/0026300 A1 | 2/2005 | Samper et al. |
| 2005/0047967 A1 | 3/2005 | Chuang et al. |
| 2005/0053952 A1 | 3/2005 | Hong et al. |
| 2005/0142663 A1 | 6/2005 | Parthasarathy et al. |
| 2005/0161326 A1 | 7/2005 | Morita et al. |
| 2005/0161669 A1 | 7/2005 | Jovanovich et al. |
| 2005/0224134 A1 | 10/2005 | Yin et al. |
| 2005/0224352 A1 | 10/2005 | Harrison et al. |
| 2005/0241941 A1 | 11/2005 | Parce et al. |
| 2005/0255000 A1 | 11/2005 | Yamamoto et al. |
| 2005/0255003 A1 | 11/2005 | Summersgill et al. |
| 2005/0255007 A1 | 11/2005 | Yamada et al. |
| 2005/0266582 A1 | 12/2005 | Modlin et al. |
| 2005/0287572 A1 | 12/2005 | Mathies et al. |
| 2006/0027456 A1 | 2/2006 | Harrison et al. |
| 2006/0057209 A1 | 3/2006 | Chapman et al. |
| 2006/0073484 A1 | 4/2006 | Mathies et al. |
| 2006/0076068 A1 | 4/2006 | Young et al. |
| 2006/0140051 A1 | 6/2006 | Kim et al. |
| 2006/0163143 A1 | 7/2006 | Chirica et al. |
| 2006/0186043 A1 | 8/2006 | Covey et al. |
| 2006/0260941 A1 | 11/2006 | Tan et al. |
| 2006/0263789 A1 | 11/2006 | Kincaid |
| 2006/0266645 A1 | 11/2006 | Chen et al. |
| 2006/0292032 A1 | 12/2006 | Hataoka et al. |
| 2007/0015179 A1 | 1/2007 | Klapperich et al. |
| 2007/0017812 A1 | 1/2007 | Bousse |
| 2007/0031865 A1 | 2/2007 | Willoughby |
| 2007/0034025 A1 | 2/2007 | Pant et al. |
| 2007/0105163 A1 | 5/2007 | Grate et al. |
| 2007/0122819 A1 | 5/2007 | Wu et al. |
| 2007/0175756 A1 | 8/2007 | Nguyen et al. |
| 2007/0184463 A1 | 8/2007 | Molho et al. |
| 2007/0202531 A1 | 8/2007 | Grover |
| 2007/0237686 A1 | 10/2007 | Mathies et al. |
| 2007/0238109 A1 | 10/2007 | Min et al. |
| 2007/0248958 A1 | 10/2007 | Jovanovich et al. |
| 2007/0297947 A1 | 12/2007 | Sommers et al. |
| 2008/0014576 A1 | 1/2008 | Jovanovich et al. |
| 2008/0014589 A1 | 1/2008 | Link et al. |
| 2008/0047836 A1 | 2/2008 | Strand et al. |
| 2008/0064610 A1 | 3/2008 | Lipovsek et al. |
| 2008/0124723 A1 | 5/2008 | Dale et al. |
| 2008/0138809 A1 | 6/2008 | Kapur et al. |
| 2008/0164155 A1 | 7/2008 | Pease et al. |
| 2008/0179255 A1 | 7/2008 | Jung et al. |
| 2008/0179555 A1 | 7/2008 | Landers et al. |
| 2008/0237146 A1 | 10/2008 | Harrison et al. |
| 2008/0242560 A1 | 10/2008 | Gunderson et al. |
| 2008/0257437 A1 | 10/2008 | Fernandes et al. |
| 2008/0281090 A1 | 11/2008 | Lee et al. |
| 2008/0302732 A1 | 12/2008 | Soh et al. |
| 2008/0311585 A1 | 12/2008 | Gao et al. |
| 2009/0004494 A1 | 1/2009 | Blenke et al. |
| 2009/0011959 A1 | 1/2009 | Costa et al. |
| 2009/0023603 A1 | 1/2009 | Selden et al. |
| 2009/0035770 A1 | 2/2009 | Mathies et al. |
| 2009/0053799 A1 | 2/2009 | Chang-yen et al. |
| 2009/0056822 A1 | 3/2009 | Young et al. |
| 2009/0060797 A1 | 3/2009 | Mathies et al. |
| 2009/0084679 A1 | 4/2009 | Harrison et al. |
| 2009/0092970 A1 | 4/2009 | Williams |
| 2009/0134069 A1 | 5/2009 | Handique |
| 2009/0137413 A1 | 5/2009 | Mehta et al. |
| 2009/0148933 A1 | 6/2009 | Battrell et al. |
| 2009/0178934 A1 | 7/2009 | Jarvius et al. |
| 2009/0181411 A1 | 7/2009 | Battrell et al. |
| 2009/0253181 A1 | 10/2009 | Vangbo et al. |
| 2009/0269504 A1 | 10/2009 | Liao |
| 2009/0286327 A1 | 11/2009 | Cho et al. |
| 2009/0311804 A1 | 12/2009 | Mcbrady et al. |
| 2009/0314972 A1 | 12/2009 | Mcavoy et al. |
| 2010/0068723 A1 | 3/2010 | Jovanovich et al. |
| 2010/0111770 A1 | 5/2010 | Hwang et al. |
| 2010/0129810 A1 | 5/2010 | Greiner et al. |
| 2010/0165784 A1 | 7/2010 | Jovanovich et al. |
| 2010/0172898 A1 | 7/2010 | Doyle et al. |
| 2010/0173398 A1 | 7/2010 | Peterman |
| 2010/0197507 A1 | 8/2010 | Rothberg et al. |
| 2010/0210008 A1 | 8/2010 | Strand et al. |
| 2010/0221726 A1 | 9/2010 | Zenhausern et al. |
| 2010/0228513 A1 | 9/2010 | Roth et al. |
| 2010/0233696 A1 | 9/2010 | Joseph et al. |
| 2010/0243916 A1 | 9/2010 | Maurer et al. |
| 2010/0266432 A1 | 10/2010 | Pirk et al. |
| 2010/0285578 A1 | 11/2010 | Selden et al. |
| 2010/0285606 A1 | 11/2010 | Philips et al. |
| 2010/0285975 A1 | 11/2010 | Mathies et al. |
| 2010/0291666 A1 | 11/2010 | Collier et al. |
| 2010/0303687 A1 | 12/2010 | Blaga et al. |
| 2010/0304355 A1 | 12/2010 | Shuler et al. |
| 2010/0326826 A1 | 12/2010 | Harrison et al. |
| 2011/0003301 A1 | 1/2011 | Raymond et al. |
| 2011/0008813 A1 | 1/2011 | Dilleen et al. |
| 2011/0027913 A1 | 2/2011 | Bau et al. |
| 2011/0038758 A1 | 2/2011 | Akaba et al. |
| 2011/0045505 A1 | 2/2011 | Warthoe et al. |
| 2011/0053784 A1 | 3/2011 | Unger et al. |
| 2011/0070578 A1 | 3/2011 | Bell et al. |
| 2011/0124049 A1 | 5/2011 | Li et al. |
| 2011/0126910 A1 | 6/2011 | May |
| 2011/0127222 A1 | 6/2011 | Chang-yen et al. |
| 2011/0136179 A1 | 6/2011 | Bin/lee et al. |
| 2011/0137018 A1 | 6/2011 | Chang-yen et al. |
| 2011/0171086 A1 | 7/2011 | Prins et al. |
| 2011/0172403 A1 | 7/2011 | Harrold et al. |
| 2011/0189678 A1 | 8/2011 | Mcbride et al. |

| | | | |
|---|---|---|---|
| 2011/0206576 | A1 | 8/2011 | Woudenberg et al. |
| 2011/0212440 | A1 | 9/2011 | Viovy et al. |
| 2011/0212446 | A1 | 9/2011 | Wang et al. |
| 2011/0223605 | A1 | 9/2011 | Bienvenue et al. |

FOREIGN PATENT DOCUMENTS

| | | | |
|---|---|---|---|
| EP | 0527905 | B1 | 11/1995 |
| EP | 1065378 | B1 | 4/2002 |
| EP | 1411340 | A2 | 4/2004 |
| EP | 1411340 | A3 | 5/2004 |
| EP | 1658890 | B1 | 5/2008 |
| EP | 2345739 | A2 | 7/2011 |
| JP | 408327594 | A | 12/1996 |
| JP | 2003-536058 | A | 12/2003 |
| JP | 2004-025159 | A | 1/2004 |
| JP | 2004-108285 | A | 4/2004 |
| JP | 2004-180594 | A | 7/2004 |
| JP | 2005-323519 | A | 11/2005 |
| JP | 2005-337415 | | 12/2005 |
| JP | 2005-345463 | A | 12/2005 |
| JP | 2007-155491 | A | 6/2007 |
| JP | 2008-513022 | A | 5/2008 |
| WO | WO 96/04547 | A1 | 2/1996 |
| WO | WO 98/52691 | A1 | 11/1998 |
| WO | WO 98/53300 | A2 | 11/1998 |
| WO | WO 98/53300 | A3 | 2/1999 |
| WO | WO 99/36766 | A1 | 7/1999 |
| WO | WO 99/40174 | A1 | 8/1999 |
| WO | WO 00/40712 | A1 | 7/2000 |
| WO | WO 00/60362 | A1 | 10/2000 |
| WO | WO 00/61198 | A1 | 10/2000 |
| WO | WO 01/38865 | A1 | 5/2001 |
| WO | WO 01/85341 | A1 | 11/2001 |
| WO | WO 02/41995 | A1 | 5/2002 |
| WO | WO 02/43615 | A2 | 6/2002 |
| WO | WO 02/043615 | A3 | 3/2003 |
| WO | WO 03/085379 | A2 | 10/2003 |
| WO | WO 2004/038363 | A2 | 5/2004 |
| WO | WO 2004/098757 | A2 | 11/2004 |
| WO | WO 2004/038363 | A3 | 12/2004 |
| WO | WO 2005/075081 | A1 | 8/2005 |
| WO | WO 2005/121308 | A1 | 12/2005 |
| WO | WO 2004/098757 | A3 | 5/2006 |
| WO | WO 2007/002579 | A2 | 1/2007 |
| WO | WO 2007/064635 | A1 | 6/2007 |
| WO | WO 2007/082480 | A1 | 7/2007 |
| WO | WO 2008/012104 | A2 | 1/2008 |
| WO | WO 2008/024319 | A2 | 2/2008 |
| WO | WO 2008/024319 | A3 | 4/2008 |
| WO | WO 2008/039875 | A1 | 4/2008 |
| WO | WO 2008/012104 | A3 | 5/2008 |
| WO | WO 2008/115626 | A2 | 9/2008 |
| WO | WO 2008/115626 | A3 | 11/2008 |
| WO | WO 2009/008236 | A1 | 1/2009 |
| WO | WO 2009/015296 | A1 | 1/2009 |
| WO | WO 2007/002579 | A3 | 9/2009 |
| WO | WO 2009/108260 | A2 | 9/2009 |
| WO | WO 2009/129415 | A1 | 10/2009 |
| WO | WO 2009/108260 | A3 | 12/2009 |
| WO | WO 2010/041174 | A1 | 4/2010 |
| WO | WO 2010/041231 | A2 | 4/2010 |
| WO | WO 2010/042784 | A2 | 4/2010 |
| WO | WO 2010/042784 | A3 | 7/2010 |
| WO | WO 2010/041231 | A3 | 9/2010 |
| WO | WO 2010/109392 | A1 | 9/2010 |
| WO | WO 2010/130762 | A2 | 11/2010 |
| WO | WO 2010/141921 | A1 | 12/2010 |
| WO | WO 2011/003941 | A1 | 1/2011 |
| WO | WO 2010/130762 | A3 | 2/2011 |
| WO | WO 2011/012621 | A1 | 2/2011 |
| WO | WO 2011/034621 | A2 | 3/2011 |
| WO | WO 2011/084703 | A2 | 7/2011 |
| WO | WO 2011/034621 | A3 | 11/2011 |

OTHER PUBLICATIONS

European search report dated Sep. 1, 2010 for Application No. 5804847.1.
International search report dated Oct. 6, 2010 for PCT Application No. US10/37545.
International search report dated Aug. 18, 2009 for PCT Application No. US09/00419.
International search report dated Sep. 25, 2007 for PCT Application No. US2007/02721.
U.S. Appl. No. 12/026,510, filed Feb. 5, 2008, Jovanovich et al.
U.S. Appl. No. 12/526,015, filed Nov. 3, 2010, Jovanovich et al.
U.S. Appl. No. 12/815,685, filed Jun. 15, 2010, Jovanovich et al.
U.S. Appl. No. 12/820,390, filed Jun. 22, 2010, Harrison et al.
U.S. Appl. No. 12/845,650, filed Jul. 28, 2010, Jovanovich et al.
U.S. Appl. No. 12/852,370, filed Aug. 6, 2010, Harrison et al.
U.S. Appl. No. 12/949,623, filed Nov. 18, 2010, Kobrin et al.
Japanese Office Action dated Apr. 27, 2010 for Application No. JP2001-540363 (in Japanese with English translation).
Japanese Office Action dated Dec. 21, 2010 for Application No. JP2001-540363 (in Japanese with English translation).
MillGat pump user manual, version 2.12, published 2005, pp. 1-28.
International search report and written opinion dated Mar. 24, 2011 for PCT Application No. US2010/058227.
International search report and written opinion dated Sep. 1, 2010 for PCT Application No. US2010/040490.
U.S. Appl. No. 13/075,165, filed Mar. 29, 2011, Eberhart et al.
U.S. Appl. No. 13/113,968, filed May 23, 2011, Majlof et al.
Armani, et al. Re-configurable fluid circuits by PDMS elastomer micromachining. Proceedings of IEEE Micro Electro Mechanical Systems: MEMS. 1999; 222-227.
European search report and search opinion dated Jun. 6, 2011 for Application No. 10011511.2.
International search report and written opinion dated Jun. 9, 2011 for PCT Application No. US2011/30973.
Notice of allowance dated Jun. 9, 2011 for U.S. Appl. No. 12/831,949.
U.S. Appl. No. 13/202,877, filed Aug. 23, 2011, Vangbo et al.
U.S. Appl. No. 13/202,884, filed Aug. 23, 2011, Jovanovich et al.
Bennett, et al. Toward the 1,000 dollars human genome. Pharmacogenomics, 6 (4) 373-382. (Jun. 2005).
Chinese office action dated Jan. 31, 2011 for CN 200580035911.7. (In Chinese with English translation).
Erratum for Margulies, et al. Genome sequencing in microfabricated high-density picolitre reactors. Nature. 2005;437(7057):376-80.: Margulies, et al. Nature. 441(7089):120. (May 4, 2006).
International search report dated Sep. 1, 2010 for PCT/US2010/040490.
U.S. Appl. No. 90/011,453, filed Jan. 21, 2011, Mathias et al.
European search report and search opinion dated Aug. 17, 2011 for Application No. 08799648.4.
Notice of allowance dated Sep. 8, 2011 for U.S. Appl. No. 12/820,390.
U.S. Appl. No. 13/287,398, filed Nov. 2, 2011, Jovanovich et al.
Chinese office action dated Jul. 8, 2011 for CN 200580035911.7. (in Chinese with English translation).
International search report and written opinion dated Jan. 5, 2012 for PCT Application No. US2011/048527.
International search report and written opinion dated Oct. 26, 2011 for PCT Application No. US11/38180.
International written opinion dated Oct. 6, 2010 for PCT Application No. US10/37545.
International written opinion report dated Jul. 30, 2010 for PCT Application No. US2010/36464.
Japanese office action dated May 27, 2011 for Application No. 2007-532553 (in Japanese with English translation).
Japanese office action dated Jul. 28, 2011 for Application No. 2008-553535 (in Japanese with English translation).
Amendment and Request for Correction of Inventorship mailed Jan. 10, 2008 in U.S. Appl. No. 10/750,533.
Anderson, et al. A miniature integrated device for automated multistep genetic assays. Nucleic Acids Research. 2000;28:e60.
Bings, et al. Microfluidic Devices Connected to Fused-Silica Capillaries with Minimal Dead Dead Volume. Analytical Chemistry. 1999;71(15):3292-3296.
Blazej, et al. Microfabricated bioprocessor for integrated nanoliter-scale Sanger DNA sequencing. Proc. Natl. Acad. Sci. USA 2006;103:7240-7245.

Blazej, et al. Polymorphism Ratio Sequencing: A New Approach for Single Nucleotide Polymorphism Discovery and Genotyping. Genome Research. 2003;13:287-293.

Brenner, et al. Gene expression analysis by massively parallel signature sequencing (MPSS) on microbead arrays. Nature Biotechnology. 2000;18(6):630-634.

Buchholz, et al. The use of light scattering for precise characterization of polymers for DNA sequencing by capillary electrophoresis. Electrophoresis. 2001;22:4118-4128.

Caplus abstract of Krohkin et al. Modified silica as a stationary phase for ion chromatography. Journal of Chromatography A. 1995;706:93-8.

Chan, et al. Microfabricated Polymer Devices for Automated Sample Delivery of Peptides for Analysis by Electrospray Ionization Tandem Mass Spectrometry. Analytical Chemistry. 1999;71(20):4437-4444.

Chiem, et al. Microchip systems for immunoassay: an integrated immunoreactor with electrophoretic separation for serum theophylline determination. Clinical Chemistry.1998;44(3):591-598.

Chiem, et al. Room temperature bonding of micromachined glass devices for capillary electrophoresis. Sensors and Actuators. 2000;B63(3):147-152.

Coleman, et al. A sequential injection microfluidic mixing strategy. Microfluidics and Nanofluidics. 2005;319-327.

Curcio, et al. Continuous Segmented-Flow Polymerase Chain Reaction for High-Throughput Miniaturized DNA Amplification. Analytical Chemistry. 2003;75(1):1-7.

Diehl, et al. BEAMing: single-molecule PCR on microparticles in water-in-oil emulsions. Nature Methods. 2006;3(7):551-9.

Doherty, et al. Sparsely Cross-linked "Nanogel" Matrices as Fluid, Mechanically Stablized Polymer Networks for High-Throughput Microchannel DNA Sequencing. Analytical Chemistry. 2004;76:5249-5256.

Doherty, et al. Sparsely cross-linked "nanogels" for microchannel DNA sequencing. Electrophoresis. 2003;24(24):4170-4180.

Dorfman, et al. Contamination-Free Continuous Flow Microfluidic Polymerase Chain Reaction for Quantitative and Clinical Applications. Analytical Chemistry. 2005;77(11):3700-3704.

Doyle et al. Self-Assembled Magnetic Matrices for DNA Separation Chips. Science. 2000;295:2237.

Dressman, et al. Transforming single DNA molecules into fluorescent magnetic particles for detection and enumeration of genetic variations. Proc Natl Acad Sci USA. 2003;100(15):8817-8822.

Emrich, et al. Microfabricated 384-Lane Capillary Array Electrophoresis Bioanalyzer for Ultrahigh-Throughput Genetic Analysis. Analytical Chemistry. 2002;74(19):5076-5083.

Ericson, et al. Electroosmosis- and Pressure-Driven Chromatography in Chips Using Continuous Beds. Analytical Chemistry. 2000;72(1):81-87.

European search report dated Dec. 18, 2009 for Application No. 03808583.3.

Ewing, et al. Base-Calling of Automated Sequencer Traces Using Phred. I. Accuracy Assessment. Genome Research. 1998;8:175-185.

Ewing, et al. Base-Calling of Automated Sequencer Traces Using Phred. II. Error probabilities. Genome Research. 1998;8:186-194.

Figeys, et al. A Microfabricated Device for Rapid Protein Identification by Microelectrospray Ion Trap Mass Spectrometry. Analytical Chemistry. 1997;69(16):3153-3160.

Figeys, et al. An Integrated Microfluidics-Tandem Mass Spectrometry System for Automated Protein Analysis. Analytical Chemistry. 1998;70(18):3728-3734.

Figeys, et al. Microfabricated Device Coupled with an Electrospray Ionization Quadrupole Time-of-Flight Mass Spectrometer: Protein Identifications Based on Enhanced-Resolution Mass Spectrometry and Tandem Mass Spectrometry Data. Rapid Communications in Mass Spectrometry. 1998;12:1435-1444.

Figeys, et al. Nanoflow Solvent Gradient Delivery from a Microfabricated Device for Protein Identifications by Electrospray Ionization Mass Spectrometry. Analytical Chemistry. 1998;70(18):3721-3727.

Francis, et al. Flow analysis based on a pulsed flow of solution: theory, instrumentation and applications. Talanta. 2002;58(6):1029-1042.

Ghadessy, et al. Directed evolution of polymerase function by compartmentalized self-replication. Proc Natl Acad Sci USA. 2001;98:4552-4557.

Giddings, et al. A software system for data analysis in automated DNA sequencing. Genome Research. 1998;8:644-665.

Goll, et al. Microvalves with bistable buckled polymer diaphragms. Journal of Micromechanics and Microengineering. 1996;6:77-79.

Grover, et al. An integrated microfluidic processor for single nucleotide polymorphism-based DNA computing. Lab on a Chip. 2005;5(10):1033-1040.

Grover, et al. Development and multiplexed control of latching pneumatic valves using microfluidic logical structures. Lab on a chip. 2006;6:623-631.

Grover, et al. Monolithic membrane valves and diaphragm pumps for practical large-scale integration into glass microfluidic devices. Sensors and Actuators. 2003;B89:315-323.

Grover, et al. Practical Valves and Pumps for Large-Scale Integration into Microfludic Analysis Devices. Micro Total Analysis Systems. 2002;1:136-138.

Hansen, et al. A robust and scalable microfluidic metering method that allows protein crystal growth by free interface diffusion. Proc Natl Acad Sci USA. 2002;99(26):16531-16536.

Harrison, et al. Micromachining a Miniaturized Capillary Electrophoresis-Based Chemical Analysis System on a Chip. Science. 1993;261(5123):895-897.

Hayes, et al. EDGE: A Centralized Resource for the Comparison, Analysis, and Distribution of Toxicogenomic Information. Molecular Pharmacology. 2005;67(4):1360-1368.

Hultman, et al. Bidirectional Solid-Phase Sequencing of In Vitro-Amplified Plasmid DNA. BioTechniques. 1991;10(1):84-93.

International Preliminary Report for corresponding PCT Application No. PCT/CA2000/01421 dated Feb. 14, 2002.

International Preliminary Report for corresponding PCT Application No. PCT/US2005/018678 dated Nov. 13, 2007.

International Preliminary Report for corresponding PCT Application No. PCT/US2005/033347 dated Mar. 20, 2007.

International Preliminary Report for corresponding PCT Application No. PCT/US2007/007381 dated Sep. 23, 2008.

International Preliminary Report for corresponding PCT Application No. PCT/US2007/02721 dated Aug. 5, 2008.

International Preliminary Report for corresponding PCT Application No. PCT/US2007/061573 dated Aug. 26, 2008.

International search report dated Apr. 5, 2001 for PCT Application No. CA2000/01421.

International search report dated May 14, 2010 for PCT Application No. US2009/06640.

International search report dated Jul. 11, 2008 for PCT Application No. US07/61573.

International search report dated Jul. 30, 2010 for PCT Application No. US2010/36464.

International search report dated Aug. 23, 2006 for PCT Application No. US2005/033347.

International search report dated Aug. 26, 2004 PCT Application No. US2003/41466.

International Search Report for PCT/US2005/033347.

Jacobson, et al. Electrokinetic Focusing in Microfabricated Channel Structures. Anal. Chem., 1997, 69 (16), pp. 3212-3217.

Ju, et al. Fluorescence energy transfer dye-labeled primers for DNA sequencing and analysis. Proc. Natl. Acad. Sci. USA. 1995;92:4347-4351.

Kan, et al. A novel thermogelling matrix for microchannel DNA sequencing based on poly-N-alkoxyalkylaclylamide copolymers. Electrophoresis. 2003;24(24):4161-4169.

Koh, et al. Integrating Polymerase Chain Reaction, Valving, and Electrophoresis in a Plastic Device for a Bacterial Detection. Analytical Chemistry. 2003;75(17):4591-4598.

Kopp, et al. Chemical Amplification Continuous-Flow PCR on a Chip. Science. 1998;280:1046-1048.

Lagally, et al. Fully integrated PCR-capillary electrophoresis microsystem for DNA analysis. Lab on a Chip. 2001;1(2):102-107.

Lagally, et al. Integrated Portable Genetic Analysis Microsystem for Pathogen/Infectious Disease Detection. Analytical Chemistry. 2004;76:3162-3170.

Lagally, et al. Monolithic integrated microfluidic DNA amplification and capillary electrophoresis analysis system. Sensors and Actuators. 2000;B63(3):138-146.

Lagally, et al. Single-Molecule DNA Amplification and Analysis in an Integrated Microfluidic Device. Analytical Chemistry. 2001;73(3): 565-570.

Lazar, et al. Subattomole-Sensitivity Microchip Nanoelectrospray Source with Time-of-Fligt Mass Spectrometry Detection. Analytical Chemistry. 1999;71(17):3627-3631.

Li, et al. Integration of Microfabricated Devices to Capillary Electrophoresis-Electrospray Mass Spectrometry Using a Low Dead Volume Connection: Application to Rapid Analyses of Proteolytic Digests. Analytical Chemistry. 1999;71(15):3036-3045.

Li, et al.. Rapid and sensitive separation of trace level protein digests using microfabricated devices coupled to a quadrupole-time-of-flight mass spectrometer. Electrophoresis. 2000;21:198-210.

Li, et al. Separation and Identification of Peptides from Gel-Isolated Membrane Proteins Using a Microfabricated Device for Combined Capillary Electrophoresis/Nanoelectrospray Mass Spectrometry. Analytical Chemistry. 2000;72(3):599-609.

Licklider, et al. A Micromachined Chip-Based Electrospray Source for Mass Spectrometry. Analytical Chemistry. 2000;72(2):367-375.

Lisec, et al. A bistable pneumatic microswitch for driving fluidic components. Sensors and Actuators. 1996;A54:746-749.

Liu, et al. Automated parallel DNA sequencing on multiple channel microchips. Proc. Natl. Acad. Sci. USA. 2000;97(10):5369-5374.

Liu, et al. Optimization of High-Speed DNA Sequencing on Microfabricated Capillary Electrophoresis Channels. Analytical Chemistry. 1999;71:566-573.

Margulies, et al. Genome sequencing in microfabricated high-density picolitre reactors. Nature. 2005;437(7057):376-80. (Abstact only).

Melin, et al. A Passive 2-Dimensional Liquid Sample Micromixer. 7th International Conference on Miniaturized Chemical and Biochemical Analysis Systems. 2003;167-170.

Mitra, et al. Digital genotyping and haplotyping with polymerase colonies. Proc Natl Acad Sci USA. 2003.100(10):15926-5931.

Norris, et al. Fully-integrated, multiplexed STR-based human identification using a single microfluidic chip and automated instrument. Available at http://www.promega.com/geneticidproc/ussymp20proc/oralpresentations/landersbienvenue.pdf. accessed Jun. 2, 2010.

Obeid, et al. Microfabricated Device for DNA and RNA Amplification by Continuous-Flow Polymerase Chain Reaction and Reverse Transcription-Polymerase Chain Reaction with Cycle Number Selection. Analytical Chemistry. 2003;75(2): 288-295.

Ocvirk, et al. High Performance Liquid Chromatography Partially Integrated onto a Silicon Chip. Analytical Methods and Instrumentation. 1995;2:74-82.

Ocvirk, et al. Optimization of confocal epifluorescence microscopy for microchip-based miniaturized total analysis systems. The Analyst. 1998;123:1429-1434.

Office Action Final dated Feb. 19, 2008 issued in U.S. Appl. No. 10/540,658.

Office Action Final dated Feb. 6, 2008 issued in U.S. Appl. No. 11/139,018.

Office Action mailed Apr. 27, 2007 in U.S. Appl. No. 11/139,018, filed May 25, 2005.

Office Action mailed Jul. 2, 2007 in U.S. Appl. No. 10/540,658, filed Jun. 23, 2005.

Office Action mailed Jul. 12, 2007 in U.S. Appl. No. 10/750,533, filed Dec. 29, 2003.

Ohori, et al. Partly disposable three-way mirovalve for a medical micro total analysis system (muTAS). Sensors and Actuators. 1998;A64(1): 57-62.

Oleschuk, et al. Trapping of Bead-Based Reagents within Microfluidic Systems: On-Chip Solid-Phase Extraction and Electrochromatography. Analytical Chemistry. 2000;72:585-590.

Olsen, et al. Immobilization of DNA Hydrogel Plugs in Microfluidic Channels. Analytical Chemistry. 2002;74:1436-1441.

Paegel, et al. High-throughput DNA sequencing with a 96-lane capillary array electrophoresis bioprocessor. Proc Natl Acad Sci USA. 2002;99:574-579.

Paegel, et al. Microchip Bioprocessor for Integrated Nanovolume Sample Purification and DNA Sequencing. Analytical Chemistry. 2002;74(19):5092-5098.

Paegel, et al. Microfluidic devices for DNA sequencing: sample preparation and electrophoretic analysis. Current Opinion in Biotechnology. 2003;14(1):42-50.

Paegel, et al. Turn Geometry for Minimizing Band Broadening in Microfabricated Capillary Electrophoresis Channels. Analytical Chemistry. 2000;72:3030-3037.

PCT Notification of Transmittal of the International Search Report and the Written Opinion of the International Searching Authority, or the Declaration, mailed Jun. 17, 2008, Application No. PCT/US2007/082568.

Peterson, et al. Enzymatic Microreactor-on-a-Chip: Protein Mapping Using Trypsin Immobilized on Porous Polymer Monoliths Molded in Channels of Microfluidic Devices. Analytical Chemistry. 2002;74:4081-4088.

Ramsey, et al. Generating Electrospray from Microchip Devices Using Electroosmotic Pumping. Analytical Chemistry. 1997;69(6):1174-1178.

Rohr, et al. Porous polymer monoliths: Simple and efficient mixers prepared by direct polymerization in the channels of microfluidic chips. Electrophoresis. 2001;22:3959-3967.

Rye, et al. High-sensitivity two-color detection of double-stranded DNA with a confocal fluorescence gel scanner using ethidium homodimer and thiazole orange. Nucleic Acids Research. 1991;19(2):327-333.

Scherer, et al. High-Pressure Gel Loader for Capillary Array Electrophoresis Microchannel Plates. Biotechniques. 2001;31(5):1150-1154.

Schomburg, et al. Design Optimization of Bistable Microdiaphragm Valves. Sensors and Actuators. 1998;A64:259-264.

Seifar, et al. Capillary electrochromatography with 1.8-mum ODS-modified porous silica particles. Journal of Chromatography. 1998; A808:71-77.

Simpson, et al. High-throughput genetic analysis using microfabricated 96-sample capillary array electrophoresis microplates. Proc Natl Acad Sci USA. 1998;95:2256-2261.

Simpson, et al. Microfabrication Technology for the Production of Capillary Array Electrophoresis Chips. Biomedical Microdevices. 1998;1:7-26.

Soper, et al. Sanger DNA Sequencing Reactions Performed in a Solid-Phase Nanoreactor Directly Coupled to Capillary Gel Electrophoresis. Analytical Chemistry. 1998;70:4036-4043.

Spiering, et al. Novel microstructures and technologies applied in chemical analysis techniques. 1997 International Conference on Solid-State Sensors and Actuators. 1997;1:511-514.

Takao, et al. A Pneumatically Actuated Full In-Channel Microvalve With MOSFET-Like Function in Fluid Channel Networks. Journal of Microelectromechanical Systems. 2002;11(5):421-426.

Takao, et al. Microfluidic Integrated Circuits for Signal Processing Using Analogous Relationship Betweeen Pneumatic Microvalve and MOSFET. Journal of Microelectromechanical Systems. 2003;12(4):497-505.

Thomas, et al. Application of Genomics to Toxicology Research. Environmental Health Perspectives. 2002;110(6):919-923.

Thorsen, et al. Microfluidic Large-Scale Integration. Science. 2002;298(5593):580-584.

Tice, et al. Formation of Droplets and Mixing in Multiphase Microfluidics at Low Values of the Reynolds and the Capillary Numbers. Langmuir. 2003;19:9127-9133.

Unger, et al. Monolithic Microfabricated Valves and Pumps by Multilayer Soft Lithography. Science. 2000;288:113-116.

Van Der Moolen, et al. A Micromachined Injection Device for CZE: Application to Correlation CZE. Analytical Chemistry. 1997;69(20):4220-4225.

Van Der Moolen, et al. Correlation Capillary Zone Electrophoresis, a Novel Technique to Decrease Detection Limits. Chromatographia. 1995;40(7/8):368-374.

Vazquez, et al. Electrophoretic Injection within Microdevices. Analytical Chemistry. 2002;74:1952-1961.

Veenstra, et al. The design of an in-plane compliance structure for microfluidical systems. Sensors and Actuators. 2002;B81:377-383.

Waller, et al. Quantitative Immunocapture PCR Assay for Detection of Campylobacter jejuni in Foods. Applied Environmental Microbiology. 2000; 66(9):4115-4118.

Weimer, et al. Solid-Phase Capture of Proteins, Spores, and Bacteria. Applied Environmental Microbiology. 2001;67(3):1300-1307.

Wen, et al. Microfabricated isoelectric focusing device for direct electrospray ionization-mass spectrometry. Electrophoresis. 2000;21:191-197.

Wikipedia brochure for defining stocahstic process. Sep. 2, 2009.

Williams, et al. Amplification of complex gene libraries by emulsion PCR. Nature Methods. 2006;3(7):545-50.

Woolley, et al. Functional Integration of PCR Amplification and Capillary Electrophoresis in a Microfabricated DNA Analysis Device. Analytical Chemistry. 1996;68(23):4081-4086.

Wright, et al. Behavior and Use of Nonaqueous Media without Supporting Electrolyte in Capillary Electrophoresis and Capillary Electrochromatography. Analytical Chemistry. 1997;69(16):3251-3259.

Xiang, et al. An Integrated Microfabricated Device for Dual Microdialysis and On-Line ESI-Ion Trap Mass Spectrometry for Analysis of Complex Biological Samples. Analytical Chemistry. 1999;71(8):1485-1490.

Xue, et al. Integrated Multichannel Microchip Electrospray Ionization Mass Spectrometry: Analysis of Peptides from On-Chip Tryptic Digestion of Melittin. Rapid Communications in Mass Spectrometry. 1997;11:1253-1256.

Xue, et al. Multichannel Microchip Electrospray Mass Spectrometry. Analytical Chemistry. 1997;69(3):426-430.

Yang, et al. A MEMS thermopneumatic silicone rubber membrane valve. Sensors and Actuators. 1998;A64(1):101-108.

Yu, et al. Preparation of Monolithic Polymers with Controlled Porous Properties for Microfluidic Chip Applications Using Photoinitiated Free Radial Polymerization. Journal of Polymer Science. 2002;40:755-769.

Yu, et al. Towards stationary phases for chromatography on a microchip: Molded porous polymer monoliths prepared in capillaries by photoinitiated in situ polymerization as separation media for electrochromatography. Electrophoresis. 2000;21:120-127.

Zhang, et al. A Microdevice with Integrated Liquid Junction for Facile Peptide and Protein Analysis by Capillary Electrophoresis/Electrospray Mass Spectrometry. Analytical Chemistry. 2000;72(5):1015-1022.

Zhang, et al. Microfabricated Devices for Capillary Electrophoresis-Electrospray Mass Spectrometry. Analytical Chemistry. 1999;71(15):3258-3264.

International search report and written opinion dated Apr. 30, 2012 for PCT/US2012/021217.

Japanese office action dated May 11, 2012 for Application No. 2008-553535 (English translation).

Office action dated May 22, 2012 for U.S. Appl. No. 12/526,015.

Grodzinski, et al. Microfluidic System Integration in Sample Preparation Chip-Sets—a Summary. Conf. Proc. IEEE Eng. Med. Biol. Soc. 2004;4:2615-2618.

Oh, et al. A Review of Microvalves. J. Micromech. Microeng. 2006;16:R13-R39.

Peoples, et al. Microfluidic Immunoaffinity Separations for Bioanalysis. J. Chromat. B. 2008;866:14-25 (available online Aug. 30, 2007).

Stevens, et al. Bacterial Separation and Concentration from Complex Sample Matrices: a Review. Crit. Rev. Microbiol. 2004;30(1):7-24.

Van Ness, et al. Isothermal Reactions for the Amplification of Oligonucleotides. Proc. Nat. Acad. Sci. USA. 2003;100 (8):4504-4509.

* cited by examiner

STR Sample Loading

STR Sample Injection

Post-amp Chip Architecture

System with Enclosure

Footprint = 2 x 2 x 2 ft

UNIVERSAL SAMPLE PREPARATION SYSTEM AND USE IN AN INTEGRATED ANALYSIS SYSTEM

STATEMENT AS TO FEDERALLY SPONSORED RESEARCH

This invention was made with Government support under Contract No. 2004*H838109*000 awarded by the Central Intelligence Agency. The Government may have certain rights in this invention.

CROSS-REFERENCE

This application is related to U.S. Ser. No. 61/184,759 filed Jun. 5, 2009, U.S. Ser. No. 61/235,664, filed Aug. 20, 2009, U.S. Ser. No. 61/349,680 filed May 28, 2010, and PCT/US2010/037545 filed Jun. 4, 2010, which are incorporated herein by reference in their entirety for all purposes.

BACKGROUND OF THE INVENTION

Sample preparation is a ubiquitous problem in biological analytical systems. The issue of providing sufficiently purified targets from diverse raw sample types to reliably perform downstream analytical assays is pervasive and covers cell biology, genomics, proteomics, metabolomics, food biology, molecular diagnostics, and many other biological and medical assays. While many advances in sample preparation have been made the chief solution has been to develop reagents that are used manually or in robotic systems that use rectilinear stages or multi-axis arms to manipulate samples.

Microfluidics and nanofluidics allow miniaturized sample volumes to be prepared for analysis. Advantages include the nanoscale consumption of reagents to reduce operating costs and full automation to eliminate operator variances. Microfluidic sample preparation can either interface with existing or future detection methods or be part of a completely integrated system. In the present application, methods and apparatuses are disclosed that integrate full volume sample preparation with volumes over 10 mL with microliter and smaller volumes for sample preparation and analysis.

Starting from the sample, the present invention can be applied to concentrate, and pre-separate components for further processing to detect and classify organisms in matrices comprising aerosol samples, water, liquids, blood, stools, nasal, buccal and other swabs, bodily fluids, environmental samples with analysis by ELISA, PCR or other nucleic acid amplification techniques, single molecule detection, protein arrays, mass spectroscopy, and other analytical methods well known to one skilled in the art.

Microfluidic nucleic acid purification can be performed to prepare the sample for nucleic acid assays. For DNA analysis, PCR amplification is one current method. Microarray DNA, RNA and protein analysis also requires extensive sample preparation before the sample can be applied to the microarray for reaction and readout.

Samples can be obtained by a wide variety of substrates and matrices. The matrix may contain complex mixtures including inhibitory compounds such as hemes, indigo, humic acids, divalent cations, and proteins etc that interfere with DNA-based amplification. Aerosols can contain large amounts of molds, metals, and soils humic and other acids that all interfere with PCR amplification—the gold standard.

Early work showed that as few as three seeded organisms could be detected from diluted samples of soil extracts followed by PCR amplification of two 16S ribosomal gene fragments. Low-melting-temperature agarose has been used to extract DNA from soil samples for 16S and 18S rDNA PCR amplification using universal primers. Spun separation gels in column format can be used, such as Sephadex columns Multistep purifications such as organic extractions combined with Sephadex columns were developed. Bead beating was found to be an effective way to prepare samples for high numbers of organisms and grinding in liquid nitrogen to detect low numbers of organisms. While these methods are effective they were best suited for research laboratory environments.

Solid phase extractions to columns, beads, and surfaces can be used to purify DNA before DNA analysis. Proteinase K followed by a Qiagen QIA Amp silica-gel membrane columns and IsoCode Stix, an impregnated membrane-based technology, followed by heating, washing and a brief centrifugation were compared for *B. anthracis* Sterne vegetative cells in buffer, serum, and whole blood and spores in buffer and found to work well.

A variety of separations can be performed using the devices and methods of the invention. For example, the devices and methods of the invention can be used to perform chromatography, phase-based or magnetic-based separation, electrophoresis, distillation, extraction, and filtration. For example, a microfluidic channel or a capillary can be used for chromatography or electrophoresis. As well, beads, such as magnetic beads can be used for phase-based separations and magnetic-based separations. The beads, or any other surfaces described herein, can be functionalized with binding moieties that exhibit specific or non-specific binding to a target. The binding can be based on electrostatics, van der Walls interactions, hydrophobicity, hydrophilicity, hydrogen bonding, ionic interactions, as well as partially covalent interactions like those exhibited between gold and sulfur. In preferred embodiments, the devices and methods of the invention utilize immunomagnetic separations.

Immunomagnetic separation (IMS) is a powerful technology that allows targets to be captured and concentrated in a single step using a mechanistically simplified format that employs paramagnetic beads and a magnetic field (see Grodzinski P, Liu R, Yang J, Ward M D. Microfluidic system integration in sample preparation microchip-sets—a summary. Conf Proc IEEE Eng Med Biol Soc. 2004; 4:2615-8., Peoples M C, Karnes H T. Microfluidic immunoaffinity separations for bioanalysis. J Chromatogr B Analyt Technol Biomed Life Sci. 2007 Aug. 30., and Stevens K A, Jaykus L A. Bacterial separation and concentration from complex sample matrices: a review. Crit Rev Microbiol. 2004; 30(1):7-24.). IMS can be used to capture, concentrate, and then purify specific target antigens, proteins, toxins, nucleic acids, cells, and spores. While IMS as originally used referred to using an antibody, we generalize its usage to include other specific affinity interactions including lectins, DNA-DNA, DNA-RNA, biotin-streptavidin, and other affinity interactions that are coupled to a solid phase. IMS works by binding a specific affinity reagent, typically an antibody or DNA, to paramagnetic beads which are only magnetic in the presence of an external magnetic field. The beads can be added to complex samples such as aerosols, liquids, bodily fluids, or food. After binding of the target to the affinity reagent (which itself is bound to the paramagnetic bead) the bead is captured by application of a magnetic field. Unbound or loosely bound material is removed by washing with compatible buffers, which purifies the target from other, unwanted materials in the original sample. Because beads are small (about 1 nm to about 1 um) and bind high levels of target, when the beads are concentrated by magnetic force they typically form bead beds of between 1 nL and 1 uL, thus concentrating the target at the same time it is purified. The purified and concentrated targets can be conveniently transported, denatured, lysed or analyzed while on-bead, or eluted off bead for further sample preparation, or analysis.

Immunomagnetic separations are widely used for many applications including the detection of microorganisms in food, bodily fluids, and other matrices. Paramagnetic beads can be mixed and manipulated easily, and are adaptable to microscale and microfluidic applications. This technology provides an excellent solution to the macroscale-to-microscale interface: beads are an almost ideal vehicle to purify samples at the macroscale and then concentrate to the nanoscale (100's of nL) for introduction into microfluidic or nanofluidic platforms Immunomagnetic separations are commonly used as an upstream purification step before real-time PCR, electrochemiluminescence, and magnetic force discrimination.

The ability to move fluids on microchips is a quite important. This invention describes technologies in sample capture and purification, micro-separations, micro-valves, -pumps, and -routers, nanofluidic control, and nano-scale biochemistry. A key component of the technology is Micro-robotic On-chip Valves (MOVe) technology (an example of which is shown in FIG. 1) and its application to miniaturize and automate complex workflows. Collectively the MOVe valves, pumps, and routers and the instrumentation to operate them can be referred to as a microchip fluid processing platform.

The heart of the microchip fluid processing platform technology are MOVe pumps, valves, and routers that transport, process, and enable analysis of samples. These novel externally actuated, pneumatically-driven, on-chip valves, pumps, and routers, originally developed in the Mathies laboratory at the University of California at Berkeley (U. C. Berkeley) (Grover, W. H. A. M. Skelley, C. N. Liu, E. T. Lagally, and R. M. Mathies. 2003. *Sensors and Actuators* B89:315-323; Richard A. Mathies et al., United States Patent Application, 20040209354 A1 Oct. 21, 2004; all of which are herein incorporated by reference in their entirety) can control fluidic flow at manipulate volumes from 20 nL to 10 µL.

The MOVe valves and pumps (FIG. 1) can combine two glass and/or plastic microfluidic layers with a polydimethylsiloxane (PDMS) deformable membrane layer that opens and closes the valve, and a pneumatic layer to deform the membrane and actuate the valve. The microfluidic channel etched in the top glass fluidic wafer is discontinuous and leads to a valve seat which is normally closed (FIG. 1A). When a vacuum is applied to the pneumatic displacement chamber by conventional-scale vacuum and pressure sources, the normally closed PDMS membrane lifts from the valve seat to open the valve (FIG. 1B). FIG. 1C shows a top view of the valve a similar scale as the other panels.

Three microvalves can be used to make a micropump on a microchip to move fluids from the Input area to the Output area on Microchip A. The fluids are moved by three or more valves. The valves can be created actuation of a deformable structure. In some implementations a valve seat is created and in other embodiments no valve seat may be needed. FIG. 2 shows MOVe devices from top to bottom: valve, router, mixer, bead capture. Self-priming MOVe pumps (FIG. 2, top) are made by coordinating the operation of three valves and can create flow in either direction. Routers are made from three or more MOVe valves (FIG. 2, top middle panel). Mixing has been a holy grail for microfluidics: MOVe mixers (FIG. 2, bottom middle panel) rapidly mix samples and reagents. MOVe devices work exquisitely with magnetic beads to pump or trap sets of beads (FIG. 2, bottom panel).

The normally closed MOVe valves, pumps, and routers are durable, easily fabricated at low cost, can operate in dense arrays, and have low dead volumes. Arrays of MOVe valves, pumps, and routers are readily fabricated on microchips. Significantly, all the MOVe valves, pumps, and routers on a microchip are created at the same time in a simple manufacturing process using a single sheet of PDMS membrane—it costs the same to make 5 MOVe micropumps on a microchip as to create 500. This innovative technology offers for the first time the ability to create complex micro- and nanofluidic circuits on microchips.

Patents and applications which discuss the use and design of microchips include U.S. Pat. No. 7,312,611, issued on Dec. 25, 2007; U.S. Pat. No. 6,190,616, issued on Feb. 20, 2001; U.S. Pat. No. 6,423,536, issued on Jul. 23, 2002; U.S. patent Ser. No. 10/633,171 Mar. 22, 2005; U.S. Pat. No. 6,870,185, issued on Mar. 22, 2005 US Application No. US 2001-0007641, filed on Jan. 25, 2001; US Application US20020110900, filed on Apr. 18, 2002; US patent application 20070248958, filed Sep. 15, 2005; US patent application US 20040209354, filed on Dec. 29, 2003; US patent application US2006/0073484, filed on Dec. 29, 2003; US20050287572, filed on May 25, 2005; US patent application US20070237686, filed on Mar. 21, 2007; US 20050224352 filed on Nov. 24, 2004; US 20070248958, filed on, Sep. 15, 2005; US 20080014576, filed on Feb. 2, 2007; and, US application US20070175756, filed on Jul. 26, 2006; all of which are herein incorporated by reference in their entirety.

SUMMARY OF THE INVENTION

The invention provides a system that can process a raw biological sample, perform a biochemical reaction and provide an analysis readout in multiplex. For example, the system can extract DNA from a swab, amplify STR loci from the DNA, and analyze the amplified loci and STR markers in the sample. The system integrates these functions by using microfluidic components to connect what can be macrofluidic functions. In one embodiment the system includes a sample purification module, a reaction module, a post-reaction clean-up module, a capillary electrophoresis module and a computer. In certain embodiments, the system includes a disposable cartridge for performing analyte capture. The cartridge can comprise a fluidic manifold having macrofluidic chambers mated with microfluidic chips that route the liquids between chambers. The system fits within an enclosure of no more than 10 ft$^3$ and can be a closed, portable, and/or battery operated system. The system can be used to go from sample to analysis in less than 4 hours.

In one aspect, this invention provides a system that fits within an enclosure of no more than 10 ft$^3$, the system comprising: (a) a sample preparation module adapted to capture an analyte from a non-microfluidic volume on a capture particle and route the captured analyte through a microfluidic channel; (b) a reaction module comprising a reaction chamber in fluidic communication with the microfluidic channel adapted to immobilized the captured analyte and perform a biochemical reaction on the analyte in a non-microfluidic volume to produce a reaction product; (c) and an analysis module in fluidic communication with the reaction chamber adapted to perform an analysis on the reaction product. In one embodiment, the system is configured to capture the analyte, perform a biochemical reaction on the analyte, and perform an analysis on the product in less than 4 hours, in less than 3 hours, or even in less than 2 hours. In one embodiment, the system further comprises a data analysis module configured to receive data about the analysis from the analysis module and comprising executable code that transforms the data and outputs a result of the analysis. In another embodiment, the system further comprises a processing module in fluidic communication with the reaction chamber and the analysis module and adapted to (1) route the reaction product through a second microfluidic channel into a non-microfluidic processing chamber; (2) process the reaction product and (3) route the processed reaction product into the analysis module. In one particular embodiment, the system fits within an enclosure of no more than 8 ft$^3$, no more than 5 ft$^3$ or no more than 2½ ft$^3$. In another embodiment of the system, the sample preparation module is adapted to release the analyte from a cell. In another embodiment of the system, the capture particle is a magnetically responsive capture particle and a reaction module comprises a source of magnetic force configured to immobilize the captured analyte. In another embodiment of the system, the reaction module is adapted to perform thermal cycling. In another embodiment of the system, the system is a closed system and/or battery operated.

In another aspect, this invention provides a system comprising a cartridge cover, a cartridge and a pneumatic manifold wherein the cartridge can be releaseably engaged with the cartridge cover and the pneumatic manifold, wherein the cartridge comprises one or more pneumatically actuated valves and one or more microfluidic channels, wherein the pneumatic manifold and the cartridge cover are each fluidically connected to at least one pressure source, and wherein the pneumatic manifold and the cartridge cover are each adapted to control fluid flow within the cartridge. In one embodiment, the pneumatic manifold is adapted to actuate the pneumatically actuated valves and the cartridge cover is adapted to apply pressure to one or more chambers in the cartridge.

In another aspect, this invention provides a system comprising: (a) a disposable cartridge comprising at least one set of fluidic chambers including a sample chamber, a mixing chamber and a thermal cycling chamber in fluid communication with each other, and a reagent card comprising reagents for performing a chemical reaction involving thermal cycling, wherein the reagent card is configured to be carried on the cartridge in a closed configuration and to be moved into fluid communication with the at least one set of fluidic chambers; (b) an actuator assembly configured to move fluids between chambers when the cartridge is engaged with the actuator assembly; (c) a thermal cycler configured to cycle temperature in the thermal cycling chamber when the cartridge is engaged with the actuator assembly; (d) a capillary electrophoresis assembly configured to accept a sample from cartridge when the cartridge is engaged with the actuator assembly and to perform capillary electrophoresis on the sample; and (e) a computerized control system configured to control the actuator assembly, the thermal cycler and the capillary electrophoresis assembly.

In another aspect, this invention provides a cartridge comprising: (a) a fluidic manifold comprising a fluidic side and a reagent card side wherein the fluidic manifold comprises: (i) at least one set of fluidic chambers, each chamber comprising a port on the fluidic side; (ii) at least one of thermal cycling chamber comprising at least one port; (iii) at least one of exit port; (iv) a slot on the reagent card side adapted to engage a reagent card, wherein the slot comprises a plurality of slot channels comprising cannulae on the reagent card side and communicating between the two sides; (b) at least one microfluidic chip comprising: at least one fluidic circuit; (ii) a plurality of ports in fluid communication with the fluidic circuit; (iii) at least one pneumatically activated diaphragm valve configured to regulate fluid flow within the fluidic circuit; wherein the at least one chip is engaged with the fluidic manifold so that the ports in the at least one chip are in fluid communication with the ports of the chambers and the slot channels wherein each fluidic chamber is in fluid communication with at least one other fluidic chamber and each cannula is in communication with a fluidic chamber; and (c) a reagent card engaged with the slot, wherein the card comprises a plurality of reagent chambers comprising reagents, each aligned with at least one of the cannulae and adapted to take a first engagement position wherein the reagent chambers are not punctured by the cannulae and a second engagement position wherein the reagent chambers are punctured by the cannulae, thereby putting the reagent chambers in fluid communication with the fluidic circuit. In one embodiment the reagents comprise reagents for performing PCR. In another embodiment, the reagents comprise primers for amplifying a plurality of short tandem repeats. In another embodiment, the at least one set of fluidic chambers is a plurality of sets of fluidic chambers. In yet another embodiment the cartridge is such that the fluidics manifold further comprises at least one auxiliary fluidic channel on the fluidic side of the manifold, the at least one chip is a plurality of chips and fluidic circuits in each of the plurality of chips are in fluidic communication with fluidic circuits of at least one other chip through the auxiliary fluidic channel. In this embodiment, the cartridge can further comprise a gasket between the chips and the manifold, wherein the gasket seals the channels on the manifold. In another embodiment of the cartridge, the fluidic chambers comprise a distribution chamber, a capture chamber, a sample chamber, and a clean-up chamber. In another embodiment of the cartridge, at least one fluidic chamber comprises magnetically responsive particles. In another embodiment of the cartridge, the at least one set of fluidic chambers is at least 4 sets or at least 8 sets. In another embodiment of the cartridge, the chips comprise at least one diaphragm valve.

In another aspect, the invention provides a system comprising: (a) a pneumatic assembly comprising: (i) a pneumatic manifold adapted to removably engage the cartridge on the fluidic side, wherein the pneumatic manifold comprises a plurality of pneumatic ports configured to engage pneumatic channels in the at least one microfluidic chip and activate the diaphragm valves; and (ii) a pressure source configured to supply positive or negative pressure to the pneumatic channels; (b) a cartridge activation assembly adapted to engage the cartridge on the reagent card side; wherein the cartridge activation assembly comprises: (i) a reagent pneumatic manifold comprising a pneumatic side and reagent card side, wherein the reagent pneumatic manifold comprises reagent pneumatic manifold channels communicating between the two sides and comprising a cannula on the reagent card side; (ii) a pressure source configured to supply positive or negative pressure to the reagent pneumatic manifold channels; and (iii) a clamp configured to move the reagent card from the first engagement position to the second engagement position, wherein clamping results in the cannulae of the reagent pneumatic manifold puncturing the reagent chambers and putting the reagent chambers in communication with the pressure source; (c) a thermal cycler configured to cycle temperature in the at least one thermal cycling chamber when the cartridge is clamped; (d) a capillary electrophoresis assembly comprising: (i) at least one separation channel fluidically engaged with the exit port when the cartridge is clamped; and (ii) an optical sub-assembly configured to detect signal from the at least one separation channel; and (e) a computerized control system configured to control pneumatic assembly, the cartridge activation assembly, the thermal cycler and the capillary electrophoresis assembly. In one embodiment of this system, clamping seals the chamber ports and the slot channels with the at least one microfluidic chip. In another embodiment of this system, the cartridge activation assembly further comprises at least one heater configured to heat at least one of the fluidic chambers when the reagent pneumatic manifold is engaged with the cartridge. In another embodiment of this system, the cartridge activation assembly further comprises movable magnets configured to move into and out of a position wherein the magnets exert a magnetic force on at least one fluidic chamber. In another embodiment of this system, the cartridge activation assembly further comprises sensors configured to detect the presence of a sample in a sample chamber of the fluidic manifold. In another embodiment of this system, the thermal cycler comprises a Peltier device. In one embodiment the system is comprised in a portable case. In one specific embodiment, the case has an internal volume of no more than 10 ft$^3$ or no more than 2½ ft$^3$. In a related embodiment of system, the invention provides for an article in computer readable form comprising code for the operating system.

In another aspect the invention provides a method comprising: producing, from a sample comprising at lest one cell comprising DNA, a computer file identifying a plurality of STR markers in the DNA, wherein the method is performed in less than 4 hours. In one embodiment the method is performed in less than 3 hours. In another embodiment the method is performed in less than 2 hours. In a related embodiment, the producing comprises extracting the DNA from the at least one cell, amplifying the STR markers from the DNA, performing capillary electrophoresis on the amplified markers, detecting the amplified markers, and performing computer analysis on the detected amplified markers to identify the markers. In one embodiment, the plurality of STR markers is at least 5 STR markers. In another embodiment the plurality of markers are CODIS STR markers. In a related embodiment, the plurality of STR markers is at least 5, 10, or 13 CODIS STR markers. In these embodiments, the at least one cell can be a plurality of cells. In some embodiments, the sample is a forensic sample. In specific embodiments, the method is performed at the site of a sample collection. The sample can comprise blood, or can comprise a cheek swab. The method can be carried out by any system described herein.

In a related aspect, the invention provides a system configured to perform a method, wherein the method comprises: producing, from a sample comprising at least one cell comprising DNA, a computer file identifying a plurality of STR markers in the DNA, wherein the method is performed in less than 4 hours.

In another aspect, this invention provides a method comprising: (a) providing a system comprising: (i) a disposable cartridge comprising at least one set of fluidic chambers including a sample chamber, a mixing chamber and a thermal cycling chamber in fluid communication with each other, and a reagent card comprising reagents for performing a chemical reaction involving thermal cycling, wherein the reagent card is configured to be carried on the cartridge in a closed configuration and to be moved into fluid communication with the at least one set of fluidic chambers; (ii) an actuator assembly configured to move fluids between chambers when the cartridge is engaged with the actuator assembly; (iii) a thermal cycler configured to cycle temperature in the thermal cycling chamber when the cartridge is engaged with the actuator assembly; (iv) a capillary electrophoresis assembly configured to accept a sample from cartridge when the cartridge is engaged with the actuator assembly and to perform capillary electrophoresis on the sample; and (v) a computerized control system configured to control the actuator assembly, the thermal cycler and the capillary electrophoresis assembly; (b) moving of the reagent card into fluid communication with at least one set of fluidic chambers; (c) providing a sample comprising a nucleic acid molecule to a sample chamber; and (d) operating the system to amplify and detect at least one nucleic acid sequence in the sample. In one embodiment the time it takes to go from step (b) to step (d) is less than 4 hours. In one embodiment, the method comprises providing each of a plurality of samples to a different sample chamber. In another embodiment, the method comprises amplifying and detecting a plurality of nucleic acid sequences in the sample. In a related embodiment, the plurality of nucleic acid sequences comprise short tandem repeats (STRs). In a specific embodiment, the short tandem repeats comprise a plurality of Combined DNA Index System (CODIS) markers. In another embodiment the CODIS markers comprise a plurality of markers selected from AMEL, D3S1358, THO1, D21s11, D18s51, D5s818, D13s317, D7s820, D16s539, CSF1PO, vWA, D8S1179, TPOX and FGA. In one embodiment, the system comprises: (a) a pneumatic assembly comprising: (i) a pneumatic manifold adapted to removably engage the cartridge on the fluidic side, wherein the pneumatic manifold comprises a plurality of pneumatic ports configured to engage pneumatic channels in the at least one microfluidic chip and activate the diaphragm valves; and (ii) a pressure source configured to supply positive or negative pressure to the pneumatic channels; (b) a cartridge activation assembly adapted to engage the cartridge on the reagent card side; wherein the cartridge activation assembly comprises: (i) a reagent pneumatic manifold comprising a pneumatic side and reagent card side, wherein the reagent pneumatic manifold comprises reagent pneumatic manifold channels communicating between the two sides and comprising a cannula on the reagent card side; (ii) a pressure source configured to supply positive or negative pressure to the reagent pneumatic manifold channels; and (iii) a clamp configured to move the reagent card from the first engagement position to the second engagement position, wherein clamping results in the cannulae of the reagent pneumatic manifold puncturing the reagent chambers and putting the reagent chambers in communication with the pressure source; (c) a thermal cycler configured to cycle temperature in the at least one thermal cycling chamber when the cartridge is clamped; (d) a capillary electrophoresis assembly comprising: (i) at least one separation channel fluidically engaged with the exit port when the cartridge is clamped; and (ii) an optical sub-assembly configured to detect signal from the at least one separation channel; and (e) a computerized control system configured to control pneumatic assembly, the cartridge activation assembly, the thermal cycler and the capillary electrophoresis assembly. In another embodiment, the system is any system named herein. In one embodiment, the sample is a forensic sample. In a related embodiment, the sample is selected from a buccal swab, blood, hair or semen. In another embodiment, the sample is a raw sample. In some embodiments, the method further comprises transporting the system to a forensic site.

In another aspect, the invention provides an optical system comprising: (a) a plurality of optically transparent channels; (b) a light source configured to direct to the plurality of optically transparent channels; (c) a dispersive element that disperses light passing through the optically transparent channels in a wavelength dependent manner; and (d) a detector configured to receive the dispersed light. In one embodiment the plurality of optically transparent channels comprises at least eight capillaries. In another embodiment the optically transparent channels are aligned in a first plane and the dispersive element disperses light along a second plane, wherein the first plane and the second plane are different. In another embodiment, the first plane is orthogonal to the second plane.

In another aspect, the invention provides an optical system comprising: (a) an excitation source configured to direct excitation light to an object; (b) a carrier for an object, wherein the object emits light other than excitation light when excited by the excitation energy; (c) a rejection filter configured to filter out excitation energy and to allow transmission of the emitted light; (d) an imaging lens configured to focus the emitted light; (e) a dichroic mirror substantially transparent to the excitation energy and configured to reflect emitted light to a detector; (f) a focusing system comprising at least one lens configured to focus light reflected from the dichroic mirror; and (g) a photodetector (CCD camera) configured to receive the reflected light. In one embodiment of the optical system, the excitation light comprises light of a wavelength between 03 microns and 1 micron. In another embodiment, the carrier comprises an array of capillary tubes and the object comprises a fluorescent species. In another embodiment, the mirror reflects emitted light and an angle between about 5 degrees and about 10 degrees off an incident angle. In another embodiment, the dichroic mirror further comprises a portion that transmits substantially all light. In another embodiment, the focusing system comprises at least one folding mirror. In another embodiment, the photodetector comprises a CCD camera. In a related embodiment, the optical system can further comprise a prism located between the object and the imaging lens.

In another aspect, the invention provides an optical system comprising: (a) an array of capillary tubes aligned substantially parallel and substantially in a plane; (b) an excitation assembly comprising an excitation source and configured to deliver excitation light from the excitation source to the array, wherein the light delivery assembly is configured (i) to deliver a thin band of light that covers the array and (ii) to deliver the light to the array at an angle other than 90 degrees to the plane; (c) a collection lens configured to collect light emitted from the array by objects in the array excited by the excitation light; wherein the excitation assembly and the collection lens are configured with respect to the array so that excitation light passing through the array substantially avoids collection by the collection lens. In one embodiment, the angle is between about 10 degrees and about 85 degrees.

In another aspect, the invention provides an instrument comprising: (a) a microfluidic component comprising a plurality of intersecting microfluidic channels and at least one controllable valve configured to regulate flow of fluid between the intersecting channels; and (b) a non-microfluidic component comprising a plurality of non-microfluidic chambers, wherein each non-microfluidic chamber is fluidically connected to at least one of the microfluidic channels; wherein the instrument is configured to flow fluid from at least one non-microfluidic chamber into another non-microfluidic chamber through a microfluidic channel and flow is regulated by at least one valve. In one embodiment of the instrument, the plurality of non-microfluidic chambers comprises at least three chambers and the at least one valve selectively directs fluid from one chamber to either of the at least two other chambers. In another embodiment, the instrument further comprises a pump to pump fluid from a non-microfluidic chamber into a microfluidic channel. In another embodiment of the instrument the at least one valve is a diaphragm valve. In a related embodiment, the pump is a diaphragm pump comprising a series of three diaphragm valves. In another embodiment, the microfluidic component comprises a monolithic device. IN another embodiment, the combination of the microfluidic component and the non-microfluidic component define a fluidic circuit and the instrument comprises a plurality of fluidic circuits. In another embodiment, the non-microfluidic component further comprises a particulate capture agent. In another embodiment, the particles are responsive to a magnetic field and the instrument further comprises a magnet configured to immobilize the particles. In another embodiment, the invention provides a device comprising a plurality of non-microfluidic chambers fluidically connected to a common microfluidic channel.

In another aspect, the invention provides a method comprising: (a) providing a device comprising: (i) a microfluidic component comprising a plurality of intersecting microfluidic channels and at least one controllable valve configured to regulate flow of fluid between the intersecting channels; and (ii) a non-microfluidic component comprising a plurality of non-microfluidic chambers, wherein each non-microfluidic chamber is fluidically connected to at least one of the microfluidic channels; wherein the instrument is configured to flow fluid from at least one non-microfluidic chamber into another non-microfluidic chamber through a microfluidic channel and flow is regulated by at least one valve; and wherein a first non-microfluidic chamber comprises a first volume of sample comprising an analyte; (b) providing an amount of particulate capture agent in the first non-microfluidic chamber to bind a selected amount of analyte from the sample; (c) moving the particulate capture agent bound to the analyte through a microfluidic channel in the microfluidic device to a second non-microfluidic chamber; (d) contacting the particulate capture agent bound to the analyte with a reagent in a second non-microfluidic chamber; and (e) performing a chemical reaction on the analyte using the reagent. In one embodiment of the method the contacting comprises flowing the reagent from a third non-microfluidic chamber through a microfluidic channel in the microfluidic device into the second non-microfluidic chamber. In another embodiment of the method, the particles are response to magnetic force and the method further comprises immobilizing the particulate capture agent bound to the analyte in the instrument with a magnetic force. In another embodiment, the method comprises suspending the particulate capture agent bound to the analyte in the instrument in a volume at least an order of magnitude smaller than the sample volume.

In another aspect, the invention provides a method comprising: (a) performing a first chemical reaction on an analyte in a first chamber which is a non-microfluidic chamber to produce a first reaction product; and (b) moving the first reaction product through a microfluidic channel into a second chamber which is a non-microfluidic chamber and performing a second chemical reaction on the first product to create a second reaction product.

In another aspect, the invention provides a method comprising: (a) performing a first chemical reaction on an analyte in a first chamber which is a non-microfluidic chamber to produce a first reaction product; and (b) moving the first reaction product through a microfluidic channel into a second chamber which is a microfluidic chamber and performing a second chemical reaction on the first product to create a second reaction product. In a related aspect of the invention, provided herein is a method comprising: (a) performing a first chemical reaction on an analyte in a first chamber which is a microfluidic chamber to produce a first reaction product; and (b) moving the first reaction product through a microfluidic channel into a second chamber which is a non-microfluidic chamber and performing a second chemical reaction on the first product to create a second reaction product. In one embodiment, the methods of these related aspects comprise cleaning the first reaction product before moving it to the second chamber. In another embodiment, the methods of these related aspects comprise at least once, moving a reaction product through a microfluidic channel into a subsequent non-microfluidic chamber and performing a subsequent chemical reaction on the reaction product to create a subsequent reaction product. In another embodiment, the methods of these related aspects comprise at least once and before moving a reaction product into a non-microfluidic chamber, moving a reaction product through a microfluidic channel into a microfluidic chamber and performing a subsequent chemical reaction on the reaction product to create a subsequent reaction product.

In another aspect of the invention, provided herein is a device comprising: (a) a sample channel having a channel inlet and a channel outlet; (b) an electrophoresis capillary having a capillary inlet and a capillary outlet, wherein the capillary comprises an electrically conductive medium and is in communication with the sample channel at a point of connection; (c) an anode and a cathode configured to apply a voltage across the capillary inlet and capillary outlet, wherein one of the anode or cathode comprises a forked electrode wherein the forks are in electrical communication with the sample channel on different sides of the point of connection; and (d) a second electrode in electrical communication with the sample channel substantially opposite the point of connection. In one embodiment of the device, the second electrode is comprised as a third fork in the forked electrode.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 96A shows three electrodes opposite a capillary inside the lumen of tubing. The third electrode is not electrically connected, but is independently electrified.

FIG. 96B shows three electrodes opposite a capillary inside the lumen of tubing. All the electrodes are electrically connected.

DETAILED DESCRIPTION OF THE INVENTION

Figure 1A:
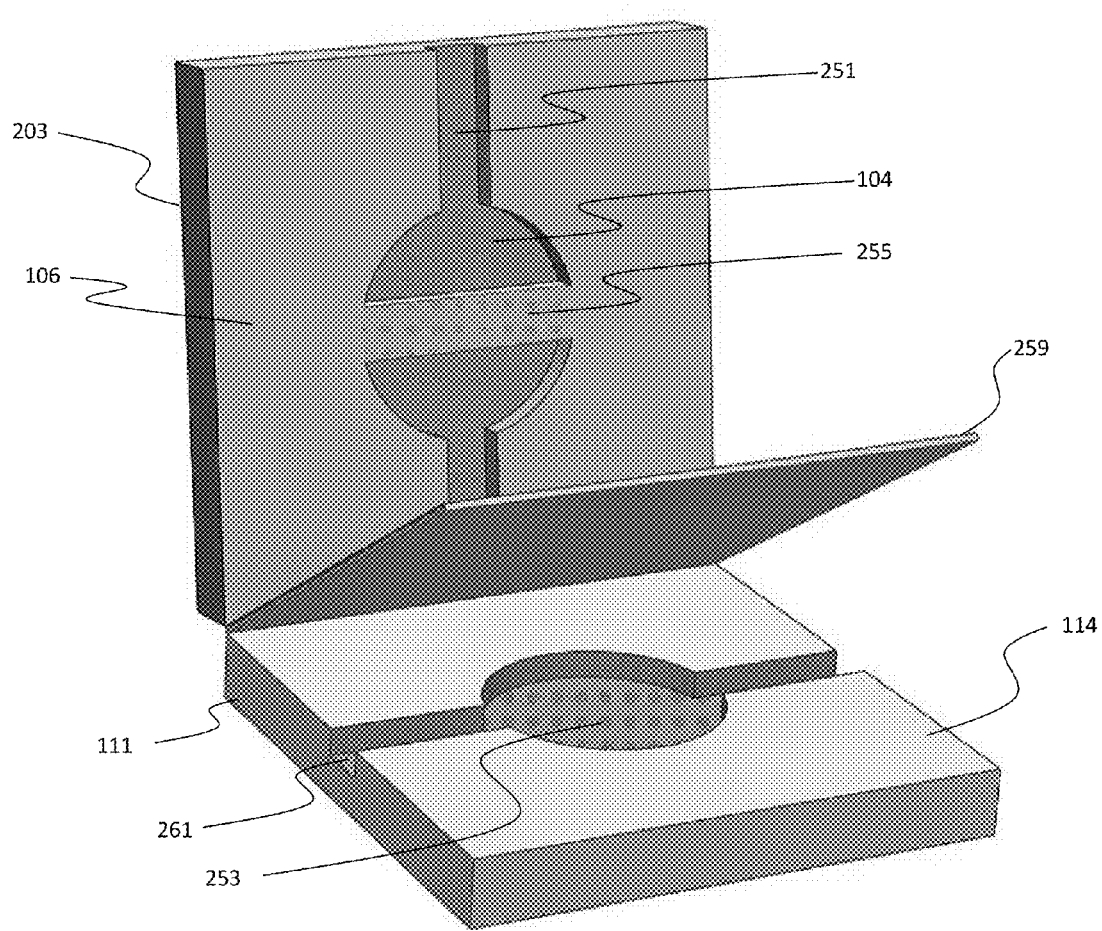
FIG. 1 depicts an example of a microscale on-chip valve (MOVe).

This invention includes devices that incorporate valves, such as microvalves (including but not limited to pneumatically actuated valves and microscale on-chip valves), into their design in order to control the movement of fluid. These devices can be used for the enrichment of a component, for sample preparation, and/or for analysis of one or more components in or from a sample.

The invention also provides devices for fluid and analyte processing and methods of use thereof. The devices of the invention can be used to perform a variety of actions on the fluid and analyte. These actions can include moving, mixing, separating, heating, cooling, and analyzing. The devices can include multiple components, such as a cartridge, a microfluidic microchip, and a pneumatic manifold.

Microfluidic-Non-Microfluidic Integration

In one aspect, this invention provides an instrument that uses microfluidic components to integrate functions performed on a non-microfluidic scale. The instrument includes non-microfluidic chambers fluidically connected to each other and to microfluidic chambers through microfluidic channels in a microfluidic device, e.g., a microfluidic chip. The microfluidic device comprises directional control mechanisms, such as valves and pumps, by which fluid can be selectively routed between different chambers and along different channels, and by which a single chamber can communicate with a number of other chambers. These connections and routing mechanisms allow automation of the functions. In certain embodiments, the instrument uses particulate capture agents that can bind an analyte, be immobilized, be suspended or re-suspended in a desired volume of fluid and be routed to and from chambers through the microfluidic channels. This simplifies in the transition of an analyte from a non-microfluidic environment to a microfluidic environment and back to a non-microfluidic environment. The amount of capture agent can be selected to capture a desired amount analyte from a sample, for example, to concentrate analyte from a dilute sample, to quantitatively capture all or substantially all of an analyte from a sample or to select a portion of an analyte from a more concentrated sample. This allows one to "tune" the amount of analyte used in a reaction and further decreases fluid handling steps. The instrument can comprise a plurality of parallel fluidic circuits by which fluidic operations can be performed in parallel. The integration of microfluidic and non-microfluidic components on the device simplifies sample handling during the performance of chemical reactions (e.g., chemical reaction, biochemical reaction and enzymatic reaction). It also allows size reduction of operations, decreasing the footprint and the total space occupied by the system. Accordingly, the instruments of this invention integrate non-microfluidic and microfluidic environments.

More specifically, this invention provides instruments that comprise a microfluidic component and a non-microfluidic component in fluid communication with each other. A microfluidic component comprises at least one microfluidic channel. A microfluidic channel generally has a cross sectional area of less than 1 mm$^2$ or at least one cross-sectional dimension in the range of from about 0.1 microns to about 500 microns, e.g., below about 350 microns. A non-microfluidic component comprises at least one non-microfluidic chamber (open or closed), that is, a chamber that holds a non-microfluidic volume e.g., at least 10 microliters, at least 20 microliters, at least 50 microliters, at least 100 microliters, at least 500 microliters, at least 1 ml, at least 10 ml or at least 100 ml. Accordingly, in the instruments of this invention, a non-microfluidic chamber is in fluid communication with a microfluidic channel. The instruments are adapted to transport fluid samples (e.g., a liquid) from a non-microfluidic chamber into a microfluidic channel and/or from a microfluidic channel into a non-microfluidic chamber or otherwise out of the microfluidic device. In other embodiments the microfluidic devices comprise microfluidic chambers in fluid communication with microfluidic channels. In this case, the instruments are adapted to transport fluid samples between microfluidic chambers and non-microfluidic chambers through microfluidic channels. Fluid moved from a microfluidic channel into a non-microfluidic chamber can be removed from the device.

Manipulation of the analyte can include a variety of steps. These can include, for example, preparing the analyte for a chemical reaction, mixing with one or more reagents in various sequences, performing a chemical reaction with the analyte, removing wastes and washing. The instrument of this invention can be used to perform these functions by routing analytes, reagents, wastes and wash solutions between compartments. Accordingly, in certain embodiments the instruments of this device comprise a plurality of non-microfluidic chambers connected to each other through microfluidic channels. Fluid can be moved from one chamber to another by any appropriate motive force, for example, continuous pressure or non-continuous pressure (e.g., positive displacement pumps), electroosmotic flow or centrifugation. Pressure can be generated internally (e.g., with on-chip diaphragm valves) or externally. The channels can comprise directional control mechanisms to selectively route fluids between chambers as desired. These mechanisms can be valves, such as the diaphragm valves described elsewhere in this specification, single use valves such as wax valves or other valves. By opening and closing valves in a proper sequence, analyte, reagents and waste can be routed into appropriate locations. In this way, the microfluidic portion of the instrument is used to route fluids between non-microfluidic environments where various functions can be performed on the analyte.

The non-microfluidic chambers can comprise capture agents to bind analytes. The capture agents generally comprise a solid substrate and are able to specifically or non-specifically bind analytes. The substrate can assert the binding force, or a molecule having binding properties can be attached to the substrate, for example, an antibody. The capture agent can be a particulate capture agent. Alternatively, the material can be a chromatographic material. In this case, a sample can be passed through the chromatographic material and separated fractions introduced into the microfluidic device. Alternatively, the capture agent can be a monolith. Alternatively, the capture agent can be attached to a surface of the chamber, such as a post, or the chamber surface can be derivatized with a capture molecule.

The device is further adapted to move particles, such as beads, between a microfluidic channel and a non-microfluidic chamber. The particles can be responsive to magnetic force, electrical forces, or other forces. For example, they can be paramagnetic or magnetic particles. This allows further manipulation of the particles within the device by application of magnetic fields using fixed or movable magnets including electromagnets. The particles can function as a capture agent to capture one or more analytes from a sample. For example, the particles can have specific or non-specific affinity for an analyte. Because the particles are solid, they allow one to transit between non-microfluidic fluid volumes and microfluidic fluid volumes by immobilizing the particles and altering the volume of the fluid in which they are contained. Particles can be immobilized in the non-microfluidic chamber or in the microfluidic device.

The instrument of this invention can be used to capture a selected amount of an analyte from a sample in a non-microfluidic chamber and transport that amount of analyte from the chamber into a microfluidic channel. Once in the microfluidic channel, the particles can be routed into a non-microfluidic chamber for storage or processing. For example, a non-microfluidic volume of a sample is provided to a chamber. The sample may be, for example, dilute or concentrated with respect to an analyte. By properly calibrating the amount of capture agent and conditions, a selected amount of the analyte can be captured by the capture agent. For example, in a concentrated sample, a small amount of capture agent can be selected so that only a portion of the analyte to be used in a reaction is captured. This allows sampling of a portion of the analyte in the sample volume, e.g., an amount sufficient or appropriate to perform a chemical reaction. Alternatively, in a dilute sample, a greater amount of capture agent can be used so that most or substantially all of the analyte present is captured on the capture agent. This effectively concentrates the analyte. Washing the analyte can remove impurities, effectively purifying the analyte from undesirable components of the sample such as inhibitors, other analytes, etc. The specificity of the capture can also be controlled by adjusting the chemistry to select broader or narrower ranges of analytes, for example longer or short pieces of DNA, differentiating DNA from RNA, or using affinity reagents with broader or narrower specificity. In some embodiments, multiple analytes may be captured by combining affinity reagents or by using multiple modes of capture either on one type of bead or by mixing multiple bead or particle types. In certain embodiments, the instrument further comprises a detector, e.g., an optical detector, for detecting molecules at some stage of the process.

A variety of reaction sequences are contemplated. A chemical reaction can be performed on an analyte. Then, the reaction product can be cleaned and subjected to a different chemical reaction. This sequence of cleaning a reaction product and performing a subsequent different reaction can be repeated. In particular, this invention contemplates performing series of biochemical or enzymatic reactions separated by clean-up steps. One example of this is Eberwine chemistry, in which a first chemical reaction, reverse transcription, is followed by a second reaction, second strand synthesis, which is followed by a third reaction, transcription. Before each subsequent reaction, and typically after the last reaction, the product is removed from contaminants in preparation of the next step. In one embodiment, a reaction product in a non-microfluidic chamber is moved through a microfluidic channel to another non-microfluidic chamber. In another embodiment, a reaction product in a non-microfluidic chamber is moved through a microfluidic channel into a microfluidic chamber, e.g., on-chip. In another embodiment, a reaction product in a microfluidic chamber is moved through a microfluidic channel into a non-microfluidic chamber. Accordingly, this invention provides the use of small analyte volumes and small reagent volumes, thereby reducing waste of reagent.

For example, the instrument can be used to perform chemical reactions on nucleic acids, such as DNA amplification. A non-microfluidic volume of a sample (e.g., several hundred microliters) comprising DNA can be collected in a non-microfluidic chamber of this device. Paramagnetic capture particles can be flowed through microfluidic circuits into the chamber to capture a calibrated amount of nucleic acid. The paramagnetic particles can be held in the chamber by magnetic force and the uncaptured sample can be removed as waste, e.g., through a microfluidic channel. Valves in the microfluidic device can then be configured to route a volume, e.g., a non-microfluidic volume, of wash solution into the chamber. The analyte and particles can be washed, immobilized and the waste can be removed. Then, the particles with captured and purified analyte can be re-suspended in a volume and moved from the chamber through a microfluidic channel into a thermal cycling chamber, which can be a non-microfluidic reaction chamber or a microfluidic reaction chamber. There, the particles can be immobilized and liquid removed. This can concentrate the particles to about the particle volume (e.g., in the nanoliter range). Reagents for performing nucleic acid amplification in an appropriate volume can be routed through a microfluidic channel into the thermal cycling chamber. Under certain conditions, the reaction mixture will elute the nucleic acids from the particles. Accordingly, this invention contemplates contacting reagents for performing a chemical reaction, such as PCR, cycle sequencing, real-time PCR, rolling circle amplification, restriction digestion, RNA fragmentation, protein digestion, etc., with the analyte attached to a particle, without first eluting the analyte from the particle and, e.g., determining concentration and selecting an amount of analyte for mixing with reagent. This is possible, in part, by properly calibrating the capture agent used to capture analyte, so that an appropriate amount of analyte is already present. After enzymatic reaction or thermal cycling, the product can be moved into a microfluidic channel for clean up, e.g., in a microfluidic chamber or into a non-microfluidic chamber. This can comprise diluting the product to decrease salt concentration. It also can comprise binding the analytes to beads, immobilizing them, and washing them. It can also comprise chromatography, solid phase extraction, or other cleanup methods at microfluidic scale or non-microfluidic scale. At this point, the microfluidic components can route the product to an appropriate location for analysis, e.g., a capillary tube for capillary electrophoresis or the product can be output into a non-microfluidic volume for analysis by an unintegrated system such as a commercial capillary array electrophoresis instrument, mass spectrometer, or other analytical instrument. The microfluidic device also can contain a waste confinement area.

In certain embodiments, the microfluidic devices of this invention are monolithic devices. In monolithic devices, a plurality of circuits are provides on a single substrate. In the case of devices comprising diaphragm valves, a monolithic device comprises a single elastic layer functioning as a diaphragm for a plurality of valves. In certain embodiments, one actuation channel can operate a plurality of valves on a monolithic device. This allows parallel activation of many fluidic circuits. Monolithic devices can have dense arrays of microfluidic circuits. These circuits function with high reliability, in part because the channels in each circuit are fabricated simultaneously on a single substrate, rather than being made independently and assembled together.

The fluidic circuits and of these devices can be densely packed. A circuit comprises an open or closed fluid conduit. In certain embodiments, the device can comprise at least 1 fluidic circuit per 1000 mm$^2$, at least 2 fluidic circuits per 1000 mm$^2$, at least 5 fluidic circuits per 1000 mm$^2$, at least 10 fluidic circuits per 1000 mm$^2$, at least 20 fluidic circuits per 1000 mm$^2$, at least 50 fluidic circuits per 1000 mm$^2$. Alternatively, the device can comprise at least 1 mm of channel length per 10 mm$^2$ area, at least 5 mm channel length per 10 mm$^2$, at least 10 mm of channel length per 10 mm$^2$ or at least 20 mm channel length per 10 mm$^2$. Alternatively, the device can comprise valves (either seated or unseated) at a density of at least 1 valve per cm$^2$, at least 4 valves per cm$^2$, or at least 10 valves per cm$^2$. Alternatively, the device can comprise features, such as channels, that are no more than 5 mm apart edge-to-edge, no more than 2 mm apart, no more than 1 mm apart, no more than 500 microns apart or no more than 250 microns apart.

Universal Sample Preparation System

This invention provides a universal sample preparation system. The system is configured to accept a biological sample comprising in analyte in an un-purified form, purify the analyte, perform at least one biochemical reaction on the analyte, and analyze the product of the biochemical reaction.

The universal sample preparation system can be configured to fit inside a volume of no more than 6 ft$^3$, no more than 7 ft$^3$, no more than 8 ft$^3$, no more than 97 ft$^3$, or no more than 10 ft$^3$. In one specific embodiment, the universal sample preparation system is configured to fit inside a volume of about 8 ft$^3$. In another specific embodiment, the universal sample preparation system is configured to fit inside a volume of about 10 ft$^3$.

The universal sample preparation system can comprise the following modules: a sample preparation module, a reaction module, a post-reaction module, an analysis module, and/or a computer module. A sample preparation module can be configured to capture in analyte, e.g., DNA, from a sample that has a non-microfluidic volume, and move the captured analyte into a first microfluidic channel. This can be accomplished using, for example, magnetically-responsive capture particles to concentrate the analyte. The reaction module is fluidly connected to the first microfluidic channel and is configured to perform at least one biochemical reaction on the analyte in a reaction chamber to produce a reaction product. Typically, the analyte in the reaction chamber is concentrated with respect to its concentration in the sample preparation module. A post-reaction module is in fluid communication with the reaction module and is configured to process the reaction product for analysis. The post-reaction module can be configured to move the reaction product through a second microfluidic channel into a non-microfluidic chamber in the post-reaction module. The analysis module is fluidly connected to the reaction module or the post-reaction module and is configured to perform an analysis, such as capillary electrophoresis, on the reaction product. The analysis module generates data about the reaction product. A computer module comprises computer executable code for processing and/or analyzing the data, including formatting the data into a universal format. The system can be further configured to access the Internet, transmit data to an off-site server and receive information from the server.

Figure 6:
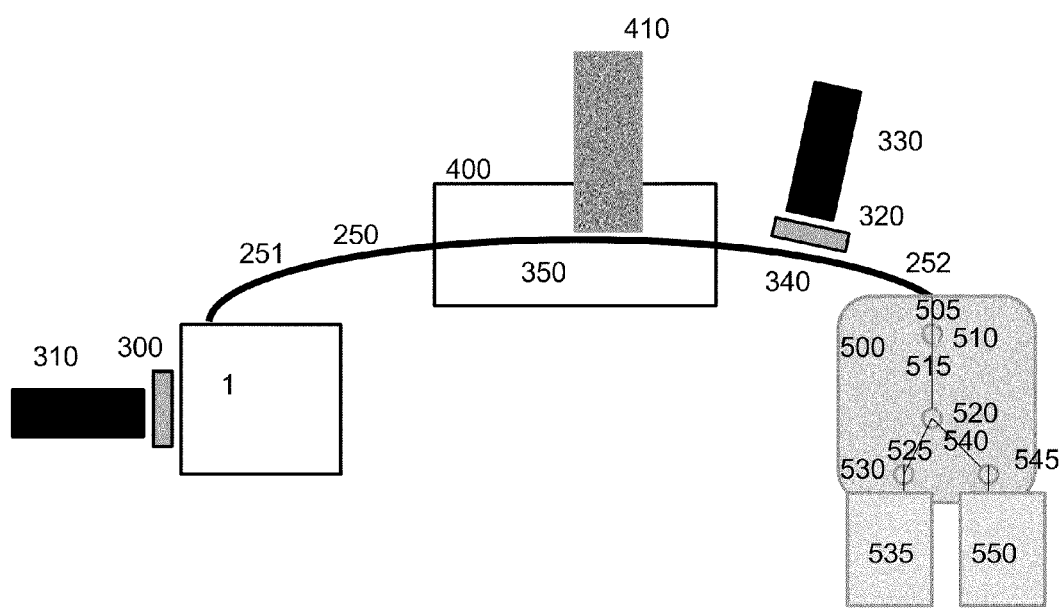
FIG. 6 shows a cartridge connected to reaction chamber and detector with downstream MOVe pumps and reagents.

An exemplary device is shown in FIG. 6. FIG. 6 shows a cartridge with integrated microchip (1), temperature modulating device (400), and downstream analysis device (500). In certain embodiments the device comprises a fluid preparation module comprising a cartridge mated or otherwise fluidically connected to a microchip; an off-chip thermal modulation module connected to the fluid preparation module through a fluid transporter with a fluidic channel, such as a tube, through the cartridge, and configured to modulate the temperature in the fluid transporter, wherein the fluid transporter is further fluidically connected to a second microchip with valves and fluidic channels that can selectively route fluid to one or more subsequent devices. This device can be used for thermal cycling or isothermal reactions.

In one application, the system is configured to prepare, from a biological sample, a CODIS-compatible file for searching a CODIS database. CODIS is a forensic system that presently uses thirteen STR (short tandem repeat) loci as genetic identity markers see, e.g., www.fbi.gov/hq/lab/html/codis1.htm. Information from fewer or more than 13 markers can be used to provide evidence of identity. The sample preparation module extracts DNA from forensic material, captures a predetermined amount of DNA on capture particles e.g. in magnetically responsive particles, and delivers the DNA to a non-microfluidic reaction chamber of a reaction module, where the particles are immobilized, e.g., with a magnetic force. There, reagents for PCR are delivered to the reaction chamber and the STR markers used in CODIS are amplified using PCR. The amplification can be performed using commercially available reagents, such as those available from Promega (e.g., the PowerPlex product series). This product uses four differently colored fluorescent markers. The PCR products are routed to the post-reaction module and diluted to a proper concentration for capillary electrophoresis. The new product is directed to the analysis module, where capillary electrophoresis is performed. Analytes in the product are detected by fluorescence detection. The data generated is then subjected to an algorithm which generates traces for each fluorescent species. These traces can then be analyzed by computer to identify the markers at the STR loci used in CODIS. Such software is commercially available from, e.g., Life Technologies, such as GeneMapper™ ID-X software or NIST software tools (www.cstl.nist.gov/biotech/strbase/software.htm). Software can convert this data into a file format compatible with CODIS. See, e.g., www.ncjrs.gov/pdffiles1/nij/sl413apf.pdf. The CODIS compatible file can be used to query a forensic database such as the CODIS database. The system can be configured to access the Internet and deliver the file to the appropriate database for analysis and to receive a report from the database indicating the probable matches between the initial sample and an individual.

I. Sample Preparation Module

The sample preparation module is configured to capture an analyte from a non-microfluidic volume onto a solid substrate and route the captured analyte through a microfluidic channel into a reaction chamber of the reaction module. The analyte can be captured from a sample in which the analyte is in non-isolated form. An analyte is non-isolated if it is present with other cellular or biomolecular components with which it is naturally associated. These can include for example, cytoplasmic components or viral components. The sample preparation module can be configured to capture and analyte from a raw sample. A raw sample is one in which the analyte is contained within a cell or a virus. For example, blood, a cheek swab and semen are raw samples containing the analyte DNA. In this case, the sample preparation module can comprise materials to lyse cells and extract DNA from the lysate.

Figure 16:
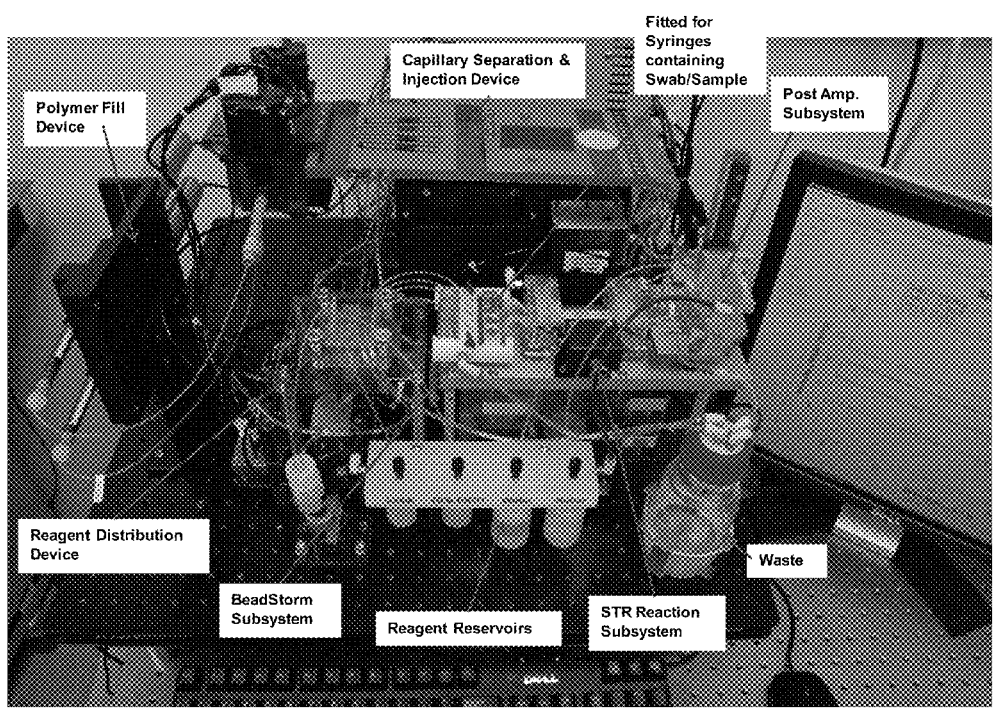
FIG. 16 shows a four module assembly.
Figure 17:
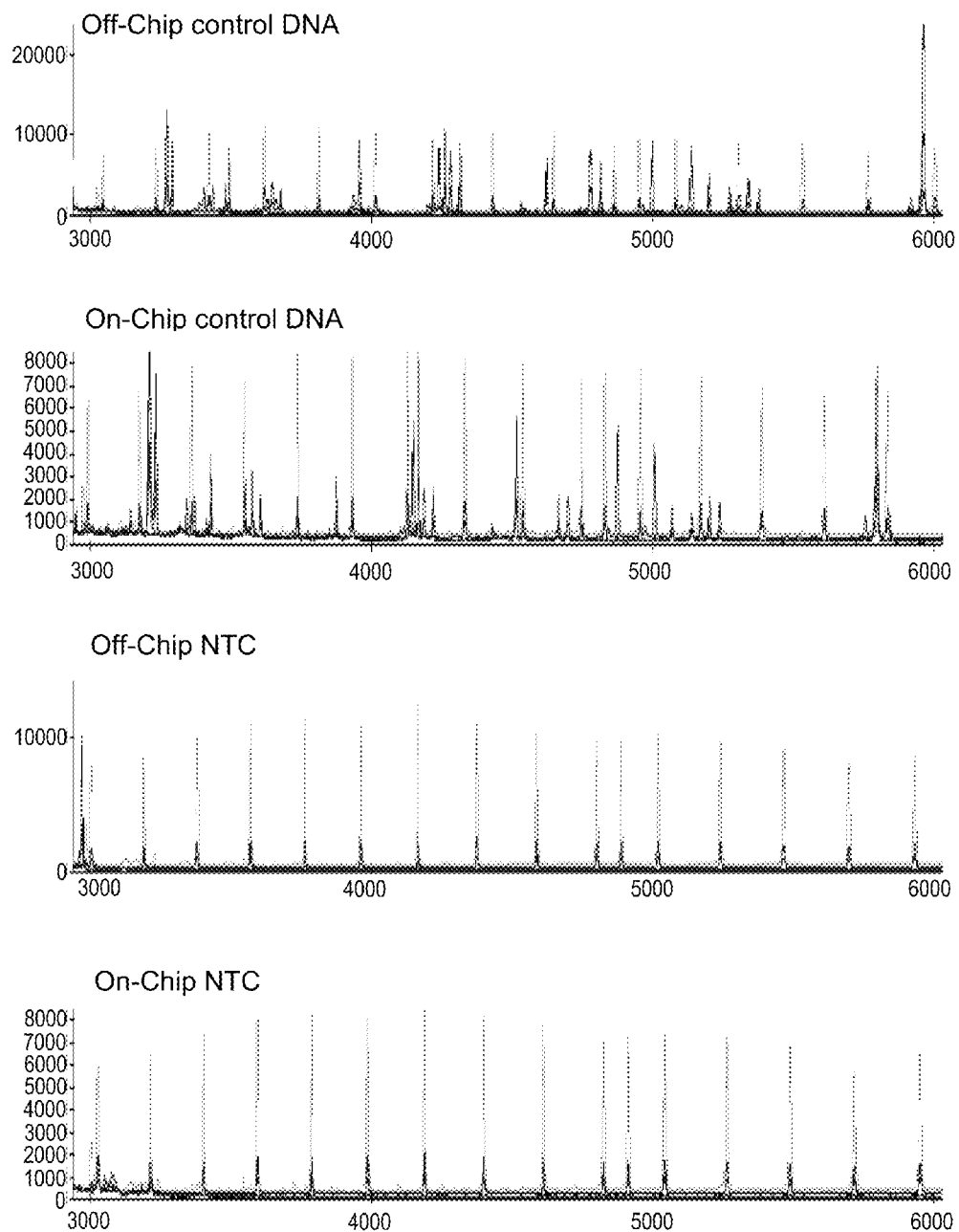
FIG. 17 shows an example of STR reactions on microchips.
Figure 21:
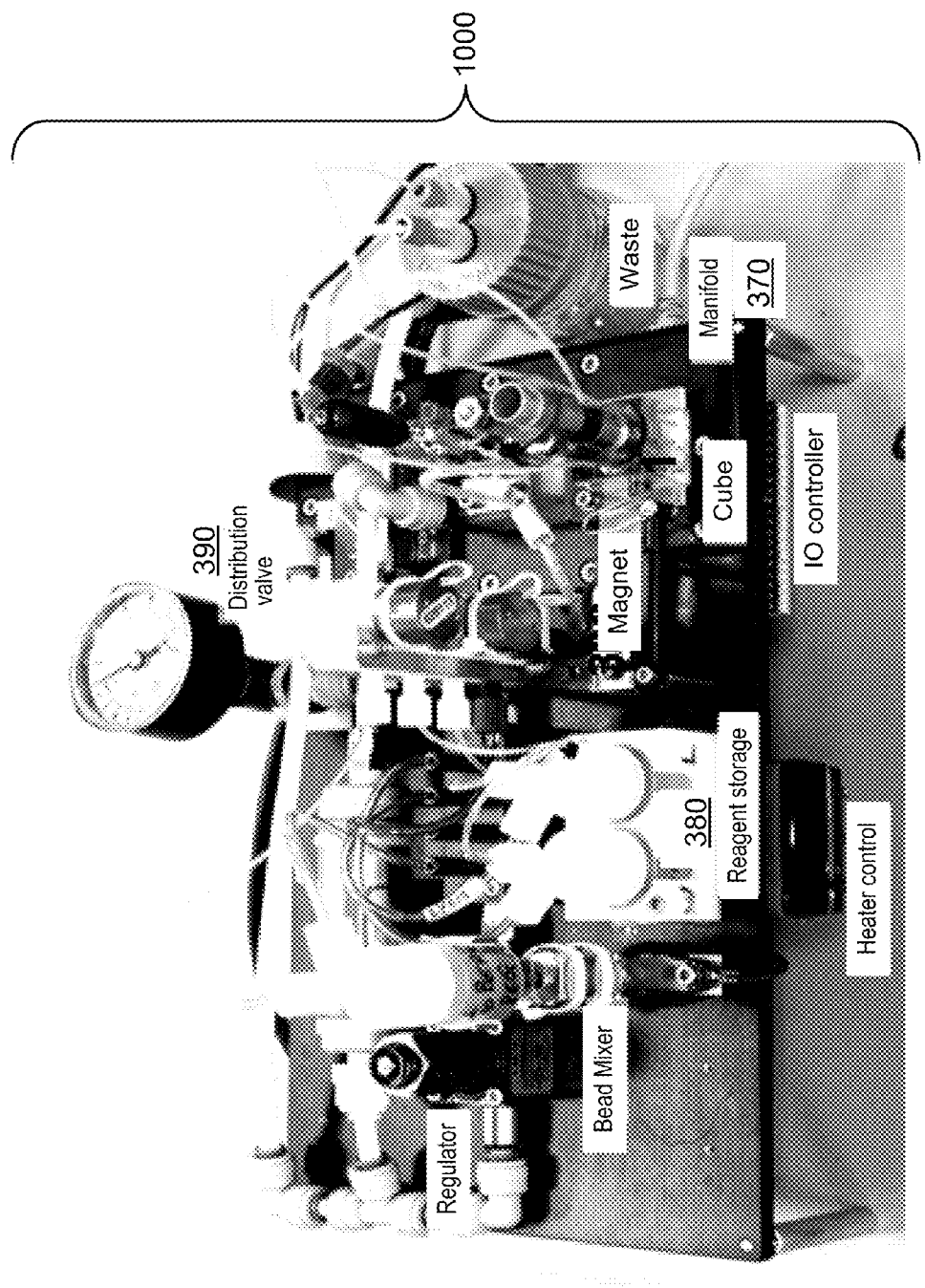
FIG. 21 shows a cartridge mounted on a computer controlled apparatus.
Figure 22:
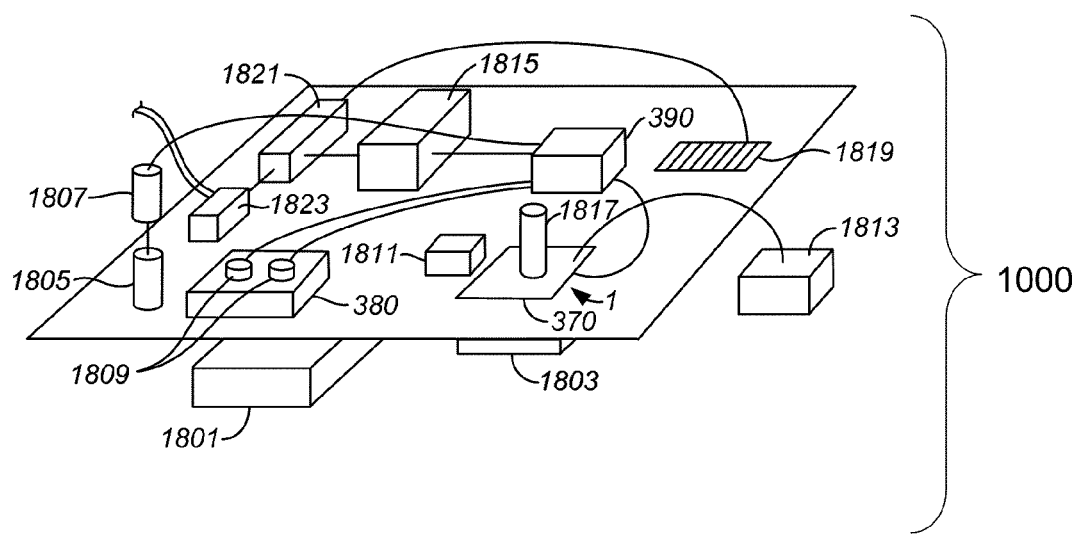
FIG. 22 shows a cartridge mounted on a computer controlled apparatus.
Figure 54:
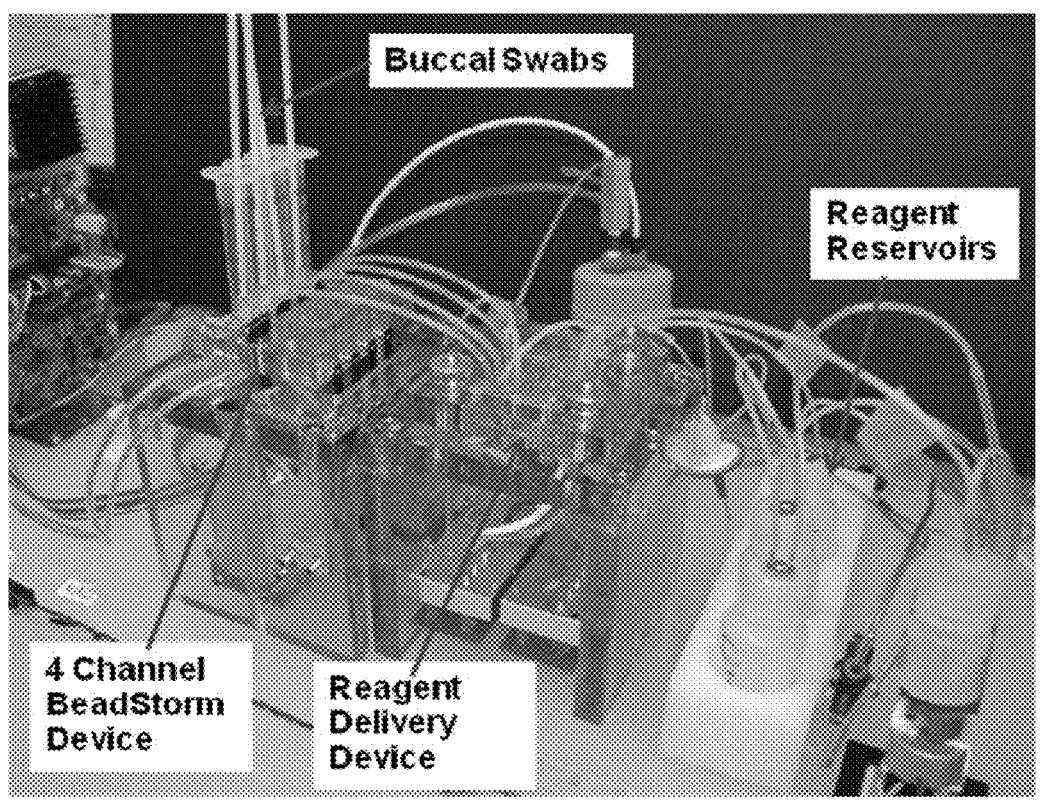
FIG. 54 shows a four-channel sample preparation device on the left and a four-channel sample preparation device mounted on a monolithic pneumatic manifold on the right.

In one aspect a sample preparation device, as shown in FIG. 16, device 1000 in FIG. 21 and FIG. 22, and FIG. 54, comprises a cartridge integrated with a microfluidic microchip that controls movement of the fluid in the cartridge through microvalves and the components to operate the cartridge. The cartridge and/or the compartments therein can be of sufficient size to process one or more milliliter of an input sample in an automated device. The cartridge can process a sample to output a component that can be moved using pressure-driven flow or vacuum modulated by microvalves. The cartridge can provide an interface with a delivery device comprising macroscale samples, such as blood, aerosol liquids, swabs, bodily fluids, swipes, and other liquid, solid, and gas samples. The cartridge can process macroscale sample volumes using microscale sample preparation and analysis. The cartridge can allow for processing of macroscale or large volume samples using microfluidic devices and components have reduced void volumes that allow for reduced loss of materials.

A. Cartridges

A cartridge, also referred to as a fluidic manifold herein, can be used for a number of purposes. In general, a cartridge can have ports that are sized to interface with large scale devices as well as microfluidic devices. Cartridges or fluidic manifolds have been described in U.S. Patent Publication US20090253181. The cartridge can be used to receive materials, such as samples, reagents, or solid particles, from a source and deliver them to the microfluidic microchip. The materials can be transferred between the cartridge and the microfluidic microchip through mated openings of the cartridge and the microfluidic microchip. For example, a pipette can be used to transfer materials to the cartridge, which in turn, can then deliver the materials to the microfluidic device. In another embodiment, tubing can transfer the materials to the cartridge. In another embodiment, a syringe can transfer material to the cartridge. In addition, a cartridge can have reservoirs with volumes capable of holding nanoliters, microliters, milliliters, or liters of fluid. The reservoirs can be used as holding chambers, reaction chambers (e.g., that comprise reagents for carrying out a reaction), chambers for providing heating or cooling (e.g., that contain thermal control elements or that are thermally connected to thermal control devices), or separation chambers (e.g. paramagnetic bead separations, affinity capture matrices, and chromatography). Any type of chamber can be used in the devices described herein, e.g., those described in U.S. Patent Publication Number 2007/0248958, which is hereby incorporated by reference. A reservoir can be used to provide heating or cooling by having inlets and outlets for the movement of temperature controlled fluids in and out of the cartridge, which then can provide temperature control to the microfluidic microchip. Alternatively, a reservoir can house Peltier elements, or any other heating or cooling elements known to those skilled in the art, that provide a heat sink or heat source. A cartridge reservoir or chamber can have a volume of at least about 0.1, 0.5, 1, 5, 10, 50, 100, 150, 200, 250, 300, 400, 500, 750, 1000, 2000, 3000, 4000, 5000 or more µL. The relative volume of a chamber or reservoir can be about 1, 2, 5, 10, 20, 50, 100, 200, 500, 1000, 2000, 5000, 10000 or more greater than a channel or valve within the microfluidic microchip. The size of the chambers and reservoirs of the cartridge, which can be mated to the microfluidic microchip, can be chosen such that a large volume of sample, such as a sample greater than about 1, 5, 10, 50, 100, 500, 1000, 5000, 10000, 50000 or more µL, can be processed, wherein the flow of fluids for processing the sample is controlled by valves in the microfluidic microchip. This can allow for a reduced amount of sample and reagent loss due to the reduced void volumes in the microfluidic microchip compared to other flow control devices, such as pipettes and large scale valves. The void volume within a microfluidic microchip can be less than 1000, 500, 100, 50, 10, 5, 1, 0.5, 0.1, or 0.05 µL. This can allow for the amount of sample or reagent loss during processing of a sample to be less than 20, 15, 10, 7, 5, 3, 2, 1, 0.5, 0.05 percent.

A cartridge can be constructed of any material known to those skilled in the art. For example, the cartridge can be constructed of a plastic, glass, or metal. A plastic material may include any plastic known to those skilled in the art, such as polypropylene, polystyrene, polyethylene, polyethylene terephthalate, polyester, polyamide, poly(vinylchloride), polycarbonate, polyurethane, polyvinyldiene chloride, cyclic olefin copolymer, or any combination thereof. The cartridge can be formed using any technique known to those skilled in the art, such as soft-lithography, hard-lithography, milling, embossing, ablating, drilling, etching, injection molding, or any combination thereof.

Figure 3:
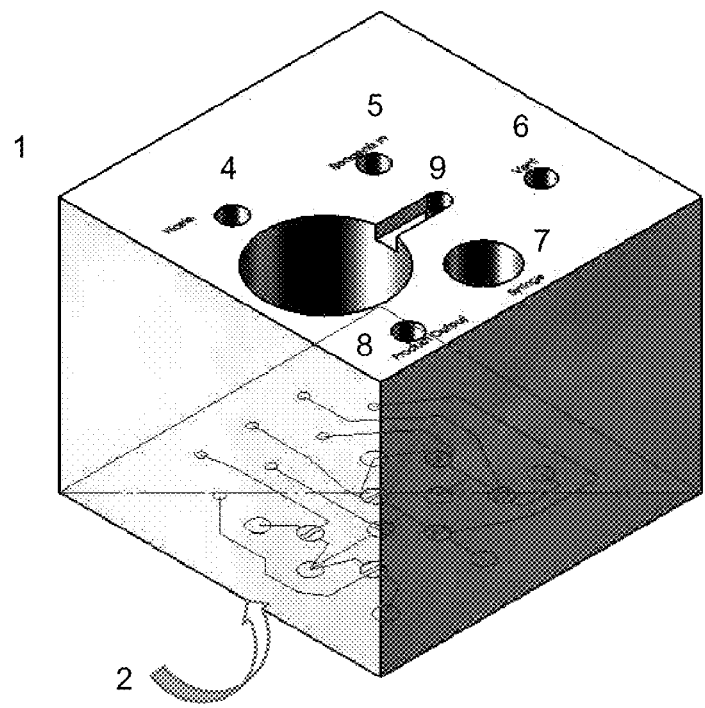
FIG. 3 shows a fluidic cartridge with MOVe microvalves.
Figure 4:
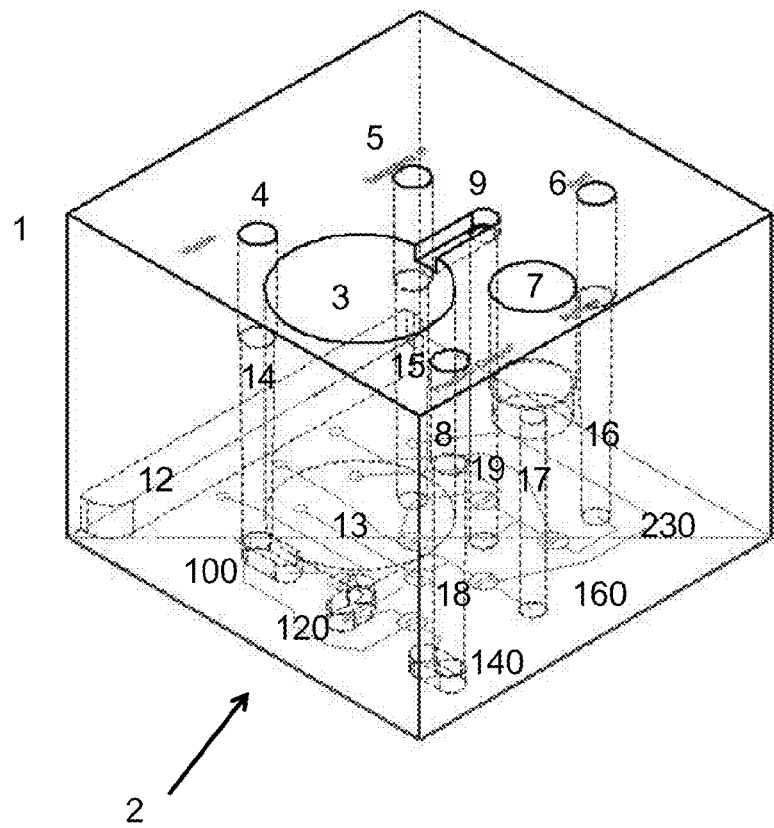
FIG. 4 shows a fluidic cartridge with ports to a microfluidic microchip with microvalves.

As exemplified in FIG. 3 and FIG. 4, a cartridge (1) can comprise a rectilinear configuration with flat sides. In another embodiment, a cartridge comprises a surface that is curved, rounded, indented or comprises a protrusion. In one embodiment a cartridge has at least one substantially flat surface which is adjacent to a microfluidic microchip. The cartridge is adapted to be fluidically connected with ports in the microchip. For example, openings in the surface of the cartridge can be aligned with ports in the microchip. When the cartridge and microchip are mated to one another, the openings align to create the fluidic connections allowing liquids to pass from the cartridge into the ports of the microchip, which are connected to channels typically having valves that form fluidic circuits.

In one embodiment a cartridge contains one or more features, including but not limited to a chamber, a port, a channel or a magnet. In one embodiment, microvalves, such as pneumatically actuated valves are combined with the microfluidic cartridge. In some embodiments the microvalves are active mechanical microvalves (such as magnetic, electrical, or piezoelectric thermal microvalves), non-mechanical microvalves (such as bistable electromechanical phase change or rheological microvalves), external microvalves (such as modular or pneumatic), passive mechanical (such as check microvalves or passive non-mechanical (such as capillary microvalves) (Oh et al., A review of microvalves, J. Micromech Microeng. 16 (2006) R13-R39)).

In another embodiment, pneumatically actuated valves, such as MOVe valves, modulate the flow of air pressure, vacuum, or fluids in a microfluidic microchip 2 or multiple microfluidic microchips. MOVe valves can be microscale on-chip valves, microfluidic on-chip valves or micro-robotic on-chip valves. In one embodiment the flow of air pressure, vacuum, or fluids is regulated by one or more variable pressure pumps, such as solenoid valves or solenoid pumps. In one embodiment, a microfluidic microchip is a structure that contains microchannels and/or microtrenches, where a microchannel is a closed structure and a microtrench is an open structure. In one embodiment a microfluidic microchip is a planar structure. In a related embodiment a microfluidic device comprises a microfluidic microchip with microvalves clustered on one side of a cartridge. In one embodiment (FIG. 3 and FIG. 4) the cartridge (1) can comprise one or more ports (4, 5, 6, 7, 8, 9) to external fluids, air, or vacuum. Functions of the ports can be for waste (4), reagent entry (5), vent (6), sample input (7), product output (8). The cartridge (1) can contain one or more sample input or reaction chambers, (7) and (3).

A single chamber within the cartridge, such as a reaction chamber, can have one or more, or at least one, two, or three fluidic connections to a microchip. For example, in FIG. 3 and FIG. 4, the reaction chamber (3) can have a fluidic connection to the microchip through connection 120, which is at the base of the chamber, and another fluidic connection to the microchip through port (9), which is connected to chamber (3) through a passageway located at the top of the chamber. The top of chamber (3), port (9), and the passageway between chamber (3) and port (9) can be closed from the exterior environment such that fluids in chamber (3) necessarily are pumped into port (9) when chamber (3) is full and vice versa. Such a chamber or combination or chamber and port can be referred to as a closed chamber. The positioning of the fluidic connections need not necessarily be at the base and top of the chamber, however, fluidic connections at the base and top positions of the chamber allow for reduced trapping of gas in the chamber. Alternatively, reaction chamber (3) can be viewed as a combination of two chambers that are fluidically connected to each other at a top position, which can be within the cartridge, and, where each chamber also has an opening at a base location. The openings at the base locations, also called chamber apertures, can be fluidically connected to port apertures on the microchip. The two fluidic connections can allow for fluids to be directed into and out of the chamber through the microfluidic microchip.

In another embodiment a device comprises a cartridge comprising at least one pneumatically actuated valve, such as a MOVe valve, located on one or more surfaces or structures in a non-linear manner. A cartridge can comprise one or more pneumatically actuated valves that are located within the cartridge, in a location other than the base of the cartridge.

Functional elements of a cartridge can include ports, channels, chambers, filters, magnets, or vents, chambers can be collectively referred to as functional elements. In one embodiment, FIG. 4, the functional elements connect to the microfluidic microchip containing microvalves at junctions 100, 120, 140, 160, and 230. The functional elements can connect with tubing or capillaries inserted into the ports, by a flush connection, or by fittings. In one embodiment a flush connection can comprise a port of a cartridge aligned directly with an aperture of a microfluidic microchip. In one embodiment the cartridge and microfluidic microchip form an integrated module. In another embodiment the cartridge and microfluidic microchip are two separate pieces which are attached together, prior to use.

A cartridge can comprise at least one chamber, a sample input port, a reagent port, an exit port, a waste port and a magnet. The magnet can be located adjacent to the chamber, so that the magnet force generated by the magnet can attract paramagnetic particles in said chamber to a wall of the chamber. In one embodiment the paramagnetic particles are beads or cells rendered magnetically responsive (e.g., cells comprising hemoglobin that are treated with sodium nitrate). The magnet can be an electric magnet or a permanent magnet, such as a rare earth metal magnet.

In one embodiment, as exemplified in FIG. 4, connections or ports (4, 5, 6, 7, 8, and 9) lead to channels in the cartridge (14, 15, 16, 17, 18, and 19) respectively. Ports (4, 5, 6, 7, and 8) show indents to reliably attach a connector or tubing to the indent, such as the indent shown for connection (7) (see the difference in diameter of connection (7) with channel (17)). In one embodiment, the ports or ports can interface with a variety of connector or tubes, such as the capillaries as described in U.S. Pat. No. 6,190,616, U.S. Pat. No. 6,423,536, U.S. application Ser. No. 09/770,412, Jan. 25, 2001, U.S. Application No. 60/402,959 or one or more microchips with modular microfluidic ports as described in U.S. Pat. No. 6,870,185 and U.S. application Ser. No. 11/229,065; all of which are herein incorporated by reference in their entirety. In one embodiment, the modular microfluidic ports enable microchips or capillaries to be reversibly joined without dead volumes or leakage.

In another embodiment chamber (3) is connected to passageway (9) and to cone (13), leading to junction (120). Chamber (3) can be used for reactions as may any of the channels. In FIG. 4 the cartridge channels lead directly to the apertures of ports on the microchip (2). The channels of the cartridge can interconnect with each other as needed. In some embodiments, at least one channel in a cartridge does not physically connect to a microfluidic microchip. In another embodiment at least one channel in a cartridge is fluidically connected to at least one microchannel in a microfluidic microchip. The connection may or may not utilize an aperture on the microfluidic microchip. An aperture can be an opening or a fitting designed to mate between the microchip and the cartridge. In some embodiments of the invention, the fitting comprises a seal such as a gasket or an o-ring.

B. Microfluidic Devices

In one embodiment a cartridge and a microfluidic microchip are integrated together to form a single modular device. The cartridge and a microfluidic microchip can be attached by a fluid or by a solid adhesive or mechanically. In one embodiment the adhesive is a polyacrylate, adhesive tape, double-sided tape, or any other adhesive known to one skilled in the art. A cartridge can comprise a feature (12), as exemplified in FIG. 4, that is capable of wicking a fluid-based adhesive into the junction between a microfluidic microchip and a cartridge. An exemplary In another embodiment a cartridge is attached to a microfluidic microchip with a non-fluidic adhesive layer. Alternatively, the cartridge and microchip can be held together by clips, clamps, or another holding device. The cartridge and microchip can be aligned prior to integration by visual cues, with or without a microscope, or by physical guiding features. Visual cues can include lines or features that are drawn, etched, or otherwise present on the cartridge, the microchip, or both. Physical guiding features include indentations, protrusions, and edges that can be 'keyed' to aid or insure proper assembly.

In some instances, the microfluidic microchip has diaphragm valves for the control of fluid flow. Microfluidic devices with diaphragm valves that control fluid flow have been described in U.S. Pat. No. 7,445,926, U.S. Patent Publication Nos. 2006/0073484, 2006/0073484, 2007/0248958, and 2008/0014576, and PCT Publication No. WO 2008/115626. The valves can be controlled by applying positive or negative pressure to a pneumatics layer of the microchip through a pneumatic manifold.

In one embodiment, the microchip is a "MOVe" microchip. Such microchips comprise three functional layers—a fluidics layer that comprises microfluidic channels; a pneumatics layer that comprises pneumatics channels and an actuation layer sandwiched between the two other layers. In certain embodiments, the fluidics layer is comprised of two layers. One layer can comprise grooves that provide the microfluidics channels, and vias, or holes that pass from the outside surface to a fluidics channel. A second layer can comprise vias that pass from a surface that is in contact with the actuation layer to the surface in contact with the pneumatic channels on the other layer. When contacted together, these two layers from a single fluidics layer that comprises internal channels and vias that open out to connect a channel with the fluidics manifold or in to connect a channel with the activation layer, to form a valve, chamber or other functional item. The actuation layer typically is formed of a deformable substance, e.g., an elastomeric substance, that can deform when vacuum or pressure is exerted on it. At points where the fluidic channels or pneumatic channels open onto or are otherwise in contact with the actuation layer, functional devices such as valves, e.g. diaphragm valves, can be formed. Such a valve is depicted in cross section in FIG. 1. Both the fluidics layer and the pneumatics layer can comprise ports that connect channels to the outside surface as ports. Such ports can be adapted to engage fluidics manifolds, e.g., cartridges, or pneumatics manifolds.

Figure 40:
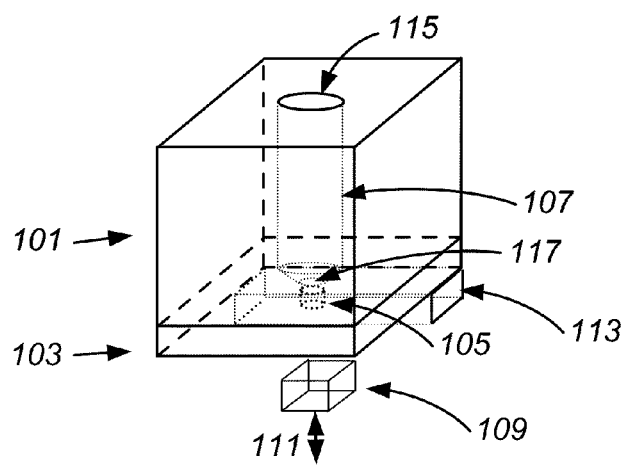
FIG. 40 depicts a device with a cartridge, microfluidic microchip, and a magnet.

As shown in FIG. 40, the microfluidic microchip (103) can be interfaced with the cartridge (101). The microfluidic microchip can have a chamber (105) with an opening that is mated to an opening (117) of the cartridge (101). The chamber can be used for a variety of purposes. For example, the chamber can be used as a reaction chamber, a mixing chamber, or a capture chamber. The chamber can be used to capture magnetic particles such as magnetic beads, paramagnetic beads, solid phase extraction material, monoliths, or chromatography matrices.

A magnetic component (109) can be positioned such that magnetic particles in the cartridge reservoir (107) and/or the microfluidic chamber (105) are captured against a surface of the microfluidic chamber (105). The magnetic component can generate a magnetic and/or electromagnetic field using a permanent magnet and/or an electromagnet. If a permanent magnet is used, the magnet can be actuated in one or more directions to bring the magnet into proximity of the microfluidic microchip to apply a magnetic field to the microfluidic chamber. In some embodiments of the invention, the magnet is actuated in the direction (111) indicated in FIG. 40.

Alternatively, any of a variety of devices can be interfaced with the microfluidic microchip. For example detectors, separation devices (e.g. gas chromatographs, liquid chromatographs, capillary electrophoresis, mass spectrometers, etc), light sources, or temperature control devices can be positioned next to the microfluidic microchip or used in conjunction with the microfluidic microchip. These devices can allow for detection of analytes by detecting resistance, capacitance, light absorbance or emission, fluorescence, or temperature or other chemical or physical measurements. Alternatively, these devices can allow for light to be introduced to a region or area of the microfluidic microchip.

A microfluidic device can be designed with multiple chambers that are configured for capture of magnetic particles. The multiple chambers and magnetic component can be arranged such that a magnetic field can be applied simultaneously to all chambers, or be applied to each or some chambers independent of other chambers. The arrangement of chambers and magnetic components can facilitate faster or more efficient recovery of magnetic particles. In particular, the arrangement can facilitate recovery of magnetic particles in multiple chambers.

Figure 41:
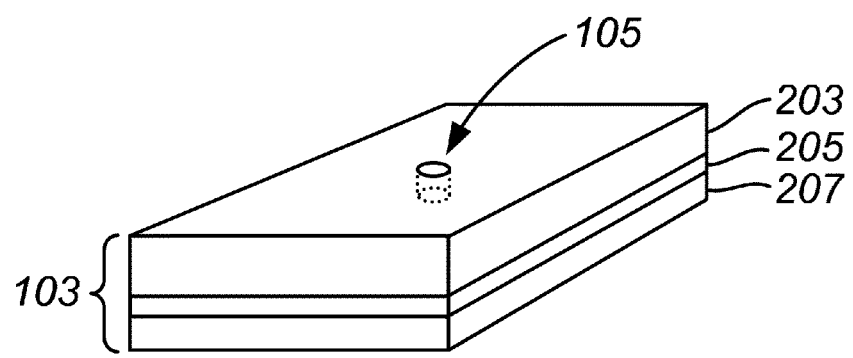
FIG. 41 depicts a microfluidic microchip with a fluidics layer, an elastomeric layer, and a pneumatics layer.

As shown in FIG. 41, the microfluidic microchip (103) can be formed of a fluidics layer (203), an elastomeric layer (205), and a pneumatic layer (207). The fluidics layer can contain features such as a chamber (105), as well as channels, valves, and ports. The channels can be microfluidic channels used for the transfer of fluids between chambers and/or ports. The valves can be any type of valve used in microfluidic devices. In preferred embodiments of the invention, a valve includes a microscale on-chip valve (MOVe), also referred to as a microfluidic diaphragm valve herein. A series of three MOVes can form a MOVe pump. The MOVes and MOVe pumps can be actuated using pneumatics. Pneumatic sources can be internal or external to the microfluidic microchip.

Figure 1B:
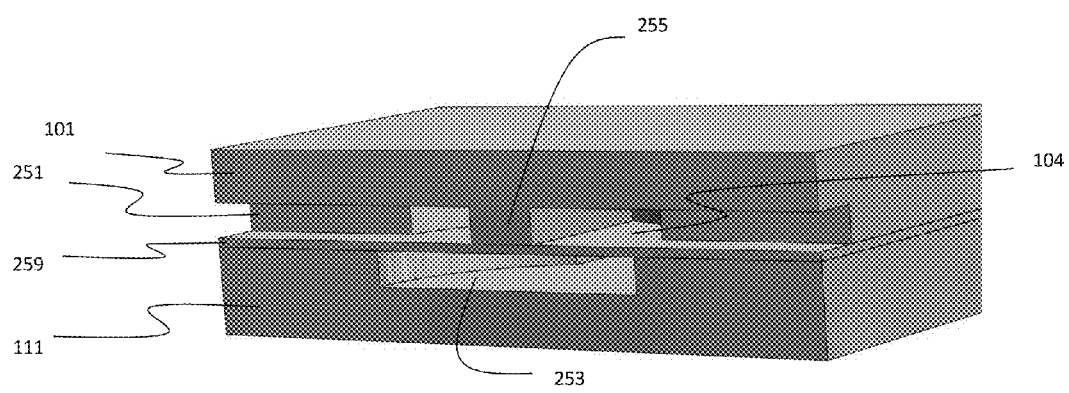

An example of a MOVe valve is shown in FIG. 1. A clamshell view of a MOVe valve is shown in FIG. 1A. A cross-sectional view of a closed MOVe valve is shown in FIG. 1B.

Figure 1C:
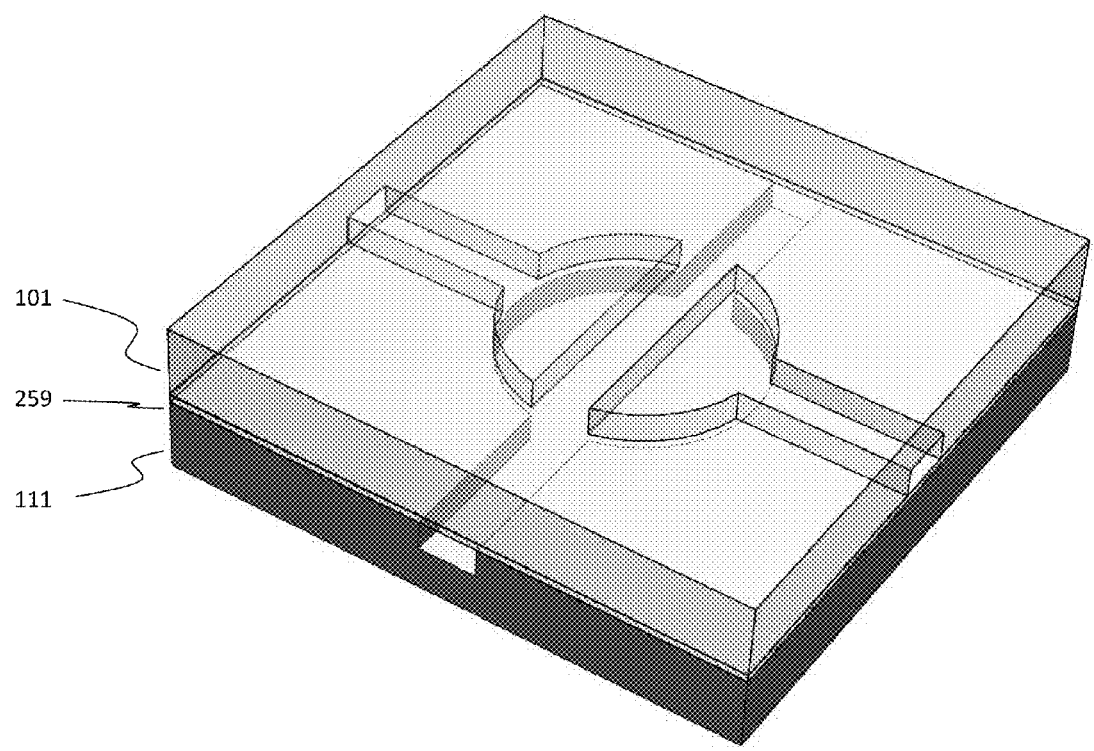

FIG. 1C shows a top-down view of the MOVe valve. A channel (251) that originates from a fluidic layer can interface with an elastomeric layer (259) by one or more vias (257). The channel can have one or more seats (255) to obstruct flow through the channel when the elastomeric layer (259) is in contact with the seat (255). The elastomeric layer can either be normally in contact with the seat, or normally not in contact with the seat. Application of positive or negative pressure through a pneumatic line (261) to increase or decrease the pressure in a pneumatic chamber (253) relative to the fluidic channel (251) can deform the elastomeric layer, such that the elastomeric layer is pushed against the seat or pulled away from the seat.

In some embodiments of the invention, a MOVe does not have a valve seat, and fluid flow through the fluidic channel is not completely obstructed under application of positive or negative pressure. This type of valve is useful as a fluid reservoir and as a pumping chamber and can be referred to as a pumping valve. The vacuum that can be applied include extremely high vacuum, medium vacuum, low vacuum, house vacuum, and pressures such as 5 psi, 10 psi, 15 psi, 25 psi, 30 psi, 40 psi, 45 psi, and 50 psi.

Three MOVe valves in series can form a pump through the use of a first MOVe as an inlet valve, a second MOVe as a pumping valve, and a third MOVe as an outlet valve. Fluid can be moved through the series of MOVes by sequential opening and closing of the MOVes. For a fluid being supplied to an inlet valve, an exemplary sequence can include, starting from a state where all three MOVes are closed, (a) opening the inlet valve, (b) opening the pumping valve, (c) closing the inlet valve and opening the outlet valve, (d) closing the pumping valve, and (e) closing the outlet valve. Since the inlet and outlet valve can have the same structure, a MOVe pump can move fluids in either direction by reprogramming of the sequence of opening inlet or outlet valves.

Figure 42:
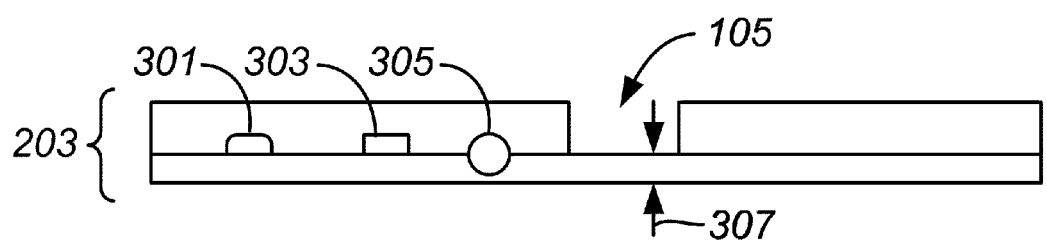
FIG. 42 depicts a fluidics layer made of two layers of material.

The fluidic layer (203) can be constructed of one or more layers of material. As shown in FIG. 42, the fluidic layer (203) can be constructed of two layers of material. Channels (301, 303, 305) can be formed at the interface between the two layers of material, and a chamber (105) can be formed by complete removal of a portion of one layer of material. The channels can have any shape, e.g., rounded and on one side (301), rectangular (303), or circular (305). The channel can be formed by recesses in only one layer (301, 303) or by recesses in both layers (305). The channels and chambers can be connected by fluidic channels that traverse the channels and chambers shown. Multidimensional microchips are also within the scope of the instant invention where fluidic channels and connections are made between multiple fluidic layers.

The thickness (307) of the second layer of material can be of any thickness. In some embodiments of the invention, the second layer has a thickness that minimizes reduction of a magnetic field in the chamber (105) that is applied across the second layer from an external magnetic component or minimizes reductions in heat transfer.

Figure 43:
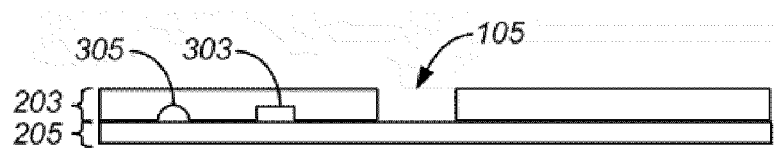
FIG. 43 depicts a fluidics layer made of a single layer of material.
Figure 44:
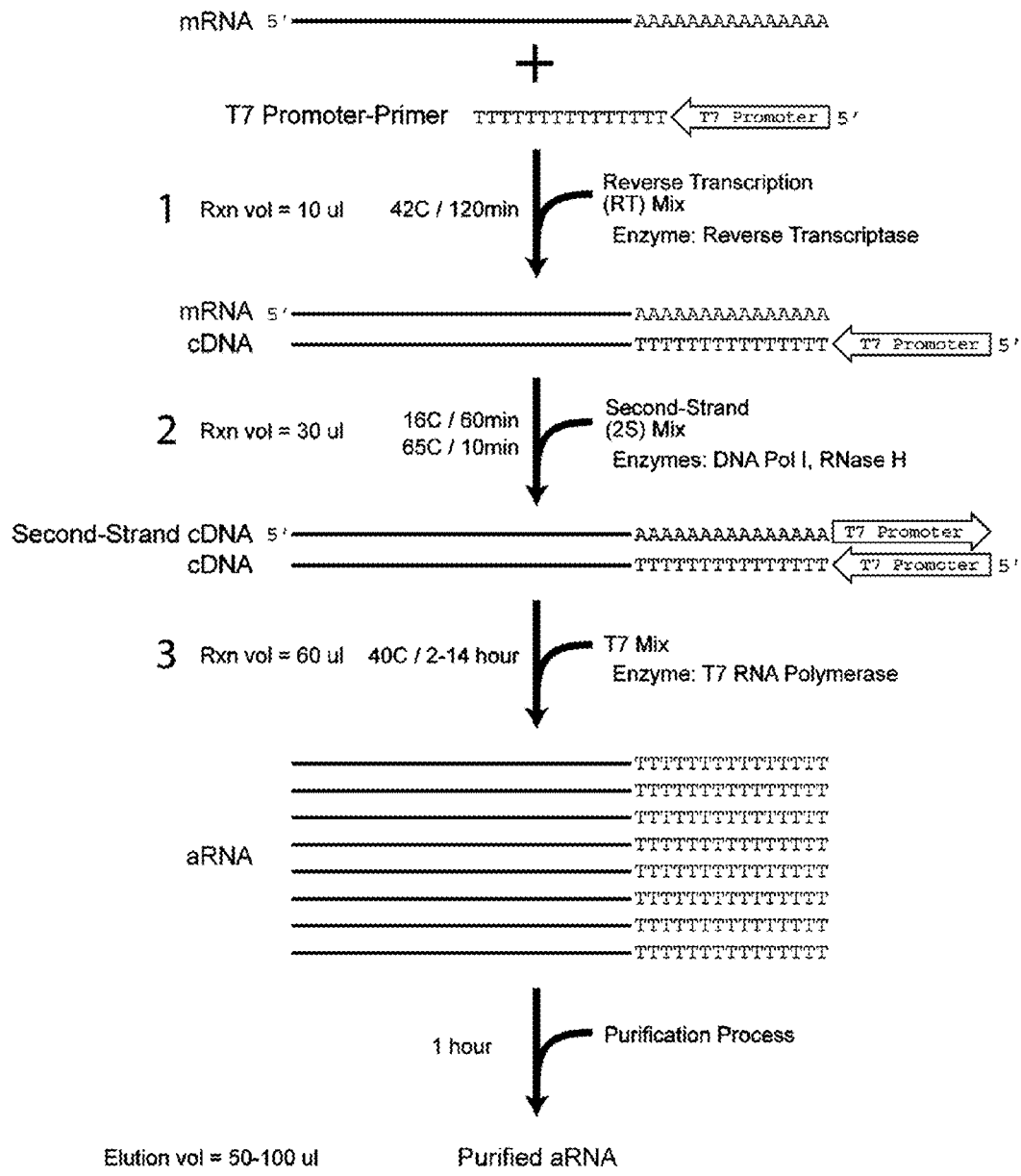
FIG. 44 depicts a reaction scheme for amplifying mRNA.

As shown in FIG. 43, the fluidic layer (203) can be constructed of a single layer of material. The single layer is then interfaced with an elastomeric layer (205), such that channels (305, 303) and chambers (305) are formed between the fluidic layer and the elastomeric layer.

The microfluidic microchip can be constructed from any material known to those skilled in the art. In some embodiments of the invention, the fluidics and pneumatic layer are constructed from glass and the elastomeric layer is formed from PDMS. In alternative embodiments, the elastomer can be replaced by a thin membrane of deformable material such as Teflon (PTFE), silicon, or other membrane. The features of the fluidics and pneumatic layer can be formed using any microfabrication technique known to those skilled in the art, such as patterning, etching, milling, molding, embossing, screen printing, laser ablation, substrate deposition, chemical vapor deposition, or any combination thereof.

Microfluidic devices can be configured so that valves are less sticky. This can be accomplished by coating valve seats and other surfaces over which fluid flows that are likely to come into contact with the elastic layer with low energy material, such a noble metal (e.g., gold) or a perfluorinated polymer (e.g., Teflon). Such devices are described in more detail in U.S. patent application Ser. No. 12/789,186.

Figure 5:
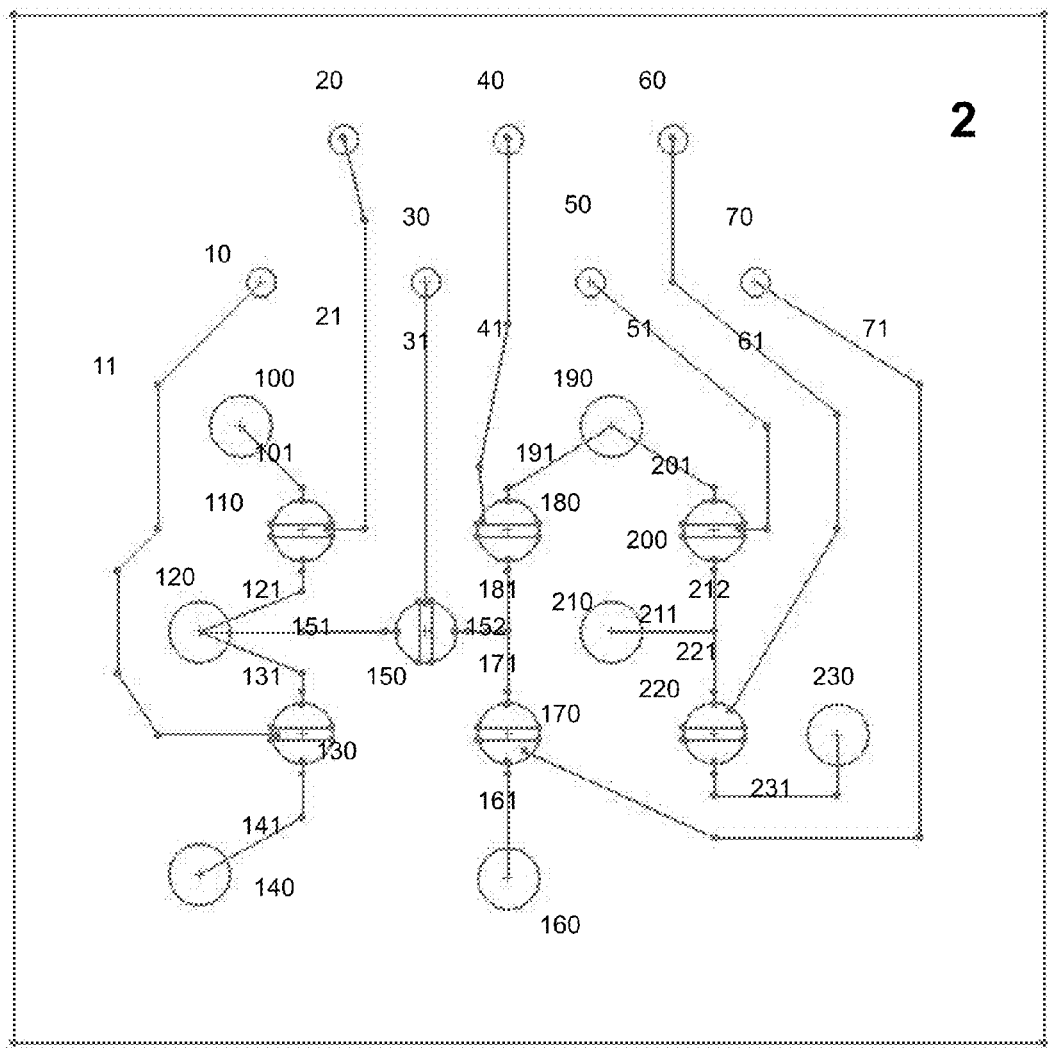
FIG. 5 shows a microfluidic microchip with MOVe valves that controls flows in a cartridge.

In one embodiment, microchannel circuits are formed on a microfluidic microchip 2, as shown in FIG. 5, linking sets of microvalves with microchannels. In one embodiment the microvalves are pneumatically actuated valves. In one embodiment the pneumatically actuated valves are MOVe microvalves. In one embodiment, the fluidic path between a cartridge and a microfluidic microchip, such as between chambers, ports, channels, microchannels, and other functional elements can be controlled by opening or closing at least one microvalve. In one embodiment the microvalve is controlled by a microprocessor control such as a computer. A computer can include an input/output controller, or any other components known to one skilled in the art such as memory storage and a processor. In one embodiment, a microvalve is a MOVe valve that is actuated by a pneumatic source, such as through pneumatic ports 10, 20, 30, 40, 50, 60, or 70. In one embodiment the pneumatic source is controlled by at least one solenoid. In one embodiment the solenoid is miniaturized and can be connected to vacuum or pressure sources. In one embodiment the pneumatic source is connected to a pneumatic port using a force such as clamping, springs, pneumatics, or a screw force, optionally with sealing provided by an o-ring.

In one embodiment FIG. 5 shows a view of the top of a microfluidic microchip (2), this side makes contact with the bottom of cartridge (1). A microvalve 110 controls the fluidic path between microchannels 101 and 121. A microvalve 130 controls the fluidic path between microchannels 131 and 141. Microvalve (150) controls the fluidic path between microchannels 151 and 152. Microvalve 180 controls the fluidic path between microchannels 181 and 191. Microvalve 200 controls the fluidic path between microchannels 201 and 212. Microvalve 220 controls the fluidic path between microchannels 221 and 231.

In one embodiment junctions can connect one or more microchannels. FIG. 5 shows the schematic for a microchip that can be mated with the cartridge shown in FIG. 4. In FIG. 5, junction 100 connects to single microchannel 101, junction 140 connects to single microchannel 141, junction 160 connects to single microchannel 161, and junction 230 connects to single microchannel 231. Junction 190 connects to two microchannels 191 and 201. Junction 120 connects to three microchannels 121, 131, and 151. In one embodiment more than three microchannels can be connected to a single junction.

The microchannels can be fabricated by one or more techniques such as photolithography, molding, embossing, casting, or milling. The microchannels can be manufactured in a material such as glass, plastic, polymer, ceramic, gel, metal, or another suitable solid.

In one embodiment the cartridge is used in a method of sample enrichment comprising: delivery of a sample to a chamber by a sample port and delivery of paramagnetic particles to a chamber by a reagent port. The paramagnetic particles (e.g. paramagnetic beads) bind to at least one component in the sample (such as DNA, RNA, micro RNA, a protein, a lipid, a polysaccharide or other ligand). The paramagnetic particles are attracted to a wall of a chamber by virtue of the magnetic force exerted by a magnet located outside the chamber. The paramagnetic particles are washed with a wash solution delivered to the chamber comprising the paramagnetic particles by a reagent port, and the wash solution is removed by a waste port. A reagent can be added to elute the component of the sample from the paramagnetic particles and output the sample component to another device for further processing or analysis. A preferred embodiment is to output the component of the sample on the paramagnetic particles.

In one embodiment a device comprising a microfluidic microchip is used in a method of diagnosis. In one embodiment the diagnosis comprises the detection of an infectious agent in a sample. In one embodiment the infectious agent is a bacteria, virus, fungi, mycoplasm or prion. In another embodiment a device comprising a microfluidic microchip is used in a method of diagnosis of a hereditary disease. In one embodiment the hereditary disease is caused by one or more DNA mutations, such mutations include but are not limited, triplet base expansions, base substitution mutations, deletion mutations, addition mutations, nonsense mutations, premature stop codons, chromosomal deletions, chromosomal duplications, aneuploidy, partial aneuploidy or monosomy. In another embodiment a device comprising a microfluidic microchip is used in a method to diagnose cancer or a predisposition to cancer. In another embodiment a device comprising a microfluidic microchip is used in a method to diagnose a hereditary disease such as autism, downs syndrome, trisomy, Tay-sachs, or other hereditary diseases. In some embodiments a sample used for diagnosis in a device comprising a microfluidic microchip is a blood sample, a mucus sample, a lung lavage sample, a urine sample, a fecal sample, a skin sample, a hair sample, a semen sample, a vaginal sample, or an amniotic sample.

In another embodiment a device comprising a microfluidic microchip is used to identify the presence of environmental contamination of an agent. In one embodiment the agent is a biological agent such as bacteria, virus, fungi, or mycoplasm in an environmental sample. In another embodiment the agent is a contaminant agent, such as a pesticide, an herbicide, or a fertilizer. In one embodiment the environmental sample is a soil sample, a water sample, an air sample, a meat sample, a vegetable sample or a fruit sample. In another embodiment, the agent is a genetically modified organism.

In another embodiment a device comprising a microfluidic microchip is used for genotyping, identification of an individual mammal (such as a human), forensics, gene expression, gene modification, microRNA analysis, or ribotyping.

In another embodiment a device comprising a microfluidic microchip is used in a method comprising molecular biological analysis, including but not limited to polymerase chain reaction (PCR) amplification of nucleic acids in a sample (such as Allele-specific PCR, Assembly PCR, Asymmetric PCR, Colony PCR, Helicase-dependent amplification, Hot-start PCR, Intersequence-specific (ISSR) PCR, Inverse PCR, Ligation-mediated PCR, Methylation-specific PCR Multiplex Ligation-dependent Probe Amplification, Multiplex-PCR, Nested PCR, Overlap-extension PCR, Quantitative PCR Reverse Transcription PCR-PCR, Thermal asymmetric interlaced-PCR, Touchdown PCR, or PAN-AC PCR), isothermal nucleic acid amplifications, (such as Loop-mediated Isothermal Amplification (LAMP); nick displacement amplification; Helicase Dependant Amplification platform (HDA);

and the primase-based Whole Genome Amplification platform (pWGA); single primer isothermal amplification (SPIA) and Ribo-SPIA for RNA; strand displacement amplification (SDA); EXPAR [Van Ness J, Van Ness L K, Galas D J. (2003) Isothermal reactions for the amplification of oligonucleotides. Proc Natl Acad Sci USA. 100:4504-9.]; rolling circle amplification (RCA); transcription-based amplification system (TAS) and its derivatives include self-sustaining sequence replication (3SR), isothermal nucleic acid sequence-based amplification (NASBA), and transcription-mediated amplification (TMA); ligase chain reaction (LCR)), sequencing reactions of DNA or RNA (such as Maxam-Gilbert sequencing, Sanger chain-termination method, Dye-terminator sequencing Emulsion PCR sequencing, massively parallel sequencing, polony sequencing, sequencing by ligation, sequencing by synthesis, or sequencing by hybridization), restriction fragment length polymorphism (RFLP) analysis, single nucleotide polymorphism (SNP) analysis, short tandem repeat (STR) analysis, microsatellite analysis, DNA fingerprint analysis, DNA footprint analysis, or DNA methylation analysis.

In one embodiment a cartridge employs beads coupled to a binding moiety, including but not limited to a binding receptor, transferrin, an antibody or a fragment thereof (such as an Fc fragment or an Fab fragment), a lectin, or a DNA or RNA sequence. In another embodiment a cartridge comprises a reagent such as an anti-coagulant, a fixative, a stabilization reagent, a preservative or precipitation reagent.

C. Pneumatic Manifold

A pneumatic manifold can be integrated with any microchip and/or cartridge described herein to facilitate distribution of air pressure or vacuum. The air pressure or vacuum can be used to actuate valves on the microchip. Alternatively, air pressure or vacuum can be supplied to a cartridge such that air pressure or vacuum is provided to microchannels within the fluidics layer of a microchip which can be used to move fluids or gases within the fluidics layer. A pneumatic manifold provides the air pressure or vacuum to operate microvalves on microchip (2) on cartridge (1) of FIG. 3 or operate microvalves in other devices.

A pneumatic manifold can be used to mate the pneumatic lines of a microfluidic microchip to external pressure sources. The pneumatic manifold can have ports that align with ports on the pneumatics layer of the microfluidic microchip and ports that can be connected to tubing that connect to the external pressure sources. The ports can be connected by one or more channels that allow for fluid communication of a liquid or gas, or other material between the ports.

The pneumatic manifold can be interfaced with the microfluidic microchip on any surface of the microchip. The pneumatic manifold can be on the same or different side of the microfluidic microchip as the cartridge. As shown in FIG. 40, a pneumatic manifold (113) can be placed on a surface of the microfluidic microchip opposite to the cartridge. As well, the pneumatic manifold can be designed such that it only occupies a portion of the surface of microfluidic microchip. The positioning, design, and/or shape of the pneumatic manifold can allow access of other components to the microfluidic microchip. The pneumatic manifold can have a cut-out or annular space that allows other components to be positioned adjacent or proximal to the microfluidic microchip. This can allow, for example, a magnetic component (109) to be placed in proximity of a chamber within the microfluidic microchip.

A pneumatic manifold can be constructed of any material known to those skilled in the art. For example, the cartridge can be constructed of a plastic, glass, or metal. A plastic material includes any plastic known to those skilled in the art, such as polypropylene, polystyrene, polyethylene, polyethylene terephthalate, polyester, polyamide, poly(vinylchloride), polycarbonate, polyurethane, polyvinyldiene chloride, cyclic olefin copolymer, or any combination thereof. The pneumatic manifold can be formed using any technique known to those skilled in the art, such as soft-lithography, conventional lithography, milling, molding, embossing, drilling, etching, or any combination thereof.

The apparatus shown in FIG. 21 and FIG. 22 can incorporate a pneumatic manifold. The apparatus can be used for sample preparation, as described herein, and can incorporate a cartridge. Cartridge (1), labeled 'cube', is attached to manifold (370) with solenoids (1819). The assembly of the cartridge and manifold is mounted on a base plate of the apparatus. The pneumatic manifold can be controlled by an IO controller (1803).

A gas supply, such as a reservoir that can be maintained at a desired pressure or vacuum, can supply gas to the manifold. The gas supply can be connected to an outside pressure or vacuum source. The gas supply feeding the gas supply manifold can have a pressure gauge to monitor the inlet pressure. The gas supply can supply gas to multiple components of the system through a gas supply manifold (1821). The gas supply manifold can supply gas to the pneumatic manifold (370) and to individual reagent containers, (1809) and (1807). The line supplying the distribution valve (390) with gas can be regulated by a regulator (1815).

Reagents and/or sample can also be supplied to the cartridge through the reagent distribution valve (390) that is connected to containers (1809) in a reagent storage region (380) and a bead solution container (1807) that is mounted on a bead mixer (1805). Adapter (1817) can be mounted and/or aligned with the cartridge such that a delivery device, such as a syringe, can deliver a material to the cartridge. The adapter (1817) can be thermally regulated by a heater control (1801). The adapter can have a thermal conductor, such as brass, to distribute heat generated by heater coil or a Peltier device. The adapter can maintain temperature between about 20 to 100, 20 to 75, or 50 to 60 degrees Celsius.

A magnet assembly (1811) can be positioned adjacent to the cartridge. A magnet (300) of the magnet assembly can be positioned adjacent to the cartridge (1) and moved by an actuator, such that the magnet can exert a magnetic field within the cartridge, or a microchip integrated, mated, or interfaced with the cartridge. The magnetic field can be used to capture paramagnetic or magnetic particles, such as beads, within the cartridge or microchip and separate material bound to the particles from waste materials. Waste from the cartridge and/or microchip can be delivered to a waste container (1813).

Figure 23:
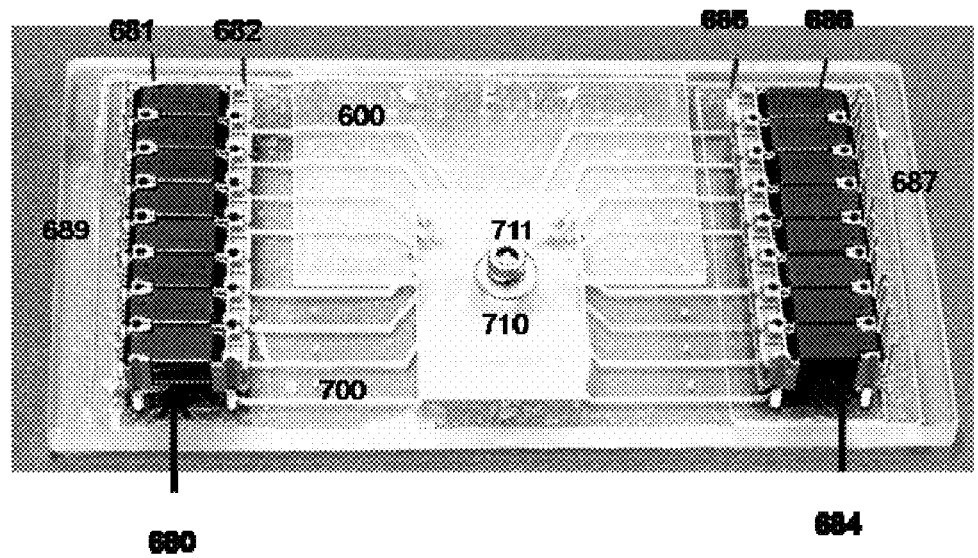
FIG. 23 shows a reagent distribution manifold based on MOVe technology that can distribute five reagents to five extraction/isolation or other devices.
Figure 24:
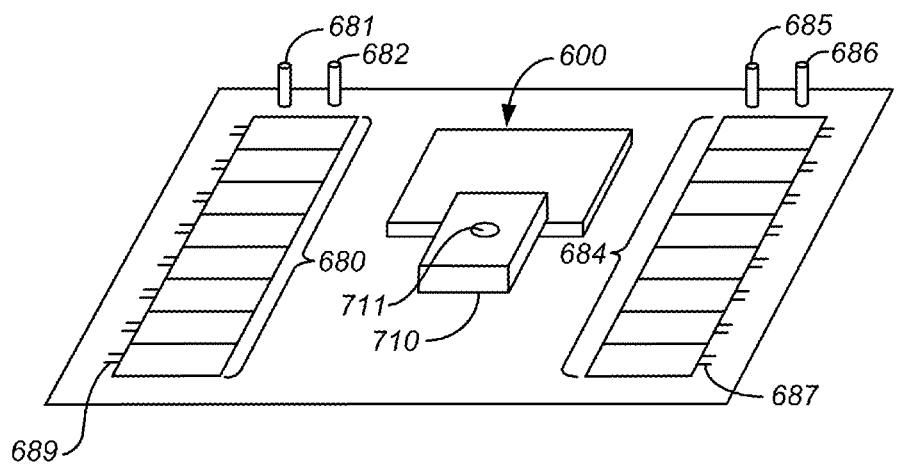
FIG. 24 shows a reagent distribution manifold based on MOVe technology that can distribute five reagents to five extraction/isolation or other devices.
Figure 25:
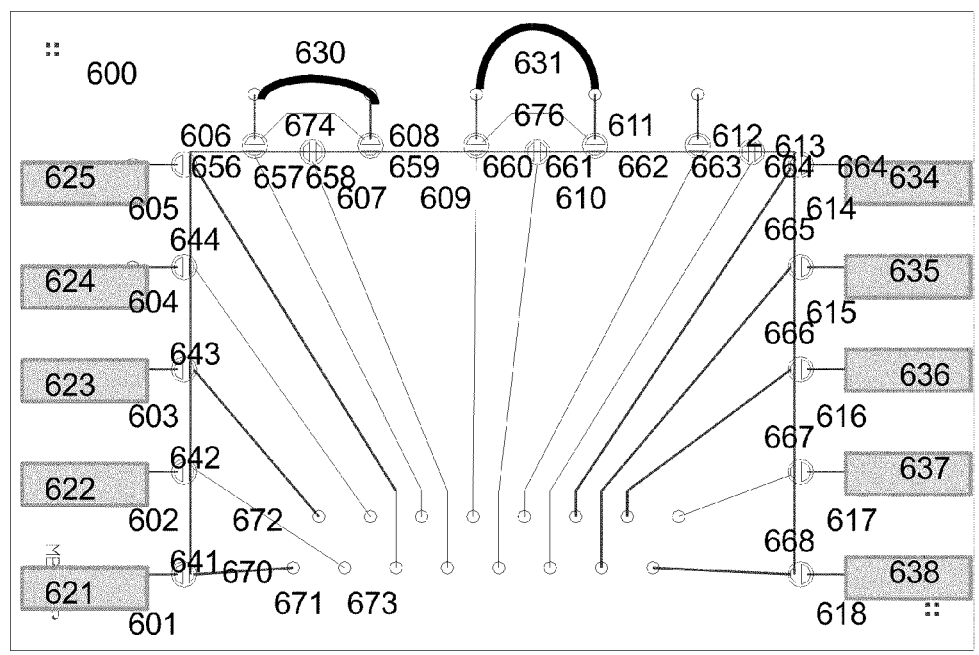
FIG. 25 shows a distribution manifold with sample loops and MOVe microvalves.
Figure 26:
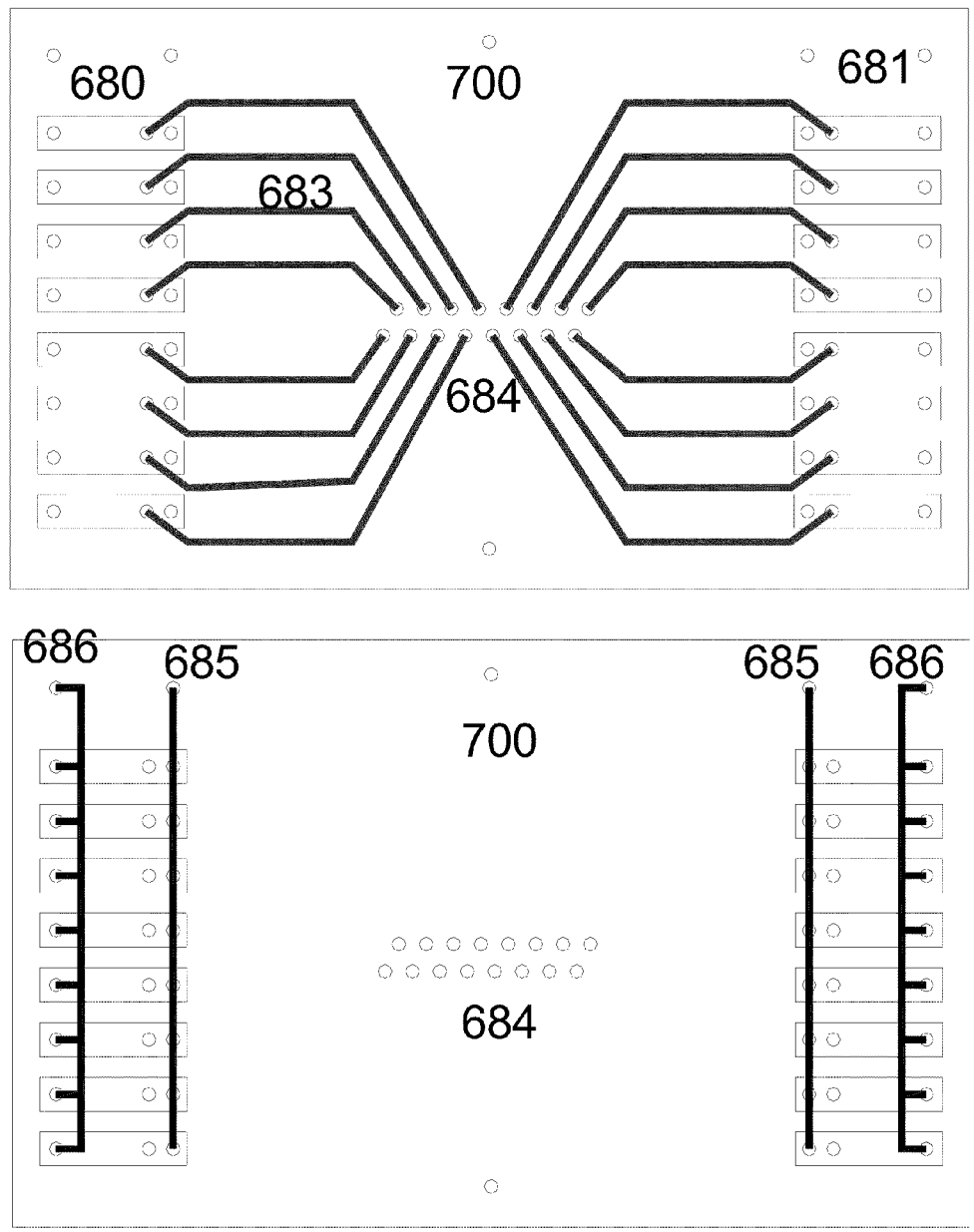
FIG. 26 shows a pneumatic manifold, top panel shows the top side and the lower panel the bottom side.

The apparatus shown in FIG. 21 and FIG. 22 can use seven solenoid valves to operate the cartridge (1). The size and complexity of the apparatus can be further reduced with MOVe microvalves. FIG. 23 and FIG. 24 show a reagent distribution device that contains microfluidic microchip 600, which is approximately two inches wide. Solenoid banks 680 and 684 provide connection to full scale external vacuum and pressure through connectors 681, 682, 685, and 686. The solenoids are controlled through electrical junctions 689 and 687. The microfluidic microchip 600, which has MOVe valves, is held in contact with the manifold 700 by attachment 711 using clamp 710. Other methods known to one skilled in the art can be used to connect the microchip to the pneumatics manifold 700.

D. Parallel Processing of Samples

In some embodiments of the invention, one or more cartridges can be operated simultaneously to allow for parallel processing of samples. FIG. 16 illustrates parallel or ganged operation of multiple cartridges with microvalves on a single pneumatic manifold in swab extraction assembly (800). The manifold (370) distributes regulated vacuum and pressure to operate four cartridges (1), indicated in the figure, using solenoids (680). Solenoids (680) control pressure to the pneumatic layer of a microchip integrated with each cartridge through the pneumatic manifold (370, 380, 390). The pneumatic manifold is formed by a top plate (370), a gasket (380) and a bottom plate (390). The top plate can have channels etched into it. The channels can be sealed by the gasket, which is sandwiched against the top plate by the bottom plate (390). Actuator 310 moves rod 810 to move magnets (320) close to or away from the cartridges (1). Clamps 805 hold cartridges (1) in place.

Figure 14:
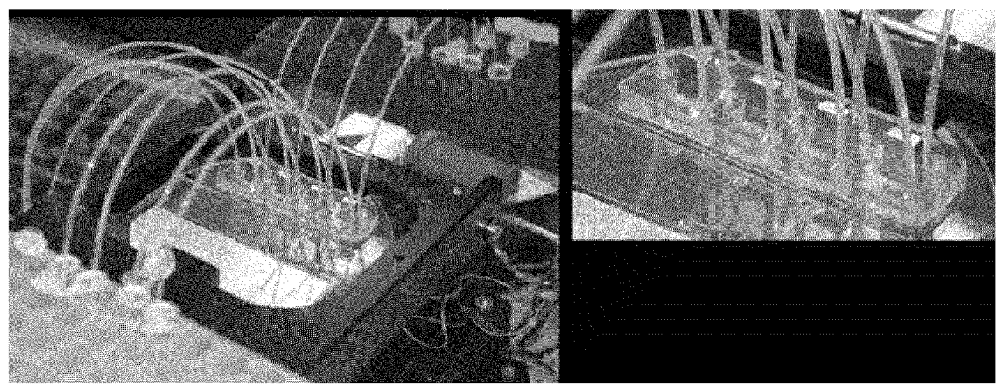
FIG. 14 shows a capture and reaction microchip using MOVe microvalves.
Figure 15:
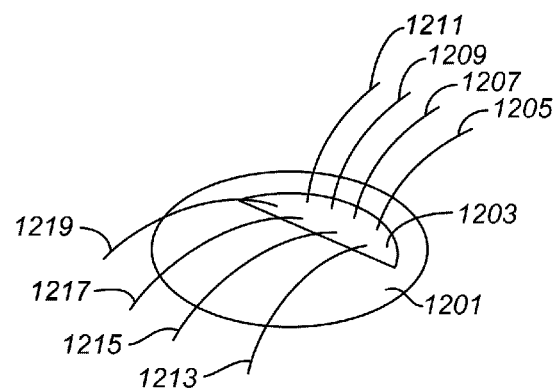
FIG. 15 shows a capture and reaction microchip using MOVe microvalves.

In other embodiments of the invention, a single cartridge integrated with a microchip can process multiple samples at one time using parallel channels. For example, the device can be configured to have 4, 8, or even 12 channels. FIG. 14 and FIG. 15 shows an assembled capture and reaction microchip with capillary feed and magnets. This microchip can capture bead solutions and perform, for example, four, STR-PCR reactions simultaneously. FIG. 14 shows a microchip (1201) with a cartridge (1203) adhered to the microchip and tubes (1205, 1207, 1209, 1211, 1213, 1215, 1217, and 1219) leading into and out of the microchip. A total of eight tubes are shown and two tubes are used per parallel reaction. For example, one unit of the parallel processing device is served by tubes 1205 and 1213.

In an exemplary embodiment, a four-channel sample preparation device combines a four-channel parallel reagent delivery device (FIG. 53) that meters and delivers reagents simultaneously to all four channels of a single integrated cartridge (FIG. 54) enabling four samples to be processed simultaneously and rapidly.

Figure 53:
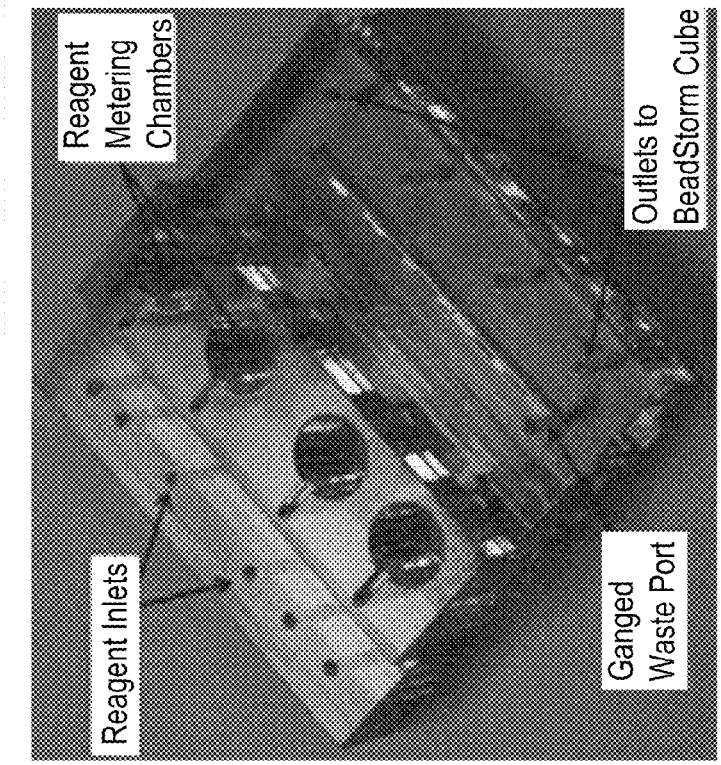
FIG. 53 shows a four-channel parallel reagent delivery device: the Chip C microchip design is shown on the top left, a fluidic manifold is shown on the bottom left, and the fabricated and assembled device is shown on the right.
Figure 53:
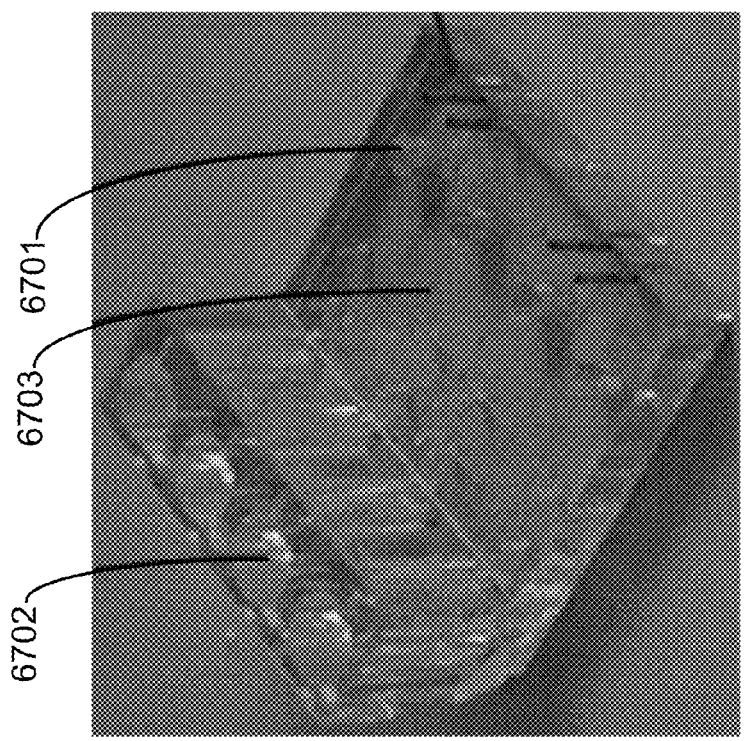

The four-channel parallel reagent delivery device combines a microchip (see FIG. 53) with a fluidics manifold mounted on a pneumatics control manifold. FIG. 53 shows a sample extraction module comprises a cartridge mated to a microfluidic chip. The cartridge comprises apertures for syringes (6701) and compartments for bead capture of analyte (6702). These compartments are fluidically connected through channels (6703) in a microfluidic chip mated to the undersurface of the cartridge. A reagent distribution cartridge can comprise compartments configured similar to those in FIG. 3. The two can be fluidically connected, e.g., by tubes, and reagents can be pumped from reagent reservoirs into the chambers on the reagent cartridge and then into the sample extraction module. 4, 8, 12 channel and devices with more channels are contemplated. Reagents are metered, using one of the two different size reagent loops, which can be similar to the sample loops described herein, for each channel, and delivered in parallel to all four channels of the sample preparation device. Delivering reagents simultaneously to all four channels of the sample preparation device using the parallel reagent delivery device can takes <4 minutes, representing a process time saving of >11 minutes as compared to the first generation serial reagent delivery device that took ~15 minutes per four samples processed.

Bonded pneumatics manifolds can be used to control both the reagent delivery and sample preparation devices by fabricating the manifolds using an adhesive bonding approach; however, these may be prone to delamination over time due to the pneumatic pressures used in the subsystem, and the size and complexity of the manifold. Thermally bonded manifolds can mitigate delamination issues, but may only be a viable approach for relatively small and low complexity manifold designs such as the reagent delivery device. A monolithic manifold made from a single piece of polycarbonate with tubing connecting pneumatic ports to the solenoid control valves can operate the four-channel sample preparation cartridge and has proved to be a viable alternative to bonded pneumatic manifolds. This pneumatic manifold design concept is also being utilized for control of the Chip A microchip on the Post-amplification STR (Short Tandem Repeat) cleanup subsystem.

Assembly processes for the microchip and fluidic manifold of the four-channel sample preparation cartridge have also been improved. Historically, silicon epoxy can be used to attach the cartridge to its associated MOVe microchip by wicking the adhesive between the microchip and the cube. An inherent lack of control of the movement of the epoxy can allow it to occasionally wick into the ports on either the microchip or the cube creating a blockage in the fluidic pathway rendering the device unusable. This process has been improved by using a double-sided adhesive tape (Adhesives Research ARcare90106) to assemble the fluidic cubes and microchips; this is now the preferred assembly method used for the four-channel reagent delivery cartridge, the sample preparation device, and the post amplification device in the Post-amplification STR clean-up subsystem described below.

Figure 55:
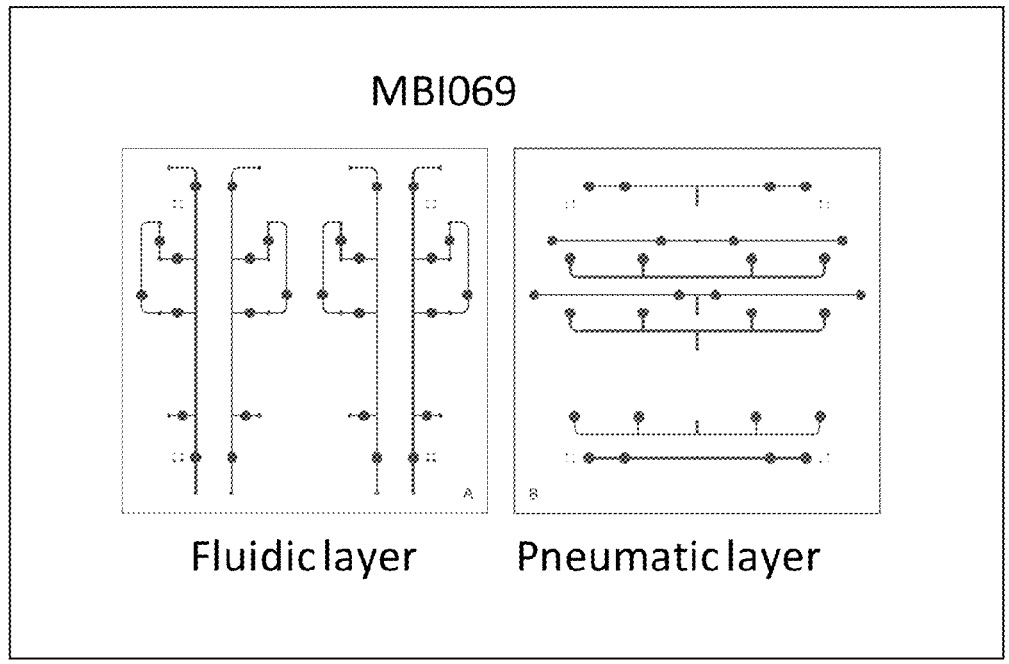
FIG. 55 shows MOVe microchip designs of the four-channel sample preparation device.
Figure 56:
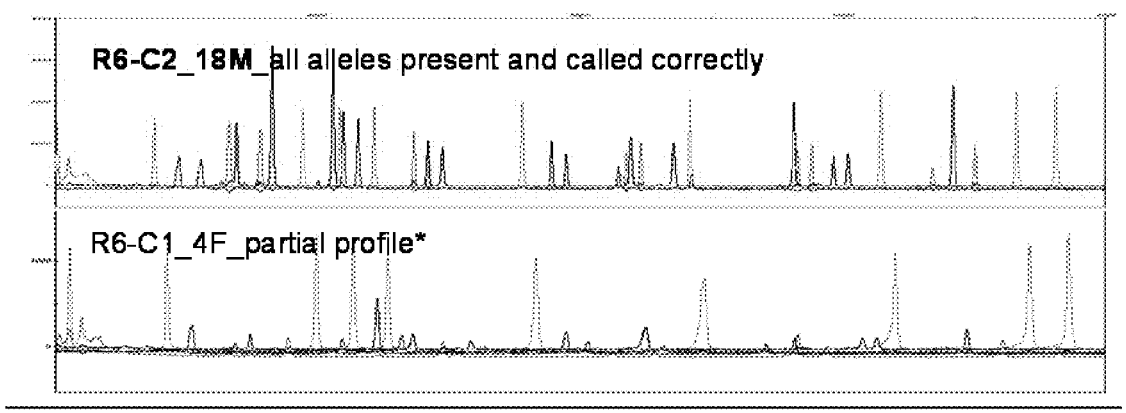
FIG. 56 shows IdentiFiler STR profiles of DNA samples prepared on the four-channel sample preparation device, where STR amplifications were performed using fast protocols (1.5 hrs) on a STR Reaction subsystem thermocycler.
Figure 57:
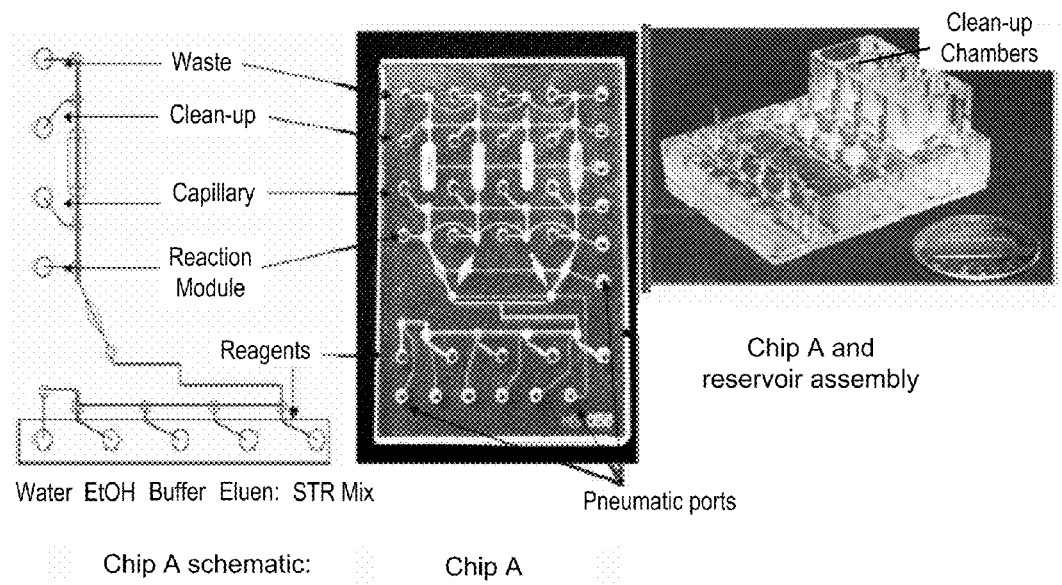
FIG. 57 shows a four-channel post amplification device combined with an Chip A microchip with a fluidics manifold: the Chip A microchip design is shown on the left, the fabricated microchip is shown in the center, and the assembled fluidic manifold and microchip is shown on the right.
Figure 58:
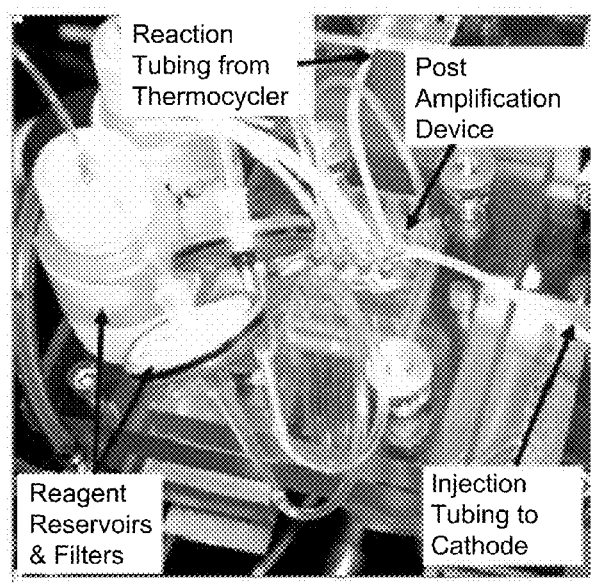
FIG. 58 shows a post-amplification STR clean-up subsystem with the post-amplification device.
Figure 59:
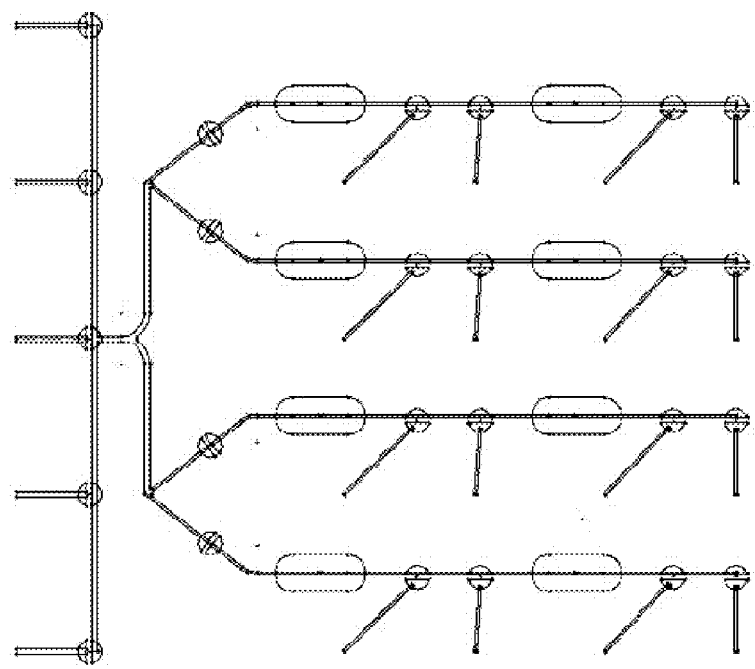
FIG. 59 shows the Chip E microchip design, which can be used in the post-amplification device.

The integrated four-channel sample preparation cartridge with the 069 microchip (see FIG. 55) was tested. The 069 microchip design is used with the sample extraction cartridge. Other chips, for example the 070 chip is used with the post-amplification cartridge.

Microchip blockages due to the inadvertent introduction of fibers into the systems and devices described herein can be problematic in microfluidics. To minimize blockages, all reagents with the exception of paramagnetic bead solutions, can be filtered prior to loading and in-line filters used to minimize microchip blockages.

E. Separation and Cleanup

A variety of separations can be performed using the devices described herein. These separations include chromatographic, affinity, electrostatic, hydrophobic, ion-exchange, magnetic, drag-based, and density-based separations. In some embodiments of the invention, affinity or ion-exchange interactions are utilized to bind materials to solid-phase materials, such as beads. The beads can be separated from fluid solutions using any method known to those skilled in the art.

Magnetic separation can be used to capture and concentrate materials in a single step using a mechanistically simplified format that employs paramagnetic beads and a magnetic field. The beads can be used to capture, concentrate, and then purify specific target antigens, proteins, carbohydrates, toxins, nucleic acids, cells, viruses, and spores. The beads can have a specific affinity reagent, typically an antibody, aptamer, or DNA that binds to a target. Alternatively electrostatic or ion-pairing or salt-bridge interactions can bind to a target. The beads can be paramagnetic beads that are only magnetic in the presence of an external magnetic field. Alternatively, the beads can contain permanent magnets. The beads can be added to complex samples such as aerosols, liquids, bodily fluids, extracts, or food. After (or before) binding of a target material, such as DNA, the bead can be captured by application of a magnetic field. Unbound or loosely bound material is removed by washing with compatible buffers, which purifies the target from other, unwanted materials in the original sample. Beads can be small (nm to um) and can bind high amounts of target. When the beads are concentrated by magnetic force they can form bead beds of just nL-µL volumes, thus concentrating the target at the same time it is purified. The purified and concentrated targets can be conveniently transported, denatured, lysed or analyzed while on-bead, or eluted off the bead for further sample preparation, or analysis.

Separations are widely used for many applications including the detection of microorganisms in food, bodily fluids, and other matrices. Paramagnetic beads can be mixed and manipulated easily, and are adaptable to microscale and microfluidic applications. This technology provides an excellent solution to the macroscale-to-microscale interface: beads can purify samples at the macroscale and then concentrate to the nanoscale (100's of nL) for introduction into microfluidic or nanofluidic platforms. Magnetic separations can be used as an upstream purification step before real-time PCR, electrochemiluminescence, magnetic force discrimination, magnetophoretic, capillary electrophoresis, field-flow separations, or other separation methods well known to one skilled in the art.

The devices of the invention can accommodate the use of magnetic beads. For example, beads or bead slurry can be supplied to a port of a cartridge. The beads can be mixed or suspended in solution within the cartridge using pumping, magnetic fields, or external mixers. The beads can then be pumped to desired chambers or reservoirs within the microfluidic device or cartridge. Beads can be captured within a chamber using a magnetic field. Beads in a solution can be captured as the solution travels through the magnetic field, or beads can be captured in a stagnant solution.

To illustrate methods of use of the cartridge, several examples are contemplated. The first example is processing of nucleic acid from a buccal swab with paramagnetic beads to purify the sample followed by PCR amplification and bead purification of the PCR products. A second example describes performing immunomagnetic separations to purify cells, proteins, or other antigenic material using a binding moiety coupled to beads. A third example describes performing molecular biology to prepare samples for sequencing technologies such as sequencing by synthesis, sequencing by hybridization, or sequencing by ligation. It would be known to one skilled in the art that many different chemistries and biochemistries can be used with the instant invention. These include, but are not limited to, enzymatic reactions, purifications on gels, monoliths, beads, packed beds, surface reactions, molecular biology, and other chemical and biochemical reactions.

The cartridge with integrated microchip can be formed of any cartridge and microchip described herein. For example, the cartridge and microchip shown in FIG. 3, FIG. 4, and FIG. 5. A movable magnet (300) can be positioned adjacent to the cartridge. The movable magnet can be moved by an actuator (310). The movable magnet can be used to apply a magnetic field within the cartridge or the microchip. In some embodiments, the movable magnet can be used to facilitate gathering or collecting of beads against a wall of a chamber within the cartridge or the microchip.

II. Reaction Module

The reaction module typically will comprise a reaction chamber fluidically connected to a microfluidic channel and the sample preparation chamber through which the analyte passes. The reaction module can be adapted to place the analyte in a volume, e.g. a non-microfluidic volume, that is smaller than the original sample volume. For example, the reaction module can comprise a chamber in communication with a magnetic force that is adapted to immobilize magnetically responsive particles on which the analyte is captured. The bead bed typically has a volume that is smaller than the original sample volume. The analyte can be released from to particles in the reaction chamber and a biochemical reaction, such as PCR, can be performed on the analyte. The liquid volume in reaction chamber can be a non-microfluidic volume e.g. between 10 and 50 microliters. Accordingly, the use of analyte capture materials that are flowable and immobilizable allows capture, transfer and concentration of the analyte.

Figure 7:
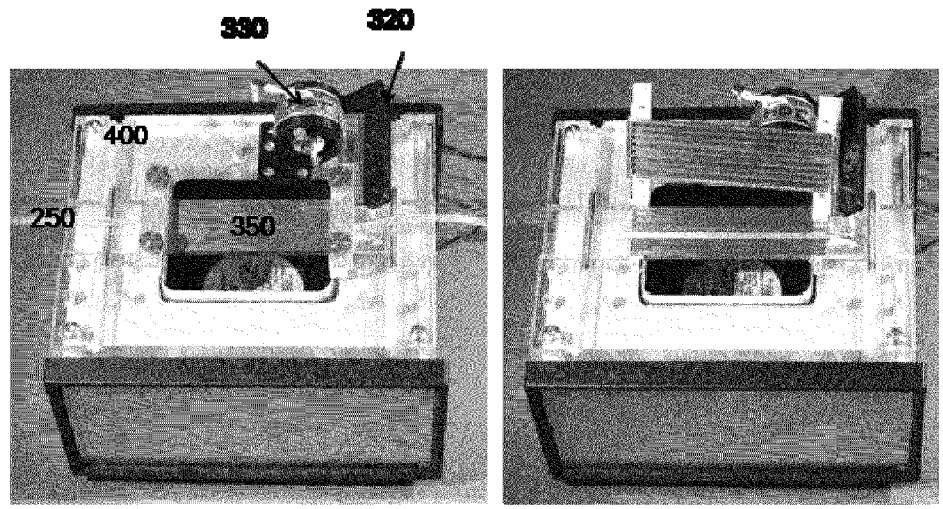
FIG. 7 shows a temperature control device that can thermal cycle and incorporates magnetic capture, pinch clamps and the capability of cycling seven reactions simultaneously.
Figure 8:
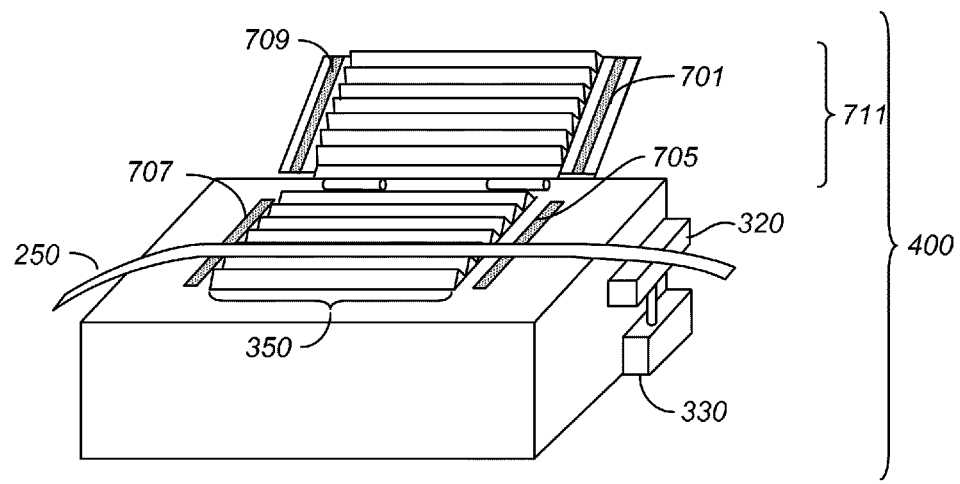
FIG. 8 shows a temperature control device that can thermal cycle and incorporates magnetic capture, pinch clamps and the capability of cycling seven reactions simultaneously.

As shown in FIG. 6, temperature modulator can be fluidically connected to the cartridge and microchip through reaction channel (250). The reaction chamber (250) can be connected at an end (251) to the cartridge. The temperature modulator can be used for thermal cycling the temperature of a reaction channel (250) containing a reaction mixture and a nucleic acid enriched from a sample (collectively referred to as the PCR reaction sample). A control mechanism can be used for controlling the operation of the temperature modulator. An optical assembly can be used to monitor or control the reaction. The optical assembly can introduce or detect light. For example, an optical assembly 410 can be used for performing Real-time PCR or other real-time or end point measurements. In certain embodiments the temperature modulator employs a thermo-coupled Peltier thermoelectric module, a conventional thermoelectric module, hot air, infra-red light or microwave. In one embodiment the temperature modulator uses a Peltier thermoelectric module external to the reaction channel to heat and cool the PCR reaction sample as desired. The heating and cooling of the thermoelectric module can be distributed over a region 350. Additional views of the temperature modulator 400 are shown in FIG. 7 and FIG. 8. FIG. 7 shows the reaction channel 250 in contact with a temperature controlled region 350. The temperature modulator can also include a movable magnet 320 that is positioned by an actuator 330. The movable magnet can be used to capture magnetic particles at position 340, as shown in FIG. 6. In some embodiments of the invention, the temperature controlled region comprises two parts. The two parts can be parts of a clamshell that are clamped, locked, or held together to maintain thermal contact with the reaction channel 250. One portion of the temperature controlled region, portion 711 of FIG. 8, can be hinged to the second portion of the temperature controlled region. The temperature controlled regions can have grooved channels for positioning of one or more reaction channels, as shown on the right side of FIG. 7 and in FIG. 8. The left side of FIG. 7 shows the temperature controlled region in a closed configuration. Additionally, the temperature controlled region can comprise one or more constriction components, shown as 709 and 701 in FIG. 8. The constricting points can pinch the reaction channel such that a portion of the reaction channel is isolated from another portion of the reaction channel. In some embodiments of the invention, the reaction channel is pinched in two locations such that a body of fluid, such as a reaction mixture, is isolated. Constriction components 709 and 701 can mate with additional constriction components 707 and 705 to facilitate pinching of the reaction channel.

Figure 51:
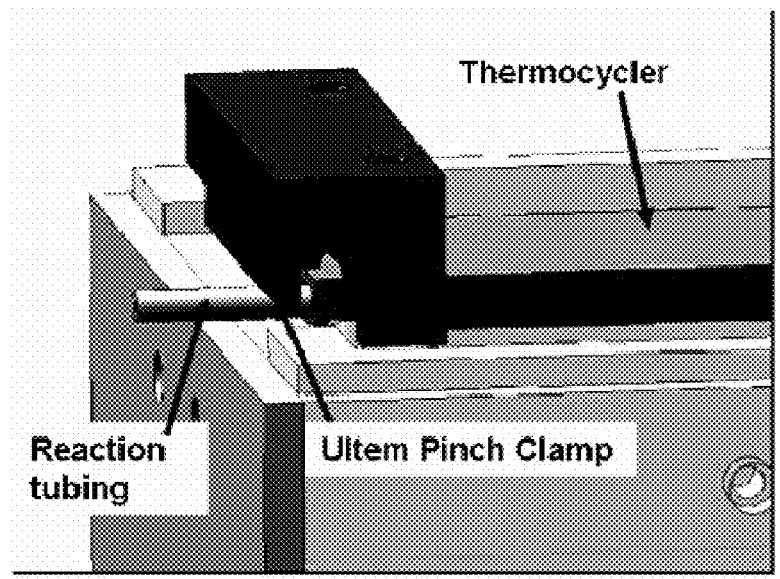
FIG. 51 shows a thermocycler with an Ultem pinch clamp.
Figure 52:
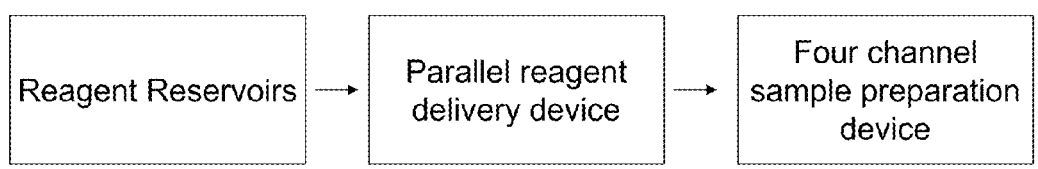
FIG. 52 shows a diagram indicating movement of reagents between components of a four channel parallel processing device.

Alternatively the temperature modulator can constrict the reaction tubing using a pinch clamp, as shown in FIG. 51. Use of the pinch clamp, which can be formed of a plastic such as Ultem, can reduce heat transfer to the reaction channel. The reduction in heat transfer can reduce the likelihood that the reaction channel has for being welded closed during thermocycling or temperature regulation. Alternatively, different material tubing can be used as the reaction channel to ensure that the reaction channel can maintains its shape before and after the thermocycling or temperature regulation process. Different material tubing can also be used to reduce rate of evaporation during the temperature modulating process. Example materials include ethylvinyl acetate, silicone, and silanized c-flex tubing.

The temperature modulating device can modulate temperatures at a rate of 0.5 to over 3 degrees Celsius per second. The heater can utilize about 25 to 100 Watts and a fan, which can be used to cool the temperature modulating device, can produce an air flow rate of at least about 75, 100, 130, 150, 200, 250, or 300 cfm.

In one embodiment a sample preparation device comprising a cartridge integrated with a microfluidic microchip, which can be used to control the movement of fluid in the cartridge, can be used in conjunction with a temperature modulator 400 as a flow-through PCR thermal cycler. Driving force for moving the fluid can be an external pressure source or an internal pressure source, such as a MOVe valves within the microchip. A flow-through PCR thermal cycler can be used when highly sensitive or high throughput PCR is desired. There are many situations in which one might want to sample air, blood, water, saliva, a cellular sample, or other medium in a sensitive PCR assay. This can be used to detect a variety of biological contaminants including influenza, bacterial pathogens, and any number of viral or bacterial pathogens. Flow-through PCR can allow PCR to be practiced in an automated manner without the need for human interaction. A flow-through PCR system can also serve as an early warning system in HVAC systems of buildings, airplanes, busses, and other vehicles, and can be used in the monitoring of blood, water, or other sample sources for the presence of an infectious agent or a contaminant.

As shown in FIG. 6, the flow-through PCR device takes a sample from a collection device, such as a buccal swab, a syringe, an air sampler, fluid sampler or other sampler and delivers it to a sample preparation device 1 (FIG. 6 is not necessarily drawn to scale). The sample is prepared in the preparation device 1, which in some embodiments may include cell lysis, DNA, RNA, or micro RNA enrichment or purification, filtration, or reverse transcription. In one embodiment at least one nucleic acid is enriched. In another embodiment at least one enriched nucleic acid is prepared for PCR by adding the nucleic acid to PCR reagents (such as at least one DNA polymerase, RNA polymerase, dNTPs, buffer or a salt) and primers, (such as assay-specific primers or broadly applicable primer sets for multiple target pathogens). These primers may be chosen to selectively amplify at least one nucleic acid isolated from a specific pathogen (such as a mold, virus, bacteria, parasite or amoeba), gene, other desired nucleic acid, or any combination thereof. The composition comprising at least one nucleic acid enriched from a sample, PCR reagents and primers is called a PCR reaction sample. In one embodiment, the flowthrough PCR can be used as a continuous flow device while in other embodiments samples are moved into the thermal cycling region and stopped.

The PCR reaction sample then flows through a reaction channel (250) to a temperature controlled device or region (350). In some embodiments the reaction channel is clear or transparent. In another embodiment the reaction channel is opaque. In one embodiment the reaction channel is a cylinder. In another embodiment the reaction channel's cross section comprises one or more planes forming a shape such as a triangle, square, rectangle, pentagon, hexagon, heptagon, octagon, nonagon, decagon, or other polygon. In one embodiment the volume of PCR reaction sample is such that it takes up a small discrete length of space in the reaction channel, the rest of which is occupied by air, gas, or a non-reactive liquid, such as mineral oil. Air, gas, or a non-reactive liquid can be used to separate individual PCR reaction samples from each other. In one embodiment the temperature controlled region (350) is thermally modulated by one or more modules, including but not limited to thermo-coupled Peltier thermoelectric module, a conventional thermoelectric module, hot air, microwave, or infrared light. In one embodiment the thermal cycler uses Peltier thermoelectric modules external to the tube to heat and cool the sample as desired. In one embodiment a detection module (410) measures fluorescence, luminescence, absorbance or other optical properties to detect a signal emitted from a PCR reaction sample while it is located with a temperature control region, or after it has left a temperature control region. A detection module can comprise a light source (such as a coherent light source or incoherent light source) used to excite a fluorescent dye (such as an intercalating dye, including but not limited to ethidium bromide or Syber green) in a PCR reaction sample, and the excitation light is sensed with a photodetector (such as a CCD, CMOS, PMT, or other optical detector). Detection electronics can evaluate the signal sent from the detection module (410).

In one embodiment, after the desired number of thermal cycles are complete, the PCR reaction sample is pumped or pushed further down the reaction channel, using pressure or vacuum, exiting the temperature controlled region and passing into a second microfluidic microchip (500). The second microchip (500) can be attached at end (252) to the reaction channel (250). Microfluidic microchip (500) can comprise microvalves (510, 520, 530, and 545). Any three microvalves such as 510, 520, and 530 or 510, 520, and 545 can form a pump. Microchannels 505, 515, 525, and 540 can connect the pumps on the microchip. Downstream devices 535 and 550 can be connected to the microchip. Flow of material to devices (535 and 550) can be controlled by the microvalves, for example, by keeping either valve 530 or 545 closed while pumping or moving fluid. In one preferred embodiment, the downstream device are analytical devices that can be used for performing electrophoresis, mass spectroscopy, or other analytical techniques known to one skilled in the art.

III. Post-Reaction Module

In certain embodiments, after the biochemical reaction is complete, the reaction product is processed before analysis. The system can include a post-reaction module adapted to process the reaction product. The post-reaction module can comprise a microfluidic device comprising on-device valves and pumps adapted to route a fluid comprising the reaction product through a microfluidic channel into a processing chamber e.g., a non-microfluidic chamber. For example, if the biochemical reaction is DNA amplification, e.g., PCR, and analysis involves e.g. capillary electrophoresis, processing can involve adjusting the salt concentration of the product containing volume. This can involve for example, diluting the reaction product volume.

In another embodiment multiple reaction channels may be used in parallel to increase sample throughput. In yet another embodiment the system may alert the user when amplification has occurred (a positive result), indicating that the target sequence is present. In one embodiment a reaction channel is used for a single use only, then disposed of. In an alternative embodiment a reaction channels can be used to amplify and detect the presence or absence of PCR amplification products in multiple samples. More than one PCR reaction samples can be loaded at intervals and interspaced with a barrier bolus of gas or liquid to prevent intermixing. In one embodiment samples are spaced apart in a manner so that as one is undergoing thermal cycling another sample is in the detection region undergoing interrogation. It will be obvious to one skilled in the art that the PCR amplification can be replaced by other nucleic acid amplification technologies which may use thermal cycling or be isothermal reactions.

In other embodiments, the device can perform isothermal reactions such as sandwich assays using affinity reagents such as antibodies or aptamers to determine if cells, proteins, toxins, or other targets are present with the detection module (FIG. 6, 410) providing a reading of the amount of target present. In these applications, the cartridge 1 may perform an affinity purification such as an IMS purification and then add a secondary antibody that may have a fluorescent label attached. The sample can then move into region 350 where the thermal control is set to optimize the reaction. Detection module (410) can then monitor the reaction. In one embodiment, a plurality of cartridges are ganged to reaction channel (250) and a series of boluses can be readout with detector 410.

IV. Device for Product Analysis (e.g., Capillary Electrophoresis)

In one embodiment a complete sample-to-answer system is provide, which can comprise microfluidics, requiring coupling all steps together to match volumes and concentrations. Sample analysis using capillary electrophoresis is a standard analytical method that can be used with microfluidic sample preparation methods as described above. Capillary electrophoresis is readily adaptable to microfluidic microchips. In the instant invention, capillary electrophoresis on microchips is combined with MOVe valves to provide control of samples, process beads to concentrate the samples, and improve the loading and separations.

Figure 48:
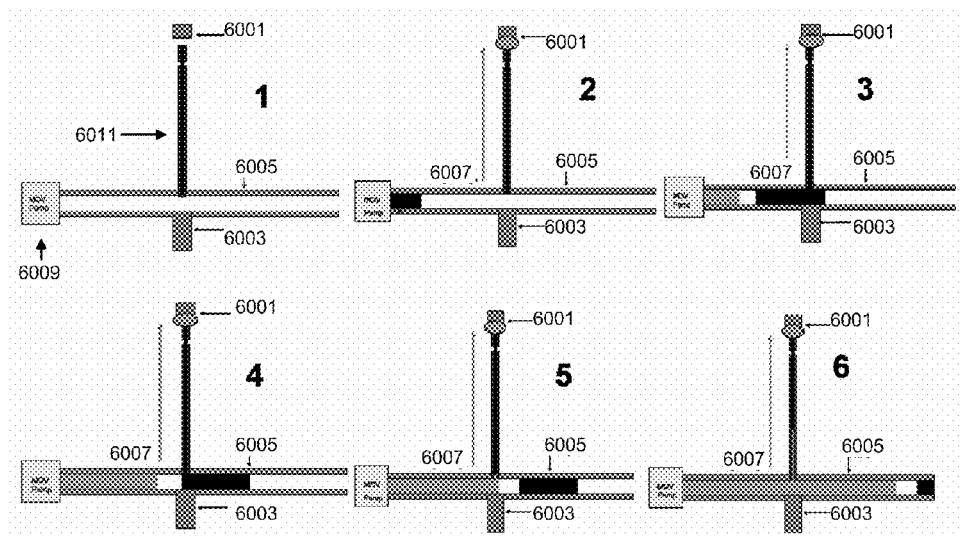
FIG. 48 shows sample injection into a separation channel.

FIG. 48 show a sample source 6009 connected to a sample channel 6005, also referred to as a loading channel, that is mated with a separation channel 6011. Two electrodes, 6003 and 6001, can be used to apply an electric field to the separation channel. In some embodiments of the invention, the sample source can pass through a MOVe pump in a microchip used to drive fluid flow within the sample channel. The sample channel can be a microfluidic channel or an injection tubing. The injection tubing can be flexible tubing or another flexible connector. Examples of flexible tubing include polytetrafluoroethylene tubing or silicon tubing. The flexible connector can also connect to another cartridge interfaced with a microchip. Alternatively, the flexible connector can return to the cartridge that it originated from. The separation channel can be a microfluidic channel, capillary tubing, or capillary electrophoresis tubing. The capillary tubing can have an outer diameter of about 150 to 500 microns and an inner diameter of about 10 to 100 microns. The capillary can be polyimide or polytetrafluoroethylene clad. The capillary can be about 2 to 100 cm long. The capillary can be mated to the injection tubing or flexible tubing by first drilling a hole into the injection tubing and then inserting the capillary into the flexible tubing. Alternatively, the capillary can be inserted into the flexible tubing without having to pre-drill the flexible tubing.

One of the two electrodes, for example electrode 6003, can be a cathode and the other electrode, for example 6001, can be an anode. The cathode can be any cathode, such as a forked cathode, described herein. The anode can be connected to the separation channel using any devices known to those skilled in the art. For example, the separation channel can be joined to a reservoir by an Upchurch fitting, which is in electrical contact with the anode, which can be a metallic electrode.

Figure 49:
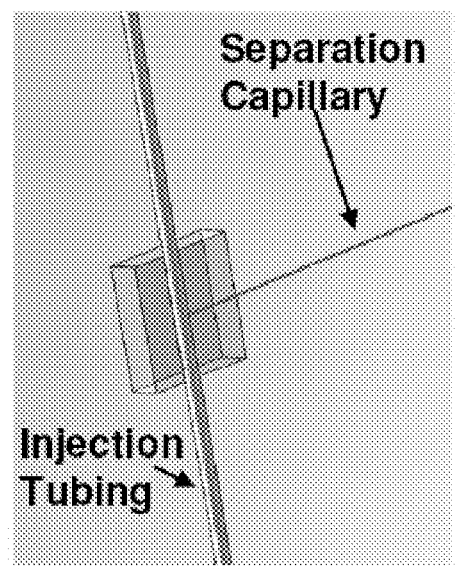
FIG. 49 shows a device for mating a separation capillary with injection tubing.
Figure 50:
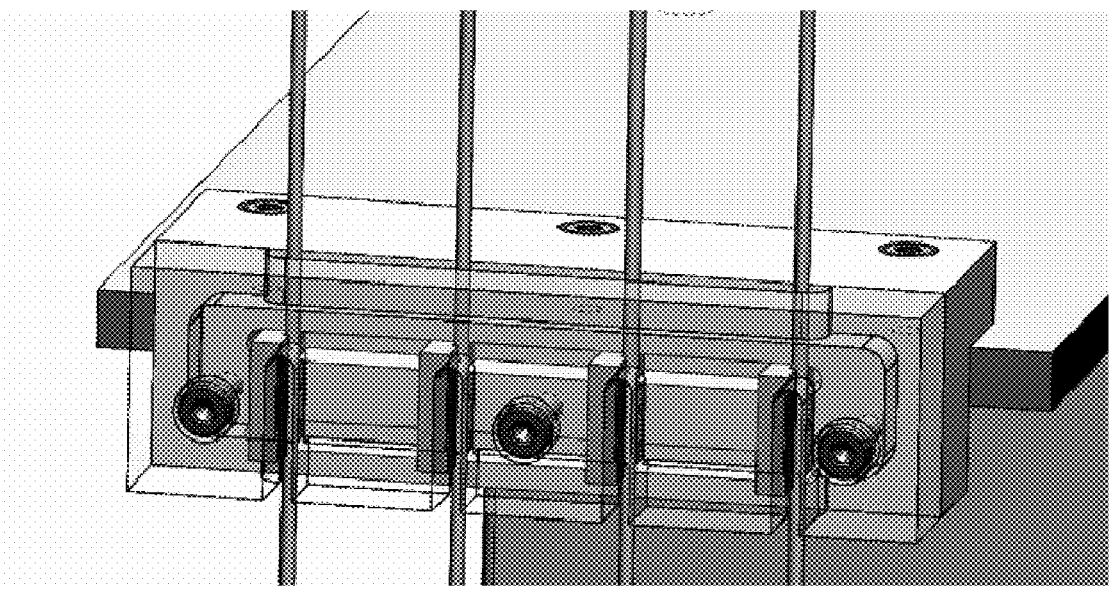
FIG. 50 shows a device for mating separation capillaries with four injection tubings.

In some embodiments of the invention, a stabilizing component, shown at the intersection of a separation capillary and injection tubing in FIG. 49, can be used to align, seal, and/or protect the connection between the separation capillary and the injection tubing. In some embodiments of the invention, multiple injection tubings are aligned with multiple separation capillaries using a stabilizing component. As shown in FIG. 50, the stabilizing component can hold four injection tubings, shown as the vertical tubings in the figure, and stabilize the connection with four separation capillaries (not shown).

Panels 1-6 of FIG. 48 show a process for injecting a sample into a separation channel. In panel 1, no sample is present in the sample channel 6005. In panel 2, sample entering the sample channel from the sample source (6009) is shown. As sample is moved down the sample channel, the sample intersects the separation capillary, as shown in panel 3. The sample can be isolated by boluses of gas upstream and downstream to the sample. Once sample is adjacent to the separation channel, an electric field, which can be between 25 and 500 V/cm, is applied between a first electrode 6003, which can be a cathode or a forked cathode, and a second electrode 6001, which can be an anode. Electrophoresis buffer, shown entering into the sample channel from the sample source, can also enter the sample channel, as shown in panel 3. The voltage potential and/or current between the anode and cathode can drop when an air bolus passes by the junction between the sample channel and the separation channel, reducing or preventing the injection of air into the separation channel. The voltage potential and/or current drop can be detected to ascertain when the sample and/or electrophoresis buffer is adjacent to the separation channel. Once the electrophoresis buffer is adjacent to the separation channel, as shown in panel 5, the current and/or voltage drop between the anode and cathode can be increased. This can allow for the separation of the analyte in the separation channel, as shown in panel 6, as the electrophoresis buffer provides ions for a high performance separation.

In one embodiment for STR analysis, the injection process is as follows:

A. The microfluidic channels can be filled with buffer.
B. The separation channel can be filled with gel while buffer is pulled across the sample channel, thus sweeping the separation polymer from the cross section formed by the separation and sample channels.
C. The STR amplified sample (desalted and captured on beads) can be captured on microchip 500, eluted in a low conductivity fluid (water) containing the size standard, and pumped into the sample channel with MOVe technology.
D. A field can be applied across the cathode and anode, with "pull back" voltage on the sample and waste arms, to drive the sample into the separation channel where it stacks at the head of the separation polymer. As the sample is injected the conductivity of the sample channel can quickly equilibrate with the buffer in the cathode arms providing a single step injection.

Figure 46:
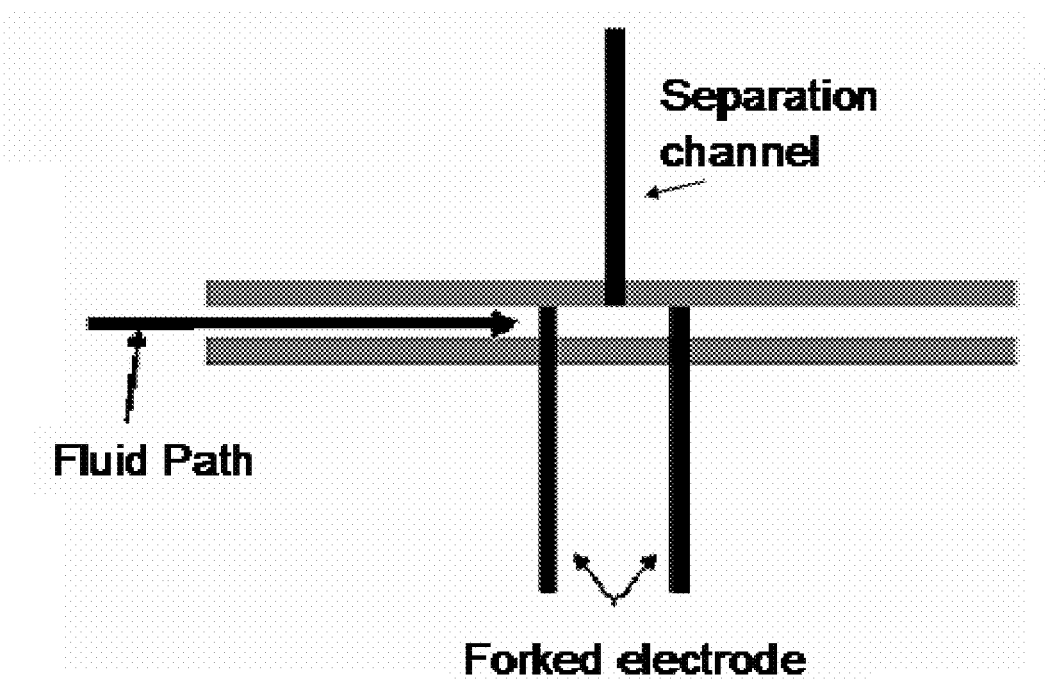
FIG. 46 shows a forked electrode.

The forked electrode or cathode can be two metallic conductors, as shown in FIG. 46. The fluid path for a sample to be analyzed, as shown in FIG. 46, can be along a loading channel. When the location of the sample is adjacent to the separation channel, the forked electrode can be used to inject the sample into the separation channel, as described herein. The conductance of the material in the sample channel can be lower than the conductance of the material in the separation channel, which can be a separation polymer. The difference in conductance can cause sample stacking when an electric field is applied through the forked electrode, which can be a cathode, and a downstream electrode, which can be an anode. The polarity of the forked electrode and the downstream electrode can be reversed such that the forked cathode is the anode and the downstream electrode is the cathode.

Figure 47:
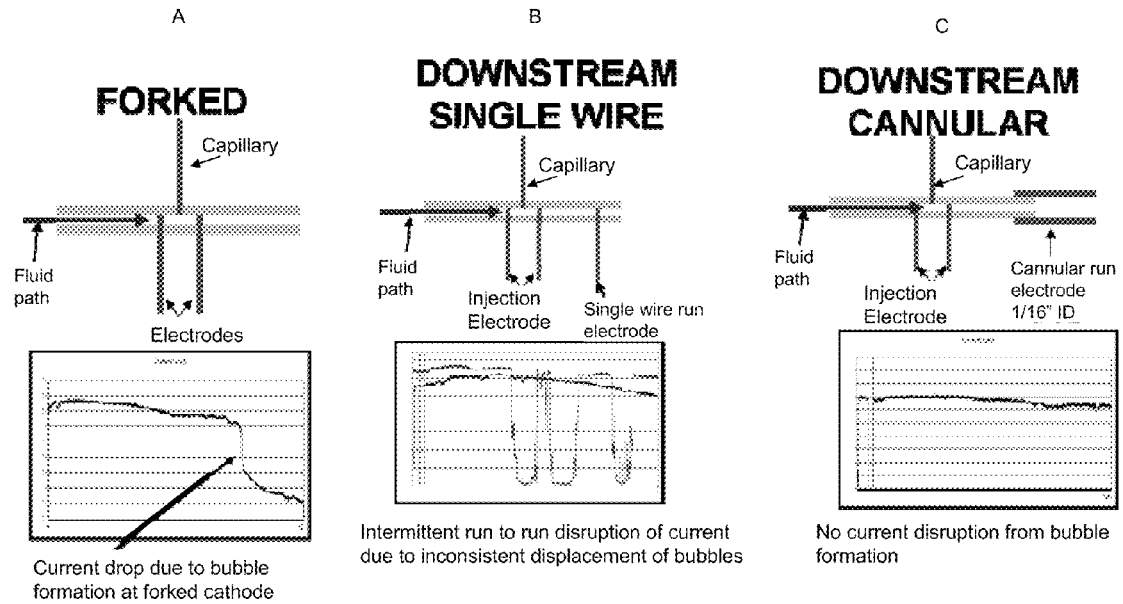
FIG. 47 shows a forked electrode, a forked electrode with a wire run electrode, and a forked electrode with a cannular electrode.

In some embodiments of the invention, an additional electrode can be used to reduce injection of gas into the separation channel or formation of bubbles within the sample loading channel which can lead to loss of the applied field on the separation channel. Injection of gas into the separation channel or formation of bubbles within the sample loading channel can cause inconsistent separation of analytes and can be detected by inconsistent current between the anode and cathode used to apply an electric field to the separation channel. Use of an additional electrode to circumvent or reduce injection of gas or bubbles into the separation channel is shown in FIG. 47. The additional electrode can be a single wire run electrode or a cannular run electrode. The increased surface area and/or larger internal diameter of the cannular run electrode can allow for a significant reduction in bubble formation or blockage and/or injection into the separation channel. In some embodiments of the invention, the cannula used for the cannular run electrode and has an inner diameter of at least about 1/64, 1/32, 1/16, 1/8, or 1/4 inches.

Figure 96:
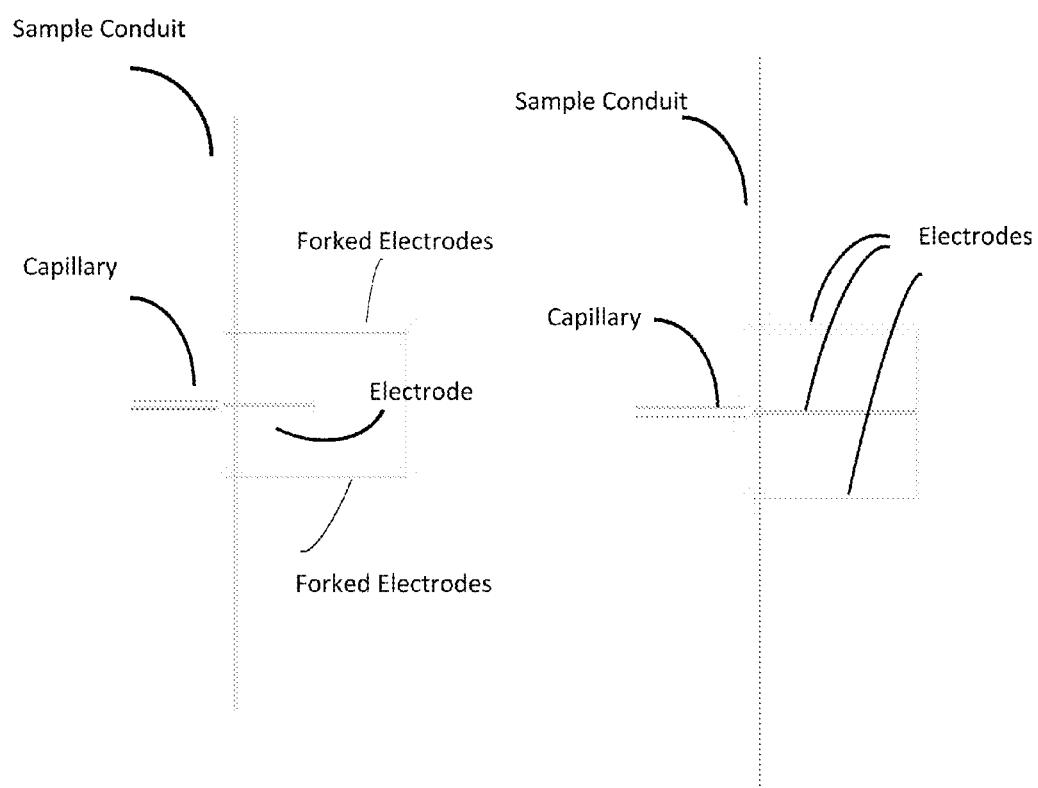
FIG. 96 shows an injection system for injecting a sample into an electrophoresis capillary.
Figure 97:
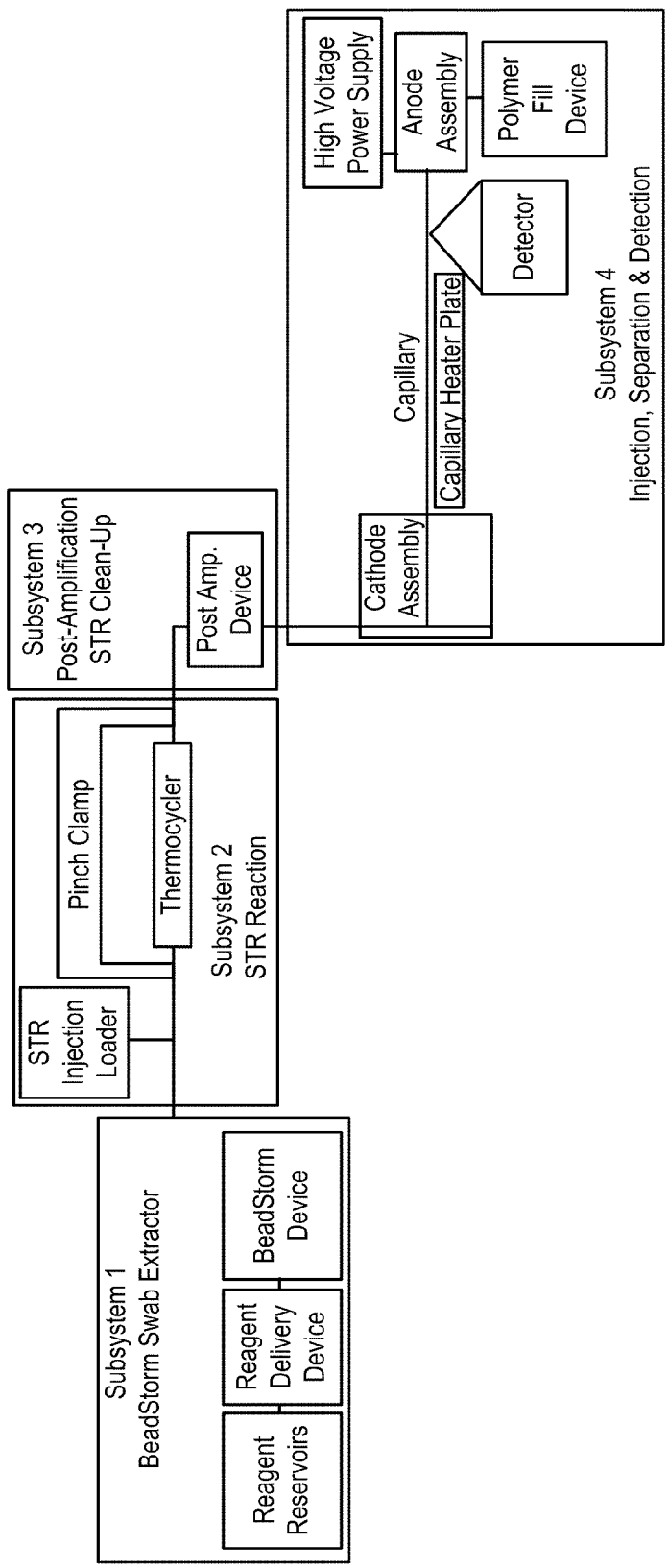
FIG. 97 shows integrated subsystems.

In another embodiment shown in FIGS. 96 A and B, the three-prong electrode arrangement can be used to pre-concentrate analytes before injection. In this method, the outside electrodes are given a charge the same as that of the analyte, and the electrode between them and opposite the electrophoresis capillary is given a charge opposite that of the analyte. For example, in the case of nucleic acids, which are negatively charged, the outside electrodes are given a negative charge and the middle electrode is given a positive charge. This causes the analyte to become concentrated between the flanking electrodes and toward the middle electrode. Then, the charge on the middle electrode is reversed and a voltage is placed across the electrophoresis capillary. This moves the analytes through the capillary tube. The shown electrode configuration for a capillary electrophoresis injector may include a forked electrode and another electrode. Both configurations shown include a forked electrode having two points of contact located distally to the connection with the electrophoresis capillary one electrode directly across from the lumen of the capillary. In one embodiment, the second electrode is a third fork in the forked electrode. In a second embodiment the second electrode is not on the same circuit as the other electrodes. This allows two circuit paths to be employed at the injector. In one method of using the three-electrode arrangement, the sample is moved into place opposite the capillary using the fluidic system. Then, the sample is injected into the capillary using only the middle electrode which is opposite the capillary. Then, the middle electrode is turned off, the flanking electrodes are turned on and are used to electrophorese the analytes through the capillary.

This invention provides a device for regulating temperature of electrophoresis capillaries, for example an array of capillaries. An embodiment is shown in FIG. 98B. The electrically insulating circuit board has a generally S-shaped path for placement of capillaries. The generally S-shaped path is broken up into 6 different sections, 12, 14, 16, 18, 20, and 22. These 6 different sections, 12, 14, 16, 18, 20, and 22 separately regulate the temperature in the portion of a capillary in thermal contact with the particular section. Each of the different sections, 12, 14, 16, 18, 20, and 22 is filled with an electrical path that runs back and forth, e.g. in a serpentine shape in that section's area to fill that section's area. This electrical path that runs back and forth is shown in detail in section 22. Although not shown for purposes of clarity in the illustration, the other sections 12, 14, 16, 18, and 20 also are filled with an electrical path that runs back and forth in that section's area to fill that section's area.

The circuit board also has a row of apertures 10 that run along both sides of the generally S-shaped path for placement of capillaries. The apertures reduce heat transfer between the generally S-shaped path of the circuit board, and a remainder of the circuit board. Because air is a good thermal insulator, heat transfer is reduced between there two parts of the circuit board. The circuit board itself is also a poor thermal conductor. In another embodiment, instead of rows of apertures, poor thermal conductive material is positioned between these two parts of the circuit board. Such reduction of heat transfer eases thermal regulation of the generally S-shaped path and the capillaries placed on the generally S-shaped path. The apertures serve to reduce the thermal mass of the thermally regulated region to substantially the generally S-shaped path and the capillaries placed on the generally S-shaped path. With less thermal mass, a desired temperature is reached more quickly for the generally S-shaped path and the capillaries placed on the generally S-shaped path.

The circuit board also includes an aperture 8 along the generally S-shaped path toward the exiting end of the generally S-shaped path. Because of the absence of circuit board material, the aperture 8 facilitates optical interaction with a capillary which is placed over the aperture 8. The aperture 8 allows for fluorescence excitation and detection using an optical configuration such as epi-fluorescent, and various skew illumination schemes.

The electrical path in various embodiments is a patterned, or etched, conductive trace bonded onto the electrically insulating circuit board. The patterned electrical path may be defined by "subtractive" patterning that removes unwanted conductive material to leave the desired conductive paths, or by "additive" patterning that adds additional conductive material to form the desired conductive paths. The circuit board may have the conductive paths on a single layer circuit board or as part of a multi-layer circuit board.

Various examples of conductive material in the electrical path are metallic material such as copper, aluminum, silver, or nonmetallic conductive material such as graphite, or conductive ink, but may be any other conductive material.

In contrast with the conductive material of the electrical path, the circuit board material is nonconductive, commonly a dielectric material.

Each electrical path creates and defines a thermal area. In one exemplary embodiment, six heating areas, each comprised of approximately 1 m of 150 um wide copper traces that is folded into the shape needed to generate the heater shapes shown below. Various embodiments vary the length of the trace to shorter or longer than 1 m, depending on a length adequate for electrophoretic separation of analytes. Various embodiments widen or narrow the width of the electrical paths, depending on an adequate resistance of the electrical paths to generate adequate heat for thermal regulation of the thermally coupled capillaries. Various embodiments increase or decrease the number of heating areas.

In some embodiments, an electrical path such as a trace has a width in the range between 0.0001 to 0.5 inches, and a length in the range between 0.25 to 750 inches.

Performing electrophoresis in a capillary allows the heat to be effectively dissipated through the capillary walls. This allows high voltages to be used to achieve rapid separations.

Figure 2:
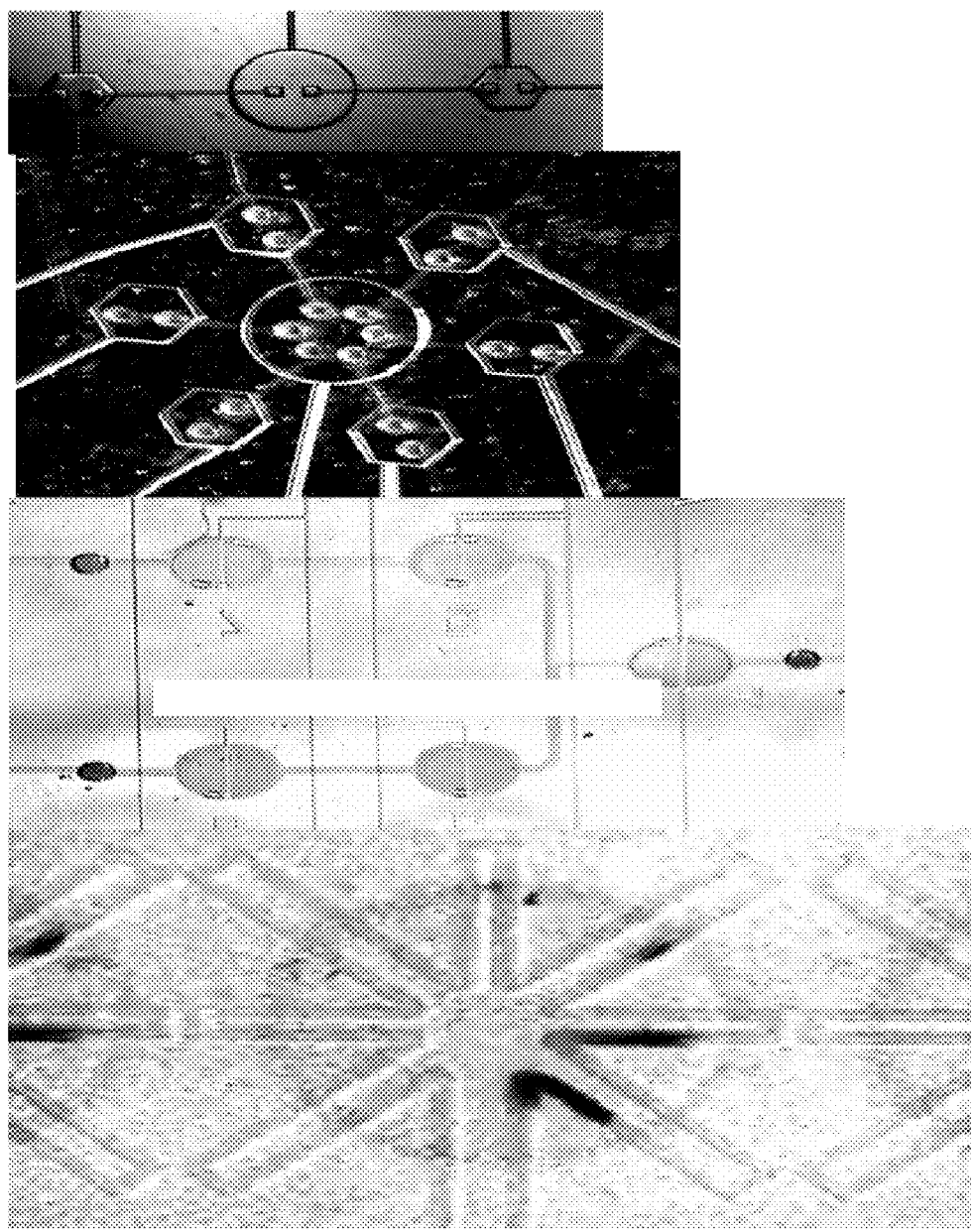
FIG. 2 shows a MOVe microvalve, a microrouter, a MOVe mixer, and bead capture on microchips.

FIG. 2 is a top view of a thermal assembly, with a circuit board, electrical paths on the circuit board, a bundle of capillaries, and temperature sensors.

Figure 98A:
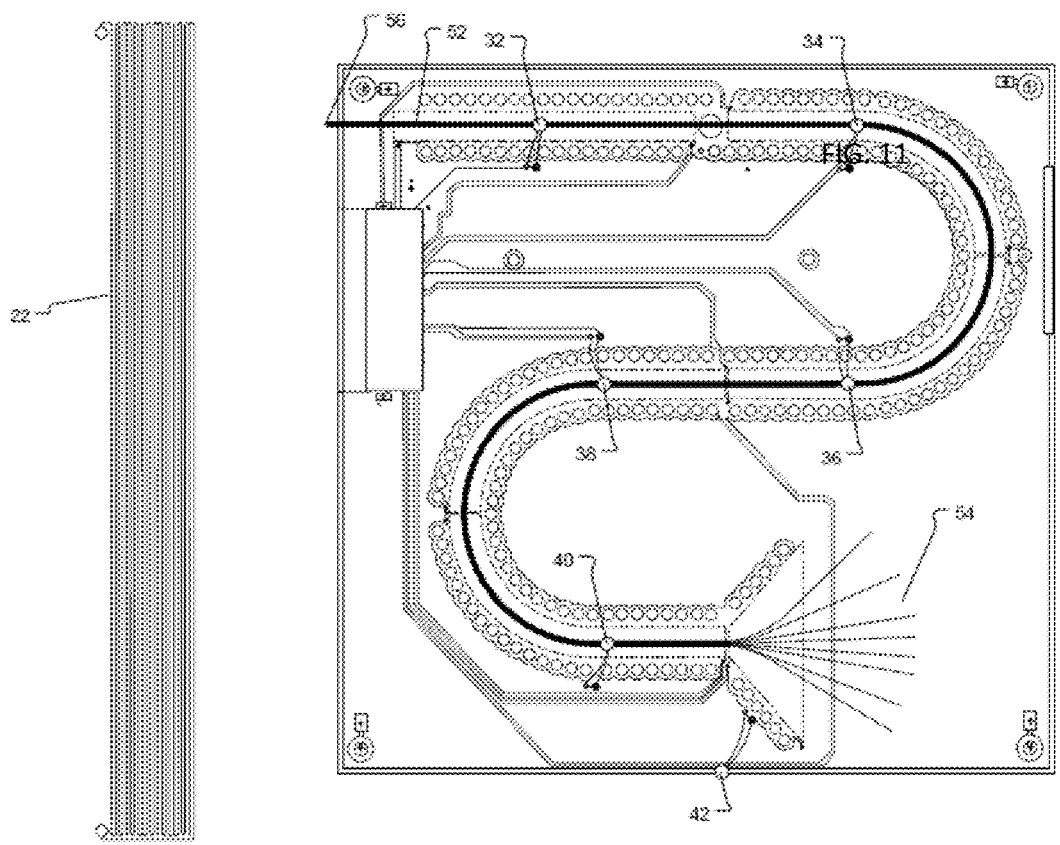
FIGS. 98A and B show embodiments of a device for regulating temperature of electrophoresis capillaries, for example an array of capillaries. The electrically insulating circuit board has a generally S-shaped path for placement of capillaries.
Figure 98B:
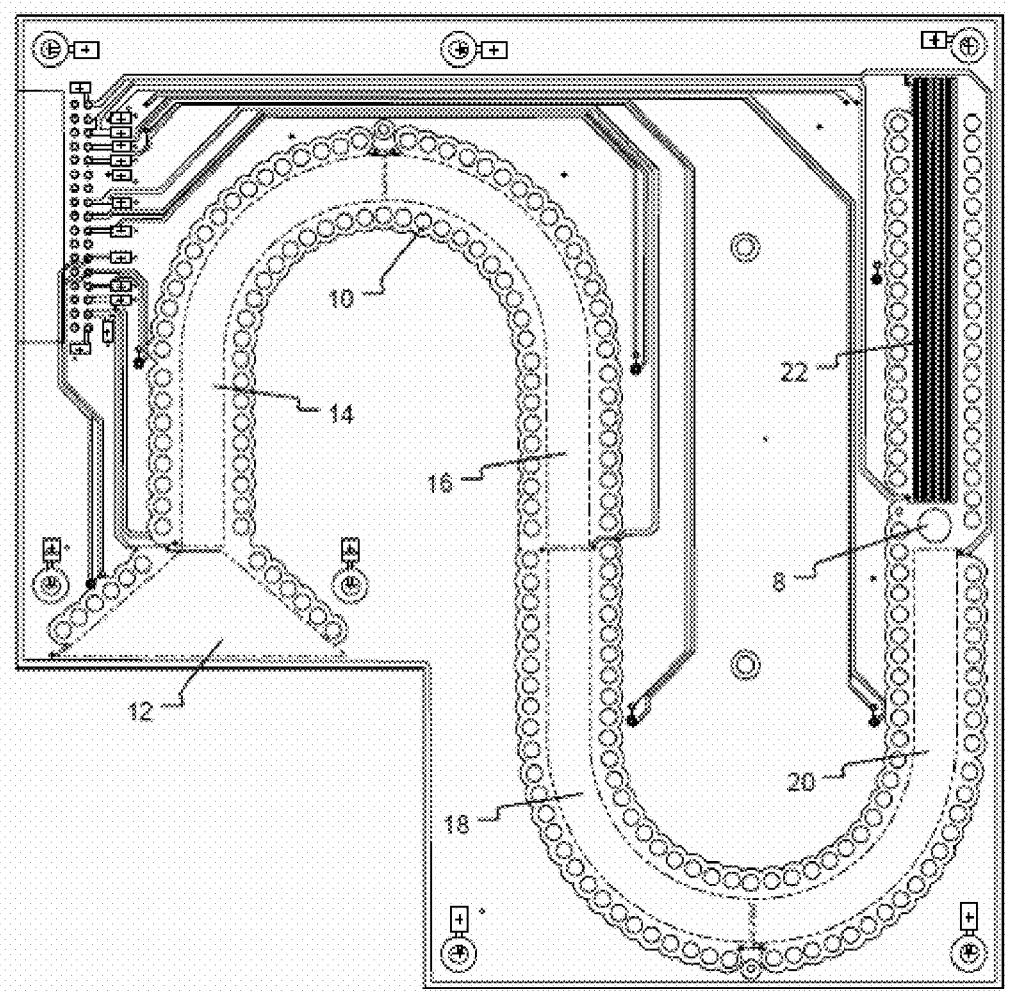

On a circuit board such as the circuit board shown in FIG. 98A, electrophoresis capillaries are attached to the generally S-shaped path, such as by adhesive material. In the shown embodiment, a bundle of 8 capillaries are attached. Other embodiments have any other number of capillaries ranging from 1 to a higher number, depending on a particular electrophoresis application's requirements for parallel processing of analytes. The entering end 54 of the capillaries have fanned out ends, to facilitate injection of analytes into the different capillaries. The exiting end 56 of the capillaries remains bundled together in the figure.

In each of the separately thermally regulated areas or sections of the generally S-shaped path, a temperature sensor is in thermal contact. The temperature sensors shown are 32, 34, 36, 38, 40, and 42. Temperature sensor 42 is in thermal contact not with the capillaries, but the circuit board itself, or alternatively the ambient air. Examples of temperature sensors are thermistors or other temperature-varying resistance, or thermocouples or other temperature-varying voltage source. In another embodiment, the temperature data of the separately thermally regulated sections is not gathered by discrete temperature sensor, but by the electrical paths themselves such as by the resistances of the electrical paths.

In the shown embodiment, temperature sensors are thermistors that are attached to traces that terminate on a portion of the circuit board outside of the array of thermal insulation apertures. The thermistors are folded down across the capillary array and embedded in the adhesive that bonds the capillary array to the board, to ensure good thermal contact between the thermistors and the capillaries, while minimizing thermal loss from the heaters.

The temperature data generated by such temperature sensors help to thermally regulate the temperature of the capillaries in thermal contact with the electrical paths. Electrical current through the electrical path deposits thermal energy in the electrical path via Joule heating. The amount of deposited thermal energy varies with the amount of electrical current and resistance of the electrical paths.

In one embodiment, the invention provides a portable eight-channel integrated automated sample-to-answer DNA forensics device. Such a device accepts buccal swab samples or blood samples; performs STR analysis; and outputs CODIS file ready for interrogation against a database.

In another embodiment, the invention provides an automated analysis for short term repeats in a sample, wherein the method comprises extracting and purifying a sample comprising an analyte comprising a short term repeat nucleic acid sequence; amplifying the short term repeat nucleic acid sequence; purifying the short term repeat nucleic acid sequence; and performing capillary electrophoresis on purified short term repeat nucleic acid sequence to determine the size of the short term repeat nucleic acid sequence.

Using standard technologies, the process from biological sample (e.g., cheek swab) to data output of a CODIS file requires more than six hours. This includes DNA extraction, qPCR, DNA normalization, STR amplification with labeled primers, post-reaction sample preparation, CE analysis and data analysis. The system of the present invention can perform this entire process in less than 5 hours, less than 4 hours less than 3 hours or even less than 2 hours.

In another embodiment, the invention provides an automated analysis for short term repeats wherein the success rate of getting the correct STR from a raw or otherwise unpurified sample is at least 60%, at least 65%, at least 70%, at least 75%, at least 80%, at least 85%, at least 90%, at least 95%, at least 96%, at least 97%, or at least 98%.

A. Detector

In one aspect, this invention provides an optical system for detecting analytes in an array of capillaries, e.g. an array of 4, an array of 8 or an array of up to 12 capillaries. In this system, the objective lens moves in relation to the capillaries, the excitation source, and the collection optics. As the objective moves, the excitation light passes through a different part of the lens and is focused at a different point in the region of the capillaries. Movement of the objective results in translation of the point of focus so that, so that each capillary can, in turn, be scanned.

Figure 99:
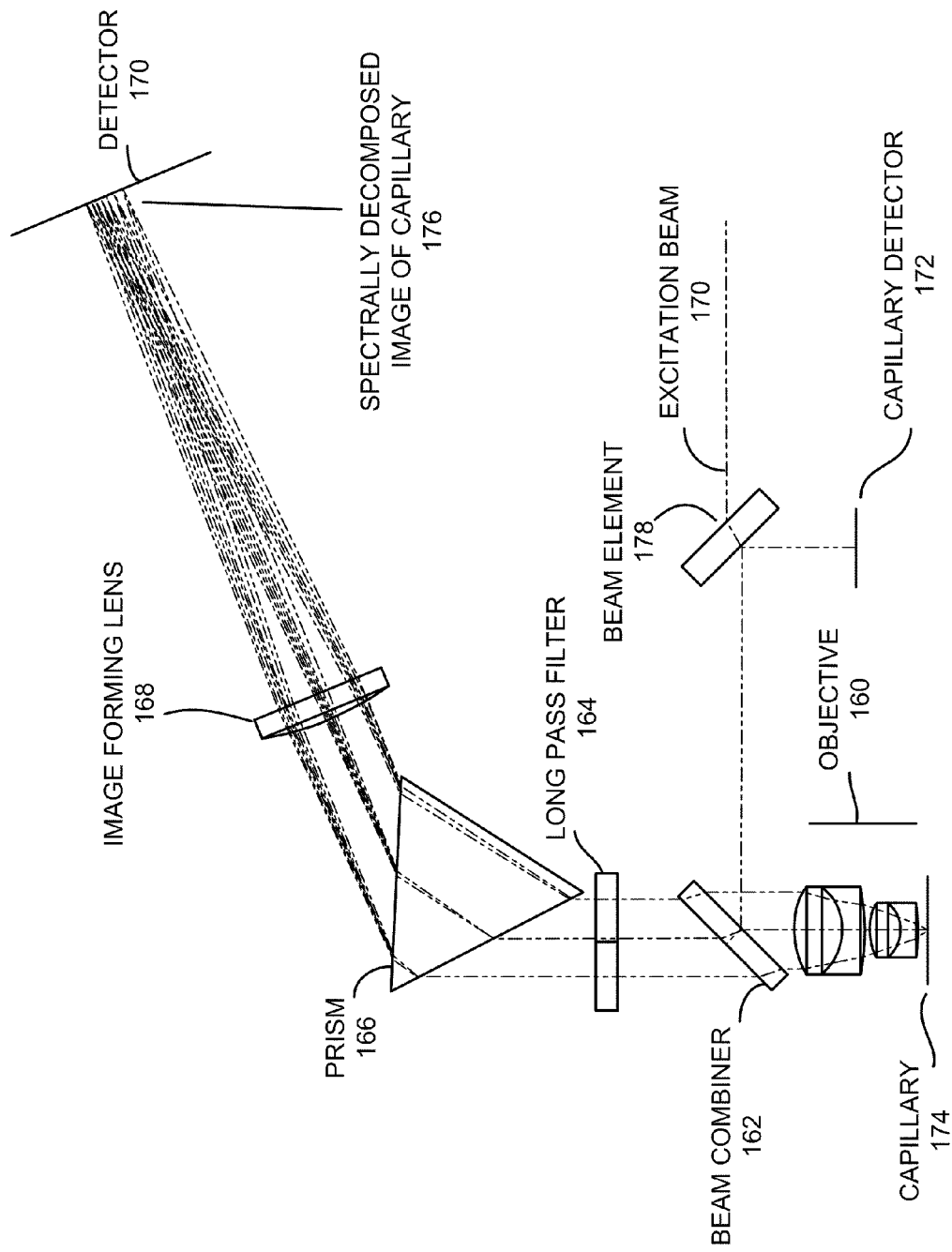
FIG. 99 shows one embodiment of the optical system for detecting analytes in an array of capillaries.
Figure 100:
FIG. 100 shows 'precious reagent' delivery one embodiment of the placement of 'precious reagent cartridges' in the device.
Figure 100:
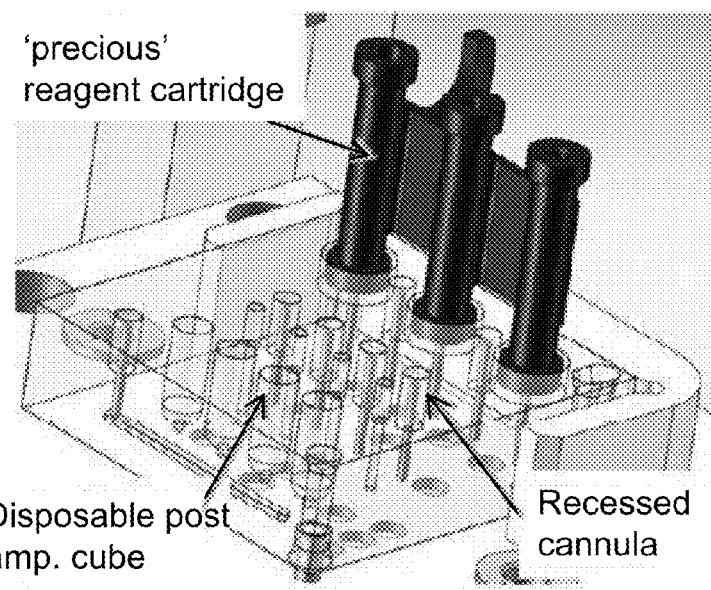
Figure 100:
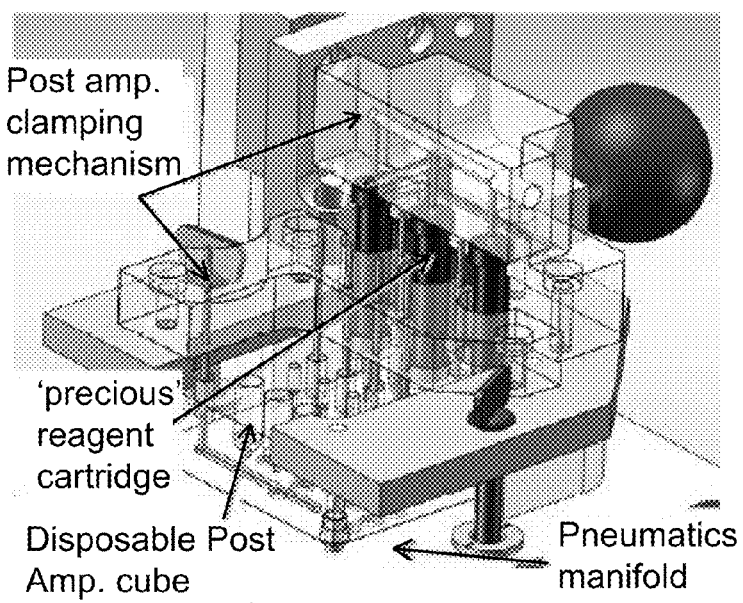
Figure 101:
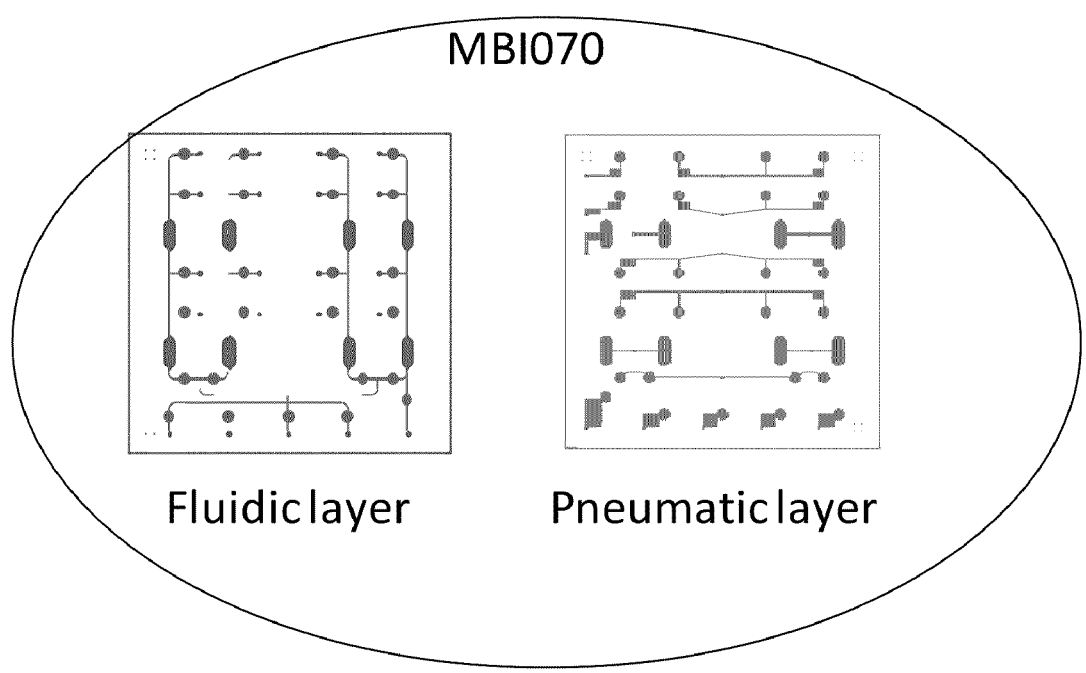
FIG. 101 shows the fluidics and pneumatics architecture of a microfluidic chip which is then mated with a fluidics cartridge to form the post amplification module.
Figure 102:
FIG. 102 shows one embodiment of the system enclosure which measure 2×2×2 ft.
Figure 103:
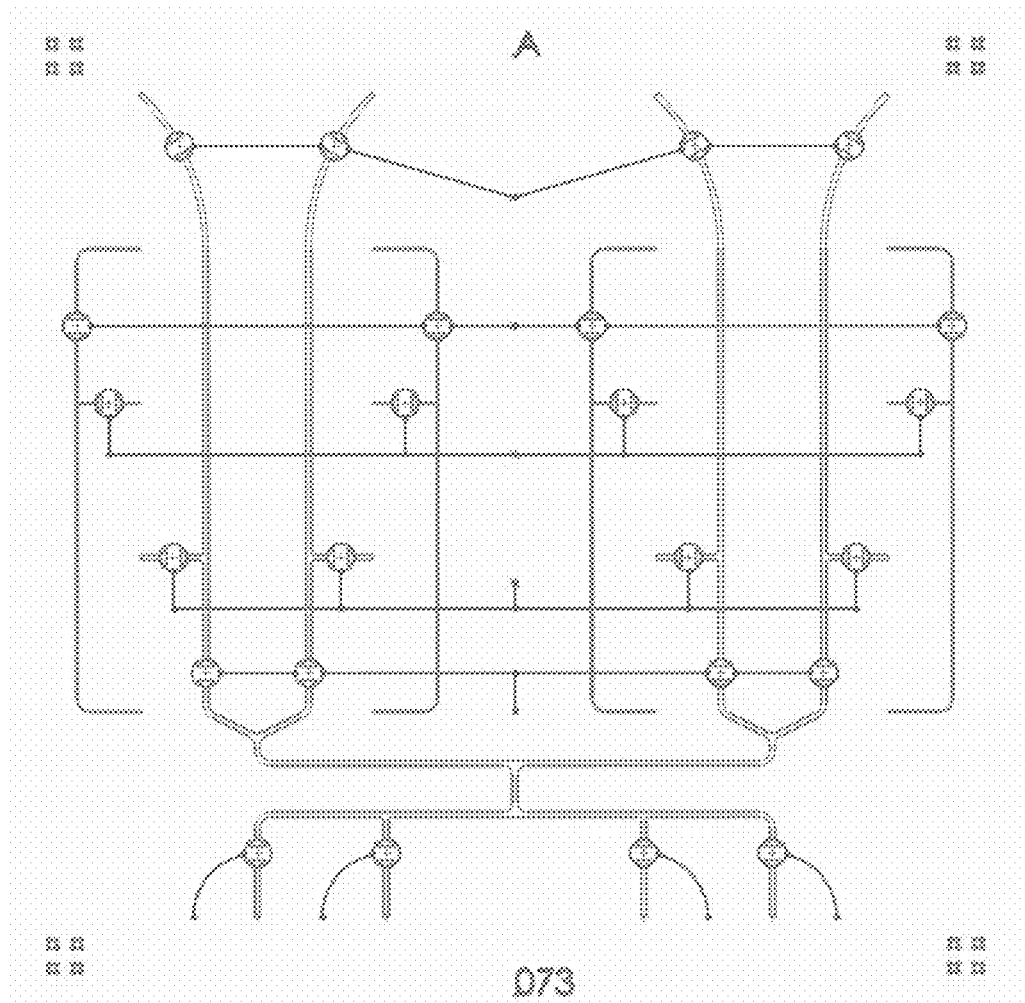
FIG. 103 shows the fluidics and pneumatics architecture of a microfluidic chip which is then mated with a fluidics cartridge to form the reagent delivery module.
Figure 104:
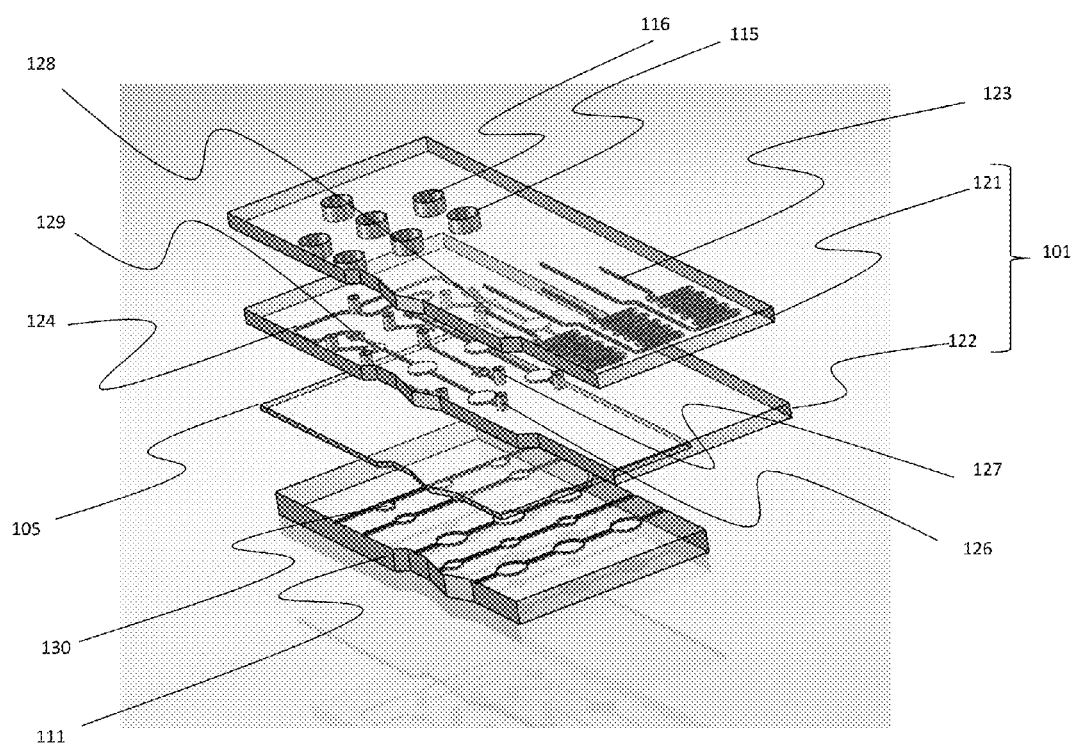
FIG. 104 shows a portion of a device in which the fluidics layer comprises a plurality of sublayers, in an exploded view. The top or external sublayer 121 is referred to as the "etch" layer and bottom or lower sublayer 122 is referred to as the "via" layer. Fluid traveling in a channel in the etch layer can flow into a conduit in the via layer that faces the elastic layer.

In FIG. 99, the excitation source of the excitation beam 170 is a solid state laser, the output of which is projected into the capillary 174 using a beam combiner 162 placed at a 45 degree angle in the optical path immediately above the objective 160. In various embodiments the beam combiner comprises a wavelength sensitive reflector or a spatial beam splitter such as a small reflective dot placed on a transparent sheet of glass. The beam combiner is wavelength dependent, which is easier to align than a spatial beam combiner.

The high numerical aperture objective is used both by the excitation beam 170 on its way to the capillary 174, and by the optical signal of emitted fluorescence from the capillary 174.

The optical signal of fluorescence emitted from the analytes of the capillary 174 is collimated by the objective 160. The optical signal passes through the wavelength sensitive reflector 162 and impinges on a long pass filter 164 that rejects the portion of the optical signal including the excitation beam 170.

The fluorescence detection scheme is prism spectrometer based. The optical signal is then projected onto a dispersive prism 166, which serves to change the angle of the rays according to wavelength. This dispersed optical signal is then focused on the plane of the detector 170 using an image forming lens 168, causing different wavelengths of the dispersed optical signal to focus at different locations in the plane of the detector 170. An example of the detector 170 is a CCD camera. An alternative is a CMOS camera or other optical sensors.

With an array that comprises 30 um diameter capillaries, the scan range for the detection device covers +/−0.8 mm for an eight channel array. This limited scan range minimizes the number of moving parts. Other embodiments widen or narrow the scan range to accommodate a different number of capillaries and/or different number of capillaries. As only the objective 160 moves, the excitation laser beam 170 remains very close to the center of the objective 160, even when the beam 170 is located at the top of the end capillary in the array. The excitation beam 170 impinges on the capillaries at different angles depending on the location of the capillary in the array.

V. Integrated Analysis System with Disposable Cartridge

The invention provides for an integrated analysis system that can interface with a disposable cartridge that integrates several functions of the system, including sample extraction, thermal cycling, and post-amplification processing. The integrated analysis system and disposable cartridge can be used to analyze a sample obtained from a source and provide information regarding the source. For example, the system and cartridge can be used to extract nucleic acid from a plurality of samples and analyze the extracted nucleic acids for short tandem repeats to obtain genetic information regarding the source.

Figure 63:
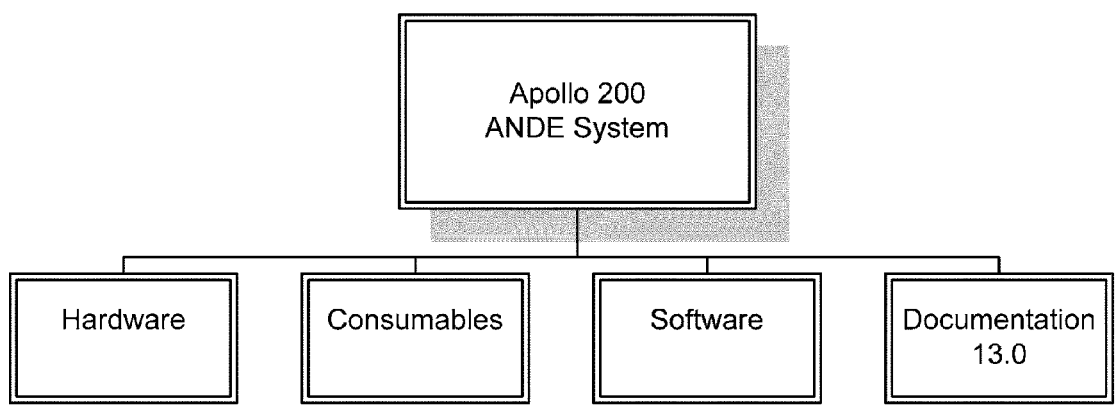
FIG. 63 depicts components of an integrated analysis system.
Figure 64:
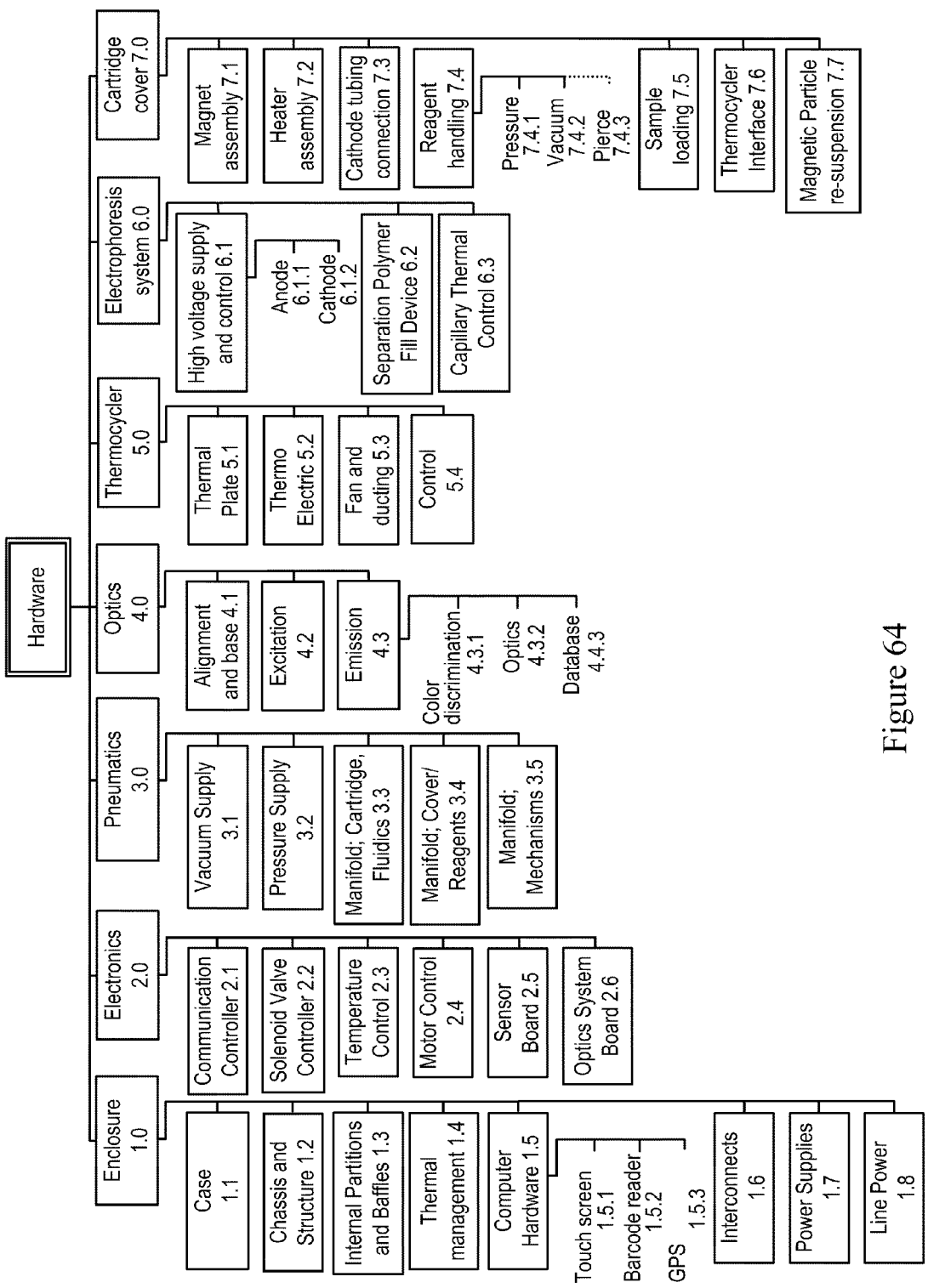
FIG. 64 depicts hardware components of an integrated analysis system.
Figure 65:
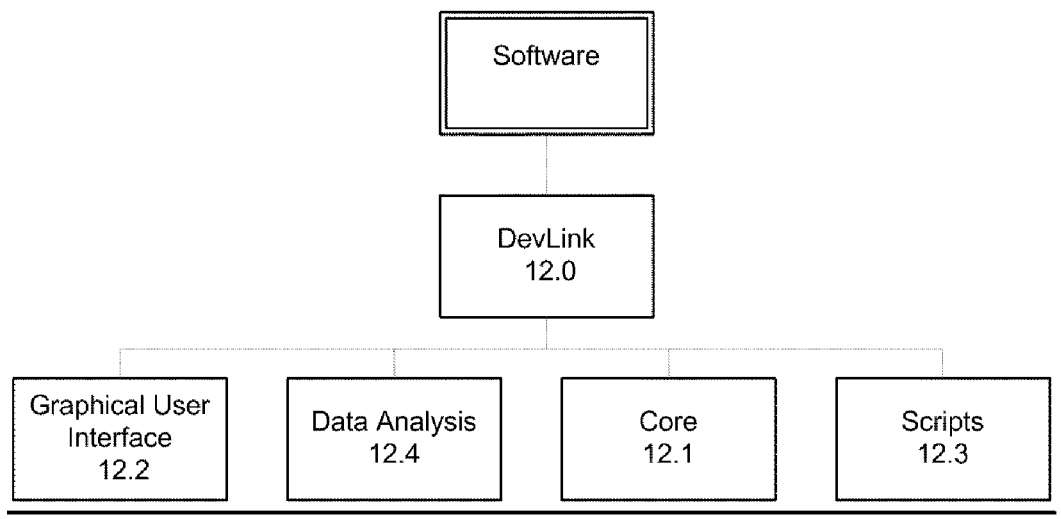
FIG. 65 depicts software components of an integrated analysis system.

An overview of the integrated analysis system and disposable cartridge is shown in FIG. 63. The integrated analysis system can include hardware, consumables, software, and documentation. As shown in FIG. 64, the hardware components of the integrated analysis system can include one or more enclosures, electronics, pneumatics, optics, thermocyclers, electrophoresis systems, and cartridge covers. Additional components of the hardware are shown in FIG. 64. The integrated analysis system can also include one or more control systems, power systems, computers, and displays. As shown in FIG. 65, the software components of the integrated analysis system can include software providing for a graphical user interface, data analysis, a core, and scripts. The core can be used for the control of the hardware. The scripts can be programs that are run. The programs can correspond to particular analytical procedures.

Figure 66:
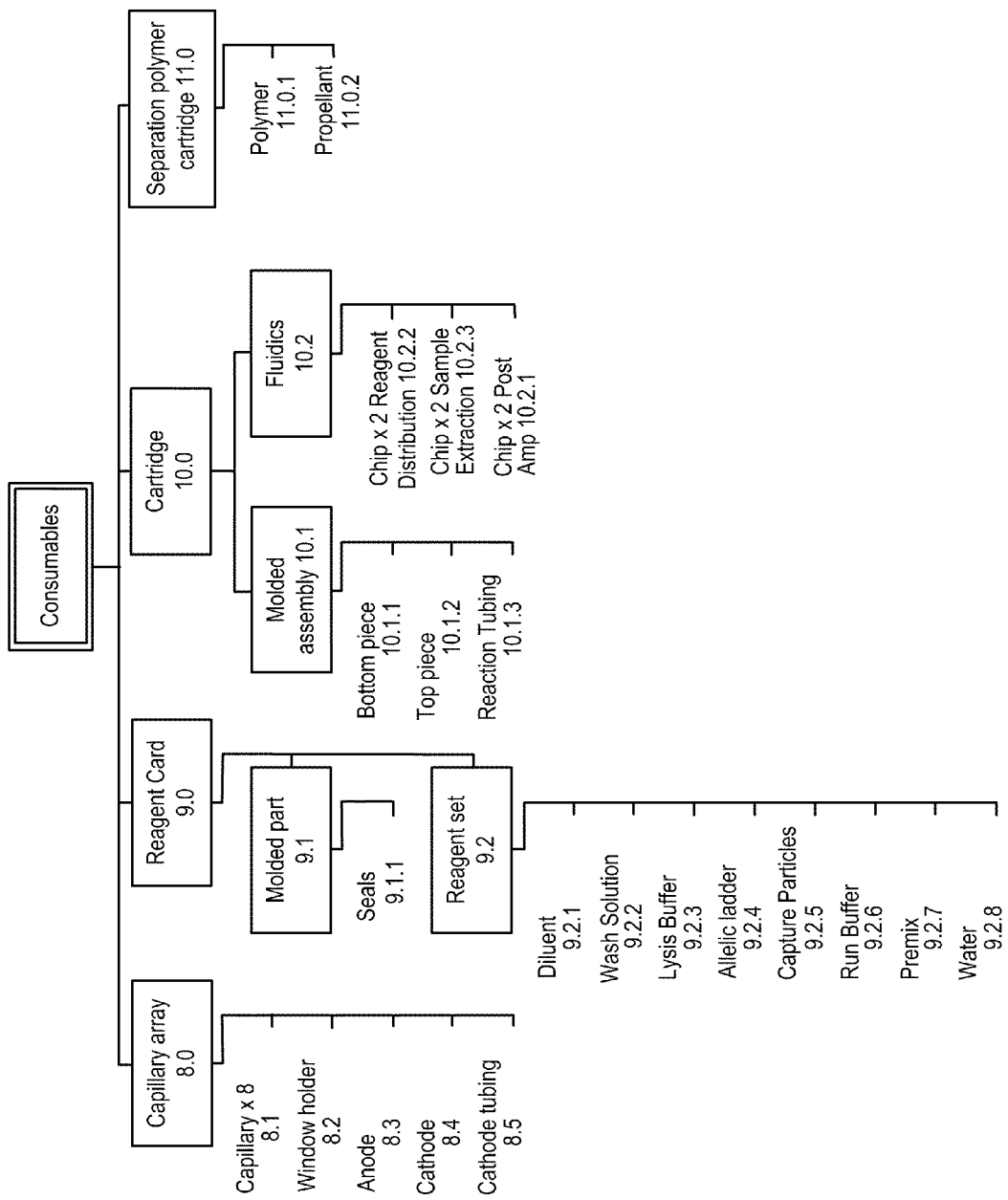
FIG. 66 depicts consumable components of an integrated analysis system.

As shown in FIG. 66, the consumables can include one or more capillary arrays, reagent cards, cartridges, and separation polymer cartridges. The reagent cards can include reagents for performing analytical reactions. The cartridge can include chambers for receiving samples and chips having one or more pneumatically actuated valves for controlling fluid transport. Other consumable components are shown in FIG. 66.

Figure 67:
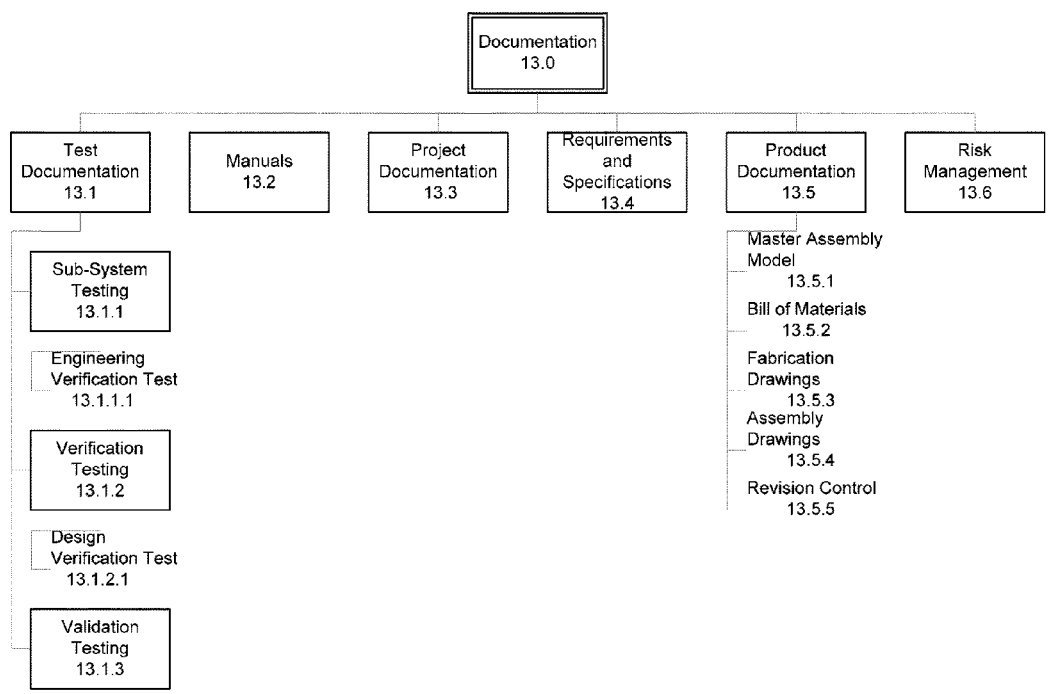
FIG. 67 depicts documentation components of an integrated analysis system.

FIG. 67 shows documentation that can be included with the integrated analysis system. Documentation can include test documentation, manuals, project documentation, requirements and specifications, product documentation, and risk management.

Figure 68:
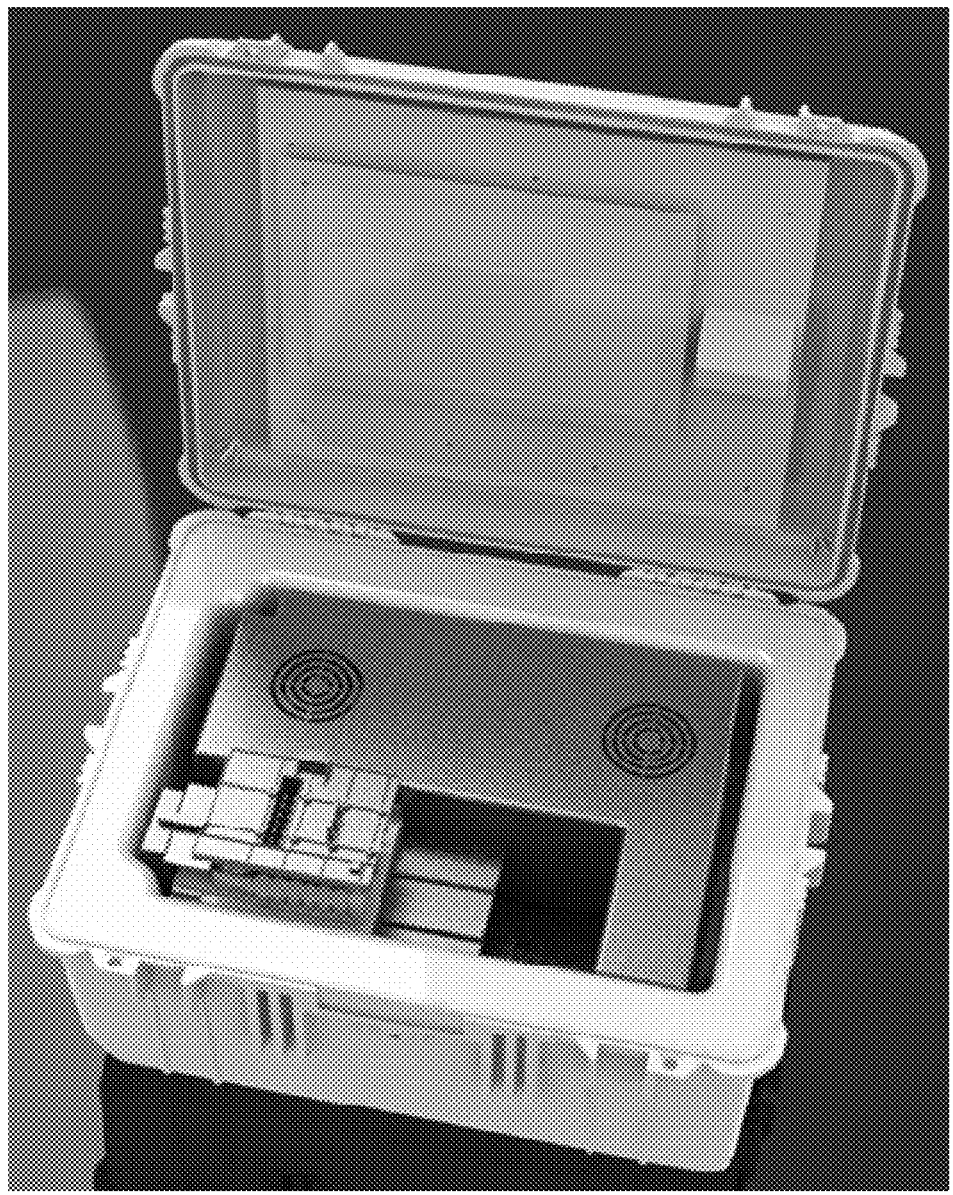
FIG. 68 shows a picture of an encased integrated analysis system.

The integrated analysis system and disposable cartridge can be enclosed in a container having a total volume of less than about 10 ft$^3$, less than about 5 ft$^3$, less than about 3 ft$^3$, less than about 2 ft$^3$, or up to about 1 ft$^3$, such as a Pelican model 1610 case. The pelican case #1610 @ 2.2 ft$^3$ can be used to contain all system parts including user control and spare cartridges. The dimensions of the container can be up to about or about 22×17×11 inches. The container can have wheels and handles for facilitating transportation of the system. The container can be padded or reinforced such that the system is protected from damage during transportation or use. The container can be securely closed or have one or more alarms to prevent and/or deter unintended entry and/or theft. An example of an encased and integrated analysis system is shown in FIG. 68. Accordingly, this system incorporates into a suitcase-sized container instrumentation to accept a biological sample and produce an analysis of the genetic content of that sample. The system is multiplexed and can perform a plurality of operations at once, for example, at least 2, at least 4, at least 6, at least 8, at least 10, or even at least 12, or more samples in parallel. In a specific embodiment, the system can perform 2, 4, 6, or 8 samples in parallel.

The case load can be <50 kg and can be shipped without protection. No additional packaging may be required, enabling rapid deployment of the device. The lid can be opened and the device can be plugged in upon arrival. The small size and two man lift can enable setup and transfer without need for lift equipment. In some embodiments of the invention, the system includes an internal power source or a power generator. The internal power source can be a battery for powering the system in the absence of an electrical source. The battery can be a rechargeable battery or can be a non-rechargeable battery. The power generator can be a fuel cell, a solar cell, or any other type of power generator known to one skilled in the art.

Figure 69:
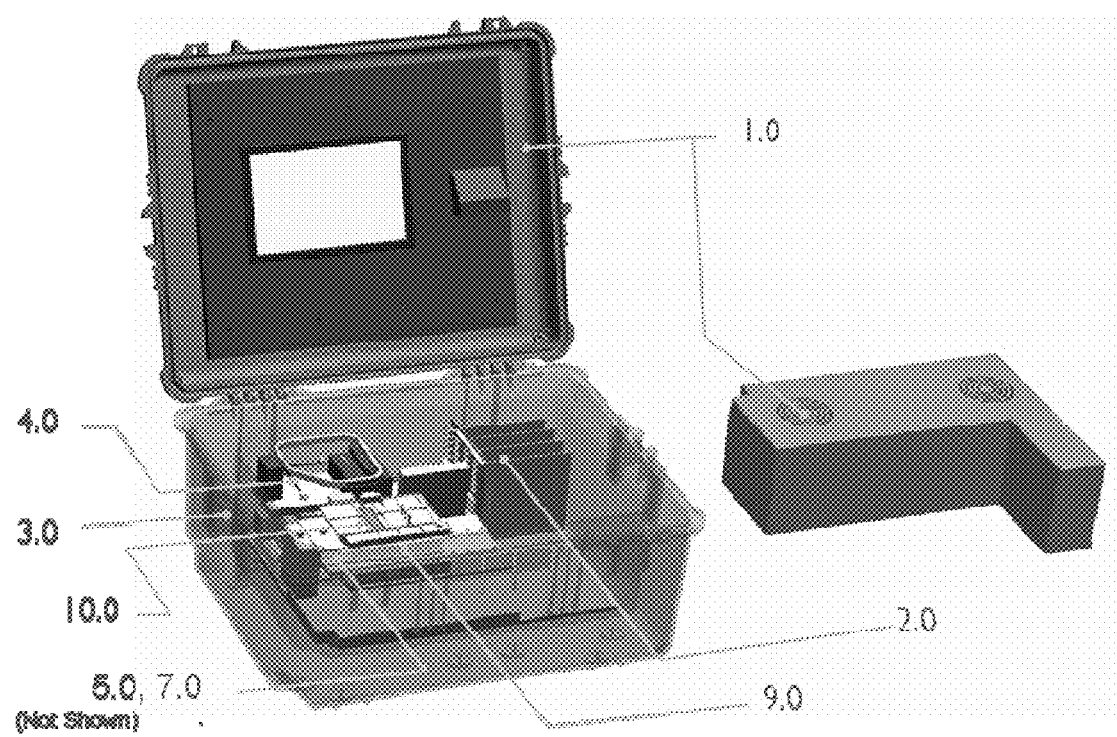
FIG. 69 shows a schematic of an encased integrated analysis system.

The container or case can also have one or more internal enclosures. The internal enclosures can protect hardware from damage or spills. An example of an internal enclosure is shown in FIG. 68. The internal enclosure has two vents with radial cutouts to allow for air-flow. FIG. 69 shows the system with the internal enclosure (1.0, bottom right) removed from the container, exposing the hardware of the integrated analysis system. FIG. 69 also indicates the location of the optics (4.0), pneumatics (3.0), cartridge (10.0), thermocyclers (5.0), cartridge cover (7.0), reagent card (9.0), and electronics (2.0).

Under operation, the system may draw hundreds of watts which may need to be exhausted from the chassis. Two rotary fans can draw air through a set of filters and provide sufficient cooling to maintain the internal chassis air temperature within 5° C. of ambient with two fans and <10° C. with a single fan. Fans can be brushless type to increase life time to >25 k-hr.

The air and temperature control subsystem manages thermal flow within the suitcase enclosure, the thermal cycler, and the CAE. The layout employs a forced-air, internal plenum with inputs at the sides of the Apollo 200 System and outputs filtered air at the front and back of the cartridge to facilitate adequate thermal management and minimize particle introduction.

Figure 70:
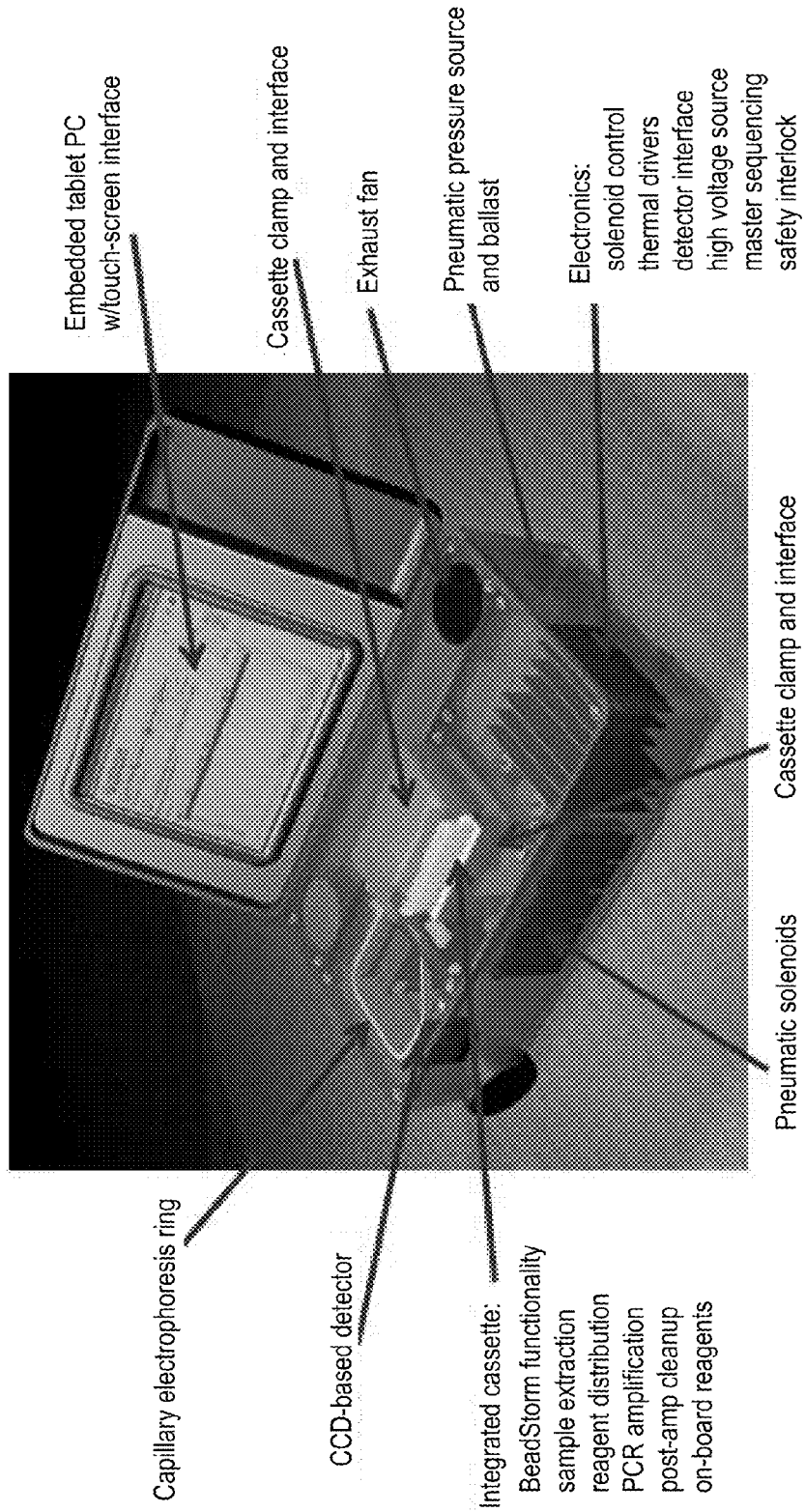
FIG. 70 shows a schematic of an encased and portable integrated analysis system.

Another diagram of an enclosed integrated analysis system is shown in FIG. 70. FIG. 70 shows a capillary electrophoresis ring for performing separations, a CCD-based detector for detecting analytes, an integrated cassette (combined disposable cartridge with reagent card), pneumatic solenoids, cassette clamp and interface (combined pneumatic manifold and cartridge cover), embedded tablet PC with touch-screen interface, exhaust fan, pneumatic pressure source and ballast, and electronics.

The computer and control software can integrate the system and provide the electronics interfaces, timing and control. The computer can be an industrial PC running Microsoft XP. Software can be Software control software. The main user interface can be a touch screen panel with auxiliary interface by monitor (VGA or higher res), external keyboard (USB) and mouse (USB) that may not included in the enclosure. A bar code reader (such as Keyence BL-180) and a GPS unit (such as an OEM module based on the Sirf-Star iii Chipset) can be connected via USB to the computer.

Figure 71:
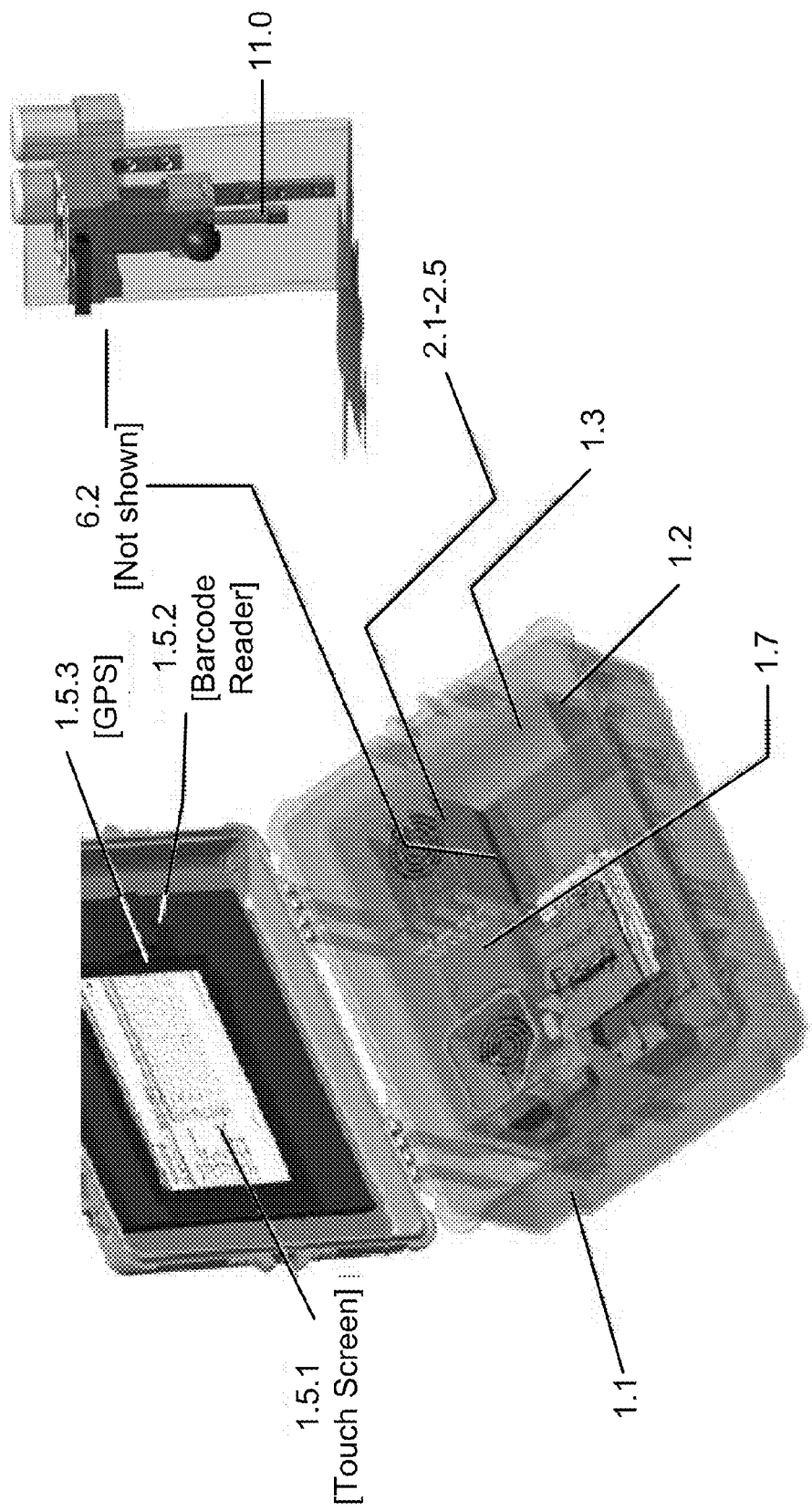
FIG. 71 shows a schematic of an encased and portable integrated analysis system and a polymer injection system.

FIG. 71 shows a view of an enclosed integrated analysis system. FIG. 71 shows a touch screen (1.5.1), barcode reader (1.5.2), GPS (1.5.3), case (1.1), power supplies (1.7), chassis and structure (1.2), Internal partitions and baffles (1.3), electronics (2.1-2.5), separation and polymer fill device (6.2), and separation polymer cartridge (11.0). The electronics include a communication controller (2.1), solenoid valve controller (2.2), temperature control (2.3), motor control (2.4), and sensor board (2.5).

Figure 72:
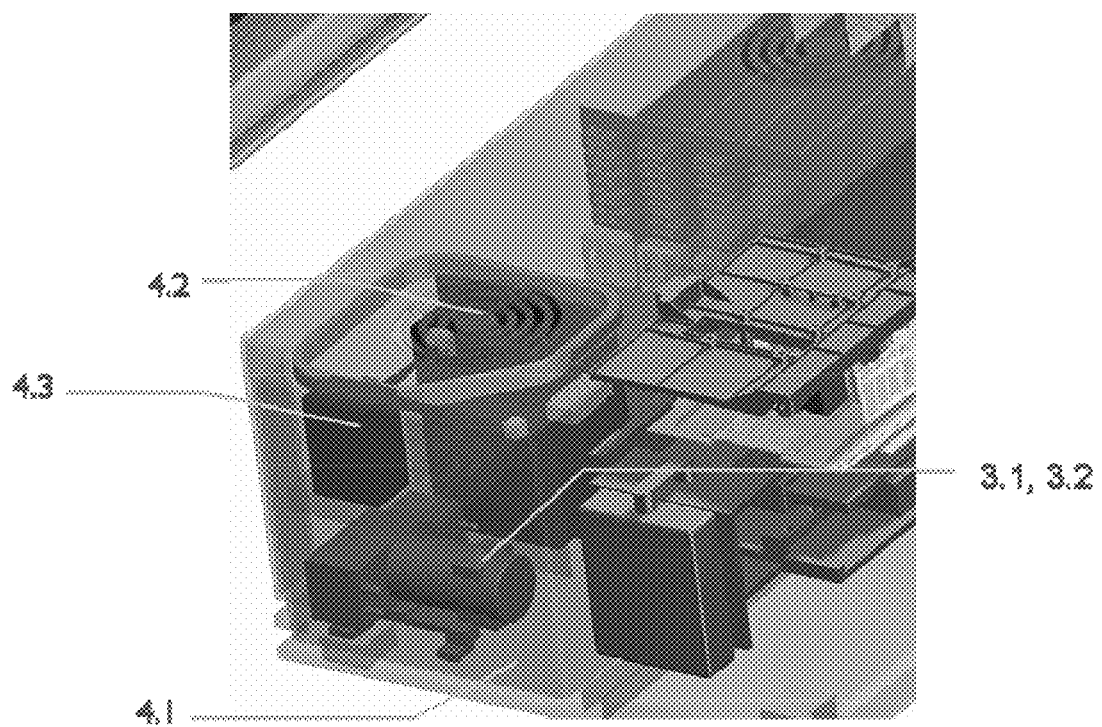
FIG. 72 shows a schematic of an optical detection system and pneumatic system.

FIG. 72 shows a close-up view of the optics and pneumatics systems of the enclosed and integrated analysis system. The optics include the alignment components and base (4.1), excitation source (4.2), detector (4.3). The pneumatics include the vacuum supply (3.1) and the pressure supply (3.2).

Industrial grade power supplies can be used to improve the life time of the system. The rating of the power supplies may not be more than 500 W. Interconnects that meet vibration standards and are proven to meet long life times can be used.

Chassis design for mounting subassemblies can include a number of structures which may utilize aluminum castings to reduce weight and cost of high volume parts. Aluminum structures can support subsystems 2, 3, 4, 5, 6 and 11 (FIG. 64). Structures utilizing sheet metal parts can support subsystems 1.5 and 2. The design can allow for reduced weight and cost while maintaining rigidity and durability to meet vibrations specifications for transportation. Structures can include internal isolation between the enclosure and system/sub-systems.

Partitions to separate the user manipulated sections, such as the cartridge loading, from the electronics and optics to avoid spillage; and baffles to keep stray light from entering the optics can be made from plastic or aluminum parts.

Figure 39:
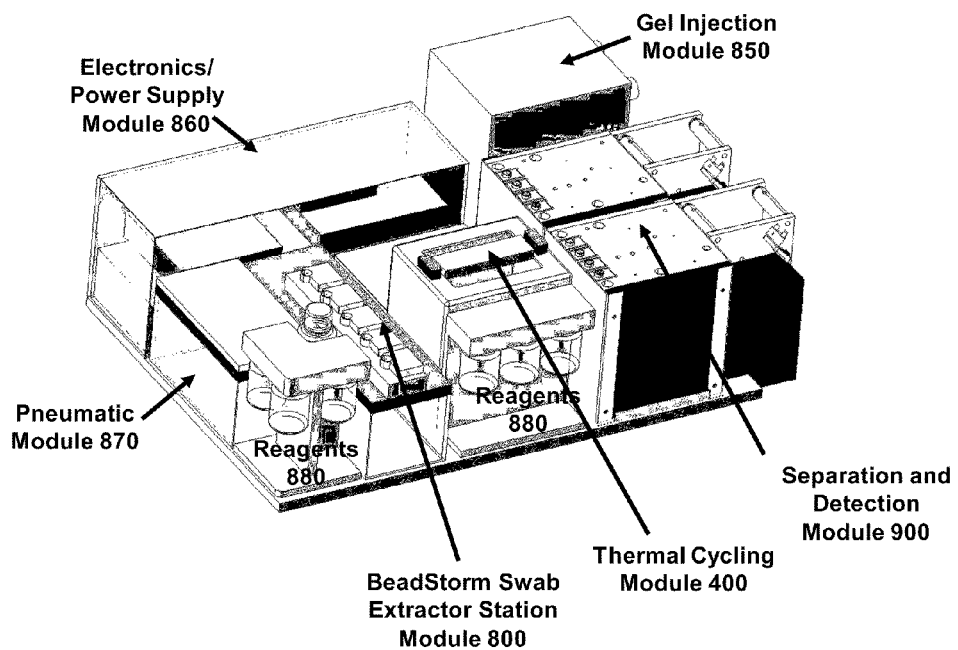
FIG. 39 shows an integrated system for nucleic acid isolation, amplification(s), separation and detection.

The chassis can be designed with a cartridge-handling subsystem. The Cartridge-Handling Subsystem interfaces the chassis with the application-specific cartridge and is located at the front center of the chassis (FIG. 39). The Cartridge-handling subsystem can be activated when the user pushes the soft button 'Load.' The Cartridge-handling subsystem can accept the cartridge from the user in a cradle similarly to a VCR mechanism which can then be actuated to move the cartridge into the chassis.

The cartridge will first move away from the user and then down. A top plate can seal the top of the cradle. Fluidic and pneumatic connections can be through the top and bottom of the cartridge through the top plate and a bottom plate both under spring force. All connections can be protected from the environment by the top plate during processing and when stored. The Cartridge-Handling Subsystem and the first cartridge are the highest risk items in the project.

As the Cartridge-Handling Subsystem completes the cartridge input, both the pneumatics and fluidics are sealed as the cartridge under the spring pressure seats onto miniature 'O-ring' seals on the bottom plate.

The unit can be constructed to meet standards in transportation vibrations and environmental extreme conditions. The unit can be utilized in a variety of case orientations. The unit can be designed to function at extreme temperatures and humidity specifications. The unit can be designed to prevent light-leaks.

Figure 73:
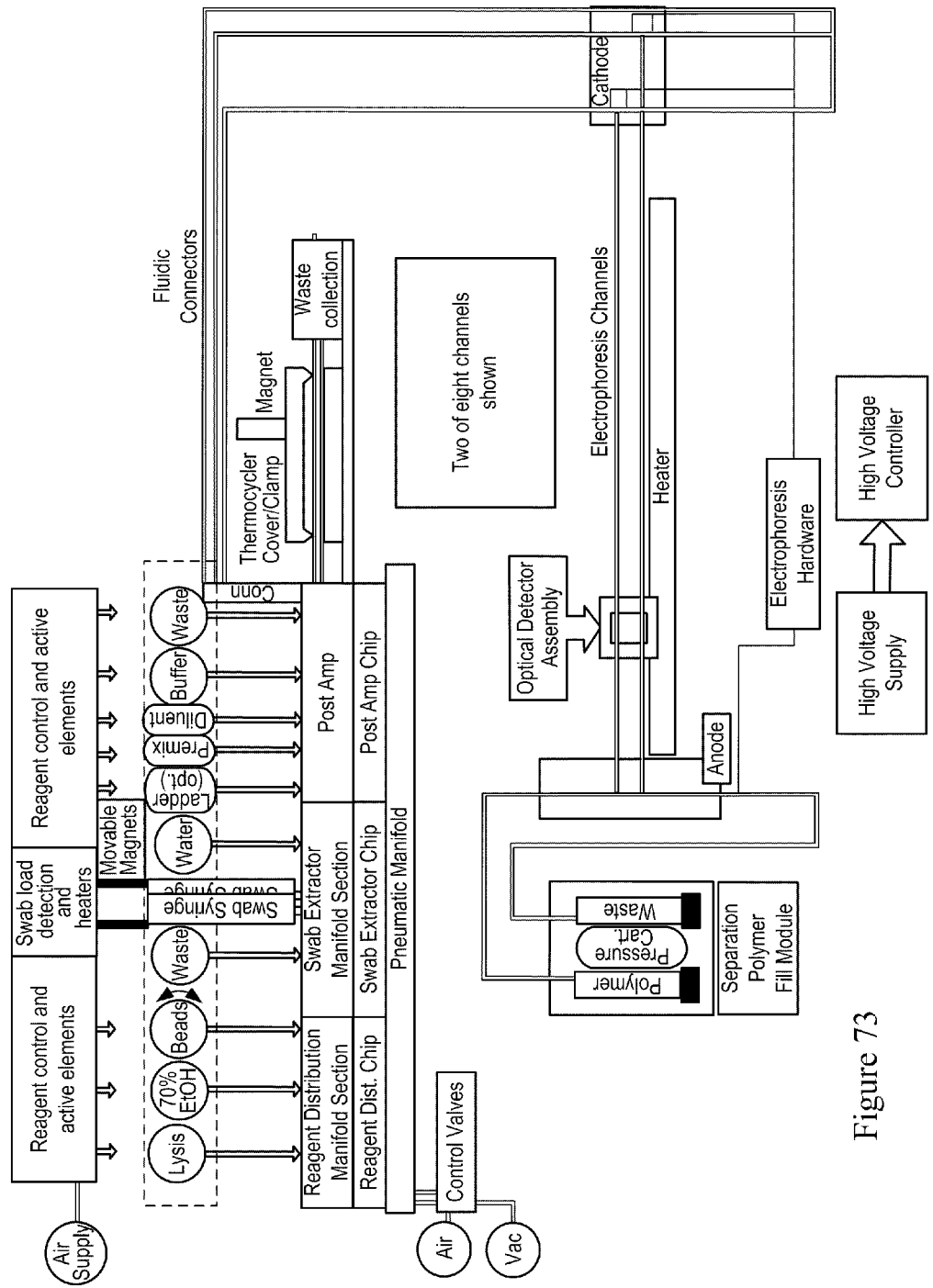
FIG. 73 shows a diagram of an integrated analysis system.

The components of the integrated analysis system and disposable cartridge are depicted in FIG. 73.

Figure 74:
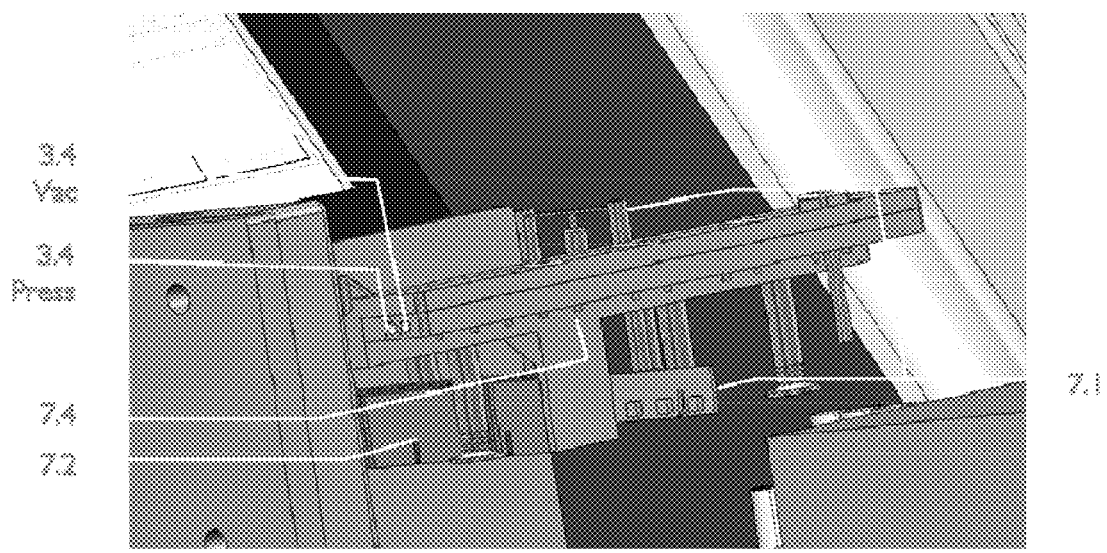
FIG. 74 shows a schematic of a cartridge cover and pneumatic components.

A reagent pneumatic assembly engages the cartridge and can perform a number of functions. A cartridge cover connected to an air supply is shown on the top left portion of the schematic shown on FIG. 73. A depiction of the cartridge cover is shown in FIG. 74. FIG. 74 shows the air supply ports for a vacuum source (3.4 Vac) and a pressure source (3.4 Press). The cartridge cover also includes a magnet assembly (7.1), reagent handling interface (7.4) and a heater assembly (7.2).

The Cartridge cover interfaces with the top of the Cartridge and the Reagent card. It can include several functions: Magnet positioning for magnetic particle capture in the sample extraction process, Heater positioning for the sample extraction lysis process, connection of the Cathode Tubing to feed diluted products to the Electrophoresis System, integration of pressure and vacuum to the Reagent Card, illumination for control of the Sample Loading process and Magnetic Particle re-suspension before Reagent Card activation.

A. A primary functionality of the Cartridge Cover is to align with the Cartridge, activate the Reagent Card and interface with the Cartridge to provide extended functionality. The functions can include the following, referring to FIG. 74.
    A. Magnet assembly (7.1): After lysis the DNA from the sample can be captured on magnetic particles and prepared for further processing by washing to remove contaminants and PCR inhibitors. To provide for the capture and re some or lease of the particles within the Cartridge the Cartridge Cover contains an assembly to facilitate the movement and location of an array of rare earth magnets in respect to the capture chamber on the Cartridge. This assembly consists of a magnet array and a mechanism. Magnets can be moved into and out of position to exert a magnetic force on compartments in the cartridge that can contain paramagnetic beads.
    B. Heater assembly (7.2): Cell lysis is carried out at elevated temperature, typically 60-80° C. The lysis takes place within the sample chamber which is heated by the Heater assembly. The Cartridge Cover positions the resistive heater around the sample chamber and provides interconnections to the Thermal management component of the Electronics. Temperature feedback is supplied by thermocouples in the heater.
    C. Cathode Tubing Connection (7.3): After PCR and dilution the sample, now diluted product, is moved to the Cathode Tubing for injection onto the capillary. The Cathode Tubing is connected through the Cartridge Cover and interfaced with the Cartridge by a low-pressure seal such as a face seal or ferrule type connection. This connection is leak free, clean and low dead volume.
    D. Reagent Handling (7.4): To maximize MOVe valve performance it is sometimes useful to feed the valves with pressurized reagents. Within the Cartridge Cover there are several ports that, when the Reagent Card is activated during system setup, pressurized specific reagent wells. In the same manner, the best scavenging of waste materials is often achieved with vacuum assist. Again, upon Reagent Card activation, specific waste wells may be evacuated to accomplish this. The interface with the Reagent Card is through cannulae, mounted in the Cartridge Cover, that pierce the top seal on the Reagent Card.
    E. Sample Loading (7.5): To facilitate the proper and controlled loading of samples, positive controls, negative controls and allelic ladder the Cartridge Cover can be fitted with sensors and illuminators that work in a closed circuit fashion with the software to monitor and control the activity. Depending on the Cartridge Type and run setup parameters the system can "activate" one or more, e.g., from five to all eight, of the Sample Chambers. A chamber can be activated by illuminating the chamber with an LED or other light source built into the Cartridge Cover. When a swab, FTA punch or control is inserted into the chamber it is detected by an optical sensor built into the Cartridge Cover. The system then turns the illumination off, effectively de-activating the chamber. If a sample is placed into a de-activated chamber the system enters an error mode. The illuminators and sensors are interfaced to the Sensor Board in the Electronics.
    F. Thermocycler Interface (7.6): The Reaction Tubing on the Cartridge is mechanically aligned to the Thermocycler components by the Cartridge Cover.
    G. Magnetic Particle Re-suspension (7.7): Before the Reagent Card is activated the Magnetic Particles can be re-suspended as they may have settled during shipping and storage. The Cartridge Cover can interface a re-suspension device, such as an ultrasonic probe, peizo vibration probe or mixing mechanism, to the Magnetic Particle well of the Reagent Card.

Figure 75:
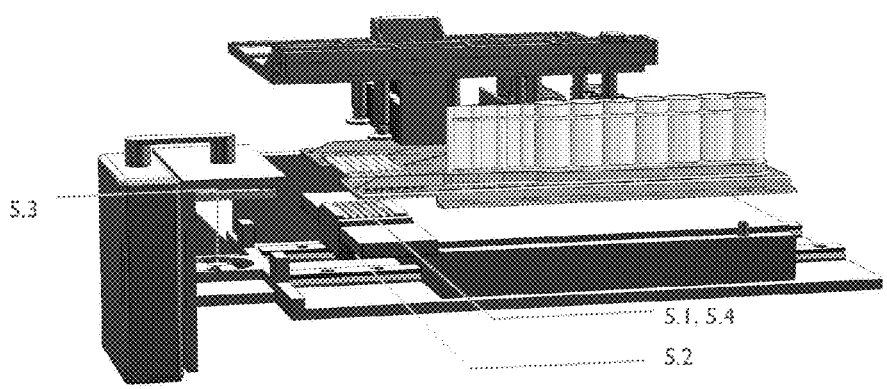
FIG. 75 shows a schematic of a cartridge cover, cartridge, pneumatic manifold, and thermocycler.

The cartridge cover can interface with a cartridge, shown within the dashed lines below the cartridge cover on FIG. 73. The cartridge cover can apply pneumatic pressure to the cartridge and/or be configured to apply a magnetic field and/or heat to one or more components of the cartridge. A depiction of a cartridge interfaced with the cartridge cover and pneumatic manifold is shown in FIG. 75. FIG. 75 also shows a fan and ducting (5.3) and thermocycling components: thermal plate (5.1), thermoelectric (5.2), and controls (5.4).

Figure 79:
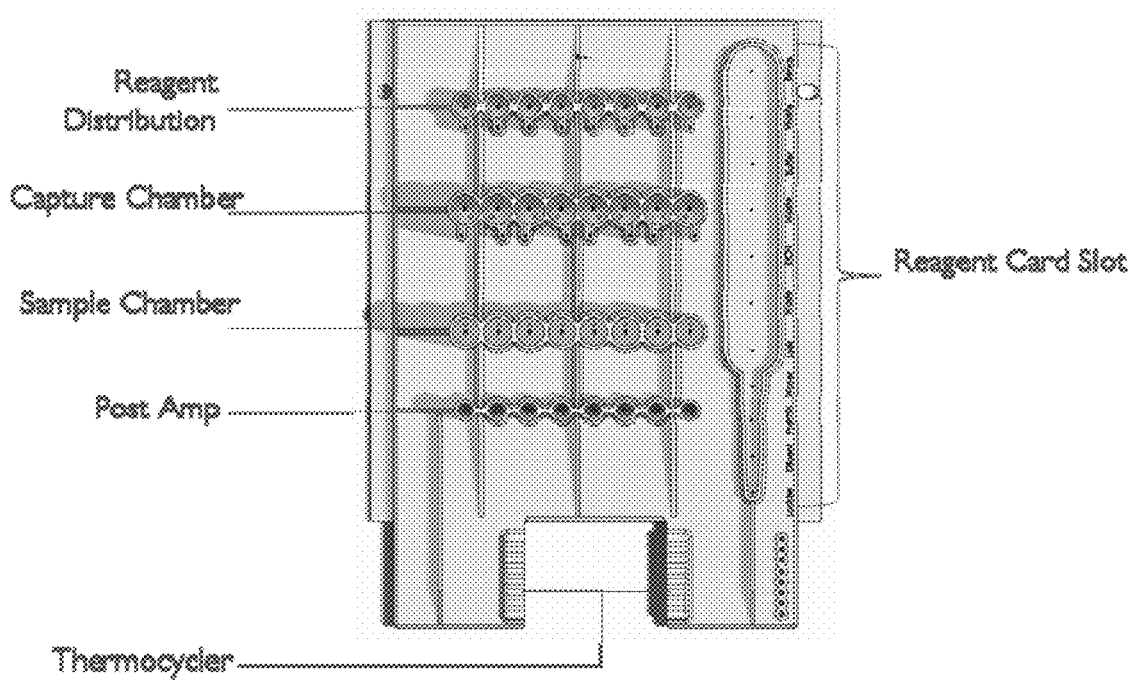
FIG. 79 depicts a top view of a cartridge without reagent cassette.

The cartridge, shown in dashed lines on FIG. 73, can include one or more chambers, fluidic connections, microchips, and/or pneumatically actuated valves. A top view of the cartridge is shown in FIG. 76, FIG. 77, FIG. 78, and FIG. 79. FIG. 79 shows reagent distribution chambers, capture chambers, sample chambers, and post amplification chambers. The cartridge can also have a receptacle for receiving reagent chambers that are on a reagent card. The reagent card can have a variety of chambers, including reagent chambers (FIG. 76, 9.0), reaction chambers, and waste chambers. The reagent card (also referred to as a removable reagent cassette) can be manufactured separately from the cartridge. The reagent card can be inserted or interfaced with a reagent card slot (shown in FIG. 79). The cartridge can be made of a piece of injection-molded plastic. The volume of the chambers, for example the sample chambers, capture chambers, and post amplification chambers can be about or up to about 0.1, 0.2, 0.5, 0.75, 1, 2, 3, 5, or 7 mL. The cartridge can have dimensions of about or up to about 1, 2, 5, 7, 10, 15, or 20 cm in width or height and about or up to about 0.2, 0.5, 0.75, 1, 2, 3, 4, or 5 cm in thickness.

The Cartridge element consists of several integrated parts. These include a piece that contains reaction chambers and that functions as a fluidic manifold. The chambers, on one side of the piece, communicate with the opposite side of the piece through ports. The opposite, or fluidic side, is engaged with fluidic chips comprising channels and diaphragm valves and pumps that move liquids between reaction chambers and reaction tubing. The chips can be attached to the fluidic side through a gasket. In certain embodiments, the cartridge comprises a plurality of chips. In this case, the fluidic manifold piece can comprise channels that fluidically connect one chip with another. Such channels are depicted, for example, in FIG. 94. They can be grooves, troughs or other depressions in the surface of the piece that are sealed by a gasket between the underside of the piece and the microfluidic chips. The Reagent Delivery fluidics, Sample extractor fluidics, the Post-amplification fluidics, the top piece, the bottom piece and the Reaction Tubing. The top piece, also referred to as the fluidic manifold, is a plastic assembly and the fluidics are three layer glass MOVe chips that direct and control the flow of reagents through the system. The assembly connects to the pneumatic manifold and interfaces with the Cartridge Cover. The Cartridge facilitates all of the sample processing up to the loading of the amplified, labeled products onto the separation column. The Cartridge contains all the waste it produces and is replaced after each run to avoid contamination.

The top piece can be a molded plastic part with chambers for the reagent fill, sample extraction particle capture, sample insertion/lysis and product dilution. It also can have a section of silicon tubing used for reactions as well as an interface section for connection to the cathode tubing and an area for interface with the reagent card. For example, the silicon tubing can be used as a thermal cycling reaction chamber that is clamped at both ends during thermal cycling. The piece is made up of several parts. The fluidics components are attached to the bottom of the top piece with double sided adhesive.

The bottom piece can function as a gasket and seals of the channels molded into the Top Piece and provides a mounting surface and passageways, called vias, to the MOVe fluidic components.

The reagent delivery fluidics can deliver a preset volume of reagent to the Sample Extractor section facilitating sample processing. This delivery relies on pressurization of the Reagent Card wells which feeds the Reagent distribution fluidic MOVe device. The MOVe device controls the filling and disposition of the reagent chamber in the top piece. Pressurized air is also available for delivery to the Sample extractor section of the Cartridge. The section is comprised of one or more MOVe chips attached to the bottom of the integrated Cartridge bottom piece. The associated manifold and chamber features are connected to the downstream sections through the top piece.

Figure 76:
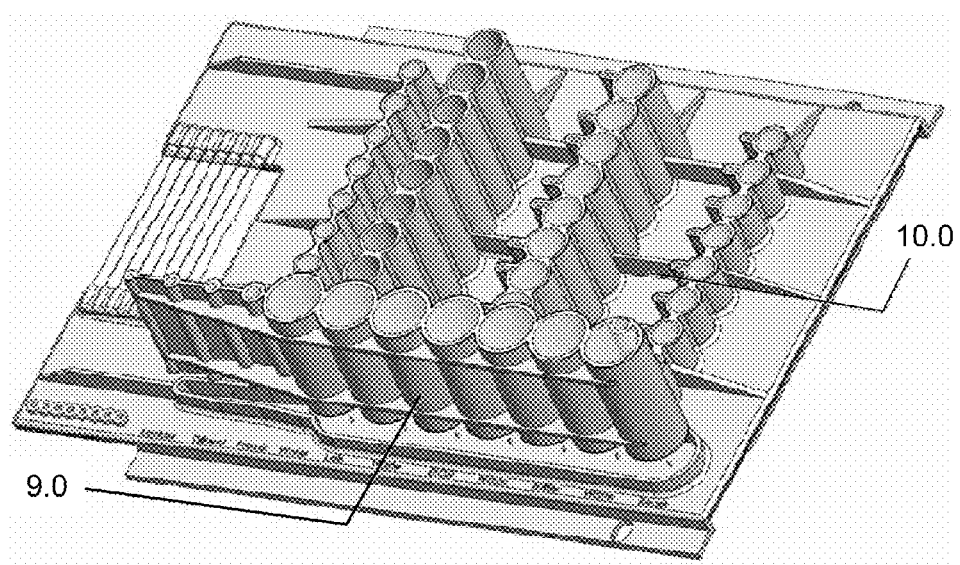
FIG. 76 depicts a cartridge with reagent cassette.

The sample extractor can include one or more syringe chambers that can be configured to receive one or more samples, such as buccal samples or swabs. In FIG. 76, the syringe chambers are the row of vertical cylinders that are second from the left. The syringe chambers are also referred to as capture chambers (shown in FIG. 79). The syringe can be heated by a component on the cartridge or by a component on the cartridge cover.

Within the Sample extractor the swab/brush/disc is rinsed, the cells are lysed, the DNA is captured on particles, the particles are cleaned and delivered to the Reaction tubing for capture. The fluidics is a three layer glass MOVe chip attached to the integrated Cartridge bottom piece. The MOVe device distributes the flow of reagents from the Reagent distribution section to; the lysis/sample insertion chamber, the capture chamber or the Post-Amplification fluidics.

The Post Amplification fluidics interfaces with the Sample Extractor section, the Dilution Chamber, the Reaction Tubing and the Cathode Tubing. These fluidics consist of one of more three layer glass MOVe devices attached to the bottom piece. The Post Amplification fluidics control the particle capture from the Sample Extractor section, meter and move premix from the Reagent card to the Reaction tubing, move product from the reaction tubing to the dilution chamber, and meters diluent from the Reagent card to the dilution chamber. It also meters and moves buffer, water and sample to the cathode tubing.

Figure 77:
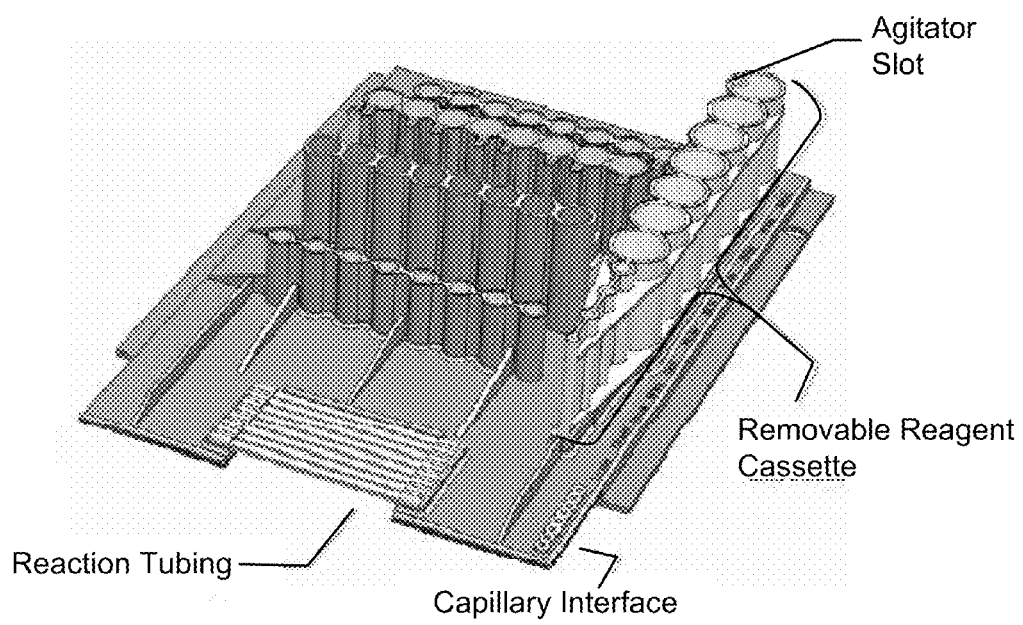
FIG. 77 depicts a cartridge with reagent cassette.
Figure 78:
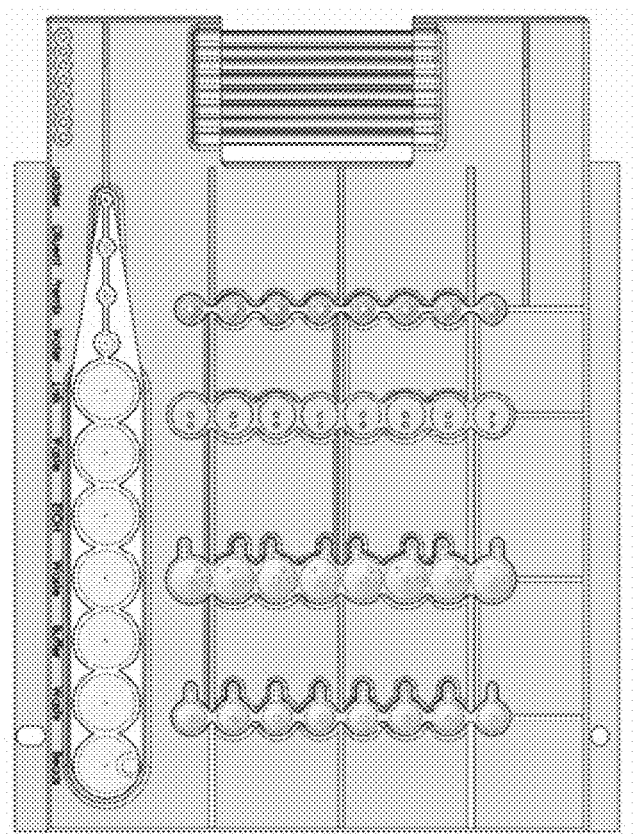
FIG. 78 depicts a top view of a cartridge with reagent cassette.

The cartridge can include reaction tubing (shown in FIG. 77). The tubes can be interfaced with a temperature controller, such as a thermocycler (shown in FIG. 73). The tubes can also be interfaced with a magnet (shown in FIG. 73).

The Thermocycler module temperature cycles the PCR-STR reactions in the Reaction tubing. It has several distinct components. The Reaction tubing is enclosed in a two piece shell that provides thermal contact and, when fully closed, pinch seals the silicon tubing. The bottom piece of the shell is part of the Cartridge. The top piece of the shell and the thermal control elements are aligned to the bottom piece and the tubing by the Cartridge cover. During particle capture and premix load the shell is in the "open" position; prior to cycling the shell is moved to the "closed" position. In the closed position the top and bottom pieces are in contact with each other which can facilitate thermal communication and pinching of the tubing which limits reaction plug evaporation and movement. Heating and cooling of the assembly is provided by a thermal electric device. The thermal control during cycling is driven by a controller which is managed by the electronics. Feed back is provided by a thermocouple permanently bonding to the top piece of the shell.

The thermal cycler temperature control can use Software objects and a thermal control board updated to 12-channels. Heating of the BeadStorm sample extraction portion of the DNA Profiling cartridge and of the capillaries of the CAE cartridge can use resistive heating monitored by thermocouples. The STR reactions can use resistive heating and fan cooling as the base case. Peltier/thermoelectric heating and cooling can also be applied as needed for extreme temperature ranges; MBI uses thermoelectric with MOVe microchips in a project with a strategic partner. The air from the thermal cycler can be output to the plenum. Control of temperature can be exerted through the MBI Temperature Control Board controlled by existing Software.

Figure 80:
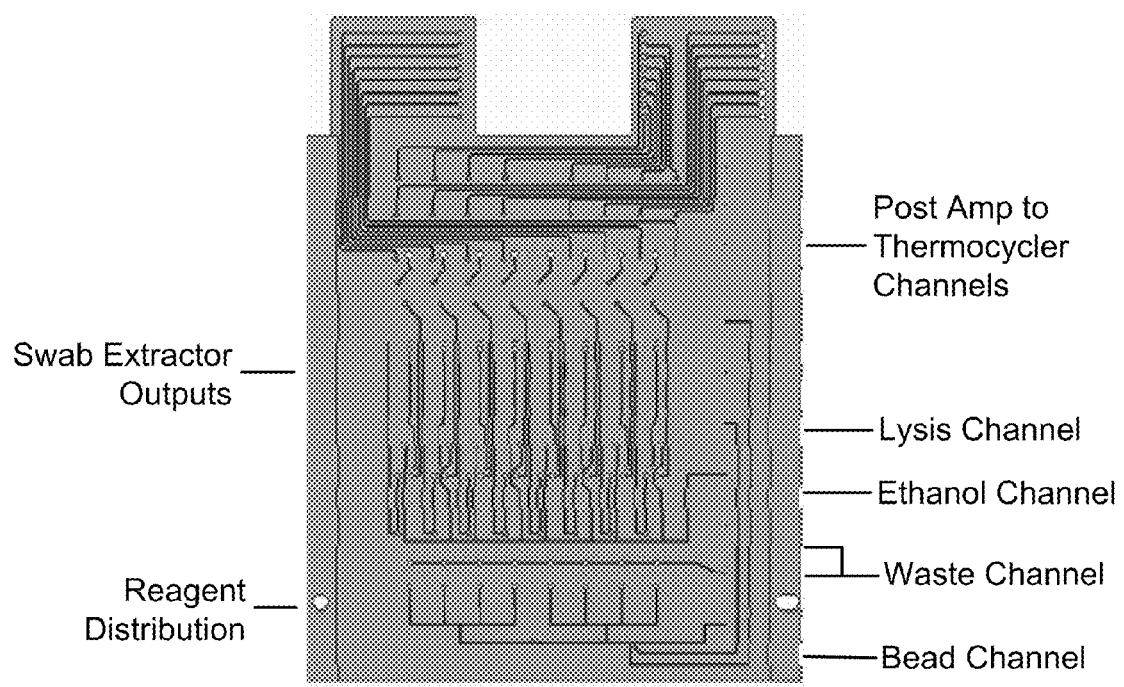
FIG. 80 depicts a bottom view of a cartridge.

The chambers can be fluidically connected to a cartridge manifold. The cartridge manifold is shown in FIG. 80. The manifolds can include one or more channels. These channels can be for swab extractor outputs, reagent distribution, post amplification to thermocycler channels, lysis channels, ethanol channels, waste channels, and bead channels.

The cartridge manifold can have one or more channels that fluidically connect the chambers on the top layer of the chip to one or more microchips. The cartridge manifold can also fluidically connect one or more microchips to each other, allowing for a fluid in one microchip to be transported to a second microchip. For example, material in the reagent chambers (shown in FIG. 73) can be transported to the swab syringe (shown in FIG. 73) by transport through the following components: the reagent distribution manifold section, the reagent distribution chip, the reagent distribution manifold section, the swab extractor manifold section, the swab extractor chip, and the swab extractor manifold section.

Figure 81:
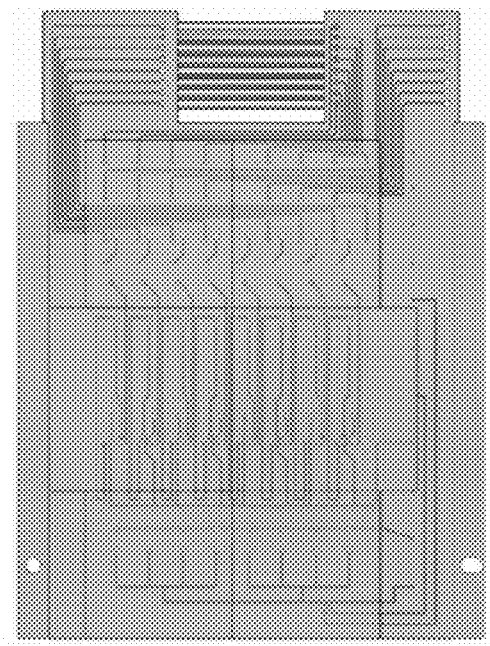
FIG. 81 depicts a bottom view of a cartridge with tubes.
Figure 82:
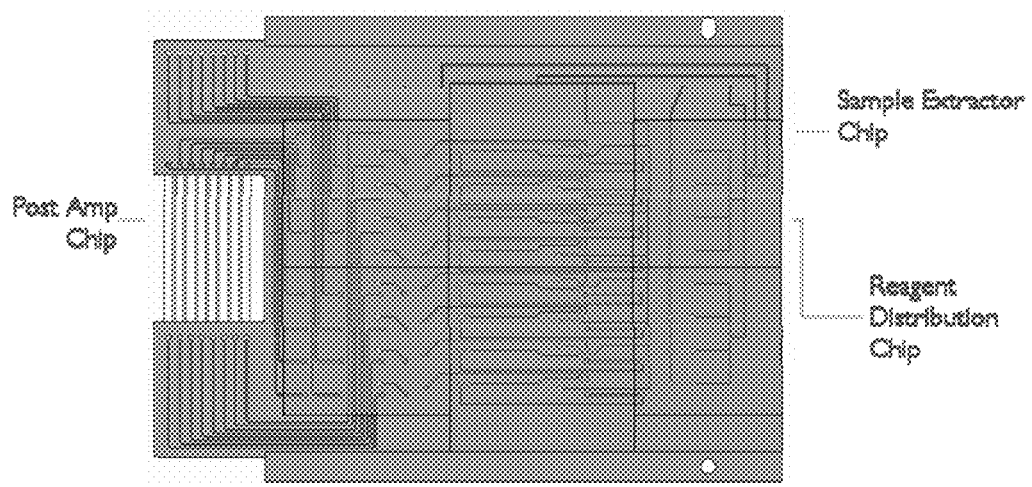
FIG. 82 depicts a bottom view of a cartridge with tubes.

Microchips are shown as square outlines in FIG. 81 and FIG. 82, which is a view of the base of a cartridge. The chips can be post amplification chips, sample extractor chips, and reagent distribution chips. The chips, also referred to as microchips herein, can have one or more pneumatically actuated valves. The valves can be used to control fluid flow by blocking or opening fluidic passages or providing a driving force for fluid movement. The valves can be controlled by a pneumatic manifold (shown in FIG. 73). The pneumatic manifold (shown in FIG. 73) can be similar to any other pneumatic manifold described herein. The pneumatic manifold can be connected to an air and vacuum source.

The chips can be fluidically connected to each other by channels in the cartridge. The channels in the cartridge can be an alternative to tubes that fluidically connected microchips, as described elsewhere herein. This can reduce the space required for the integrated analysis system and the time required to perform an analysis reaction.

As shown in FIG. 73, the reagent card can include reagent chambers for, e.g., lysis, ethanol, bead, waste, syringe, water, ladder, premix, diluent, buffer, and waste chambers. The premix can be any premix described herein. In some embodiments, the premix is a premix for performing a nucleic acid amplification reaction. The reagent chambers can have a volume of about or up to about 0.1, 0.2, 0.5, 0.75, 1, 2, 5, 7, or 10 mL. The chambers can include features or mechanisms for keeping reagents cooled, heated, or mixed. For example, the chambers can include agitators or mixers. The reagent chambers can be sealed prior to engaging the cartridge. Engaging the reagent card with the cartridge can reversibly or irreversibly place the reagent chambers in fluidic connection with the cartridge. In some embodiments, the cartridge has one or more cannulae that puncture a seal that encloses the reagent chamber. The seal can be a plastic seal or a rubber seal. In some embodiments of the invention, the rubber seal can effectively re-seal the chamber after dis-engagement. Accordingly, the card can be engaged with the cartridge in an inactive configuration. When the cartridge is engaged with a pneumatic manifold, the cover can depress the card into an active position in which the cannulae puncture the reagent chamber on one side and the cover punctures the reagent chambers from another side. This places the reagent chambers in fluid communication with the reaction chamber through channels connected by the microfluidic chips. This also allows positive pressure to be exerted to present reagent to the chips, which pump it to directed locations, as well as allowing vacuum to be exerted to pull waste presented by the chips into waste chambers on the card.

The card is designed with chambers to accommodate specific fill volumes without entrapping air. Both sides of the chambers are sealed with an elastomeric membrane. This eliminates the need for centrifugation before use. The card is fixed to the Cartridge and locked into a raised "safe" position. This is how the card ships with the Cartridge. In this position the bottom seal is aligned to the cannula on the top of the Cartridge. A safety mechanism assures that the card does not move to the lower "active" position where the cannulae on the Cartridge pierce the reagent cards seals.

The following are components of the reagent card, referring to FIG. 66.

A. Reagent Set (9.2): The Reagent Set and Reagent Card loading process and equipment are loaded with reagents adapted for performing the particular chemical reaction desired. For example, they can include reagents for performing STR analysis on one or more CODIS markers. The card can contain the following reagents:

B. Diluent (9.2.1): The diluent is used to lower the salt concentration of the PCR reaction product and introduce a size standard. The size standard in the diluent can have fragments from approximately 60 to 600 bp.

C. Wash Solution (9.2.2): The wash solution is used to clean the magnet particles and facilitate transfer to the Reaction Tubing.

D. Lysis Buffer (9.2.3): The Lysis Buffer is used to lyse the cells in the sample.

E. Allelic Ladder (9.2.4): The Allelic Ladder is included on one type of Cartridge. The Allelic Ladder is used to establish a standard position for all the possible Loci sizes. When used, the Allelic Ladder takes the place of one channel, during the sample loading process this channel may not be loaded with a standard or sample.

F. Capture Particles (9.2.5): The Capture Particles are used to facilitate the isolation, purification and volume reduction of the sample DNA.

G. Run Buffer (9.2.6): The Run Buffer is used as an electrolyte in the electrophoresis process.

H. Premix (9.2.7): The Premix supplies the primers, buffer and enzyme to run the PCR reaction I. Water (9.2.8): Water is used to prepare the Cathode Tubing for the reaction products.

A single or set of small, quiet pumps can be used along with ballasts and precision regulators to supply the required pressure and vacuum. The regulators can be factory set and monitored by the system through electronic pressure transducers to assure accurate and predictable pneumatic performance at all times. MOVe valves have very low flow but require well regulated pressure. The Cartridge Fluidics manifold provides primarily for MOVe valves. The Cartridge Cover/Reagents manifold supplies the pressure feed reagents and internal pressurized air requirements of the cartridge as well as vacuum for the waste wells. This is slightly higher flow than the MOVe valves. The Mechanisms manifold is higher flow but usually may not require the same accuracy of regulation.

The pneumatic manifold provides for the mounting of the Cartridge and the control interface to the MOVe fluidics. The manifold has 3-way solenoids with a delivery port switching between vacuum and pressure. The solenoids are addressed by the Solenoid Valve Controller component of the electronics sub-system. The solenoids are mounted in a manifold that distributes the pneumatics to ports that align with inputs on the bottom of the MOVe microfluidic chips that are part of the Cartridge. This manifold also serves as the alignment and interface component to the cartridge.

Figure 83:
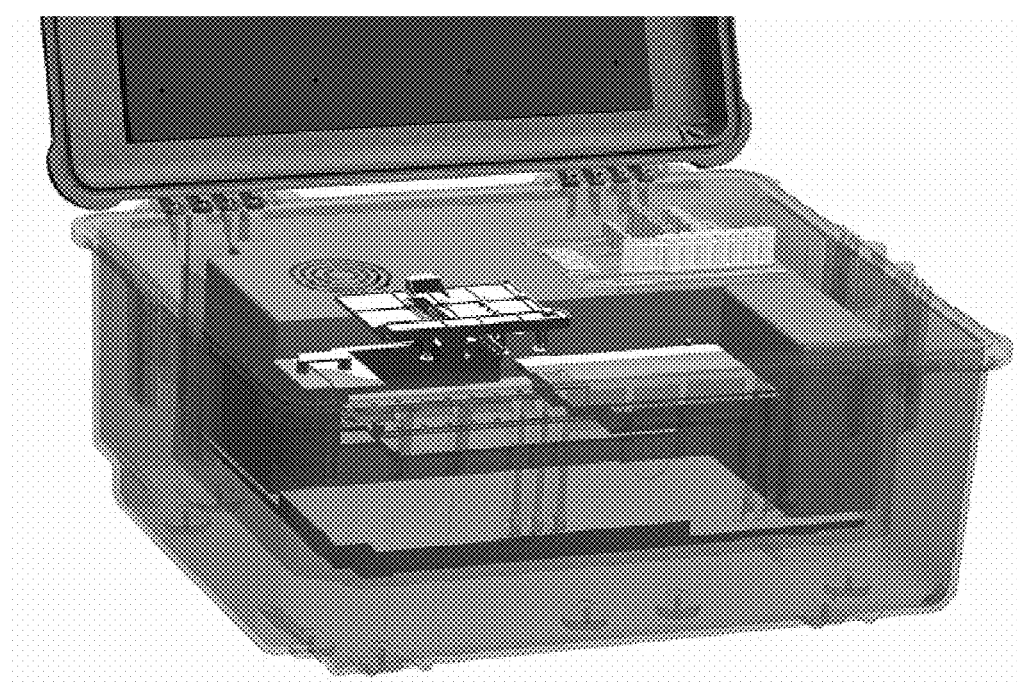
FIG. 83 depicts loading of a cartridge into an encased integrated analysis system.
Figure 84:
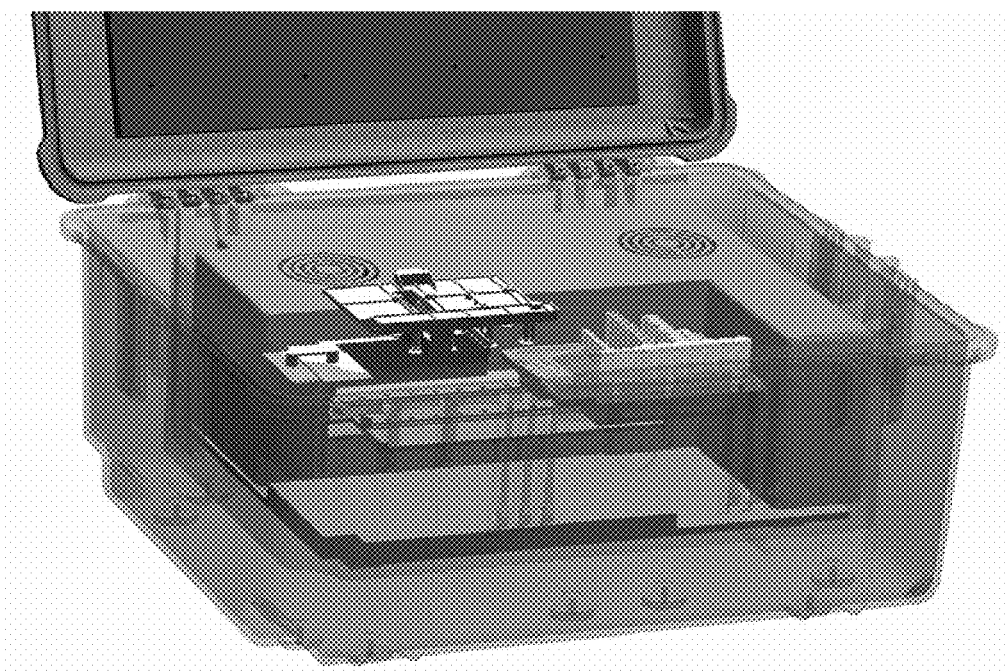
FIG. 84 depicts loading of a cartridge into an encased integrated analysis system.
Figure 85:
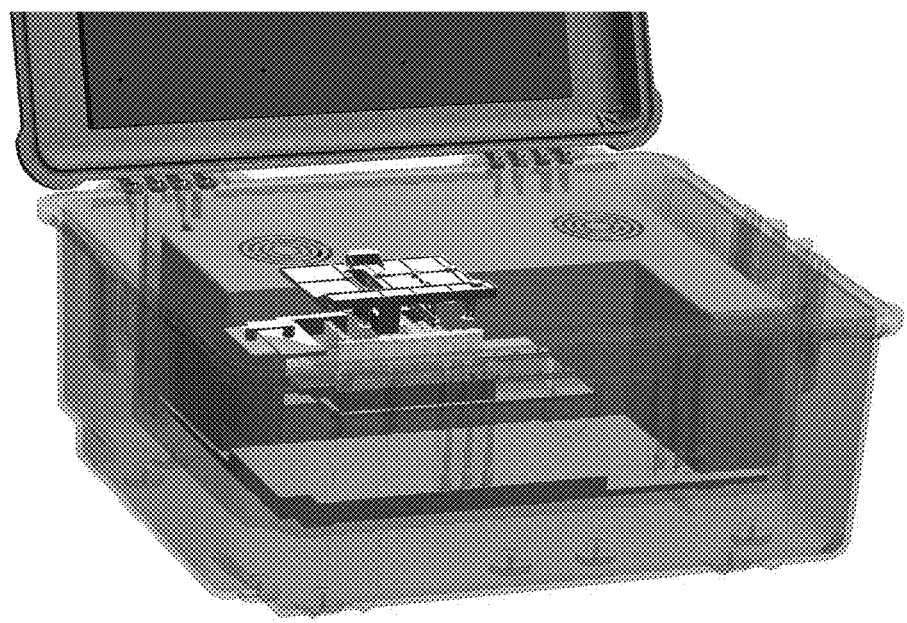
FIG. 85 depicts loading of a cartridge into an encased integrated analysis system.

The pneumatic manifold can be integrated into the chassis of the encasement such that the pneumatic manifold can be moved away from underneath the cartridge cover. This can facilitate loading of the cartridge into the integrated analysis system. FIG. 83, FIG. 84, and FIG. 85 show loading of a cartridge into an integrated an encased analytical system. FIG. 83 shows the pneumatic manifold in a position that is not underneath the cartridge cover. In FIG. 83, the cartridge is positioned above the pneumatic manifold. FIG. 84 shows the cartridge engaged with the pneumatic manifold. The pneumatic manifold can then be moved or slid to a position such that the cartridge can be engaged with the cartridge cover, as shown in FIG. 85. FIG. 69 shows the cartridge in a position such that the cartridge is engaged and fluidically connected with the cartridge cover and pneumatic manifold.

To maximize MOVe valve performance it is sometimes can be useful to feed the valves with pressurized reagents. Within the Cartridge Cover there are several ports that, when the Reagent Card is activated during system setup, pressurized specific reagent wells. In the same manner, the best scavenging of waste materials is often achieved with vacuum assist. Again, upon Reagent Card activation, specific waste wells may be evacuated to accomplish this. This manifold is a mixed manifold of 3-way solenoids delivering either pressure or vacuum to the output port. The third port is generally vented to atmosphere. The solenoids interface with the Solenoid Valve Controller component of the electronics.

Pneumatic cylinders are used to move and set a variety of mechanisms within the system. These include the Thermocycler, Cartridge Cover and components within the cover. The mechanism manifold is pressure only, utilizing 3-way solenoids to deliver pressure to the output port and vent to atmosphere with the third port. The solenoids interface with the Solenoid Valve Controller component of the electronics.

The cartridge cover, cartridge, and pneumatic manifold can be used to extract nucleic acids and perform amplification reactions, as described elsewhere herein. Amplified nucleic acids can be delivered to one or more electrophoresis channels (shown in FIG. 73) through fluidic connectors (shown in FIG. 73). The electrophoresis channels can be electrically connected to a cathode and anode. The cathode and anode can be electrically connected to a high voltage controller (shown in FIG. 73). The electrophoresis channels can be filled with separation polymer using the separation polymer module (shown in FIG. 73).

The Electrophoresis hardware consists of the High Voltage Supply and Control, the Separation Polymer Fill Device and the Capillary Array Thermal Control. It also facilitates the mounting of the Capillary array. The thermal control provides precise heating of the capillaries during electrophoresis.

The cathode is part of the Capillary array and held in place by the Electrophoresis System hardware. The anode is part of the Separation Polymer Fill Module and is connected to the Electrophoresis System hardware. The high voltage control is an MBI HV board switching an OEM high voltage source. This action is managed and monitored by the electronics. High voltage is supplied to the anode electrode while sixteen cathode electrodes (two per channel) are held at ground. Current monitoring is done between the cathodes and ground and is monitored for individual channels on the MBI HV board. The cathode electrodes are part of the Capillary Array and connections are made to the HV system during array installation. The anode electrode is part Separation polymer fill module and the electrical connection to the cathode is through electrode immersion in the separation polymer.

The Separation polymer fill provides separation polymer to the capillaries through an interface at the anode. It connects to the Electrophoresis System hardware for anode high voltage supply and control. The Separation Polymer Fill Cartridge attaches to the module and supplies pressure and reagent for every run. The system is pressure driven and controlled by solenoids managed by the electronics. Pressure can be monitored by electronic transducers monitored by the Electronics. Safety can be provided by passive and active pressure relief paths.

The Separation Polymer Cartridge contains the separation polymer, a pressure canister, and a waste receptacle. The assembly is installed in the system before the run. During the run the system uses the pressure to flush the anode and refill it with fresh polymer then forces the polymer into the capillary array.

The high voltages used in capillary array electrophoresis (CAE) produce substantial thermal loads that can be managed to eliminate the likelihood of thermal runaway, due to Joule heating, disturbing the electrophoretic process. CAE is generally run at elevated temperature, 40-80° C., producing a requirement of uniform thermal characteristics of the capillaries during the heat producing electrophoresis process. Affective transfer of Joule heating is required along with thermal uniformity to produce predictable, high resolution electropherograms. The heating and physical thermal management of the capillaries resides in the Capillary Array assembly. The interface and control of the temperature is through the Capillary Thermal Control component of the Electrophoresis System and the Temperature Control component of the Electronics.

The Capillary array includes the anode end connection, cathode tubing and electrical connections, window holder, heater, holder and eight capillaries; it provides for the separation of the labeled products and interfaces with the Electrophoresis System (6.0) and the Optics (4.0). The assembly is reusable and requires replacement by a trained technician at a prescribed interval, likely during regular maintenance. Replacement includes removing the old assembly, connecting the new assembly and aligning the capillaries to the Optics assembly. The anode piece interfaces the capillaries with the Separation Polymer Fill Device (6.2) and the anode electrode (within 6.1). It is also connected to a waste. The cathode tubing provides an interface between the capillaries and the Cartridge (10.0). It is also connected to a waste. The flow-through TREKI injection system utilizes two cathode injection electrodes which are permanently fixed and removed with the assembly. The window holder places and holds the detection window in the optical path and interfaces with the alignment system on the Optics assembly. The eight fused quartz polyamide coated capillaries, when filled with the separation polymer, facilitate the size mediated separation of the labeled products. Windows in the polyamide allow for the excitation and detection of the products as they move through the system. Capillary thermal control is by close contact to a material with high thermal transfer. Temperature control of the assembly is by resistive element and is driven by the Temperature Control electronics (2.3). Feed back is provided by a thermocouple.

The high voltages used in capillary array electrophoresis (CAE) produce substantial thermal loads that can be managed to eliminate the likelihood of thermal runaway, due to Joule heating, disturbing the electrophoretic process. CAE is generally run at elevated temperature, 40-80° C., producing a requirement of uniform thermal characteristics of the capillaries during the heat producing electrophoresis process. Affective transfer of Joule heating is required along with thermal uniformity to produce predictable, high resolution electropherograms. The system can utilize materials with high thermal transfer characteristics and good thermal uniformity such as aluminum and graphite coupled with powerful, flexible resistive heaters and fine resolution thermal control and monitoring to maintain tight thermal tolerances.

A detector (shown in FIG. 73) can be used to observe or monitor materials in the electrophoresis channels. The detector can be a CCD camera-based system, or any other detection system described herein.

The Optical detector assembly detects the separated labeled products and sends the data to the software. The assembly consists of excitation and collection optics, an excitation source, a prism and a camera. The excitation source is a DPSS laser which passes through specialized optics which shape the beam into a line. The line is focused on the capillary windows. The emission generated by the excitation of the fluors as they pass through the window area is collected by an objective and passed through a prism which separates the light into its component wavelengths. The output of the prism is focused on a camera which collects data in which the capillary array is in one axis and the emission spectra is in the other. Based on off the shelve reagent kits, the emission spectra can initially be separated into five bands. The number of discrete bands can increase to over seven without changing the physical design.

The electrophoresis channels and the optical detection assembly, including the detector and light source, can occupy a volume of about or less than about 0.1, 0.2, 0.3, 0.4, 0.5, 0.75, 1, 1.25, 2, or 5 ft$^3$.

In some embodiments of the invention, the integrated analytical system can include other types of analytical devices. These analytical devices can include devices for performing mass spectrometry, gas chromatography, liquid chromatography, or any other type of analysis described herein.

The control systems, including the computer and software, can allow for a user to select analysis parameters, control the hardware, and obtain data. The electronics of the instrument are built in a highly modular fashion using distributed micro controllers to handle peripheral control and management tasks, such as temperature control, switching of solenoids, and control of other actuators used in the system. A main "application processor" is responsible for communicating with computer running the user interface, and controlling and coordinating the activities of the system.

The primary user interface can be a 13" tablet-style, embedded touch screen mounted in the lid of the enclosure. Night mode with severely reduced light emission can be an option for the display. An application-specific GUI can overlay the Software instrument control and analysis software.

The user can turn on an On/Off switch, scan their fingerprint or enter through the touch screen. For the Standard User, four buttons can be displayed: Insert Cartridge, Load Samples, Start, and Stop. The GUI can be designed to also provide a gateway to an Expert User mode and an Admin Mode for replacement of the CAE cartridge, and instrument calibration and service. In the Expert Mode, the GUI can also provide the user with various options for data analysis and display and output, USB ports and plug in keyboards can also be enabled per the particular usage scenario and device configuration.

Each peripheral sub system is designed with hardware feedback and safety mechanisms to ensure that the firmware responsible for the operation of the module can determine whether the sub-system is operating properly from an electronics point of view. For example, current through solenoids and motors is monitored to make it possible to determine that the actuator connected and that it is drawing an appropriate amount of current. (It is possible, for instance, to determine whether a DC motor is stalled, running properly, or disconnected from its load simply by correlating the current through the motor to the voltage applied to drive it.)

Similarly, critical fluidics paths are monitored using optical sensors to determine whether they contain fluid, bubbles or air.

In certain critical systems, such as temperature control, redundant sensors and hardware over temperature protection are integrated to ensure that firmware errors cannot cause damage to the system. Further, the temperature sensors used for feedback to the control firmware are biased to a tightly controlled voltage that makes it possible to determine whether the sensor is attached or not.

Redundant interlock circuits are employed to ensure operator safety with regards to high voltage, exposure to fluorescence excitation light and other potential hazards.

The system uses CAN bus for communication between the micro controllers in the distributed network. (CAN is a robust serial network.) It enables fast and reliable communication of messages between modules, and can be set up enable master-slave control schemes that are highly responsive to real time events in the instrument.

The control of the instrument can be hierarchical. The user interface computer sends high level commands to the main "applications processor" which translates them to sequences of commands for the individual micro controllers. Each step of such a sequence is executed by sending a message to the appropriate controller. Commands are always acknowledged, either by the returning the requested data or with a specific response indicating the receipt of the command. When a module has completed a command of this latter type, it can send a message to the "applications processor" indicating whether the completion was successful or not. (There are commands defined that let the "applications processor" query for detailed status that may explain any failure.)

Any node on the CAN network can send a message to any other node at any time. The system uses this to deal with exceptions to normal operations. If for instance, the temperature control module cannot maintain the temperature within given limits, it can send spontaneous error message to the "applications processor" to "inform" it of the problem. Similarly the controller monitoring fluid lines for air or bubbles would send a spontaneous message to enable the appropriate action to be taken by the system (or the user) in response to the problem. Depending on the specifics of the problem, the control application may choose to abort the run, solicit user action, or simply log and ignore the issue.

When the system is started, all sub-systems run through a basic confidence test to ensure that all parts of the instrument are operating properly. The application can also choose to invoke all or part of this test at the beginning of each experiment. During operation, each module monitors its hardware feedback for signs of errors. If an error is detected, a message to that effect is sent to the "applications processor" which can take appropriate action to mitigate the problem (which may cause it to be escalated to the user via the GUI.). All errors and other significant events are logged in non-volatile memory for later retrieval to assist in troubleshooting and maintenance of the instrument.

Referring to FIG. 64, the electronic components can include the following: a communications controller (2.1) that communicates with the computer and in turn with other electronics modules to relay and monitor execution of commands; a Solenoid Valve Controller (2.3) that is responsible for operating the MOVe valves to implement various pumping and valve control modes. The controller can also operate solenoids for reagent and waste handling, as well as mechanism operation; a Temperature controller (2.3) that runs the thermoelectric devices to implement thermal cycling and reagent temperature control, as well as resistive heating elements to maintain heated regions (e.g. separations subsystem); a Motor Controller (2.4) that operates magnet mover and other moving elements; a Sensor Board (2.5) that is an analog and digital input device that monitors the state of various sensors within the system.

Software runs all applications, controls HW and provides GUI functionality. Software is designed for the interfacing and control of instrumentation and automation components. This architecture is simple, flexible, and designed to allow rapid implementation of laboratory protocols. Software utilizes a standardized state machine model that uses XML files, scripted code, and standard libraries to describe the devices needed to carry out a given process. A state machine defines operational logic for a hardware component or software service, defines methods that are externally available, and provides details about current state and data. Initial data analysis is done by MBI software while the final base calling is done by a third party expert system. The data is background subtracted and filtered then spectrally separated into its four or five dye channels. Further filtering is performed before the data is formed into an AB compatible file and the expert software analysis and call is initiated Software is composed of four primary sets of code, as follows, referring to FIG. 65:
  A. Core (12.1): A windows service and set of libraries that implement a set of state machines (one for each hardware module). A state machine defines operational logic for a hardware component or software service, defines methods that are externally available, and provides details about current state and data.
  B. GUI (12.2): A simple graphical user interface communicates with the core to allowing the operator to run and monitor process scripts.
  C. Scripts (12.3): Process scripts constitute the operation logic that controls the hardware to carry out the logic of defined protocols. Scripts are compiled and run dynamically, thus providing great flexibility in modifying the logic of the system.
  D. Data Analysis (12.4): Initial data analysis is done by MBI software while the final base calling is done by a third party expert system. The data is background subtracted and filtered, then spectrally separated into its four or five dye channels. Further filtering is performed before the data is formed into an AB compatible file and the expert software analysis and call is initiated.

VI. Example of Operation

Figure 86:
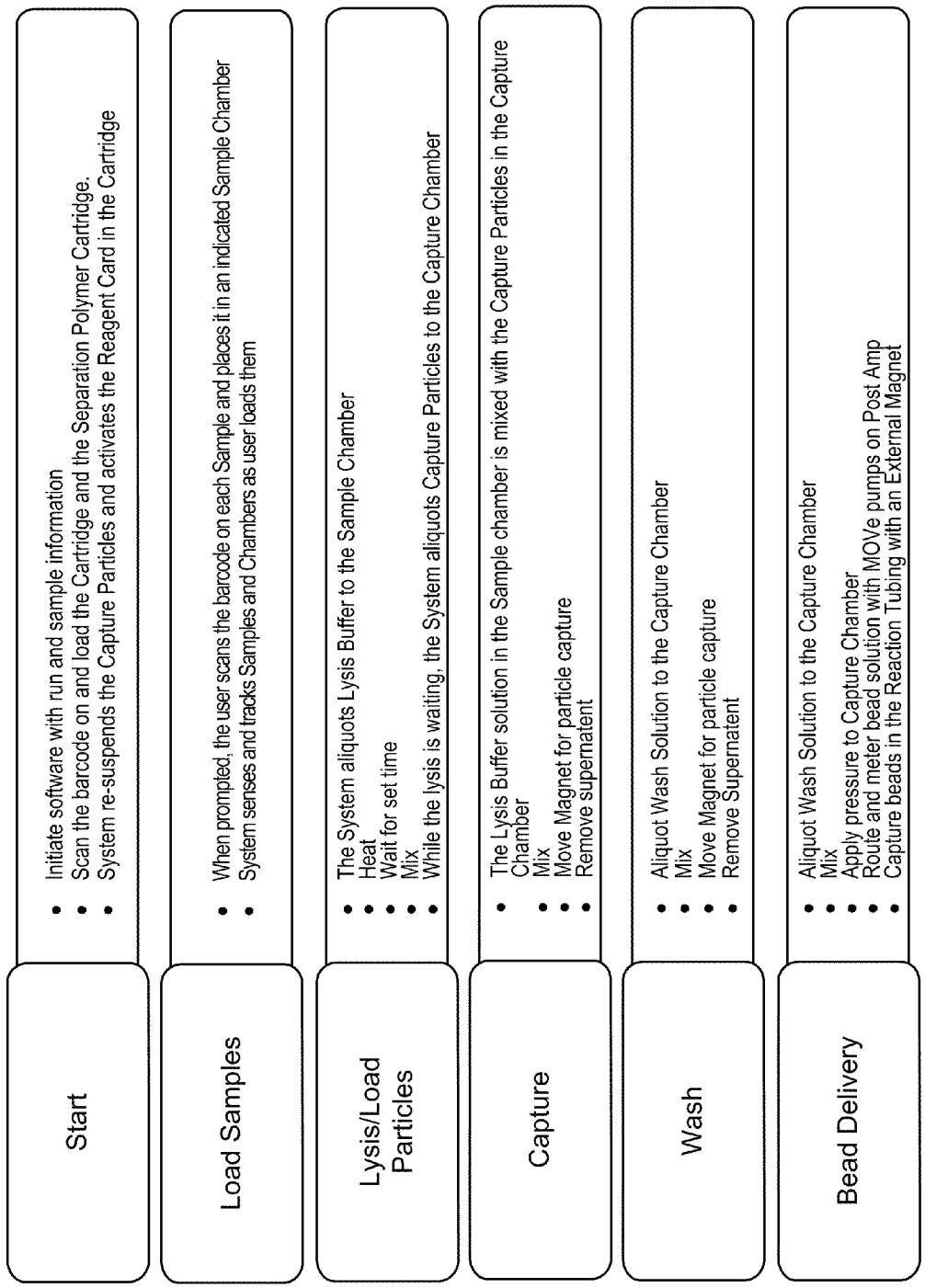
FIG. 86 shows a diagram of a sample analysis procedure.
Figure 87:
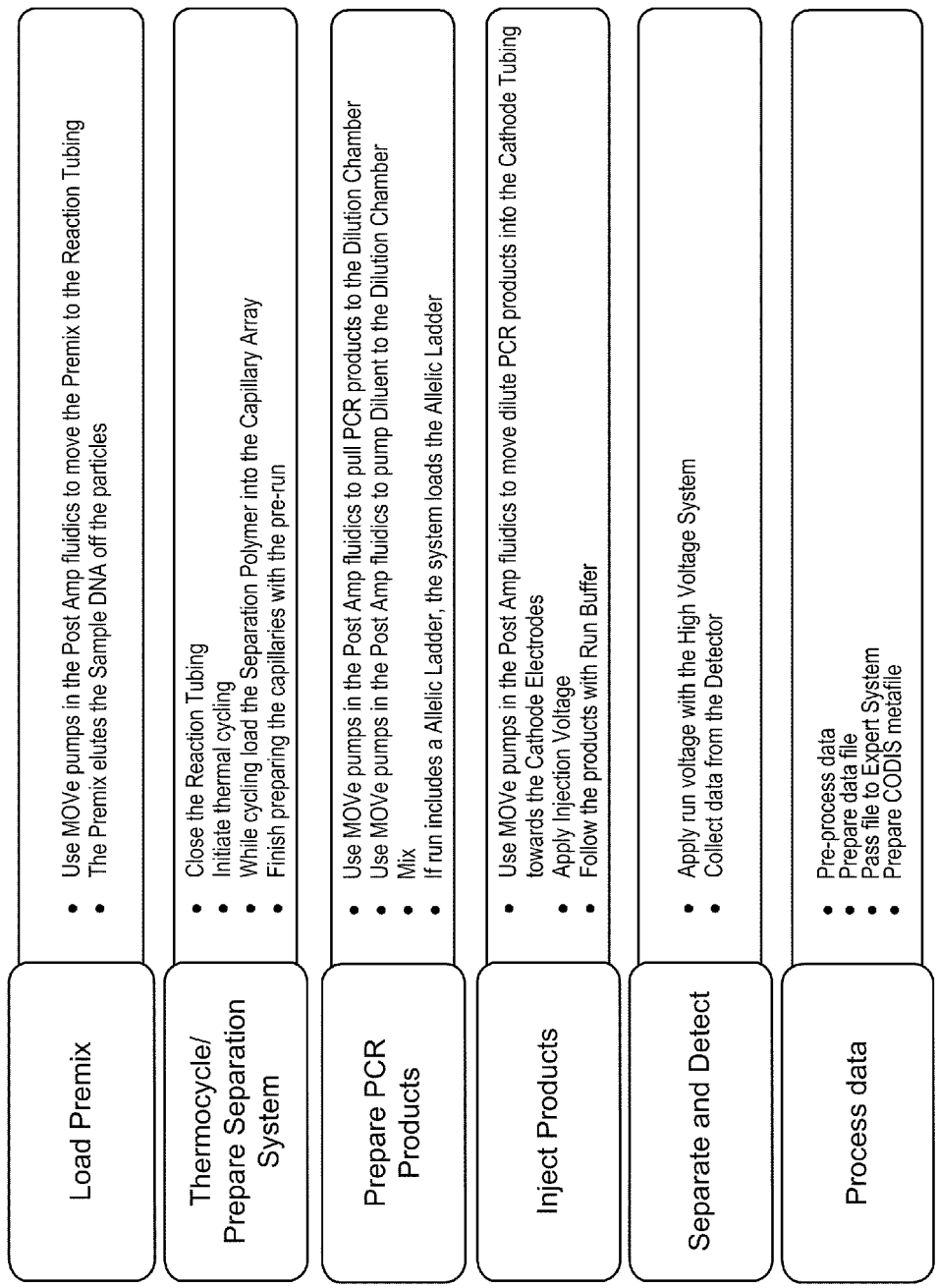
FIG. 87 shows a diagram of a sample analysis procedure.

An example of operating the encased and integrated system is shown in FIG. 86 and FIG. 87.

After powering on the system and logging on by fingerprint recognition or password, the user can push "Load' on the touch screen display. A cartridge-handling mechanism can open and the user can insert the cartridge into a mechanism which can then seat and automatically connect all liquid and pneumatic interfaces.

The user can then be prompted to add each sample. Optical barcodes can provide the chain-of-custody for sample identity and connection to associated biometric information such as photo, fingerprint, or iris scan. RFID tags may be used to transfer any associated information. Once the samples are loaded and the user touches "Go", the user's interaction can end until the system reports the results.

The cartridge is then processed by the chassis using reagents on the cartridge. The cartridge can contain all reagents and a positive and negative control. The processing of the samples in the DNA Profiling can take about 1¼ hrs. Any biological reaction can be performed in the integrated and enclosed analysis system. For example, SNP analysis or any other analysis reactions described herein can be performed.

The DNA Profiling cartridge can have four main functional areas held in a frame:
  A. Pre-processing and nucleic acid extraction using a BeadStorm-based device,
  B. STR reaction chambers in tubing,
  C. Microfluidic handling using MOVe micropumps to manipulate precious reagents and post-process microscale samples and,
  D. Reagent and waste storage The chassis Pneumatic subsystem, driven by the Control subsystem, controls all fluidic operations on the cartridge including reagent metering and distribution, mixing, and bead-based purifications. The samples are moved into the 'BeadStorm-based' area extracts nucleic acids from large volume raw and/or otherwise unprocessed samples including swabs and milliliters of liquid using MOVe microvalves to control pressure-driven flow.

The Thermal subsystem performs the thermal cycling for STR amplification in the cartridge. The pre-processed samples on beads are moved into the Thermal subsystem and the samples eluted off the beads in STR mix, and thermal cycled. The thermal cycler can be based upon the present MBI thermal cycler. The thermal cycled STR products are then diluted into size standards and pumped by MOVe micropumps to the CAE subsystem.

The CAE subsystem performs the automated separation of the STR products using capillary array electrophoresis (CAE) on a reusable CAE cartridge in about 45 min. The CAE subsystem on the chassis can have a high voltage supply and control, heat controller, and a laser-induced fluorescent detector with an imaging system capable of high sensitivity detection and data collection of separated STR products or other fluorescently labeled biomolecules.

The CAE cartridge performs the actual electrophoretic separation of the labeled products in an array of 12 separation capillaries. The CAE cartridge has the capillary array, anode and cathode assemblies, window holder, and a detection window, attached to a frame containing embedded heating segments. A separation polymer fill device accesses polymer and buffer on the single use DNA Profiling cartridge and replaces the separation polymer through an interface at the anode.

When the single-base resolution separation is complete, the digital data is processed to remove background and noise, and perform a spectral separation by MBI's Trace Analyzer. An expert system based on FSS's IQ3 then processes the data to a CODIS metafile. The metafile is queried against local and remote databases and answer if the sample's identify is produced on the screen in 2 hr after loading.

Figure 88:
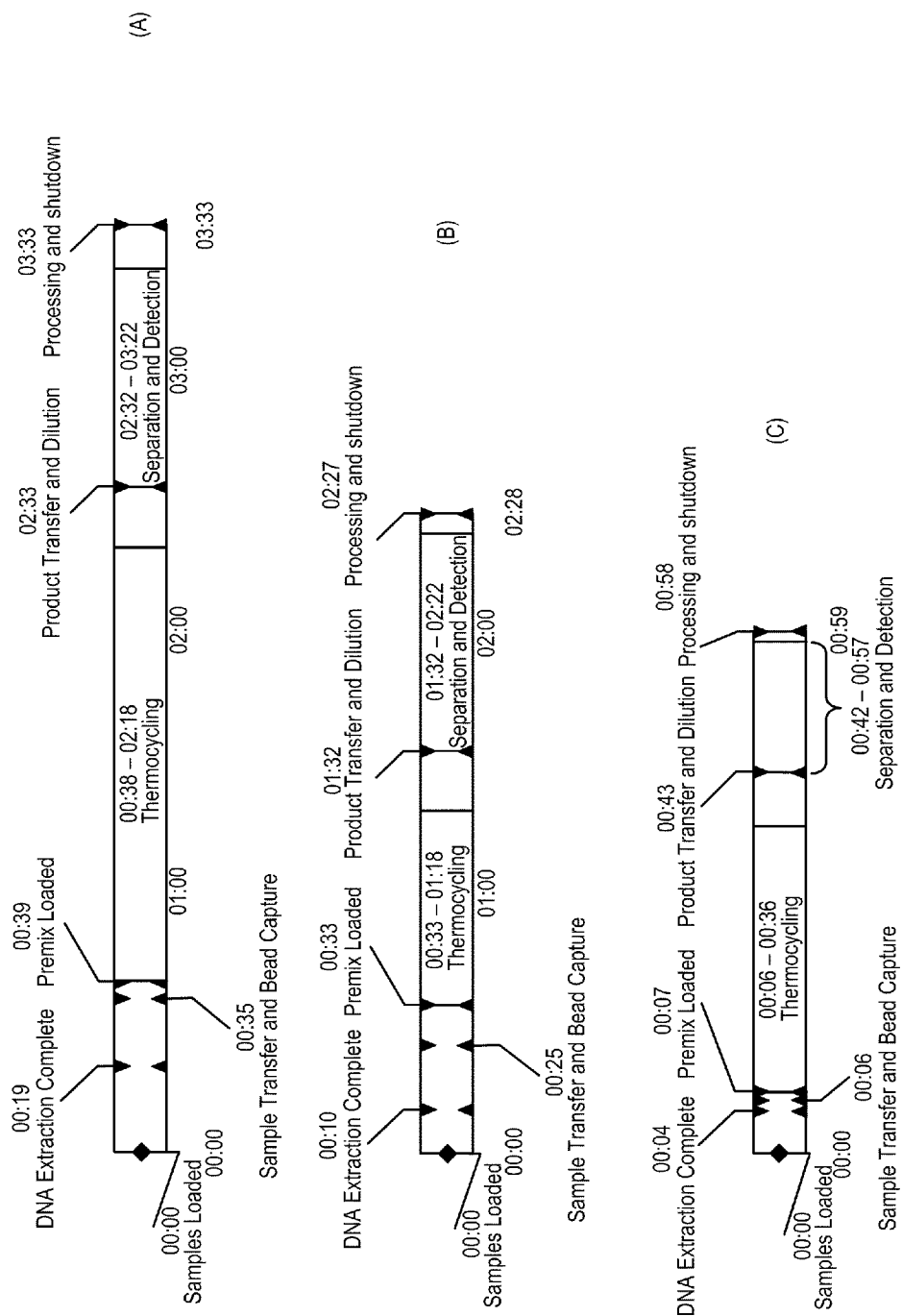
FIG. 88A shows a timeline of a sample analysis procedure.
FIG. 88B shows a timeline of a sample analysis procedure.
FIG. 88C shows a timeline of a sample analysis procedure.

The MBI integrated single channel ANDE device can have a run time of three to three and one half hours depending on the run conditions. This includes the sample entry, lysis, extraction, purification, transfer, elution, thermo-cycling of the 16-plex reaction, transfer, dilution, injection, separation and detection of the products (see FIG. 88A). The biggest single segment of time, the thermo-cycling at 100 minutes, can be significantly reduced. For example, the thermo-cycling time can be reduced to 45 minutes or less. Off system testing has shown good results with cycling times of less than one hour. Combining the intelligent primer design of the PowerPlex with advanced buffer, enzyme and dye chemistries and with efficiencies in the fluidic and separation process can allow for a processing time of less than two and one half hours (see FIG. 88B). Processing times less than 1 hr may be achieved (see FIG. 88C).

VII. Optical Detection System

The invention provides for a systems approach for the implementation of an eight channel capillary fluorescence detection and excitation sub-system.

Fluorescently labeled molecules are transported through a sieving matrix in the capillaries (200 µm ID and 50-75 µm OD). Four or more different dyes are present in the capillaries and the detector part of the system has to be able to distinguish their individual spectral signatures. Excitation of all dyes is accomplished using a solid state laser operating at 488 nm.

Figure 89:
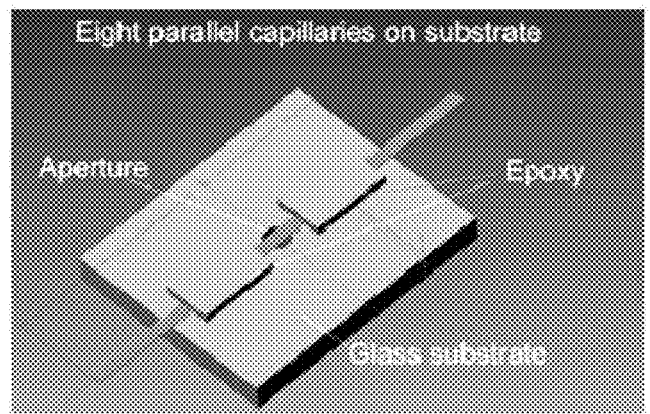
FIG. 89 shows a platform that carries an array of microcapillaries and that comprises an aperture that limits the amount of stray light collected by the optics.

As shown in FIG. 89, eight of these capillaries are held in parallel on a glass (or other substrate with similar thermal expansion properties) with epoxy adhesive. The substrate has an aperture that allows the optical system unrestricted access to the top and bottom of the capillaries.

The main purpose of the aperture is to limit the amount of material that is impinged upon by the excitation beam, which minimizes the background fluorescence of the system.

The detection system can be comprised of five elements:

A. An objective with high numerical aperture (NA=0.65) with field of view that is large enough to image the eight capillaries (1.6 mm), B. A laser rejection filter, capable of suppressing the excitation laser by at least five orders of magnitude.

C. A dispersive element (a prism) that separates the images of the capillaries by wavelength.

D. An imaging optic that projects an image of the spectrally dispersed light from the dispersive element onto the detector.

E. An area detector that is capable of capturing images of the eight parallel, spectrally separated, images of the capilliaries at a rate of five to ten images per second.

Software that is capable of separating the images of the eight capillaries and generating the spectral profile of the contents of the capillary is also an integral part of the system.

Figure 90:
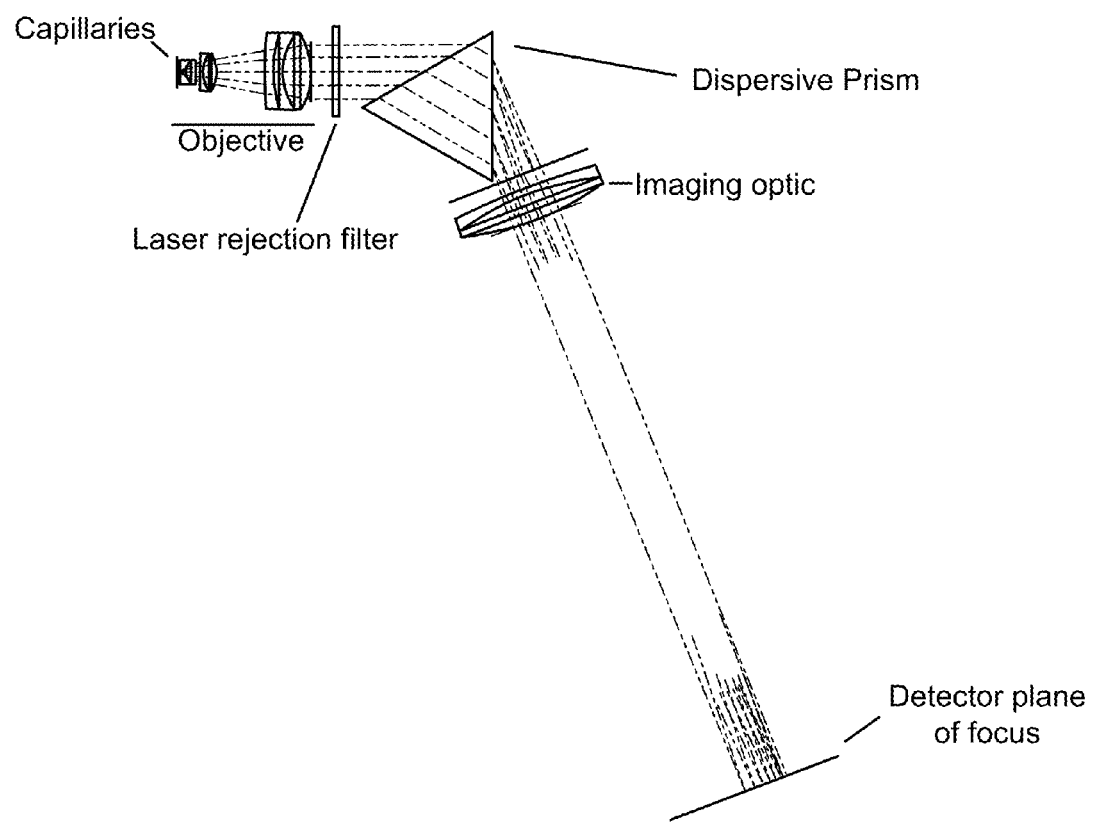
FIG. 90 shows an optical assembly.

An embodiment of the main part of the optical system is show in FIG. 90. The configuration is similar to that of a modern microscope, with an "infinity corrected" design. The objective collects the emitted light from the capillaries and collimates it at its back aperture. A prism is inserted in the collimated path to separate the image of the capillaries into its spectral components. The imaging optic (known as a "tube lens" in a microscope) then projects that spectrally separated image onto the primary focal plane of the detector.

Figure 91:
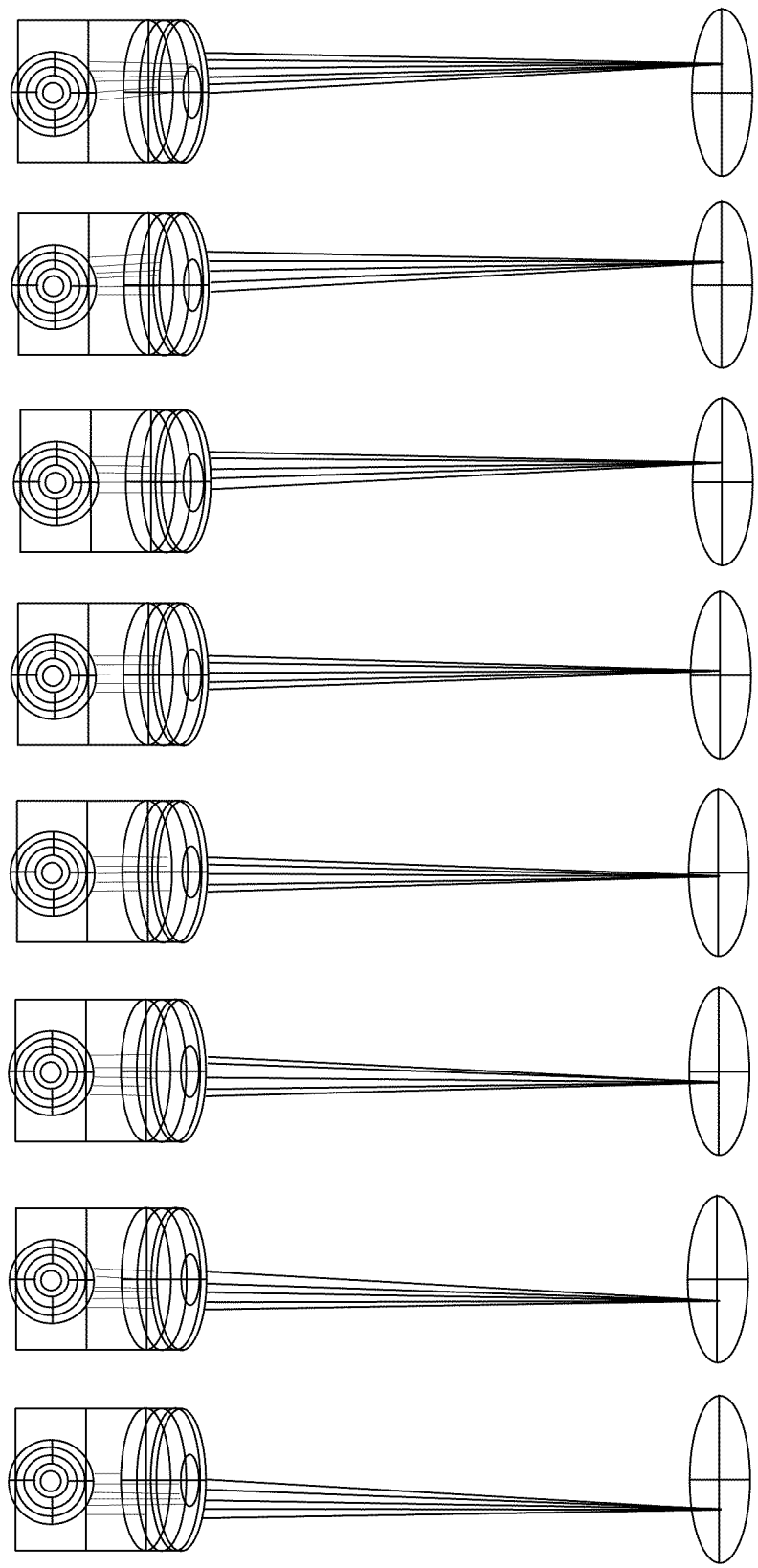
FIG. 91 shows transmission of light through a plurality of capillaries, each forming a separate image.

As shown in FIG. 91, each capillary forms its own spectrally separated image as is shown in the following image. It shows an "end view" of the optical path projecting each of the capillary images onto the primary image plane.

Although the components used in the optical path of the detection system are chosen to be low noise, there is still an opportunity for this system to generate, collect and deliver stray light to the main primary focal plane. Much of such light can arrive at that focal plane at angles that are substantially different from that of the desired signal.

Figure 92:
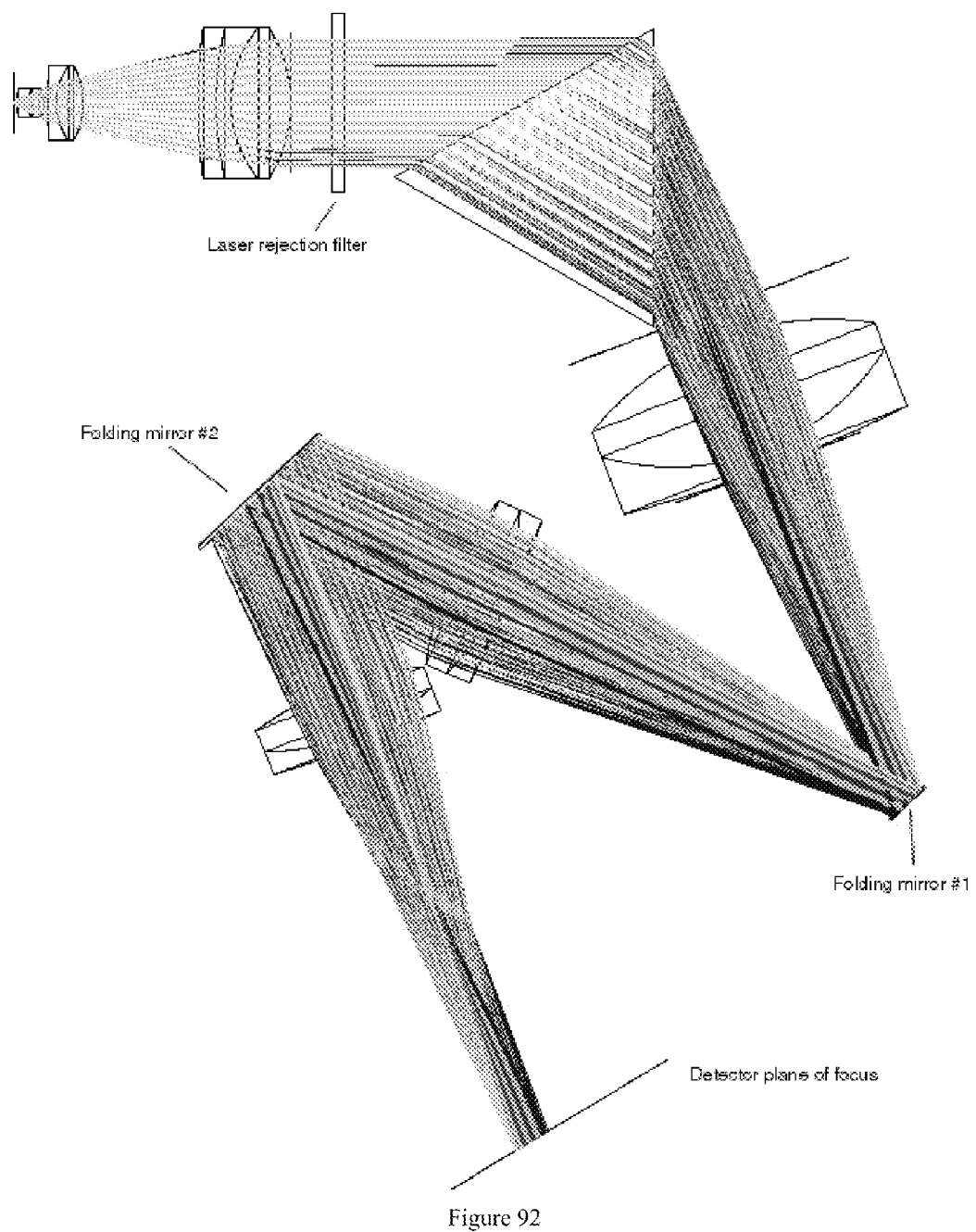
FIG. 92 shows an optical assembly comprising a dichroic mirror (folding mirror 1) that allows transmission of light from the excitation source and a second folding mirror that decreases the footprint of the assembly.

The alternative optical configuration takes advantage of that by inserting an aperture in the primary focal plane. It then images that plane to the detector using a relay optic that effectively suppresses light from outside the desired image of the capillaries. A further refinement on the idea with the aperture, is to place a dichroic mirror, the size of the image, in the primary focal plane. With properly chosen cut on wavelength for the coating, this can reject more than 90% of laser light that may have made it past the laser rejection filter. The mirror is positioned at an angle to direct light toward a detector. FIG. 92 shows the dichroic mirror as folding mirror #1.

The purpose of folding mirror #2 is primarily to reduce the foot print of the optical path, and to provide an easy way to align the image on the detector. The coating on that mirror could, however, also be of the same kind as that of folding mirror #1, in which case further laser rejection would be possible.

The detector for the system can comprise any photodetector. In one embodiment, the photodetector is a scientific grade, moderately cooled, two dimensional CCD camera.

Figure 93:
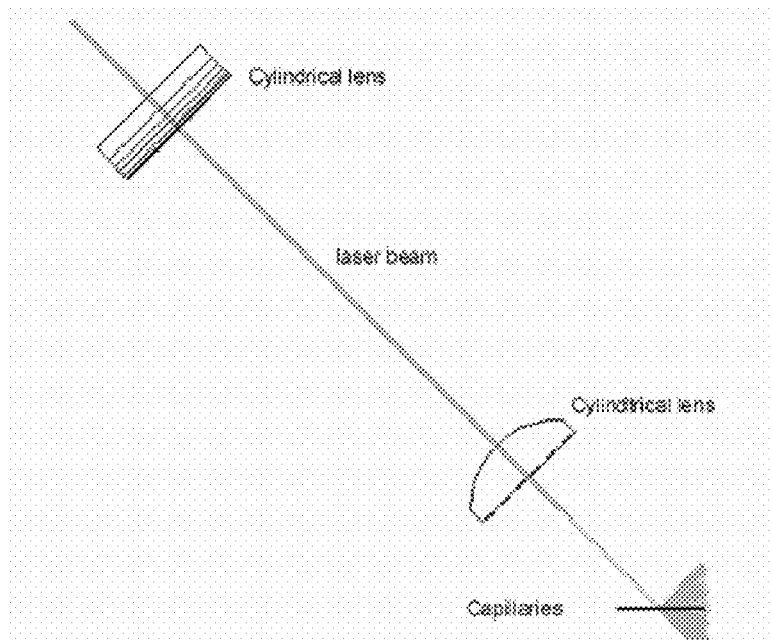
FIG. 93 shows the direction of excitation light at an oblique angle to the plane on which an array of capillaries is arranged, such that light passing through the capillaries is not directed normal to the plane where emitted fluorescent light can be collected.

The excitation of the fluorescent dyes in the capillaries can be done using a 488 nm solid state laser. The laser is projected onto the capillaries from a direction opposite of the detection system, as shown in FIG. 93. The capillaries are arrayed substantially in a plane. If light is directed orthogonally to the plane, the excitation light passes through the capillaries and is detected by the optics, interfering with sensitivity of detection. In order to avoid capturing the majority of the laser light in the collection system, the excitation is projected onto the capillaries at an oblique angle with respect to the normal orientation. In this way, the light passing through the capillaries avoids and is not collected by the collection optics.

The optical model shows how the laser beam is scattered in the capillaries, generating a "plume" of scatter that is outside the capture aperture of the collection optic. (It would be "looking" straight up at the intersection between the laser beam and the capillaries in the image above.)

Figure 94:
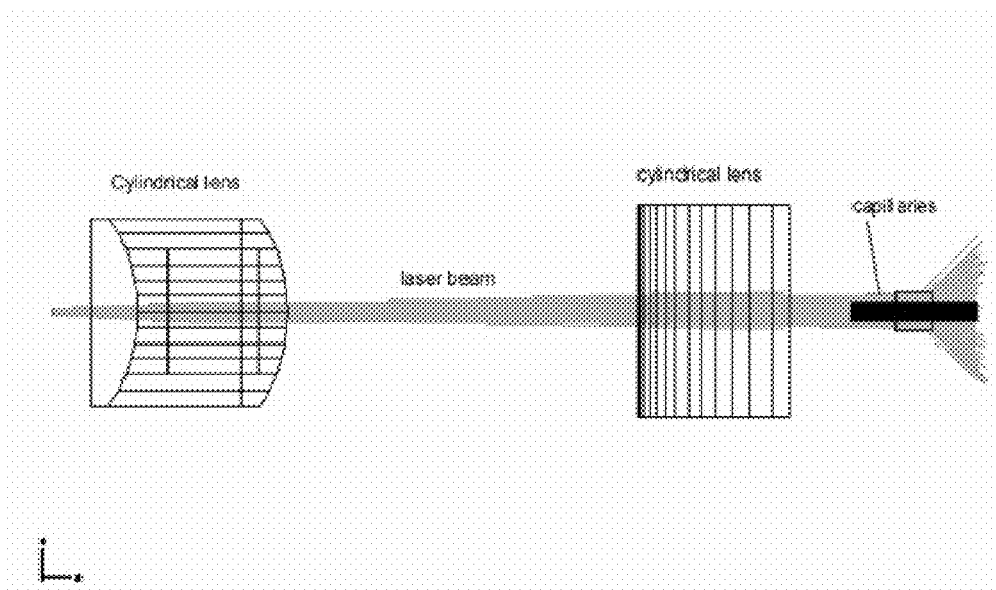
FIG. 94 is a top-down view of the configuration of FIG. 93.

FIG. 94 shows the excitation path from above. It shows the laser beam slightly diverging from its source. That is because the system uses either an "Engineered Diffuser" or a Powell lens to convert the Gaussian intensity profile of the laser to a uniformly illuminated line of light. This line is then projected (by the cylindrical lenses) directly onto the capillaries which act as very short focal length cylindrical lenses, effectively focusing the illumination energy inside the themselves.

Figure 95:
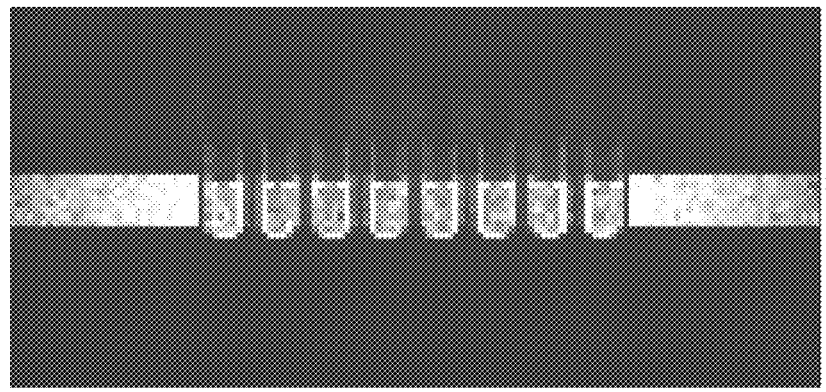
FIG. 95 shows an image produced by eight capillary tubes that carry a fluorescent species and that have been excited by light.

FIG. 95 shows a simulated image of the capillaries showing the illumination intensity in pseudo color.

EXAMPLES

Example 1

Operation of a Cartridge for Nucleic Acid Purification

Figure 45:
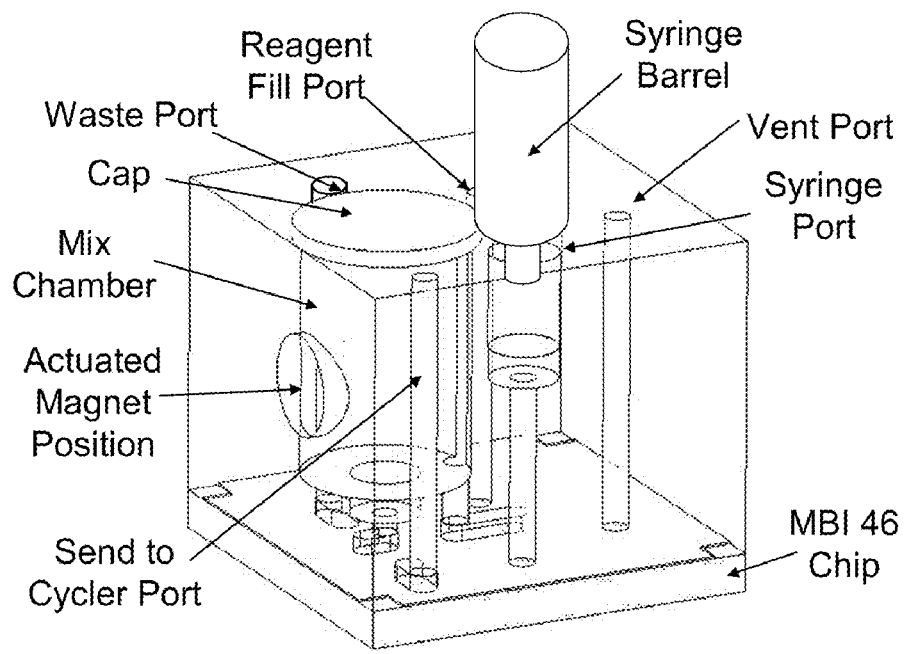
FIG. 45 shows a microfluidic microchip with MOVe valves that controls flows in a cartridge.

This example refers to the use of a device comprising a cartridge mated to a microchip. The numbers refer to the cartridge of FIG. 3 and FIG. 4 mated to a microchip with the circuit architecture of FIG. 5. This sub-assembly also can be fluidically connected other sub-assemblies in the instrument of FIG. 6. For reference, a cartridge mated with a microchip also is shown in FIG. 40 and FIG. 45.

Nucleic acids can be purified from a wide variety of matrices for many purposes including, but not limited to, genotyping, identification, forensics, gene expression, gene modification, microRNA analysis, ribotyping, diagnostics, or therapeutics. The input sample can be a solid, swab, liquid, slurry, aerosol or a gas.

For molecular diagnostics and forensics, swabs are commonly used. A buccal swab can be taken using a swab with an ejectable tip and the swab ejected into a syringe attached to connection 7 of FIG. 4. Connection 5 of FIG. 4 leads by tubing or capillary to a reagent manifold that can select a single reagent from multiple reagents by opening a full scale valve or by opening a MOVe valve with the reagents either under pressure or moved by vacuum. MOVe or other micropumps on microchip 2 of FIG. 4 can also move the fluids or gases.

In one embodiment, human and other cells in a swab are first lysed using a buffer with a heated chaotrophic agent and/or other commercial-off-the shelf (COTS) chemistries in a syringe inserted into port 7. The lysate is transported to a DNA isolation chamber (FIG. 4 #3) where paramagnetic beads have been added from a reservoir to adsorb nucleic acids onto the beads. A moveable magnet is then actuated to capture the beads onto the side of the isolation chamber where they are washed automatically using a buffer. The purified DNA, still bound to beads, is then pumped through a small diameter tube 250 where multiplexed PCR is performed. Pre-scripted Software automates the complete process. The Software defines a set of communication and command protocols in a standardized automation architecture that is simpler, more flexible, and quicker to implement than other software development approaches. The Software implementation framework is based on core technologies that span multiple operating systems, development languages, and communication protocols. Software drivers wrap individual smart components of the system, greatly reducing the time needed for typical de novo system software development. This makes it relatively straightforward to integrate the operation of multiple system modules (pumps, valves, temperature controllers, I/O controllers, etc.) that are either COM- or .NET-based. Software provides a professional quality software development system for prototyping through product release and maintenance.

While DNA amplification is useful for positive identification of microorganisms, samples can be obtained from a wide variety of substrates and matrices that contain compounds that are inhibitory to DNA amplification reactions. Raw samples are most often complex mixtures that can include inhibitors such as hemes, metal ions, humic and fulvic acids, chelators, DNases, proteases, and molds. While the initial isolation of target organisms and toxins from the sample matrix by IMS may remove most of these inhibitors, lysed cell components and lysis agents can also need to be removed or diluted from nucleic acid samples so that they do not interfere with successful amplification. Raw samples are otherwise unprocessed samples, and may environmental, biological, and the like.

In one embodiment, a small volume nucleic acid purification is used. These purification methods can be used with a wide range of samples, such as blood, to aerosols, to buccal swabs. Paramagnetic beads can be used in a disclosed device to purify DNA from various sample sources. In one embodiment a microfluidic microchip can be used to sequence a nucleic acid using magnetic beads and reagents to purify nucleic acid products for sequencing in microscale reactions. In one embodiment, the microfluidic microchip is a 24-channel microfluidic microchip.

In one embodiment, polyethylene glycol (PEG)-based nucleic acid purification is used on carboxylated magnetic beads. This PEG-facilitated process can produce yields of over 80% from upstream immunomagnetic separations (IMS) captured samples. Development of a universal sample preparation module (USPM) can partly involve porting the PEG-based nucleic acid purification onto a device containing a cartridge such as the devices shown in FIG. 21 or FIG. 16. In another embodiment, Agencourt Orapure or Promega DNA IQ chemistries are used in conjunction with a device of the present invention.

Bead Dispensation and Delivery.

To purify nucleic acids, paramagnetic beads with different surface chemistries can be mixed in a reagent container. Pressure is then applied to send the reagents to connection 5. MOVe microvalves or other valves may be closed unless referred to as open. To move the paramagnetic beads into the reaction chamber (3), microvalves 180 and 150 are opened.

The beads are moved through connection 5 into channel 15 which leads to junction 190 and microchannel 191. Because microvalves 180 and 150 are open and microvalves 200 and 170, and the other microvalves, are closed, an open microfluidic connection is from microchannel 191 through microvalve 180 to microchannel 181 through microchip 152 to open microvalve 150 and microchip 151 to junction 120. Junction 120 leads to cone 13 and chamber 3, which can be filled with beads. The volume of beads supplied to chamber 3 can be controlled by timing the opening of the reagent valves and the microvalves or by filling and emptying a sample loop connected to the microchip or the cartridge.

Commercial bead based chemistries can be used in the disclosed system, including but not limited to Orapure from Agencourt (Waltham Mass.) and DNA IQ from Promega (Madison, Wis.). Orapure uses a carboxylated bead surface and SPRI chemistry while DNA IQ is an example of a silica bead and chaotrophic chemistry. Other embodiments of paramagnetic beads or chemistries to process nucleic acids can be used in conjunction with the disclosed system, including but not limited to beads with oligonucleotides, locked nucleic acids, degenerate bases, synthetic bases, conformation, nucleic acid structures, or other hybridization and specific capture methods.

Filling Chamber (3) with Beads.

For Orapure or DNA IQ beads, 450 microliters can be moved into chamber (3) using three fills of a 150 microliter sample loop 630 or 631. A movable magnet 300 attached to actuator 310 can then be moved towards cartridge (1) near the side of 3 to pull the beads to the side of chamber (3). Magnet size and orientation can be adjusted to generate magnetic fields appropriate to specific applications. Pressurized air can then be applied through the reagent manifold with microvalve 180, 150, and 110 open. The opening of microvalve 110 connects from junction 190 which connects to the reagent manifold through junction 120 and microchannels 121 and 101 to connection 100 which leads through channel 14 to connection (4) and to waste. The air can move any remaining liquid through the circuit. Air or other gases can also be used to dry beads, volatilize solvents, or for bubble-enabled mixing (described herein).

Bubbling of Gas through Chamber (3)

If microvalves 180, 150, and 220 are open, and all other microvalves closed, the pressure can force air through chamber (3) to channel 9 and down channel 19 to junction 210 through microchannels 211 and 221, through open microvalve 220 and microchannel 231 to junction 230, through channel 16 to connection 6 which can be a vent. This sequence can bubble air or other gases through chamber (3) and can be used to mix reactions in chamber (3) or to change the gas phase.

Moving Liquids and Beads from Chamber (3) to Waste

Liquids and beads can be moved from reaction chamber (3) or any other location to waste. This can be used to wash beads, flush channels, move liquids or beads to waste. When pressure is applied to connection 6 with microvalves 220 and 110 open, and all other microvalves closed, the pressure can force air through channel 16 to junction 230 to microchannel 231, through open microvalve 220 and microchannels 222 and 221, though junction 210, and channels 19 and 9 into reaction chamber (3) and through junction 120 through microchannel 121, open microvalve 110, microchannel 101, channel 14 and to connection 4.

The equivalent effect can be obtained by applying vacuum to connection (4) if connection 6 is a vent without any additional control of air pressure. The air pressure or vacuum can move any liquids in chamber (3) to the waste connection 4.

When magnet 300 is close to chamber (3), paramagnetic beads can remain on the side of chamber (3) and the result is that the liquid is removed. When magnet 300 is far enough from chamber (3), paramagnetic beads can not remain on the side of chamber (3) and the result is that the liquid and beads are removed.

To clean paramagnetic beads, the beads are pulled to the side of chamber (3) with magnet 300 (see FIG. 6) and the liquid removed to waste. 450 microliters of buffer can be dispensed from the reagent manifold and added to chamber (3) by opening microvalves 180 and 150. The beads can be released if desired and then recaptured by moving the magnet 300 and the liquid then removed. This is repeated for a total of three times to produce beads ready to process samples.

Lysis and Extraction of Nucleic Acids from Cells on the Swab

A swab can be loaded into a syringe barrel inserted into connection 7 and then be lysed by addition of lysis buffer through reagent connection 5 with microvalves 180 and 170 opened. In some embodiments Orapure or DNA IQ chemistries are used.

Movement of the Lysed Cellular Material to Chamber (3) and Mixing with Beads The material in the syringe connected to connection 7 can be moved into chamber (3) by applying pressure to the syringe or by applying vacuum to vent 6. When vacuum is used, microvalves 170, 150, and 220 are opened. The vacuum connects through microchannels 231, 221, 211, and channels 9 and 19 through chamber (3), microchannels 151, 152, 171, and 161 to pull material from connection 7 into chamber (3). When paramagnetic beads are loaded and cleaned in chamber (3), the lysed sample material mixes with the beads in chamber (3) with the magnet is the far position.

Purification of Nucleic Acids on the Beads

The paramagnetic beads are then incubated with the lysed sample. Continued air or gas flow can aid mixing. The magnet 300 is then moved to the closed position and the beads are captured on the wall of chamber (3). The sample lysate can then be removed from chamber (3) to waste and multiple volumes of wash solution added according to manufacturers' specifications for the Orapure chemistry or DNA IQ chemistry. The sample components on the beads have now been purified and are ready for reactions in the cartridge or exporting to the sample product connection. In one embodiment the beads are used to enrich a nucleic acid component from a sample.

Exporting Samples through the Sample Product Connection 8

The purified sample components on the beads can be moved to connection 8 by applying pressures on reagent connection 5 with microvalves 180, 150, and 130 open. In one embodiment, connection 8 is connected with reaction channel 250 such as C-flex tubing (Cole Parmer) and additional reactions are performed in the reaction channel.

Multiplexed PCR Amplification of STR Markers

DNA amplification can be performed by PCR amplification. The present invention enables PCR reactions as well as many other DNA amplification and modification reactions. The reactions can be performed in chamber (3), in reaction channel 250 attached to connection 8 which can be a tube 250 (FIG. 3, FIG. 4, FIG. 6), or in another device or microdevice connected to tube 250. This demonstrates the utility of the sample preparation for DNA reactions including thermal cycling.

Capture of Nucleic Acid Containing Beads in a Reaction Channel

The purified DNA output through the sample product connection 8 is moved into a reaction channel 250 at end 251 by applied pressure or alternatively through vacuum applied to end 252. An actuator 330 moves a magnet 320 under software control into a position close to bead capture region 340. Fixed magnets of different sizes and shapes (such as rare earth magnets) as well as electromagnets or superconducting magnets can be used. As the solution containing the beads moves through region 340, the magnetic field attracts the beads to the side of the reaction channel and holds them in place. The fluid is then followed by air pressure through reagent connection 5 leaving the beads region 340 in air.

Addition of Reagents and Movement of Samples into Reaction Region

Reagents can be added from the reagent manifold as described. In one embodiment, reagents are added from end 252 of reaction channel 250. End 252 is attached to a microfluidic microchip 500 comprising microvalves 510, 520, 530, and 540. Any three microvalves such as 510, 520, and 530 or 510, 520, and 540 can form a pump. Microvalve 530 connects through a microchannel to a downstream device 535, which can connect to tubing leading to a reagent reservoir. Microvalve 540 connects through a microchannel to downstream device 545, which can connect to tubing that leads to a reagent reservoir.

Reaction mixes (such as at least one DNA polymerase, dNTPs, buffer and a salt) including but not limited to master mixes and primers, (such as assay-specific primers or broadly applicable primer sets for multiple target pathogens), or complete PCR master mixes such as PowerPlex 16 from Promega (Madison, Wis.) or IdentiFiler or MiniFiler from Applied Biosystems (Foster City, Calif.) in reagent reservoir 600 can be delivered by a micropump formed by microvalves 530, 520, and 510 through tubing 610 and microchannels 531, 521, 511, and 512, into end 252 of reaction channel 250, as shown in FIG. 6. MOVe microvalves can precisely position fluids and move the fluid to region 340 where the reaction mix encounters the beads comprising nucleic acids. Magnet 320 is moved away from reaction channel 250 by actuator 330 which releases the beads from the inner surface of the reaction channel 250. The MOVe microvalves on microchip 500 pump the beads into device 400 with an area of reaction channel 250 forming temperature controlled region 350. The region 350 can be held at isothermal temperatures or thermal cycled or other varied as is well known to one skilled in the art. The region 350 can be a temperature modulator or thermally coupled to a temperature modulator.

FIG. 7 shows a temperature control device 400 that is capable of thermal modulation using a temperature modulator for heating and cooling to thermocycle the reaction channel. In one embodiment the temperature modulator comprises a Peltier module, infra-red module, microwave module, a hot air module or a light module. In another embodiment a PCR reaction sample is moved inside the reaction channel past one or more constant temperature zones.

Figure 9:
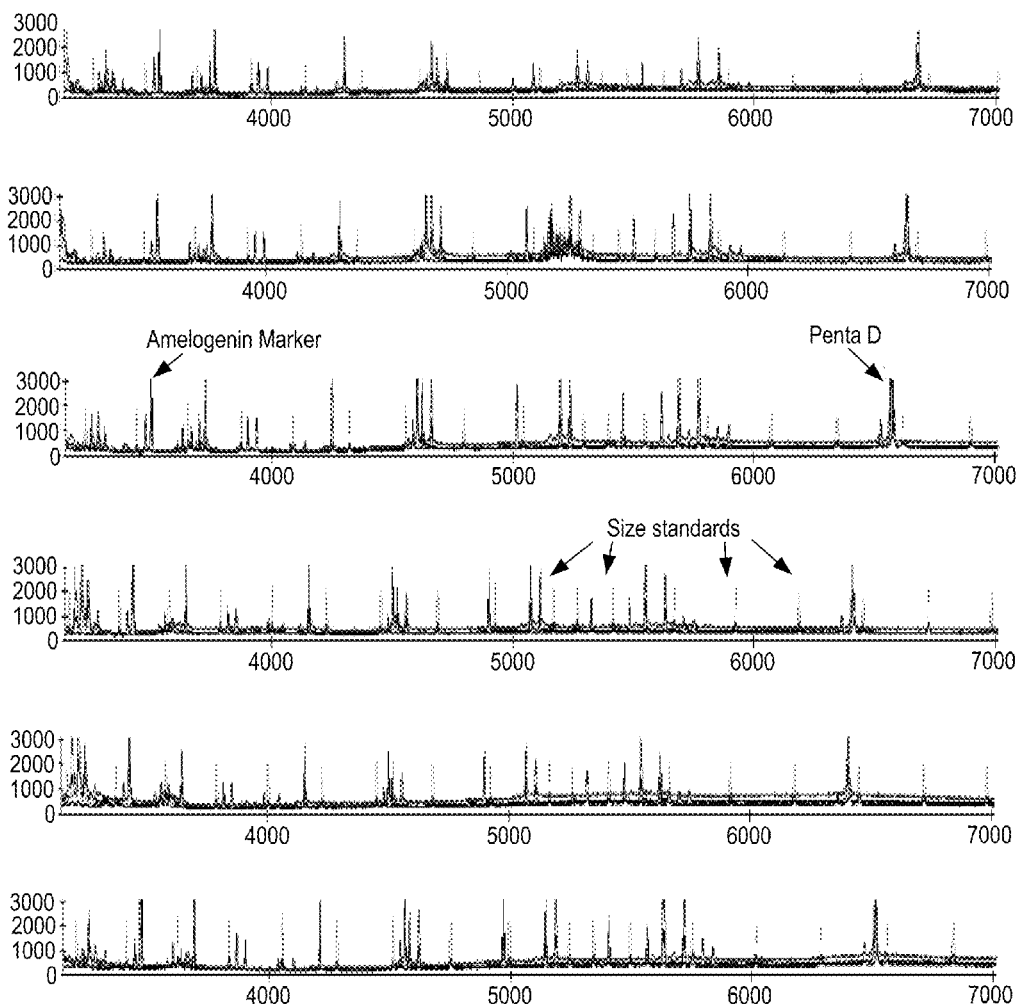
FIG. 9 shows PowerPlex16 STR (Short tandem repeat) amplification reaction performed in a passive, Teflon (PTFE) based Tube reaction chamber.

FIG. 9 shows the amplification of PowerPlex 16 STR reactions that have been prepared in a cartridge (1) from buccal swab samples and processed in reaction channel 250 using the temperature control device 400 in FIG. 7. The STR markers are amplified from standard conditions with Mg optimized for the apparatus 1000.

The temperature control device 400 can also have a detector 410. The detector can detect optical detection such as absorbance, fluorescence, chemiluminescence, imaging, and other modalities well known to one skilled in the art or measurement such as IR, NMR, or Raman spectroscopy. The detector can comprise a light source is used to excite a fluorescent or luminescent dye in the PCR reaction sample, and the excitation light is sensed with a photodetector (such as a CCD, CMOS, PMT, or other optical detector). In one embodiment the light source is a coherent light source, such as a laser or a laser diode. In another embodiment the light source is not a coherent light source, such as a light emitting diode (LED) or a halogen light source or mercury lamp.

For nucleic acid amplification, real-time PCR is one example of a nucleic acid assay method that can be performed in tube 250 in temperature controlled region 350 and detected with detector 410.

Example 2

Universal Sample Preparation

The previous example illustrated one embodiment in which the disclosed apparatus can be used to prepare samples for analysis and showed one example of STR amplification. Another embodiment involves the use of a Universal Sample Preparation Module (USPM). The USPM device can consist of a sample processing cartridge (1), accompanying apparatus to operate the cartridge, a microprocessor, and software that can readily be interfaced to downstream analytical devices. In one embodiment the USPM can be tightly integrated with analytical devices to form a modular sample-to-answer system. The cartridge can be configured as a disposable single-use device that can process swabs or liquids (including aerosol samples) for field monitoring processes, or as a reusable, flow-through format for remote operations with rare positives. Target specificity of the USPM is imparted through the use of specific antibodies (that bind selected targets) attached to paramagnetic beads; different cartridges can be supplied with various mixtures of targets.

Figure 18:
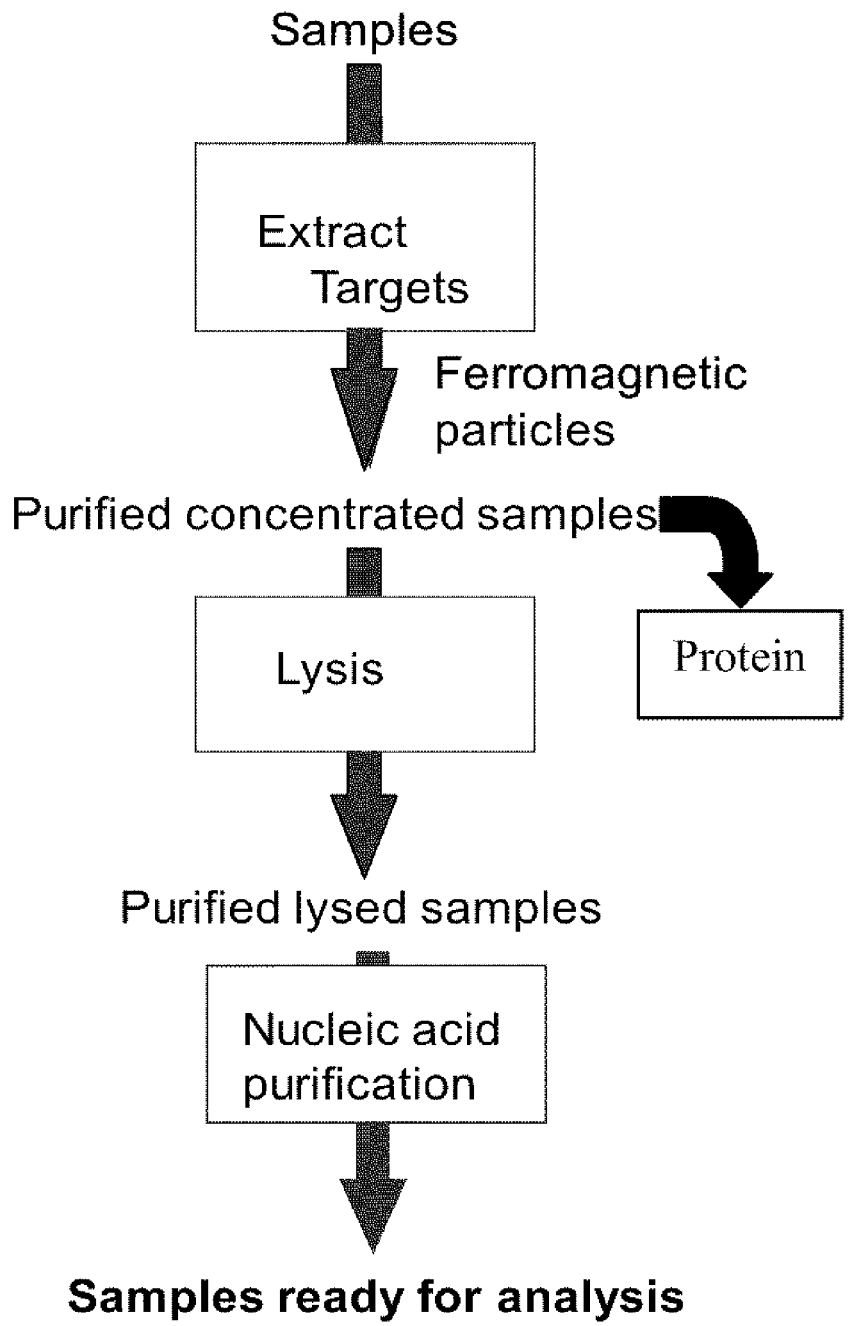
FIG. 18 shows a universal sample preparation workflow to prepare nucleic acids and toxins.
Figure 19:
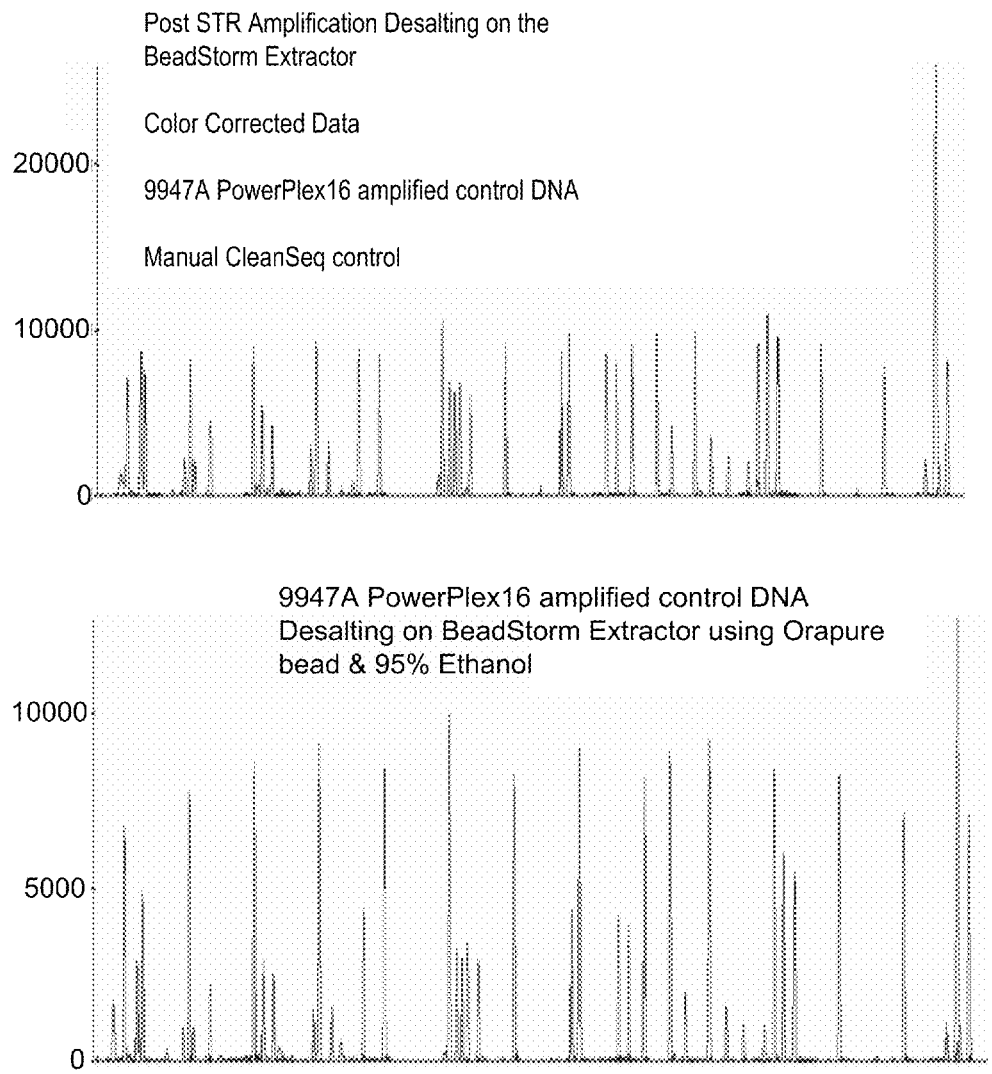
FIG. 19 shows purification of samples in a cartridge using paramagnetic beads.
Figure 20:
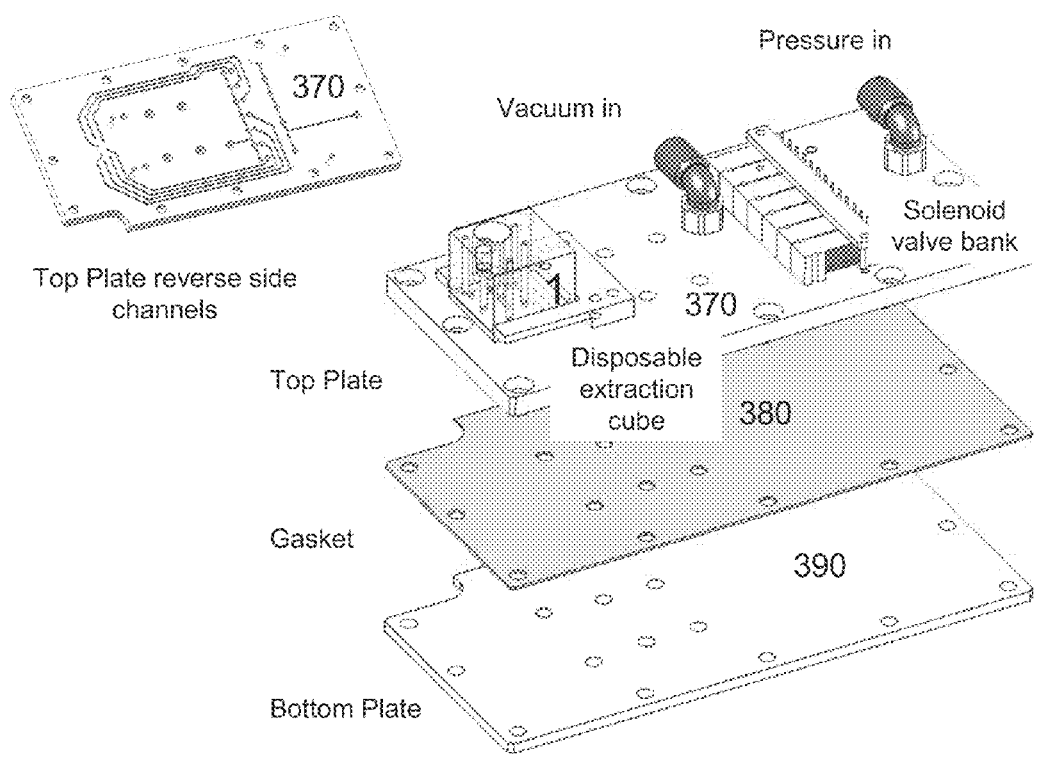
FIG. 20 shows an integrated pneumatic manifold to operate the MOVe microvalves in cartridge.

A USPM can use a multistep fully automated process to prepare biological samples for downstream analysis. One example in FIG. 18 can use swabs or liquids; the operator can select the sample type and then insert samples into input port(s). The first step can apply immunomagnetic separations (IMS) to capture, concentrate, and purify target molecules from solution onto paramagnetic beads. Targets already tested include cells, spores, viruses, proteins, or toxins. For toxin and protein detection, or for use as a triggering device, the captured targets from the IMS can be exported directly to the downstream analytical device. For nucleic acid detection, the second step can lyse the cells or spores to release the DNA and/or RNA using mechanical or other lysis techniques. The third step, nucleic acid purification, can adsorb, concentrate, and purify the nucleic acids onto a second set of paramagnetic beads and output the beads with nucleic acid, or purified desorbed nucleic acid, for downstream analysis.

Referring to cartridge (1), the immunomagnetic separation can be performed by using reagent beads that have antibodies or other immunomagnetic, affinity magnetic, or surface chemistry magnetic separations. For example, immunomagnetic beads with antibodies can be added to cartridge (1) to capture, purify, and concentrate cells, viruses, spores, toxins and other biomolecules onto bead.

Upstream sample processing for the USPM can be done in the sample preparation devices, which can process samples over 0.6 mL in a microfluidic cartridge (1) (FIG. 21). The sample processing cartridge, about 1 in cubed dimension, (FIG. 3, FIG. 21) was developed to automatically remove collected buccal cells from a swab, lyses the cells, and purifies released cellular DNA on magnetic beads. The bead beds are typically 100 nL and can be used for downstream STR analysis with microfluidics devices or full scale qPCR reactions.

The sample preparation device uses a MOVe microvalve microchip interfaced with the bottom of the cube (FIG. 3, arrow labeled 2) to direct pressure-driven flows consisting of fluids, beads, and samples among the reagent and reaction reservoirs. The MOVe microvalves replace conventional valves and tubing between the reservoirs, thereby providing a non-leakable, directable fluid transport and enable miniaturization of the entire cube and sample preparation device.

Figure 10:
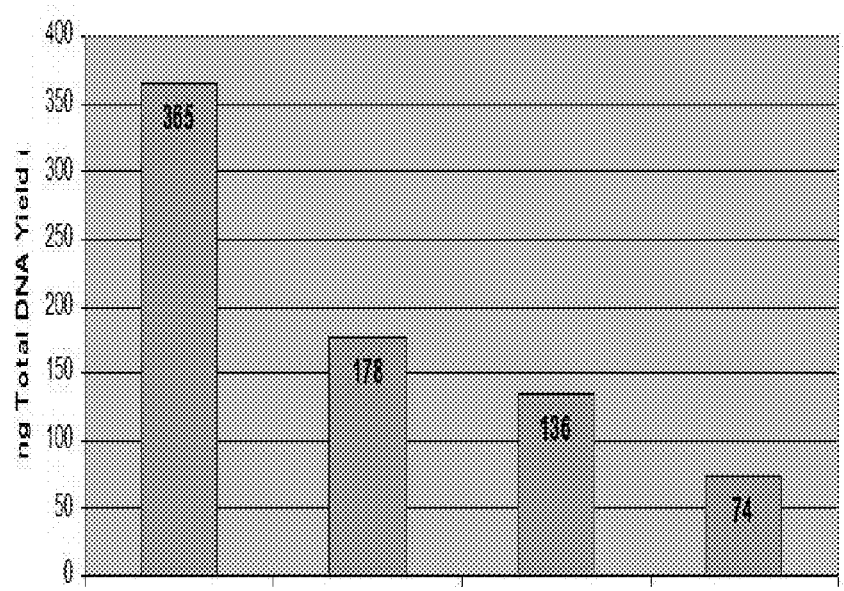
FIG. 10 shows purification of DNA from 25 uL of blood at 69', 23.5', 10.5', and 4.5'; yield in ng is shown on the bars.
Figure 11:
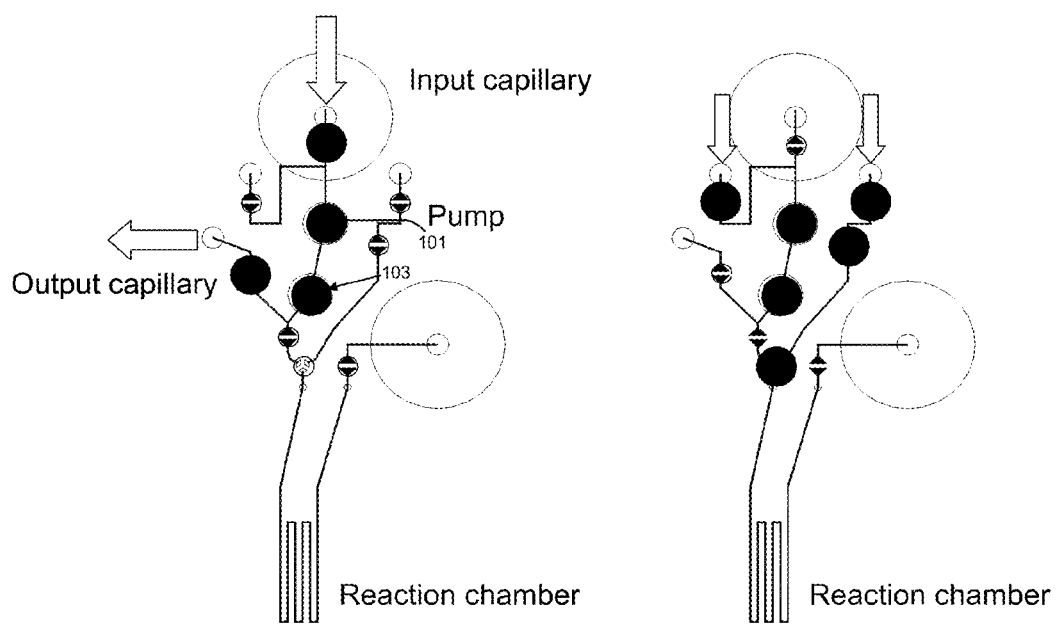
FIG. 11 shows a schematic of using microvalves to capture beads on a microchip.
Figure 12:
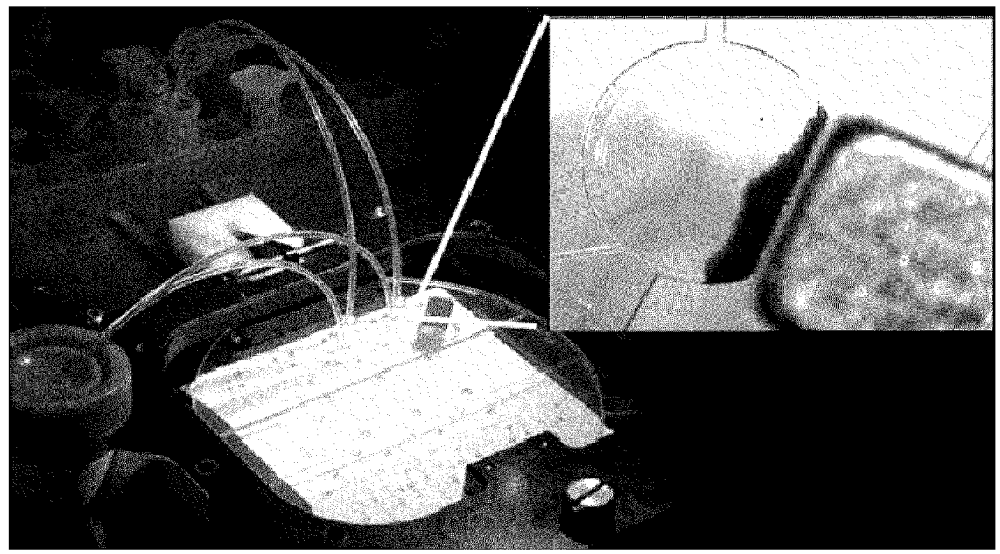
FIG. 12 shows bead capture from a cartridge on a microchip using a MOVe microvalve.
Figure 13:
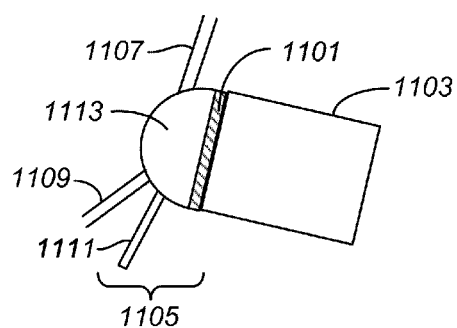
FIG. 13 shows bead capture from a cartridge on a microchip using a MOVe microvalve.

This sample preparation device technology has been used to automate DNA extraction from buccal swabs as described above. FIG. 10 shows automated preparation of DNA from 25 uL of blood in the automated sample preparation device using pressure driven flows, vibrational mixing, MOVe valves, actuated magnets, and magnetic beads. The fully automated process produced DNA ready for STR analysis in less than five minutes.

Figure 27:
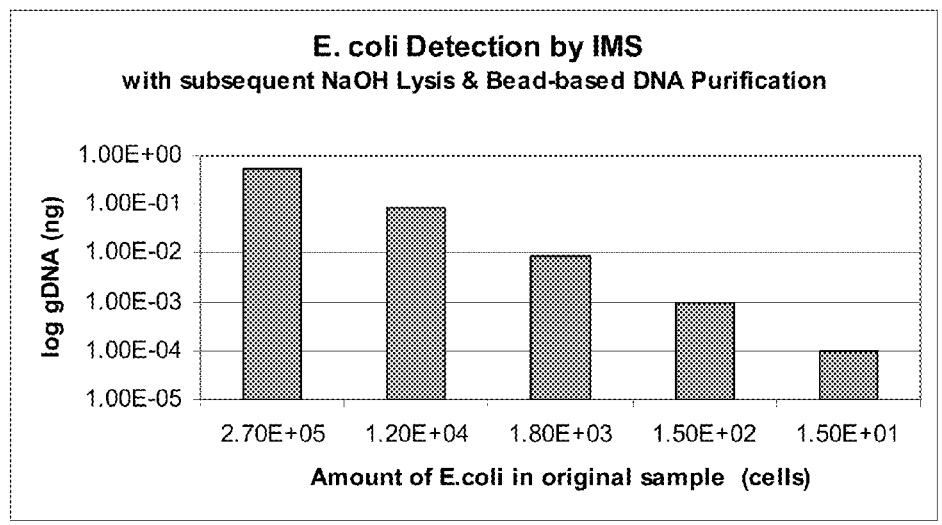
FIG. 27 shows detection of E. coli by immunomagnetic separation, followed by alkaline lysis and PEG-facilitated capture on magnetic beads, and analyzed by real-time PCR.
Figure 28:
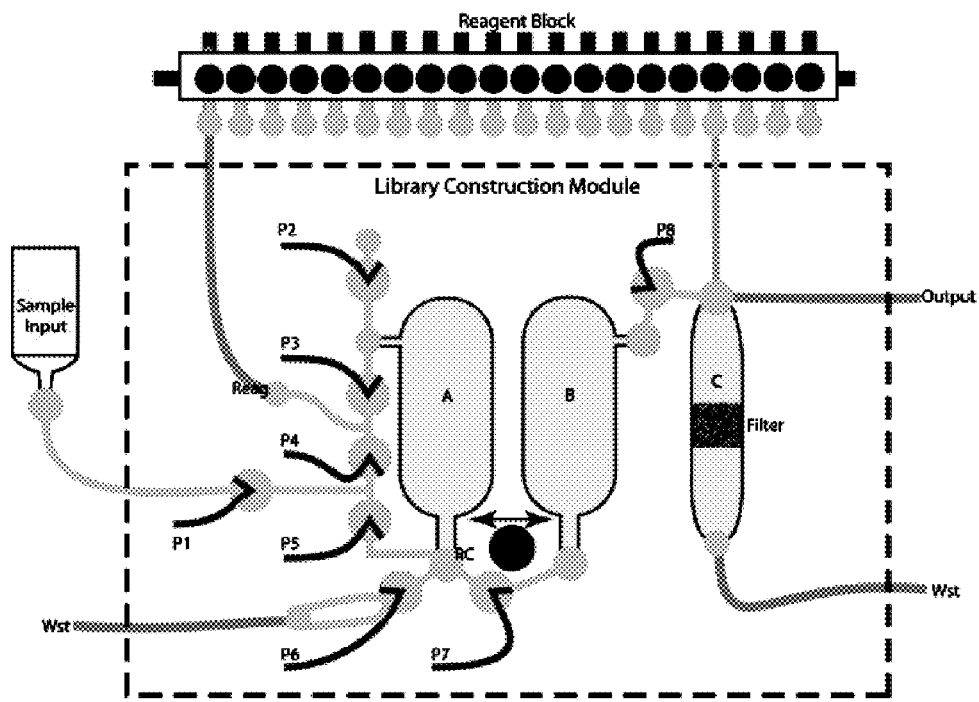
FIG. 28 shows application of a cartridge with three chambers that can be used to construct genomic libraries and other applications.
Figure 29:
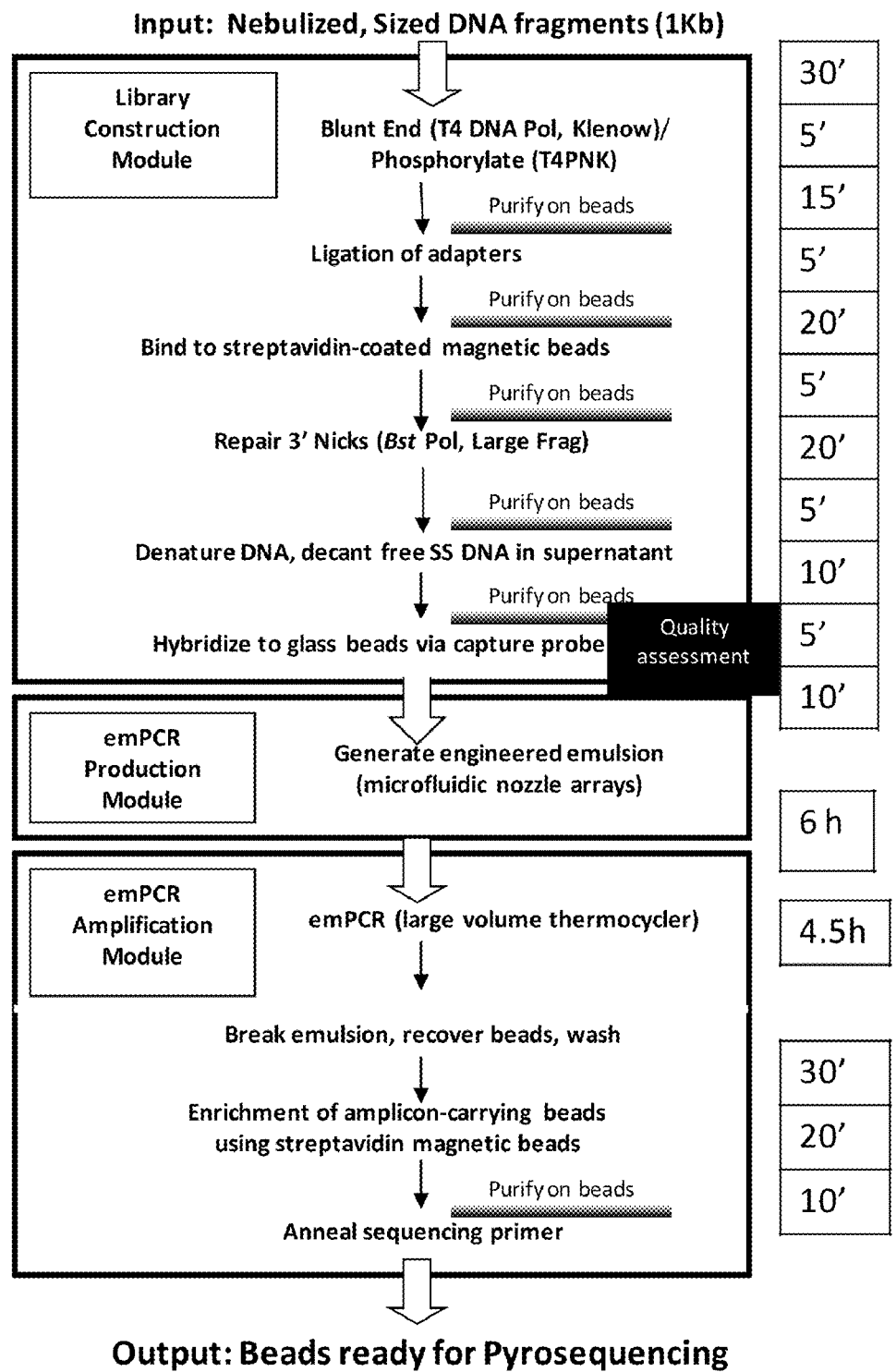
FIG. 29 shows the workflow to prepare genomic libraries using the cartridge.
Figure 30:
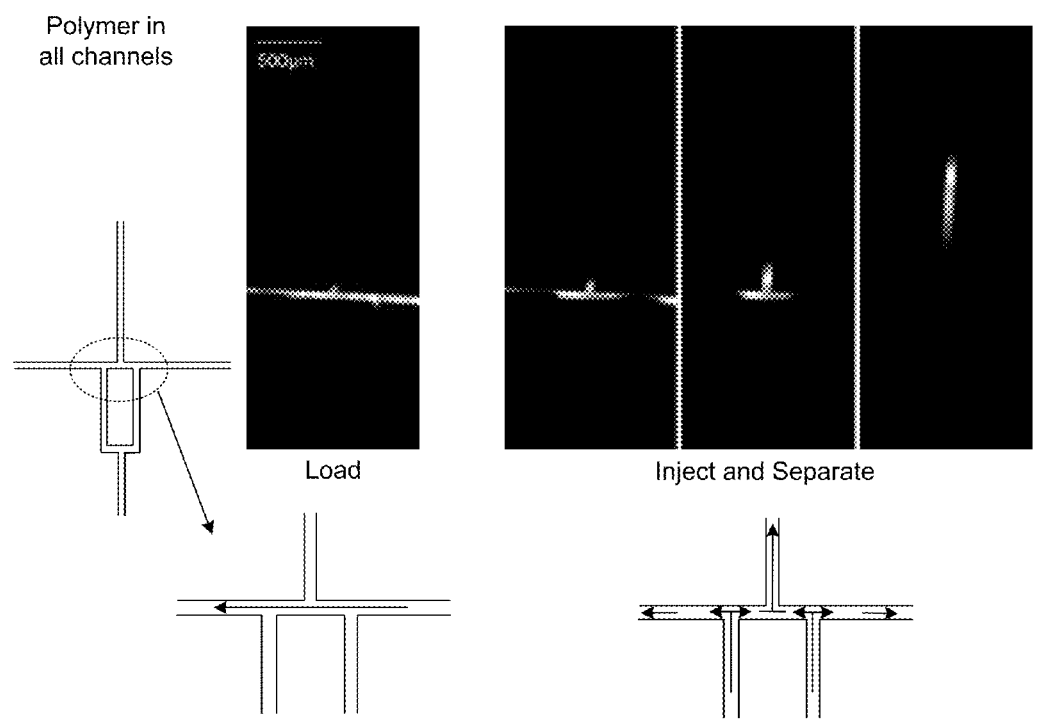
FIG. 30 shows a forked injector for microchip based electrophoresis.
Figure 31:
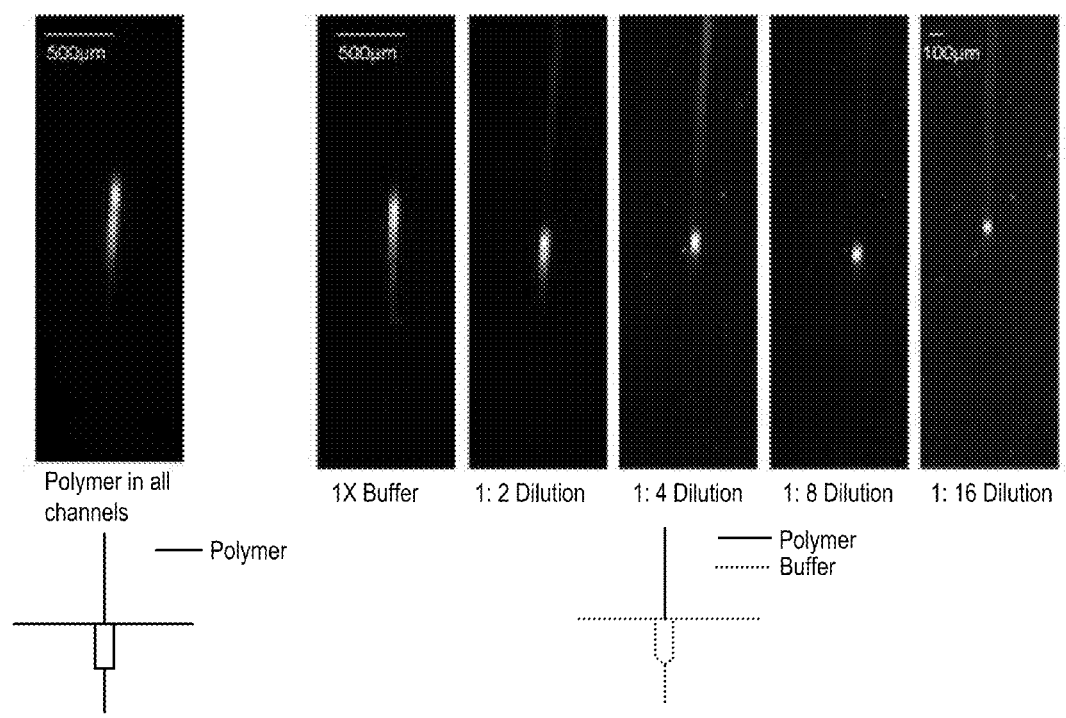
FIG. 31 shows sample stacking with a forked injector.

An automated system has been developed for capturing, concentrating, and purifying cells, viruses, and toxins from liquid samples (1-10 mL) using magnetic beads coated with antibodies specific to targets of interest. Thus, a variety of targets have been concentrated and purified with this automated system. Using this approach, *E. coli* cells were captured and detected at cell concentrations as low as 15 cells/mL/sample (FIG. 27). Similar results of greater than 90% capture efficiency were obtained using *Bacillus* spores, Gm$^+$ and Gm$^-$ vegetative cells, a model virus (bacteriophage fd), SEB, and ovalbumin as targets. Purified samples can be further processed in the sample preparation device (e.g., lysis and nucleic acid purification), moved onto a microchip for analysis, or used with an off-chip PCR/qPCR device.

IMS capture has been shown to work well in complex samples such as aerosols and in the presence of biological clutter (See U.S. Patent Publication No. 20080014576, herein incorporated by reference in its entirety). For clutter, we showed that up to $10^5$-fold levels of added bacteria produced only a two-fold reduction in capture efficiency. For complex samples, add-back experiments using many different aerosol samples established that aerosol samples reduce the binding of *B. cereus* spores to IMS beads by less than 50%. Therefore, there is less than a two-fold loss of sensitivity in complex, real-world samples.

IMS has been used to capture, concentrate, and detect toxins. We have developed IMS assays for ovalbumin and SEB, multiplexed the assays, and developed two generations of completely integrated microfluidic systems that automate the IMS assays. Less than 10 ng of SEB can be reliably detected in a one mL samples with no interference from closely related *Staphylococcal* enterotoxins.

IMS can:
A. Select target organisms from samples with high backgrounds of interferents (selectivity),
B. Discriminate between two different strains or species of bacteria (specificity),
C. Effectively capture cells and toxins across a wide range of concentrations from a wide range of samples (sensitivity, robustness)
D. Reduce target sample volume significantly, from mL to nL volume The instant invention and the apparatus and methods are capable of implementing IMS and coupling it to nucleic acid extractions.

Figure 60:
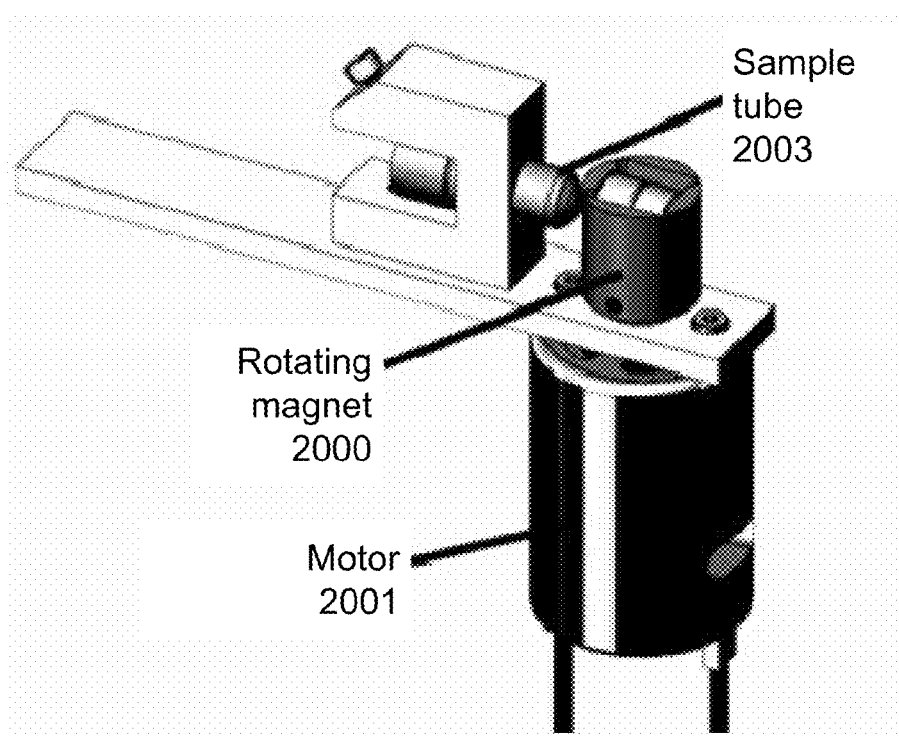
FIG. 60 shows a diagram of a mixer.
Figure 61:
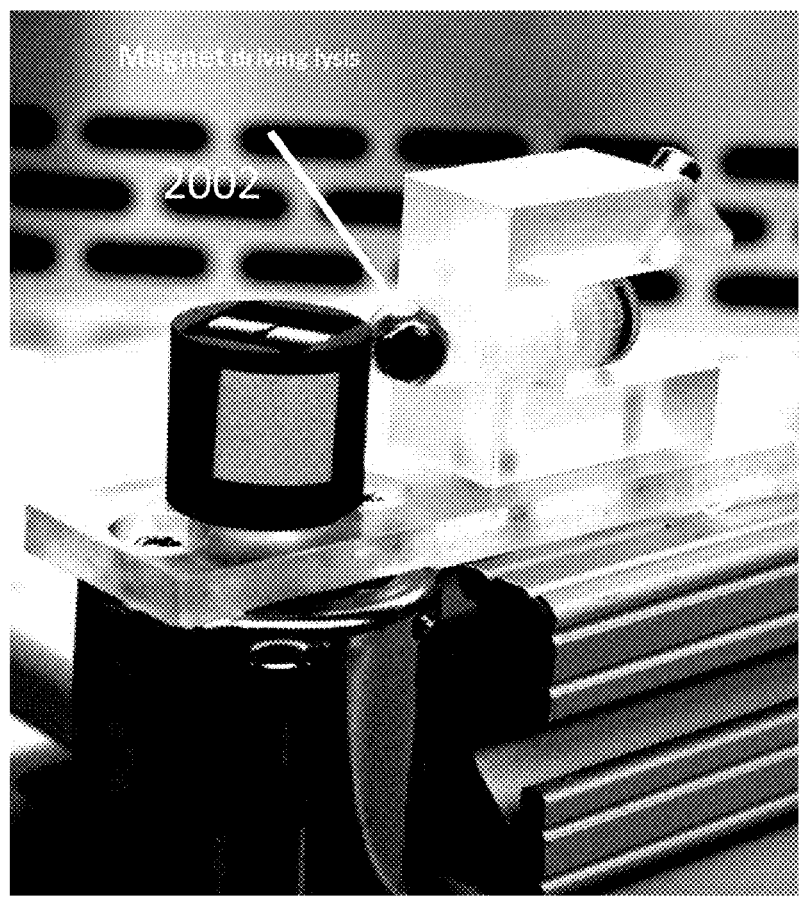
FIG. 61 shows a diagram of a mixer.

The next step in the USPM is the lysis of the captured target when it is a cell, virus, prion, or spore. Lysis of spores is particularly challenging. A MagMill or magnetically driven lysis or homogenizing device has been developed for efficient lysis of Bacillus and other spores, as well as vegetative cells. The MagMill consists of a rapidly rotating magnet 2000 actuated by a motor 2001 (FIG. 60) that drives rotation of another magnet 2002 contained within a sample-containing vessel 2003 or compartment (FIG. 61). The magnet 2002 contained within the sample-containing vessel can have any shape. For example, the magnet can have a bar, spherical, cylindrical, rectangular, oval, hexagonal, or propeller shape. Alternatively, the magnet can have holes through it, such that liquid may be forced through the holes and increase the shear force applied to the sample when the magnet is rotated by a magnetic field. The same basic components can be miniaturized, incorporated into a microfluidic format, or connected to a microfluidic format. The overall effect is analogous to a magnetic stir plate, with the sample being rapidly vortexed within the sample tube. Using magnetically driven sample agitation by MagMill treatment, spore lysis is achieved without silica, zirconia or other beads. Lysis may be accomplished by shear forces generated as the spore passes between the magnet and the vessel walls. The magnet can rotate at a rate of greater than about 10, 50, 100, 150, 200, 250, 500, 750, 1000, 1500, 2000, 2500, 5000, or 10000 rpm.

Figure 62:
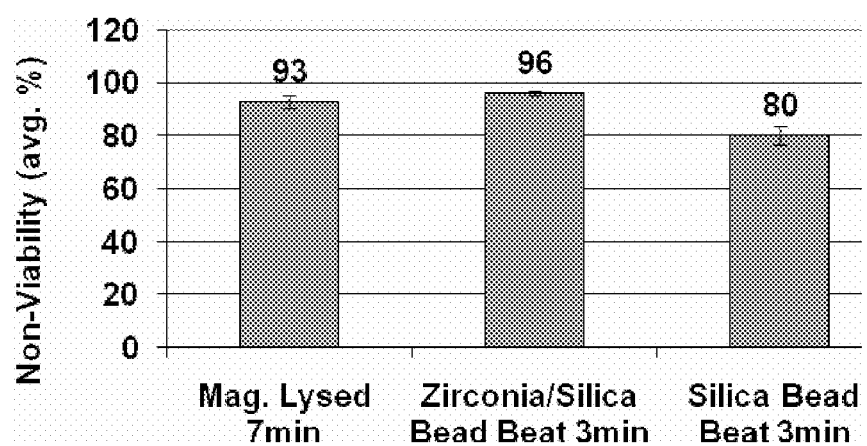
FIG. 62 shows results of using a mixer to lyse cells.

This device disrupts spores with similar efficiency as traditional bead beating that employs silica/zirconia beads (FIG. 62). Spores ($3.2 \times 10^7$) were lysed in a volume of 1 ml with viability was determined by plating on Tryptic Soy Agar; results are an average of two separate experiments each run with duplicate samples (total n=4). The non-viability of magnetically-driven spore lysates was 93% compared to traditional bead beating (BioSpec beater) lysates using either Zirconia/silica which was 96% or silica beads which was 80%. The same pattern was confirmed by qPCR The advantage of using the MagMill (versus traditional bead beating) is that the design is more mechanically robust and thus able to withstand many cycles of use without failure, and samples can be lysed using just the agitation of the magnet in the sample, without the need for inclusion of silica/zirconia beads that have been shown to bind released DNA causing a loss in follow-on detection sensitivity. The basic features of the MagMill can be reconfigured in a miniaturized format that can be integrated into a sample preparation device. The system can potentially be down-sized to fit into a microfluidic microchip. Despite changes in configuration, however, the principle driving lysis, that of a rapidly rotating magnet contained within a sample vessel, remains the same.

Example 3

Figure 32:
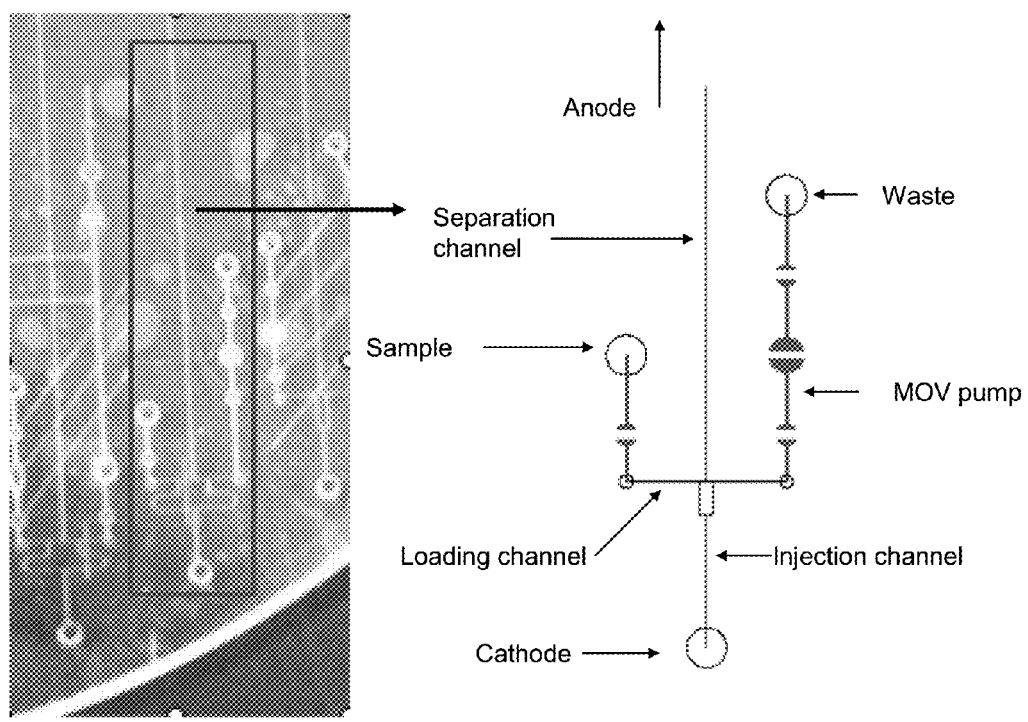
FIG. 32 shows a forked injector coupled to MOVe microvalves.
Figure 33:
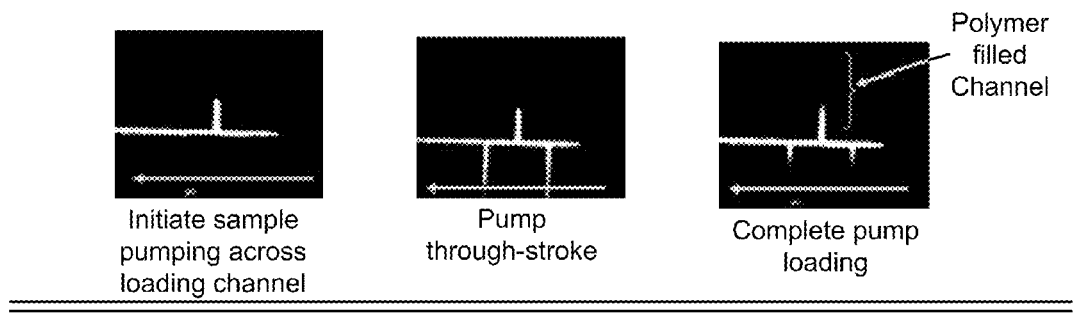
FIG. 33 shows a forked cathode injector coupled with a MOVe microchip.
Figure 33:
Figure 34:
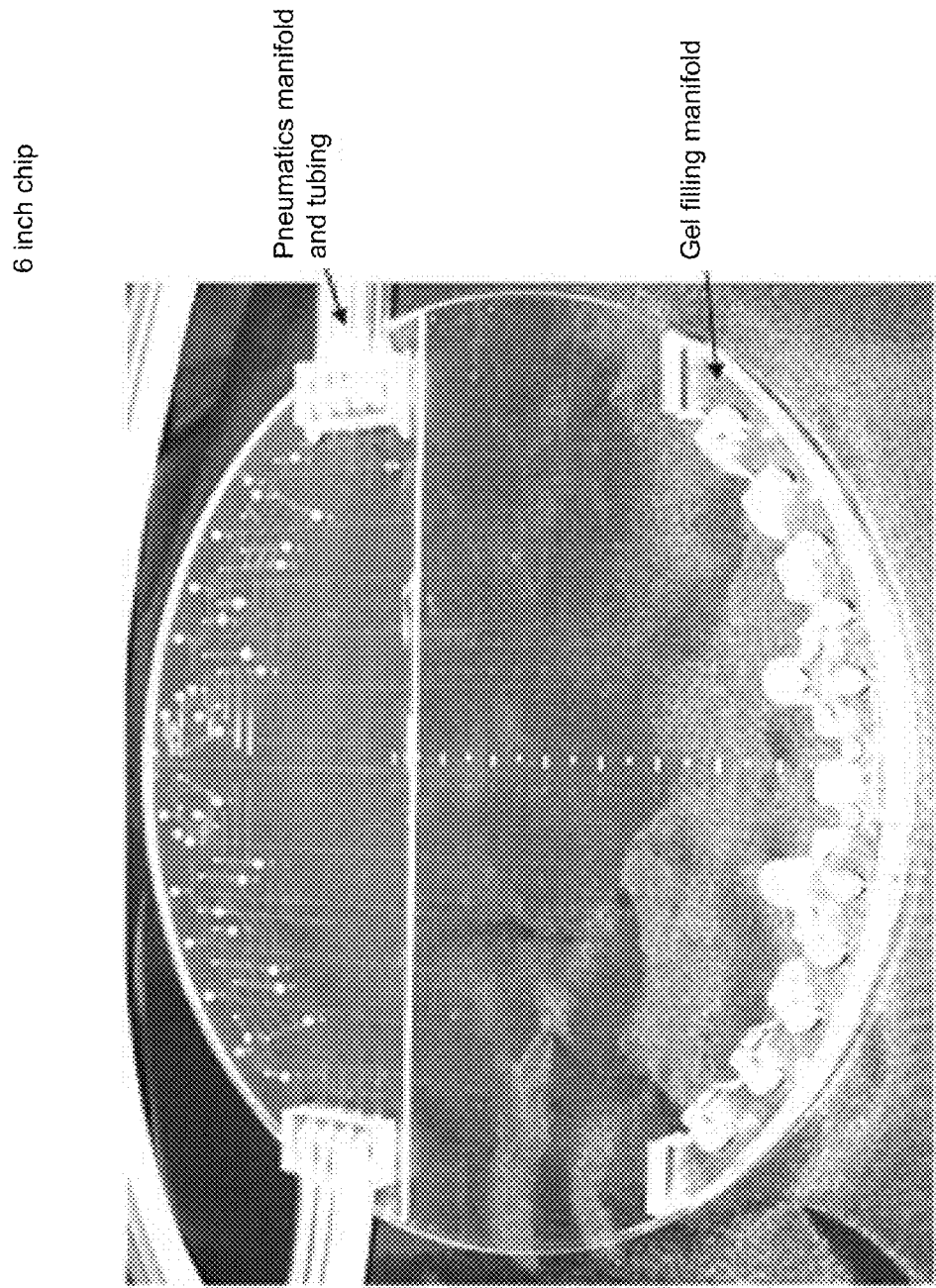
FIG. 34 shows a photograph of a microchip with the forked injector.
Figure 35:
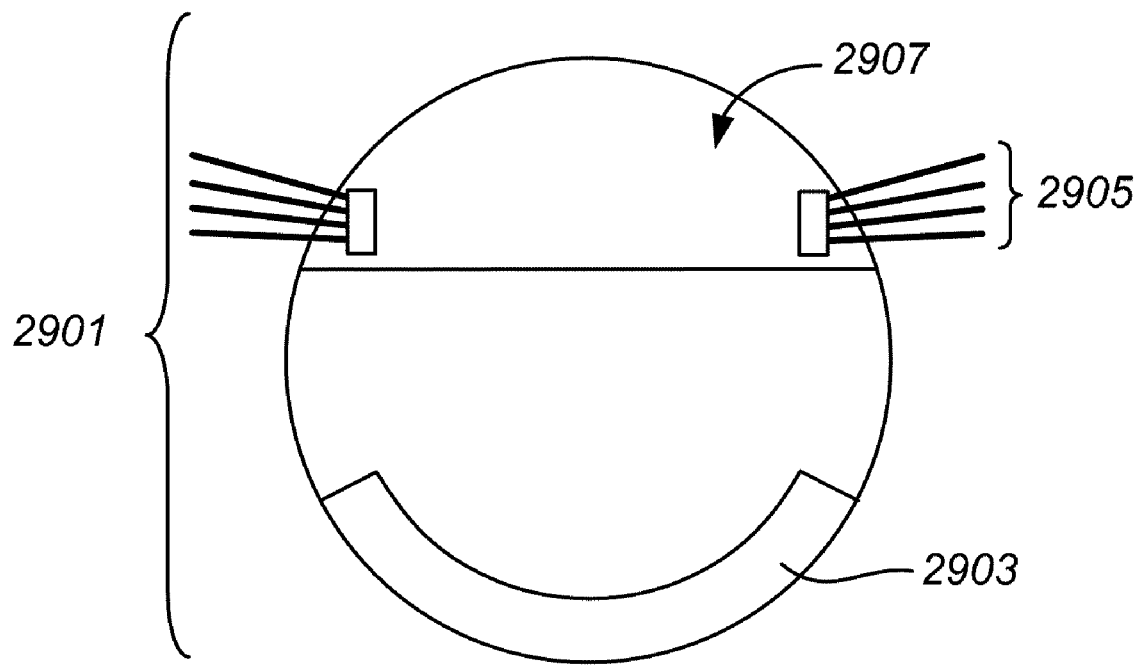
FIG. 35 shows a photograph of a microchip with the forked injector.
Figure 36:
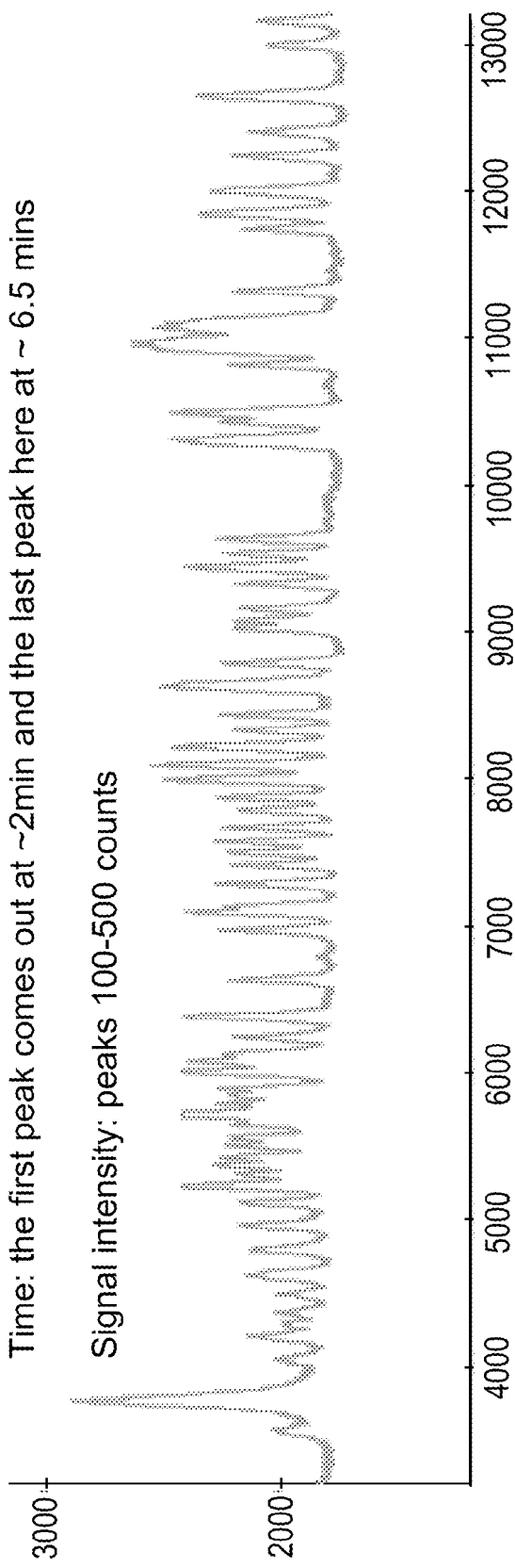
FIG. 36 shows an electropherogram of a single color from a DNA sequencing trace from a forked cathode injector.

Coupling of a Sample Preparation Device with a Microchip-Based Sample Cleanup and Separation FIG. 34 and FIG. 35 show a device with a cartridge (2907) and microchip (2901) that was designed to incorporate the Forked Injector design, as shown in FIG. 32, a gel filling manifold (2903), and associated components. The cartridge is fluidically connected to a pneumatics manifold and tubing (2905). Different configurations of the injector design, separation channel length and separation polymer were tested. FIG. 36 show an electropherogram of an M13 T track injected and separated on a microchip channel using the Forked Cathode injector, with sample detection on a confocal microscope breadboard system. The sample was injected uniformly with short and long DNA fragments represented equally. The results show that an M13 T track DNA ladder can be uniformly injected and single base pair resolution can be obtained out to approximately 330 base pairs in less than 20 minutes. Higher sample signal strengths were obtained compared to injections using a conventional twin T design. When integrated with a detection system, the microchip is held at a constant 50° C. in order to obtain separations with good resolution.

Figure 37:
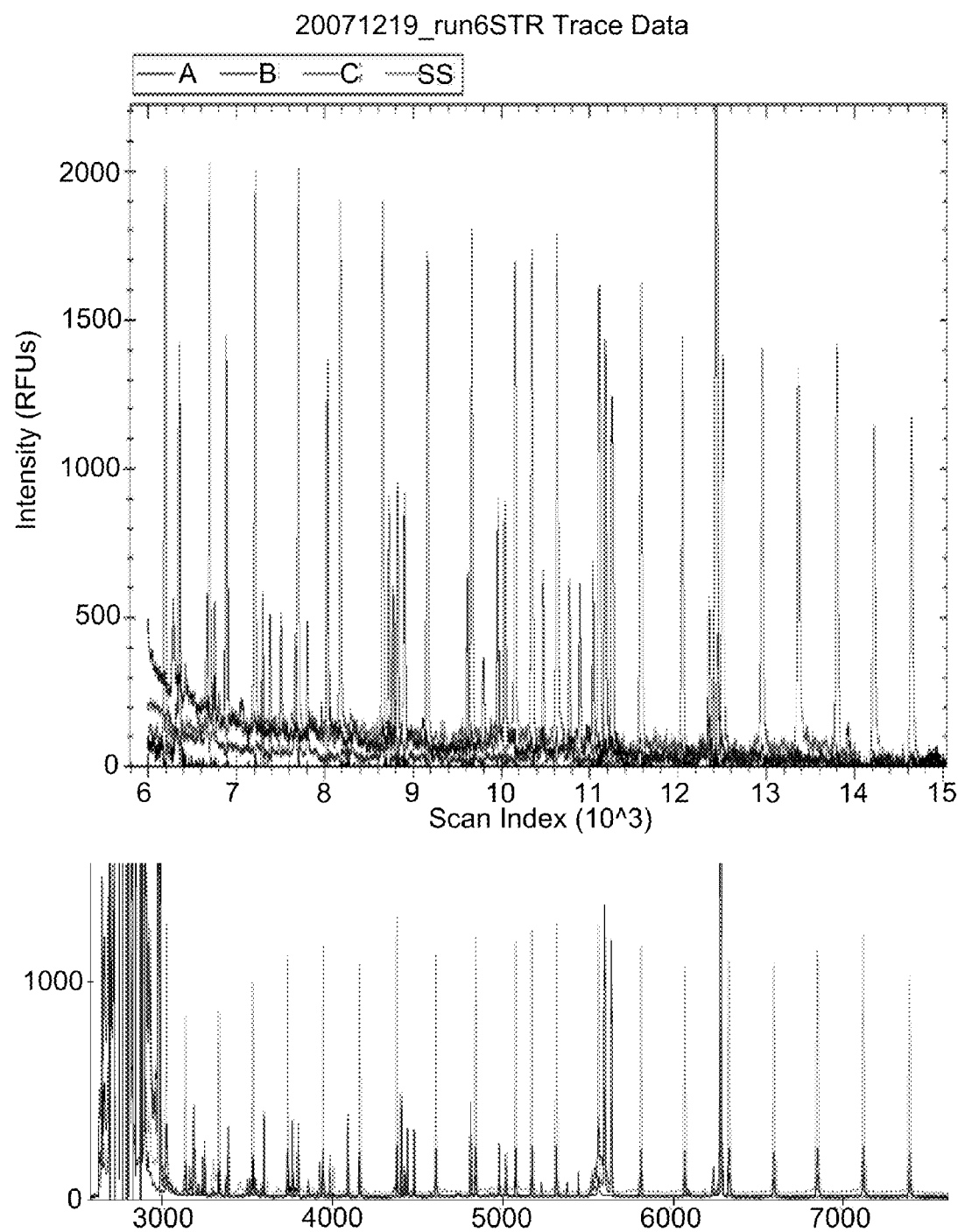
FIG. 37 shows STR separations on a forked cathode injection system.

Using these processes, excellent results were obtained for MOVe integrated, field amplified stacking injections of liquid samples (FIG. 37). This data was generated with all sample loading, manipulation and injection processes carried out under software control using MOVe microvalves. The data has been minimally processed, color corrected from a detector that uses eight diode channels to four dye traces.

Figure 38:
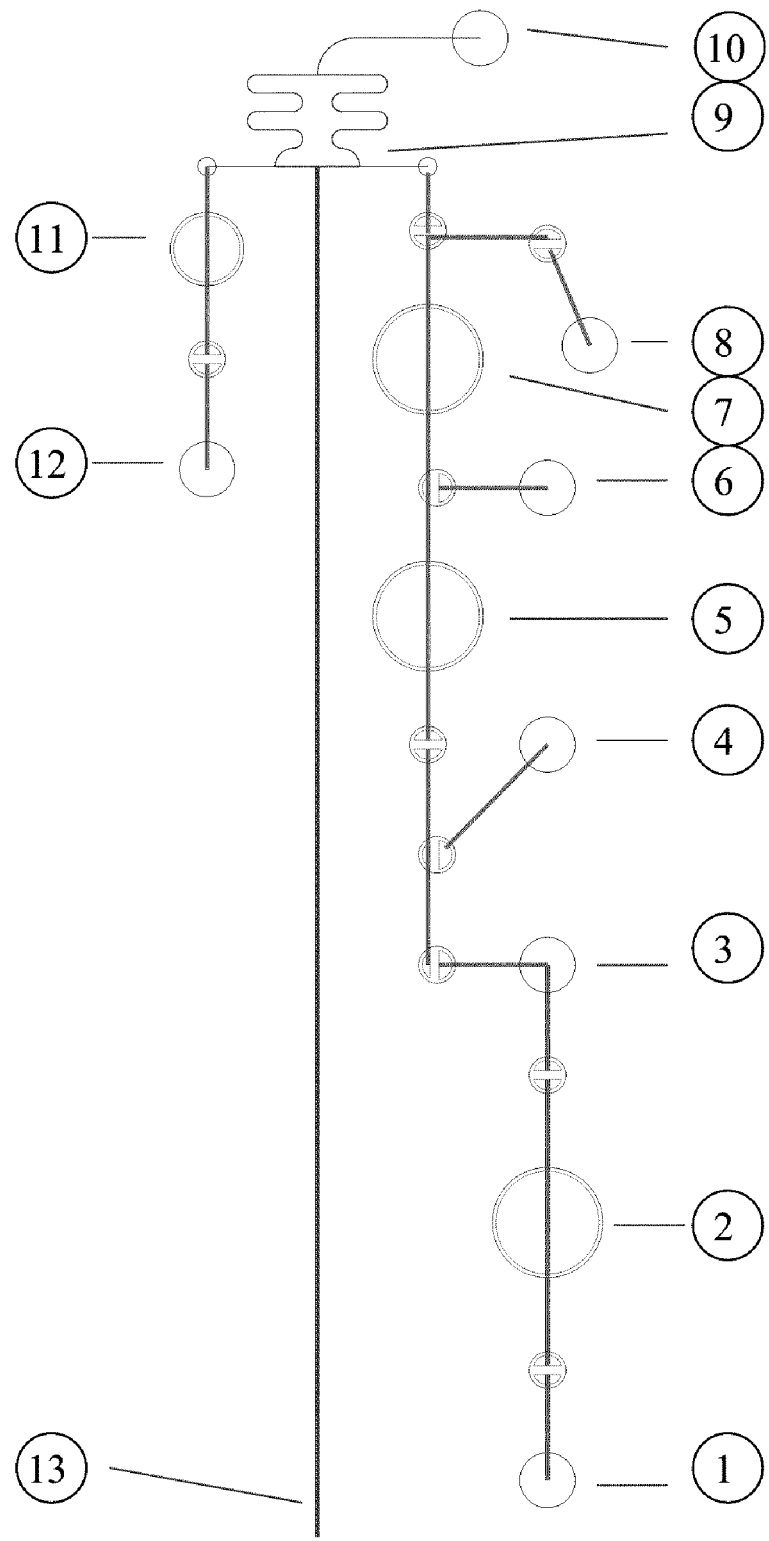
FIG. 38 shows a forked cathode with MOVe microfluidics for shuttle loading.

One embodiment of a microchip that combines the forked cathode with a MOVe sample preparation device is shown in FIG. 38. This device comprised additional processes that enable integration with the rest of the system, i.e., the sample preparation device (1000 shown in FIG. 22), the reaction channel (250 shown in FIG. 6), and the output of the STR purification as described in the STR example. FIG. 38 shows a forked cathode with MOVe fluidics and shuttle sample loading for integration with post amplification STR purification system. The parts are: 1—Reagent input port, 2—Reagent pump head, 3—Sample input port, 4—Size Standard/eluent input port, 5—Capture valve, 6—Waste port, 7—Elution valve, 8—Sample waste port, 9—Cathode, 10—Cathode port, 11—Sample valve, 12—Sample port, and 13—Separation channel. The anode port, which is downstream of the channel, is not shown.

The sample to be separated is introduced as a bead solution in ethanol. This can be the purified reaction products on beads output as described above. In one embodiment, the sample is an STR reaction. In other embodiments, the sample can be nucleic acid fragments of different lengths produced by other reaction chemistries including DNA sequencing by Sanger chemistry. The solution containing the sample is flowed from the Sample input port to the Sample waste port with the Capture valve and other intervening valves open. The open Capture valve facilitates a slowing of the stream flow and bead capture by a fixed magnet placed above or below the valve. The ethanol solution is completely run through the system followed by air yielding a relatively dry and clean bead bed, with purified products, in the valve. At this point the valve is closed and reopened (in coordination with other valves) to fill it eluent solution from the associated port. For an STR analysis or other analyzes where an internal size standard is needed, the eluent can contain a size standard. The solution is moved between the Elution valve and the Capture valve to facilitate mixing, ending with the solution in the Elution valve. The Sample valve is then opened in coordination with the Elution valve closing to "shuttle" the sample through the sample channel leaving it filled. The sample FASS injection is carried out as previously described. An additional noteworthy function of the device is that in one embodiment the Reagent input port and Reagent pump are used to provide metered STR reaction premix to the reaction channel (250 shown in FIG. 6) after the swab extraction of DNA on the sample preparation device; in other embodiments, the device can provide other nucleic acid reaction reagents such as cycle sequencing mixture or provide PCR reagents to perform a PCR amplification followed by providing cycle sequencing reagents to perform cycle sequencing with bead-based cleanup reactions integrated as needed. Other chemistries will be apparent to one skilled in the art.

While preferred embodiments of the present invention have been shown and described herein, it will be obvious to those skilled in the art that such embodiments are provided by way of example only. Numerous variations, changes, and substitutions will now occur to those skilled in the art without departing from the invention. For example, any MOVe valve, pump, router, or other MOVe device described herein can be replaced with any pneumatically actuated valve, pump router or other device. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A method comprising:
   extracting DNA from at least one cell in a sample;
   isolating the extracted DNA;
   amplifying a plurality of short tandem repeat (STR) markers of the isolated DNA;
   separating a plurality of amplified STR markers by electrophoresis;
   detecting a plurality of separated STR markers; and
   performing computer analysis of a plurality of detected STR markers to produce a computer file identifying a plurality of detected STR markers;
   wherein the method is performed in less than 4 hours using a system that comprises:
   a) a sample preparation module adapted to extract DNA from at least one cell in a sample in a non-microfluidic volume, to capture the extracted DNA from the non-microfluidic volume on capture particles, and to route the captured DNA through a first microfluidic channel;
   b) a reaction module comprising a reaction chamber in fluidic communication with the first microfluidic channel and adapted to immobilize the captured DNA and to perform an amplification reaction on the immobilized DNA to produce a reaction product;
   c) a separation and detection module in fluidic communication with the reaction chamber and adapted to separate the reaction product by electrophoresis and to detect the separated reaction product; and
   d) a data analysis module adapted to receive data about the separation and detection of the reaction product from the separation and detection module and comprising computer-executable code that transforms the data and produces a computer file identifying the separated and detected reaction product;
   wherein the sample preparation module and the reaction module are integrated in a disposable cartridge comprising:
   i) at least one set of fluidic chambers including a sample chamber, a capture chamber and a thermal cycling chamber in fluidic communication with each other; and
   ii) a reagent cartridge comprising reagents for performing an amplification reaction involving thermal cycling, wherein the reagent cartridge is configured to be carried on the disposable cartridge in a closed configuration and to be placed into fluidic communication with the at least one set of fluidic chambers.

2. The method of claim 1 wherein the method is performed in less than 3 hours.

3. The method of claim 1 wherein the method is performed in less than 2 hours.

4. The method of claim 1 wherein the plurality of STR markers is at least 5 STR markers.

5. The method of claim 1 wherein the plurality of STR markers is a plurality of CODIS STR markers.

6. The method of claim 5 wherein the plurality of STR markers is at least 5 CODIS STR markers.

7. The method of claim 1 wherein the at least one cell is a plurality of cells.

8. The method of claim 1 wherein the sample is a forensic sample.

9. The method of claim 1 performed at the site of collection of the sample.

10. The method of claim 1 wherein the sample comprises blood, semen or hair.

11. The method of claim 1 wherein the sample comprises a buccal swab.

12. The method of claim 1, wherein the system further comprises a processing module in fluidic communication with the reaction chamber and the separation and detection module and adapted to:
   (1) route the reaction product through a second microfluidic channel to a non-microfluidic processing chamber;
   (2) process the reaction product; and
   (3) route the processed reaction product to the separation and detection module.

13. The method of claim 1, wherein the system fits within an enclosure of no more than 5 ft$^3$.

14. The method of claim 1, wherein the system fits within an enclosure of no more than 2½ ft$^3$.

15. The method of claim 1, wherein the capture particles are magnetically responsive capture particles and the reaction module further comprises a source of magnetic force configured to immobilize the captured DNA.

16. The method of claim 1, wherein the reaction module is adapted to perform thermal cycling.

17. The method of claim 1, wherein the system is a closed system.

18. The method of claim 1, wherein the system is battery operated.

19. The method of claim 1, wherein the system further comprises a cartridge cover and a pneumatic manifold,
   wherein the disposable cartridge can be releaseably engaged with the cartridge cover and the pneumatic manifold,
   wherein the disposable cartridge comprises one or more pneumatically actuated valves and one or more microfluidic channels,
   wherein the pneumatic manifold and the cartridge cover are each fluidically connected to at least one pressure source, and
   wherein the pneumatic manifold and the cartridge cover are each adapted to control fluid flow within the disposable cartridge.

20. The method of claim 19, wherein the pneumatic manifold is adapted to actuate the one or more pneumatically actuated valves of the disposable cartridge and the cartridge cover is adapted to apply pressure to one or more chambers in the disposable cartridge.

21. The method of claim 1, wherein the system further comprises:
   e) an actuator assembly configured to move fluid between chambers when the disposable cartridge is engaged with the actuator assembly;
   f) a thermal cycler configured to cycle temperature in the thermal cycling chamber when the disposable cartridge is engaged with the actuator assembly;
   g) a capillary electrophoresis assembly configured to accept a reaction product from the disposable cartridge when the disposable cartridge is engaged with the actuator assembly and to perform capillary electrophoresis on the reaction product; and
   h) a computerized control system configured to control the actuator assembly, the thermal cycler and the capillary electrophoresis assembly.

22. The method of claim 1, further comprising washing the isolated DNA to purify the isolated DNA prior to amplifying.

23. The method of claim 1, wherein the computer analysis of a plurality of detected STR markers produces a profile of a plurality of detected STR markers.

24. The method of claim 1, wherein the reaction module is adapted to perform an amplification reaction on the immobilized DNA in a non-microfluidic volume to produce a reaction product.

25. The method of claim 1, wherein the capture chamber comprises magnetically responsive particles.

26. The method of claim 1, wherein the reagents in the reagent cartridge comprise reagents for performing PCR.

27. The method of claim 1, wherein the at least one set of fluidic chambers further includes a wash chamber, a waste chamber or a dilution chamber, or a combination thereof.

28. The method of claim 1, wherein the chambers of the at least one set of fluidic chambers are non-microfluidic chambers.

29. The method of claim 1, wherein fluid is selectively routed between the chambers of the at least one set of fluidic chambers using diaphragm valves.

30. The method of claim 1, wherein the disposable cartridge comprises a plurality of sets of fluidic chambers.

31. The method of claim 30, further comprising providing each of a plurality of samples to a different sample chamber and performing the method on the plurality of samples in parallel.

32. The method of claim 1, wherein the disposable cartridge comprises:
   a) a microfluidic component comprising a plurality of intersecting microfluidic channels and at least one controllable valve configured to regulate flow of fluid between the intersecting microfluidic channels; and
   b) a non-microfluidic component comprising a plurality of non-microfluidic chambers, wherein each non-microfluidic chamber is fluidically connected to at least one microfluidic channel;
   wherein at least one valve regulates flow of fluid from at least one non-microfluidic chamber to another non-microfluidic chamber through a microfluidic channel.

33. The method of claim 1, wherein the separation and detection module comprises an electrophoresis system comprising:
   a) at least one electrophoresis sample channel having a channel inlet and a channel outlet;
   b) at least one electrophoresis capillary having a capillary inlet and a capillary outlet, wherein the at least one electrophoresis capillary comprises an electrically conductive medium and is in communication with the at least one electrophoresis sample channel at a point of connection; and
   c) an anode and a cathode configured to apply a voltage across the capillary inlet and the capillary outlet of the at least one electrophoresis capillary, wherein one of the anode or the cathode comprises a first electrode comprising at least two forks, and wherein the at least two forks of the first electrode are in electrical communication with the at least one electrophoresis sample channel on different sides of the point of connection.

34. The method of claim 1, wherein the separation and detection module comprises an optical system comprising:
   a) an excitation source configured to direct excitation light to at least one fluorescent molecule, wherein the at least one fluorescent molecule emits light other than the excitation light when excited by the excitation light;
   b) a rejection filter configured to filter out the excitation light and to allow transmission of the emitted light;
   c) an imaging lens configured to focus the emitted light;
   d) a dichroic mirror substantially transparent to the excitation light and configured to reflect the emitted light to a detector;
   e) a focusing system comprising at least one lens configured to focus the light reflected from the dichroic mirror; and
   f) a photodetector configured to receive the focused light.

35. The method of claim 1, wherein the system further comprises an article in computer-readable form comprising code for operating the system.

36. The method of claim 1, wherein the electrophoresis is capillary electrophoresis.

37. The method of claim 1, wherein the sample is a raw sample.

38. The method of claim 1, wherein the system fits within an enclosure of no more than 10 ft$^3$.

39. The method of claim 12, wherein processing the reaction product comprises diluting the reaction product.

40. The method of claim 21, wherein the thermal cycler comprises a Peltier device.

41. The method of claim 5, wherein the plurality of CODIS STR markers is selected from the group consisting of D3S1358, TH01, D21S11, D18S51, D5S818, D13S317, D7S820, D16S539, CSF1PO, vWA, D8S1179, TPDX and FGA.

42. The method of claim 5, wherein the plurality of STR markers is at least 10 CODIS STR markers.

43. The method of claim 5, wherein the plurality of STR markers is at least 13 CODIS STR markers.

* * * * *

UNITED STATES PATENT AND TRADEMARK OFFICE
CERTIFICATE OF CORRECTION

Page 1 of 1

PATENT NO. : 8,394,642 B2
APPLICATION NO. : 12/795515
DATED : March 12, 2013
INVENTOR(S) : Stevan B. Jovanovich et al.

It is certified that error appears in the above-identified patent and that said Letters Patent is hereby corrected as shown below:

Title page, Related U.S. Application Data (60), below the priority claims to the listed provisional patent applications, add -- Continuation of International Application No. PCT/US2010/037545, filed on Jun. 4, 2010. --

Column 1, lines 15 to 19, "This application is related to U.S. Ser. No. 61/184,759 filed Jun. 5, 2009, U.S. Ser. No. 61/235,664, filed Aug. 20, 2009, U.S. Ser. No. 61/349,680 filed May 28, 2010, and PCT/US2010/037545 filed Jun. 4, 2010, which are incorporated herein by reference in their entirety for all purposes." should be changed to
-- This application is a continuation patent application of PCT Application No. PCT/US2010/037545, filed Jun. 4, 2010, and claims priority to U.S. Ser. No. 61/184,759 filed Jun. 5, 2009, U.S. Ser. No. 61/235,664, filed Aug. 20, 2009, and U.S. Ser. No. 61/349,680 filed May 28, 2010, which are incorporated herein by reference in their entirety for all purposes. --

Signed and Sealed this
Thirty-first Day of March, 2015

Michelle K. Lee
*Director of the United States Patent and Trademark Office*